(12) United States Patent
Pajerowska-Mukhtar et al.

(10) Patent No.: US 10,584,346 B2
(45) Date of Patent: *Mar. 10, 2020

(54) HSF-LIKE TRANSCRIPTION FACTOR, TBF1, IS A MAJOR MOLECULAR SWITCH FOR GROWTH-TO-DEFENSE TRANSITION IN PLANTS

(71) Applicant: Duke University, Durham, NC (US)

(72) Inventors: Karolina M. Pajerowska-Mukhtar, Vestavia Hills, AL (US); Guoyong Xu, Durham, NC (US); Xinnian Dong, Durham, NC (US)

(73) Assignee: Duke University, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/003,289

(22) Filed: Jun. 8, 2018

(65) Prior Publication Data
US 2018/0273965 A1  Sep. 27, 2018

Related U.S. Application Data

(63) Continuation of application No. 14/576,304, filed on Dec. 19, 2014, now Pat. No. 10,017,773, which is a continuation of application No. 14/310,320, filed on Jun. 20, 2014, now abandoned, which is a continuation-in-part of application No. PCT/US2012/070838, filed on Dec. 20, 2012.

(60) Provisional application No. 61/578,632, filed on Dec. 21, 2011.

(51) Int. Cl.
| C12N 15/82 | (2006.01) |
| C07K 14/62 | (2006.01) |
| C07K 14/415 | (2006.01) |

(52) U.S. Cl.
CPC ........ *C12N 15/8216* (2013.01); *C07K 14/415* (2013.01); *C07K 14/62* (2013.01); *C12N 15/8274* (2013.01); *C12N 15/8279* (2013.01); *C12N 15/8281* (2013.01); *C12N 15/8282* (2013.01); *C12N 15/8283* (2013.01); *C12N 15/8285* (2013.01)

(58) Field of Classification Search
None
See application file for complete search history.

(56) References Cited

U.S. PATENT DOCUMENTS

| 6,031,153 | A | 2/2000 | Ryals et al. | |
| 7,291,767 | B2* | 11/2007 | Oriedo | ........... C07K 14/415 |
| | | | | 435/320.1 |
| 7,635,798 | B2* | 12/2009 | Weglarz | ........... C12N 15/8243 |
| | | | | 435/320.1 |
| 10,017,773 | B2* | 7/2018 | Pajerowska-Mukhtar | .............. |
| | | | | C07K 14/62 |
| 2004/0031072 | A1 | 2/2004 | La Rosa et al. | |
| 2004/0123343 | A1 | 6/2004 | La Rosa et al. | |
| 2006/0143729 | A1* | 6/2006 | Alexandrov | ........... C07K 14/415 |
| | | | | 800/278 |
| 2009/0094717 | A1 | 4/2009 | Troukhan et al. | |
| 2009/0151015 | A1 | 6/2009 | Adam et al. | |
| 2010/0138958 | A1 | 6/2010 | Mullinbaux et al. | |

(Continued)

FOREIGN PATENT DOCUMENTS

| EP | 1033405 | 9/2000 |
| WO | WO 2013096567 | 6/2013 |

OTHER PUBLICATIONS

Xu et al. (2010). One-step, zero-background ligation-independent doing intron-containing hairpin RNA constructs for RNAi in plants. New Phytologist 187: 240-250.

(Continued)

*Primary Examiner* — Medina A Ibrahim
(74) *Attorney, Agent, or Firm* — Alston & Bird LLP

(57) ABSTRACT

The present invention relates to new methods to study and control the expression of plant genes, particularly nucleotide sequences located downstream from regions comprising binding sites for transcription factors, such as the cis-element translocon 1 (TL1) comprising GAAGAAGAA and similar sequences. The invention relates to isolated nucleotide sequences comprising a regulatory region comprising a promoter operably-linked to one or more upstream open reading frames (uORFs) and one or more downstream open reading frames (dORFs) encoding one or more functional polypeptides, including transcription factors such as TBF1, reporter polypeptides, and polypeptides conferring resistance to drugs, resistance of plants viral, bacterial, or fungal pathogens, and polypeptides involved in the growth of plants. Related aspects include the use of a region which encodes one or more polypeptides designated uORF1 and uORF2 from *Arabidopsis* plants, natural and synthetic variants of these polypeptides, and their homologues and orthologues isolated from other plant species, including crop plants, plus vectors, cells, plant propagation material, transgenic plants, and seeds comprising nucleic acids comprising said all or portions of said regulatory region. Other aspects relate to methods of using these regulatory elements to generate and screen for transgenic plants having improved resistance microbial and viral plant pathogens, and engineered cells and plants comprising these one or more of these genetic elements to facilitate the production of proteins for use in structure/function studies, in industrial, medical, and agricultural applications, particularly in the discovery of metabolic pathways involved in the and development of disease-resistant plants.

18 Claims, 24 Drawing Sheets
Specification includes a Sequence Listing.

(56) References Cited

U.S. PATENT DOCUMENTS

2015/0113685 A1   4/2015   Pajerowska-Mukhtar

OTHER PUBLICATIONS

Xu et al. (2012). Plant ERD2-like proteins function as endoplasmic reticulum luminal protein receptors and participate in programmed cell death during innate immunity. The Plant Journal: Cell Molec. Biol. 72: 57-69.
Zhang et al. (2012). Agrobacterium-mediated transformation of *Arabidopsis thaliana* using the floral dip method. Nature Protocol 1: 641-646.
Zhang et al. (1996). Effects of Fis on ribosome synthesis and activity and on rRNA promoter activities in *Escherichia coli*. J. Mol. Biol. 259: 27-40.
Zhang et al. (1999). Interaction of NPR1 with basic leucine zipper protein transcription factors that bind sequences required for salicylic acid induction of the PR1 gene. Proc. Natl. Acad. Sci. USA 96: 6523-6528.
Zhao, Y. (2010). Auxin biosynthesis and its role in plant development. Annu. Rev. Plant Biol. 61: 49-64.
Zheng et al. (2006). *Arabidopsis* WRKY33 transcription factor is required for resistance to necrotrophic fungal pathogens. Plant J. 48: 592-605.
Zipfel et al. (2006). Perception of the bacterial PAMP EF-Tu by the receptor EFR restricts Agrobacterium-mediated transformation. Cell 125: 749-760.
Bailey et al. Plant Cell 15:2497-2501 (2003).
Bailey-Serres et al. Plant biology: an immunity boost combats crop disease. Nature 2017. 545(7655):420.
Ball et al. (1986). Molecular cloning and characterization of ARO7-OSM2, a single yeast gene necessary for chorismate mutase activity and growth in hypertonic medium. Mol. Gen. Genet. 205: 326-330.
Baniwal et al. (2004). Heat stress response in plants: a complex game with chaperones and more than twenty heat stress transcription factors. J. Bioscl. 29: 471-487.
Boscheinen et al. (1997). Heat stress transcription factors from tomato can functionally replace HSF1 in the yeast *Sacchoromyces cerevisiae*. Mol. Gen. Genet. 255: 322-331.
Brooks et al. (2002). Evolution of amino acid frequencies in proteins over deep time: inferred order of introduction of amino acids into the genetic code. Mol. Biol. Evol. 19: 1645-1655.
Busch et al. (2005). Identification of novel heat shock factor-dependent genes and biochemical pathways in *Arabidopsis thaliana*. Plant J. 41: 1-14.
Calvo, S.E., Pagliarini, D.J. & Mootha, V.K. Upstream open reading frames cause widespread reduction of protein expression and are polymorphic among humans. Proc. Natl Acad Sci. USA 106, 7507-7512 (2009).
Cao et al. (1997). The *Arabidopsis* NPR1 gene that controls systemic acquired resistance encodes a novel protein containing ankyrin repeats. Cell 88: 57-63.
Clough et al. (1998). Floral dip: a simplified method for Agrobacterium-mediated transformation of *Arabidopsis thaliana*. Plant Journal 16: 735-743.
Curtis et al. (2003). A gateway cloning vector set for high-throughput functional analysis of genes in planta. Plant Physiol. 133: 462-469.
Czarnecka-Verner et al. (2004). Plant class B HSFs inhibit transcription and exhibit affinity for TFIIB and TBP. Plant Mol. Biol. 56: 57-75.
Czarnecka-Verner et al. (2000). Plants contain a novel multi-member class of heat shock factors without transcriptional activator potential. Plant Mol. Biol. 43: 459-471.
Dangl et al. (2013). Pivoting the plant immune system from dissection to deployment. Science 341: 746-751.
Deplancke et al. (2004). A Gateway-Compatible Yeast One-Hybrid. System Genome Res. 14: 2093-2101.
Deplancke et al. (2006). A gene-centered C. elegans protein-DNA interacion network. Cell 125: 1192-1205.
Deplancke et al. (2006). Gateway-compatible yeast one-hybrid screens. Cold Spring Harb. Protoc.
Dey et al. (2007). Conserved intermolecular salt bridge required for activation of protein kinases PKR, GCN2, and PERK. J. Biol. Chem. 282: 6653-6660.
Dong et al. (1991). Induction of *Arabidopsis* Defense Genes by Virulent and Avirulent Pseudomonas syringae Strains and by a Cloned Avirulence Gene. The Plant Cell 3(1): 61-72.
Dong et al. (2000). Uncharged tRNA activates GCN2 by displacing the protein kinases moiety from a bipartite tRNA-binding domain. Mol. Cell 6: 269-279.
Dunbar, T.L., Yan, Z., Balla, K.M., Smelkinson, M.G. & Troemel, E.R. C. elegans detects pathogen-induced translational inhibition to activate immune signaling. Cell Host Microbe 11, 375-386 (2012).
Durrant et al. (2007). *Arabidopsis* SNI1 and RAD51D regulate both gene transcription and DNA recombination during the defense response. Proc. Natl. Acad. Sci. USA 104: 4223-4227.
Durrant et al. (2004). Systemic acquired resistance. Annu. Rev. Phytopathol 42: 185-209.
Ercikan-Abali et al. (1996). Active site-directed double mutants of dihydrofolate reductase. Cancer Res. 56: 4142-4145.
Ercikan-Abali et al. (1996). Variants of human dihydrofolate reductase with substitutions at leucine-22: effect on catalytic and inhibitor binding properties. Mol. Pharmacol. 49: 430-437.
Eulgern et al. (2000). The WRKY superfamily of plant transcription facotrs. Trends Plant Sci. 5:199-206.
Fabro et al. (2008). Genome-wide expression profiling *Arabidopsis* at the stage of Golovinomyces cichoracearum haustorium formation. Plant Physiol. 146: 1421-1439.
Gfeller et al. (2010). *Arabidopsis* jasmonate signalling pathway. Sci. Signal 3, cm4.
Guo et al. Proc. Natl. Acad. Sci. USA 101:9205-9210 (2004).
Hall et al. (1983). Expression and regulation of *Escherichia coli* IacZ gene fusions in amammalian cells. Mol. Appl. Genet. 2(1): 101-109.
Harding et al. (2000). Regulated translation initiation controls stress-induced gene expression in mammalian cells. Mol. Cell 6: 1099-1108.
Hayden et al. (2007). Identification of novel conserved peptide uORF homology groups in *Arabidopsis* and rice reveals ancient eukaryotic origin of select groups and preferential association with transcription factor-encoding genes. BMC Biol. 5, 32.
Heidel et al. (2004). Fitness Costs of Mutations Affecting the Systemic Acquired Resistance Pathway in *Arabidopsis thaliana*. Genetics 168: 2197-2206.
Hill et al. Functional Analysis of Conserved Histidines in ADP-Glucose Pyrophosphorylase from *Escherichia coli*. Biochem. Biophys. Res. Comm. 244:573-577 (1998).
Hinnebusch, A.G. (2005). Translational regulation of GCN4 and the general amino acid control of yeast. Annu. Rev. Microbiol. 59: 407-450.
Holsters et al. (1980). The funcational organization of the nopaline A. tumefacins plasmid pTiC58. Plasmid 3: 212-230.
Holton et al. (1995). Genetics and Biochemistry of Anthocyanin Biosynthesis. Plant Cell 7: 1071-1083.
Humphry et al. (2010). A regulon conserved in monocot and dicot plants defines a functional module in antifungal plant immunity. Proc. Natl. Acad. Sci. USA.
International Search Report and Written Opinion for PCT/US12/70838 dated Jul. 1, 2013 (7 pages).
Jefferson, R.A. (1987). Assaying chimeric genes in plants: The GUS gene fusion system. Plant Mol. Biol. Rep. 5: 287-405.
Jefferson et al. (1987). GUS fusion: Beta-Glucuronidase as a sensitive and versatile gene fusion marker in higher plants EMBO J. 6:3901-3907.
Johnson et al. (2007). The genome sequence of avian pathogenic *Escherichia coli* strain O1:K1:H7 shares strong similarities with human extraintestinal pathogenic E. coli genomes. J. Bacteriol. 189(8): 3228-3236.
Jones et al. (2006). The plant immune system. Nature 444: 323-329.

(56) References Cited

OTHER PUBLICATIONS

Kawai-Yamada et al. (2001). Mammalian Bax-induced plant cell death can be down-regulated by overexpression of *Arabidopsis* Bax Inhibitor-1 (AtBI-1). Proc. Natl. Acad. Sci. USA 98: 12295-12300.
Kay et al. (2007). A baterial effector acts as a plant transcription factor and induces a cell size regulator. Science 318: 648-651.
Kinkema et al. (2000). Nuclear localization of NPR1 is required for activation of PR gene expression. Plant Cell 12: 2339-2350.
Kohrer et al. (2008). The many applications of acid urea polyacrylamide gel electrophoresis to studies of tRNAs and aminoacyl-tRNA synthetases. Methods 44: 129-138.
Kotak et al. (2007). Complexity of the heat stress response in plants. Curr. Opin. Plant Biol. 10: 310-316.
Kozak, M. (1991). An analysis of vertebrate mRNA sequences: intimations of translational control. J. Cell Biol. 115: 887-903.
Kumar et al. Heat Shock Factors HsfB1 and HsfB2b Are Involved in the Regulation of Pdf1/2 Expression and Pathogen Resistance in *Arabidopsis*. Molecular Plant. 2008. 2(2): 152-165.
Kwon et al. (2008). Secretory pathways in plant immune response. Plant Physiol. 147: 1575-1583.
Lageix et al. (2008). *Arabidopsis* eIF2alpha kinase GCN2 is essential for growth in stress conditions and is activated by wounding. BMC Plant Biol. 8:134.
Lawless, C. et al. Upstream sequence elements direct post-transcriptional regulation of gene expression under stress conditions in yeast. BMC Genomics 10, 7 (2009).
Lebel et al. (1998). Functional analysis of regulatory sequences controlling PR-1 gene expression in *Arabidopsis*. Plant Journal 16:223-233.
Leister et al. (2003). From genes to photosynthesis in *Arabidopsis thaliana*. Int. Rev. Cytol. 228: 31-83.
Li et al. (2001). Activation of an EDS1-mediated R-gene pathway in the snc1 mutant leads to constitute, NPR1-independent pathogen resistance. Mol. Plant Microbe in 14: 1131-1139.
Li et al. (2002). Plant expansins are a complex multigene family with an ancient evolutionary origin. Plant Physiol. 128: 854-864.
Li et al. (2009) Specific ER quality control components required for biogenesis of the plant innate immune receptor ERF. Proc. Natl. Acad. Sci. USA 106: 15973-15978.
Li et al. (Jan. 2013). The GCN2 homologue in *Arabidopsis thaliana* interacts with uncharged tRNA and uses *Arabidopsis* eIF2alpha molecules as direct substrates. Plant Biol. (Stuttg) 15(1):13-8.
Lu et al. (2009). Uncoupling of sustained MAMP receptor signalling from early outputs in an *Arabidopsis* endoplasmic reticulum glucosidase II allele. Proc. Natl. Acad. Sci. USA 106: 22522-22527.
Marois et al. (2002). The Xanthomonas type III effector protein AvrBs3 modulates plant gene expression and induces cell hypertophy in the susceptible host. Mol. Plant Microbe Interact 15: 637-646.
Miller et al. (1990). Cis-acting sequences involved in the translational control of GCN4 expression. Biochim. Biophys. Acta 1050: 151-154.
Miller, J.H. (1972). Experiments in molecular genetics. [Cold Spring Harbor, N.Y.] Cold Spring Harbor Laboratory.
Morris et al. Molecular and Cellular Biology (2000), pp. 8635-8642.
Nover et al. (2001). *Arabidopsis* and the heat stres transcription factor world: how many heat stress transcription factors do we need? Cell Stress Chaperones 6: 177-189.
Nekrasov et al. (2009). Control of the pattern-recognition receptor EFR by an ER protein complex in plant immunity. EMBO J. 28: 3428-3438.
Nishimura et al. (2010). *Arabidopsis* and the plant immune system. Plant J. 61: 1053-1066.
Office Action for U.S. Appl. No. 14/576,304 dated Mar. 3, 2016 (26 pages).
Office Action for U.S. Appl. No. 14/576,304 dated Nov. 25, 2016 (55pages).
Office Action for U.S. Appl. No. 14/576,304 dated Jul. 13, 2017 (13 pages).
Office Action for U.S. Appl. No. 14/576,304 dated Dec. 1, 2017 (9 pages).

Oliveros, J.C. (2007). VENNY. An interactive tool for comparing lists with Venn Diagrams. Http://bioinfogp.cnb.csic.es/tools/venny/index.html.
Padyana et al. (2005). Structural basis for autoinhibition and mutational activation of eukaryotic initiation factor 2alpha protein kinases GCN2. J. Biol. Chem. 280: 29289-29299.
Pajerowska-Mukhtar et al. (2008). Natural variation of potato allene oxie synthase 2 causes differential levels of jasmonates and pathogen resistance in *Arabidopsis*. Planta 228: 293-306.
Pajerowska-Mukhtar, K.M. et al. The HSF-like transcription factor TBF1 is a major molecular switch for plant growth-to-defense transition. Curr. Biol. 22, 103-112 (2012).
Panstruga et al. (2009). SnapShot: Plant immune response pathways. Cell 136(978): e971-973.
Piquerez, S.J.M., Harvey, S.E., Beynon, J.L. & Ntoukakis, V. Improving crop disease resistance: lessons from research on *Arabidopsis* and tomato. Front. Plant Sci. 5 (2014).
Prandl et al. (1998). HSF3, a new heat shock factor from *Arabidopsis thaliana*, derepresses the heat shcok response and confers thermotolerance when overexpressed in transgenic plants. Mol. Gen. Genet. 258: 269-278.
Prasher et al. (1992). Primary structure of the Aequorea victoria green-fluorescent protien. Gene 111(2): 229-233.
Rahmani, F. et al. (2009). Sucrose control of translation mediated by an upstream open reading frame-encoded peptide. Plant Physiol. 150, 1356-1367 (2009).
Riley et al. (2006). *Escherichia coli* K-12: a cooperatively developed annotation snapshot—2005. Nucleic Acids Res. 34(1): 1-9.
Saijo et al. (2009). Receptor quality control in the endoplasmic reticulum for plant innate immunity. EMBO J. 28: 3439-3449.
Song et al. (2011). DNA Repair Proteins Are Direction Involved in Regulation of Gene Expression during Plant Immune Response. Cell Host Microbe 9: 115-124.
Sugano et al. (2010). Role of OsNPR1 in rice defense program as revealed by genome-wide expression analysis. Plant Mol. Biol. 74: 549-562.
Takahashi et al. (2012) BAIUCAS: a novel BLAST-based algorithm for the identification of upstream open reading frames with conserved amino acid sequences and its application to the *Arabidopsis thaliana* genome. Bioinformatics 28(17): 2231-2241.
Tsuda et al. (2009). Network properties of robust immunity in plants. PLoS Genet. 5, e1000772.
Tucker et al. (2001). A yeast sensor of ligand binding. Nat. Biotechnol. 19: 1042-1046.
Vaughn et al. (2012) Known and novel post-transcriptional regulatory sequences are conserved across plant families. RNA 18:368-384.
Walter et al. (2002). Binding of tobramycin leads to conformational changes in yeast tRNA(Asp) and inhibition of aminoacylation. EMBO J. 21: 760-768.
Wang et al. (2006) A genomic approach to identify regulatory nodes in the transcriptional network of systemic acquired resistance in plants. PLoS Pathog 2, e123.
Wang et al. (2005). Induction of protein secretory pathway is required for systemic acquired resistance. Science 308: 1036-1040.
Wang et al. (2007). Salicylic Acid Inhibits Pathogen Growth in Plants through Repression of the Auxin Signaling Pathway. Curr. Biol. 17: 1784-1790.
Watanabe et al. (2009). Bax Inhibitor-1, a conserved cell death suppressor, is a key molecular switch downstream from a variety of biotic and abiotic stress signals in plants. Intl. J. Molec. Sci. 10: 3149-3167.
Wichmann et al. (2004). Effector genes of Xanthomonas axonopodis pv. Vesicatoria promote transmission and enhance other fitness traits in the field. Genetics 166: 693-706.
Winzeler et al. (1999). Functional characterization of the S. cerevislae genome by gene deletion and parallel analysis. Science 285: 901-906.
U.S. Appl. No. 14/576,304, Notice of Allowance dated Mar. 12, 2018.

(56) References Cited

OTHER PUBLICATIONS

Whalen et al., "Identification of Pseudomonas syringae Pathogens of *Arabidopsis* and a Bacterial Locus Determining Avirulence on Both Ambidopsis and Soybean," The Plant Cell, 3:49-59, (1991).

* cited by examiner

The yeast strains used in the Y1H assay
A
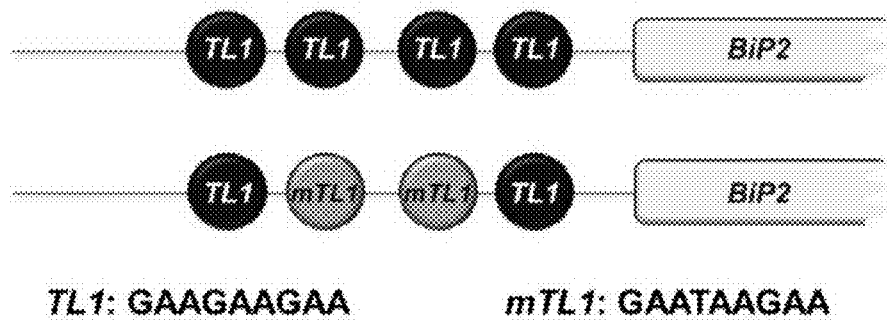
TL1: GAAGAAGAA    mTL1: GAATAAGAA
B
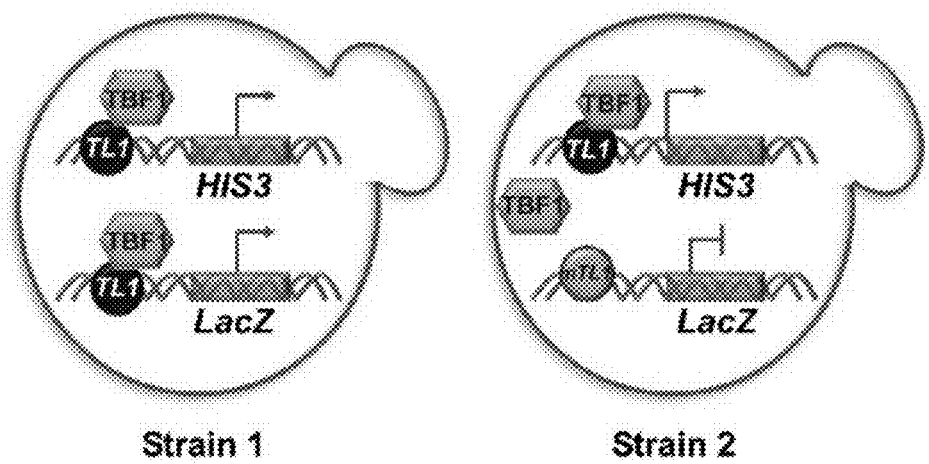
Strain 1                Strain 2
Fig. 2, Related to Figs 1A and 1B

**TBF1 transcript levels in the *tbf1* T-DNA insertion mutant**
A
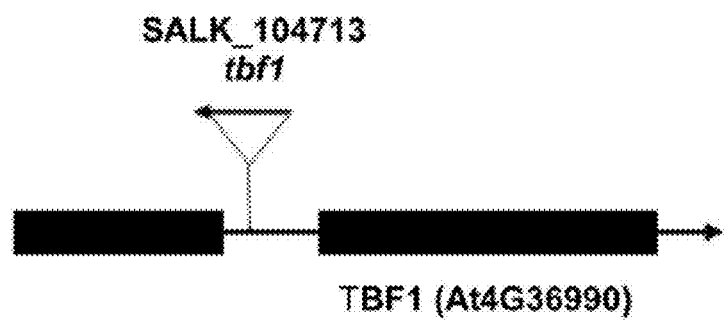
B
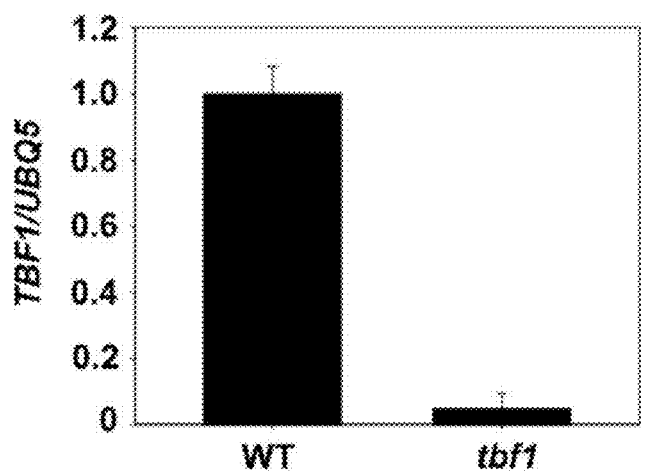
Fig. 3, Related to Fig 1C

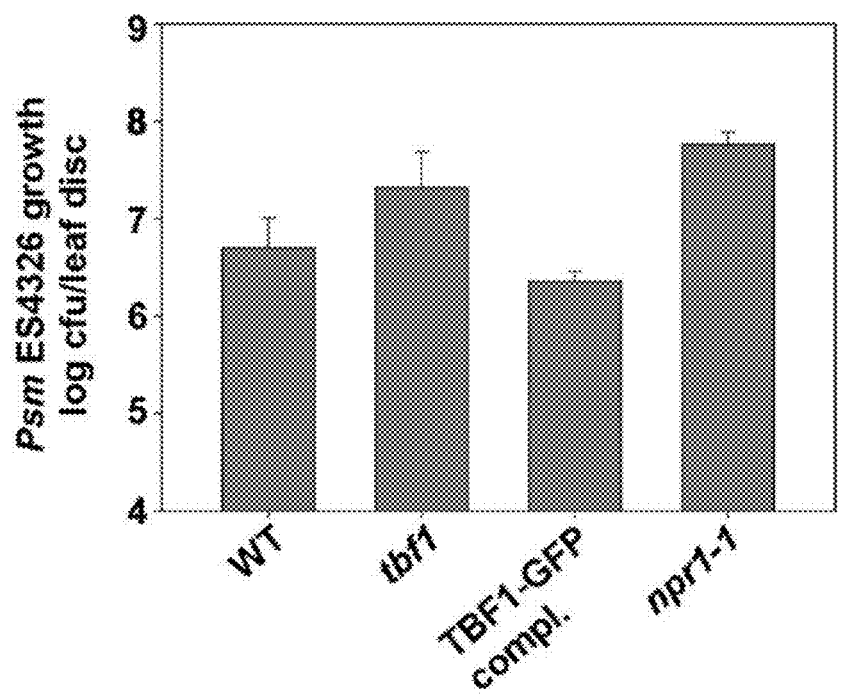
Fig. 4, Related to Fig. 1D

SA-induced accumulation of ER chaperones BiP1/2 is affected in the *tbf1* mutant
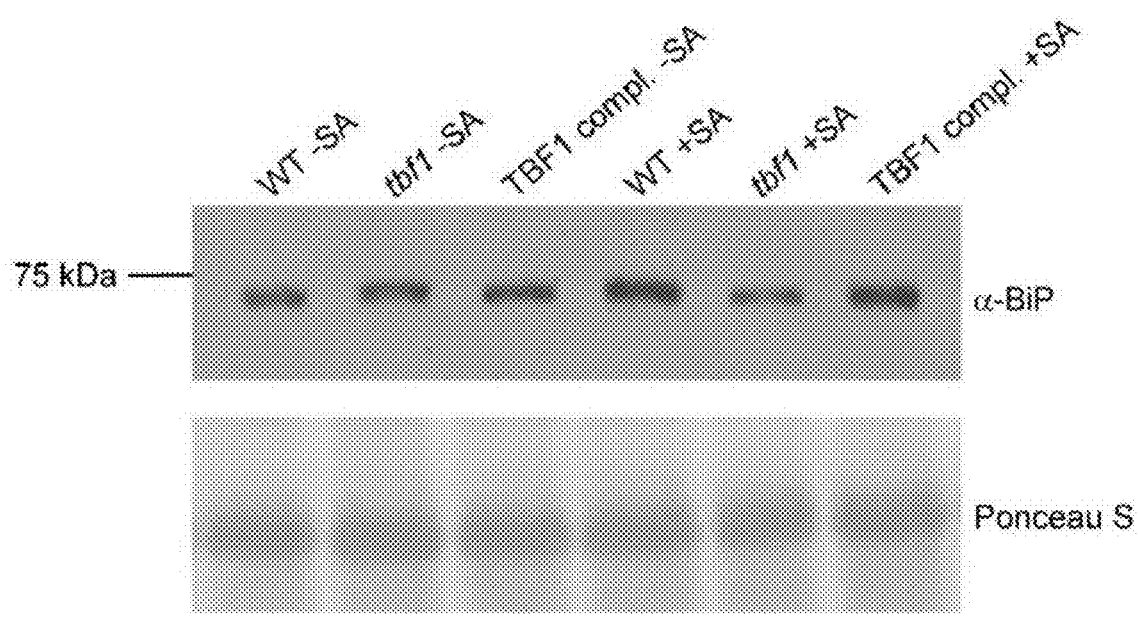
Fig. 6, Related to Fig. 5A

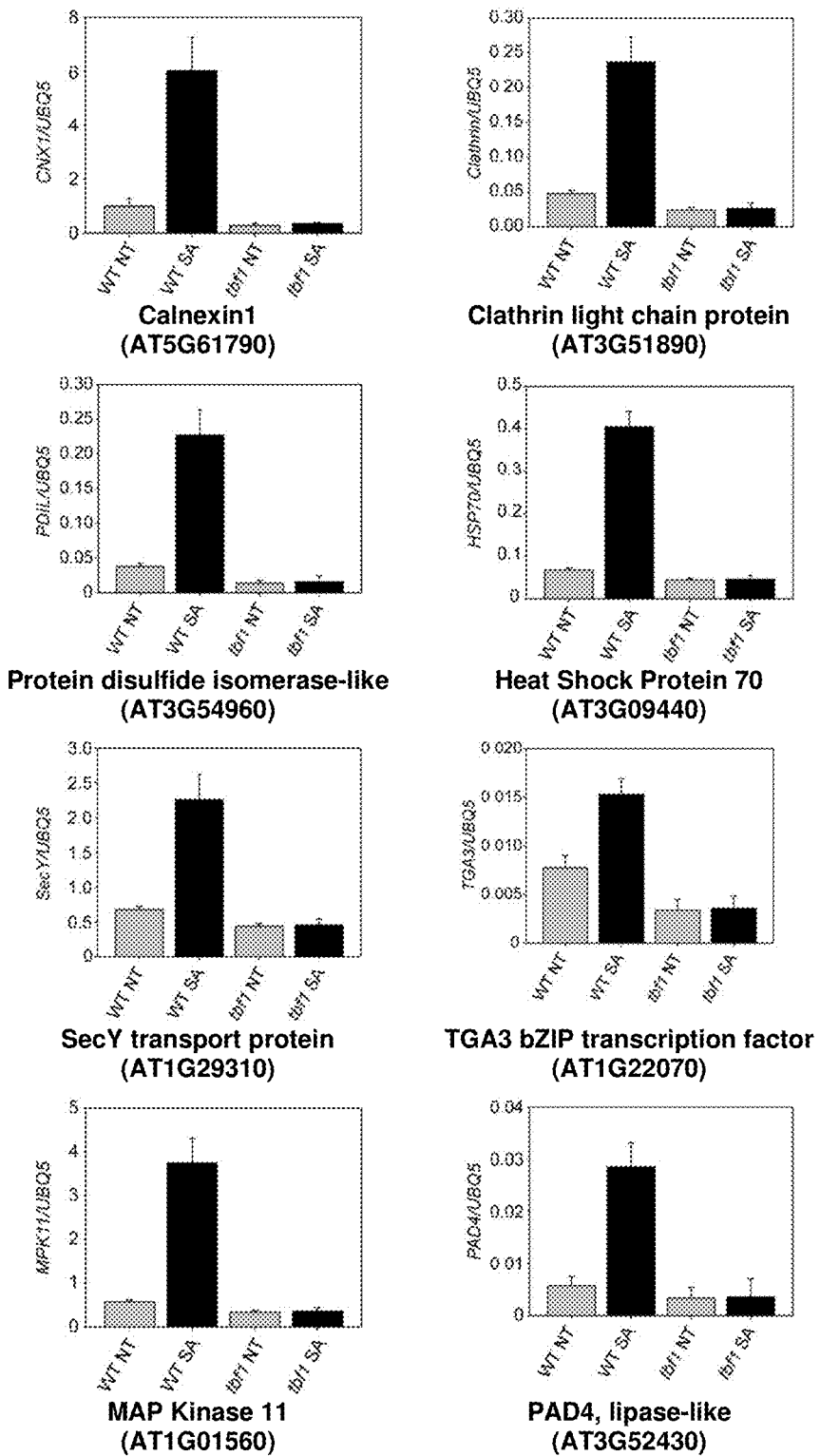
Fig. 7, related to Fig. 5D

Validation of the microarray data using qRT-PCR analysis of selected genes
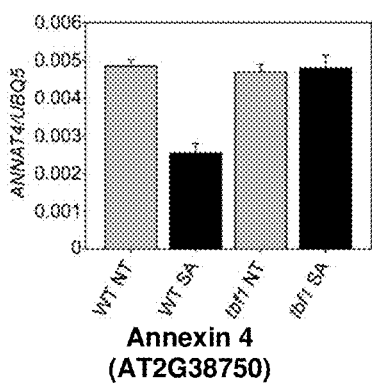
Annexin 4
(AT2G38750)
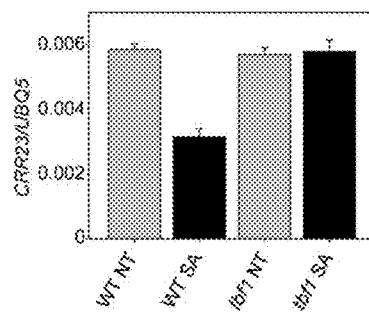
Chlororespiratory Reduction 23
NAD(P)H dehydrogenase (AT1G70760)
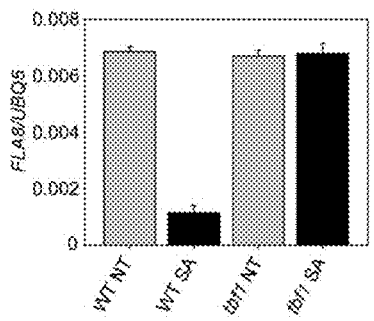
Fascilin-like arabinogalactan
protein 8 (AT2G45470)
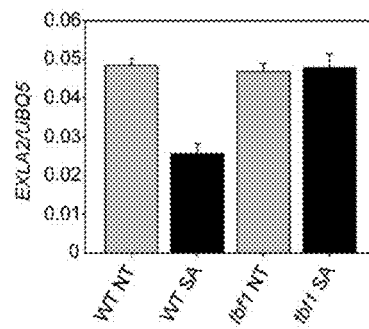
Expansin L2
(AT4G38400)
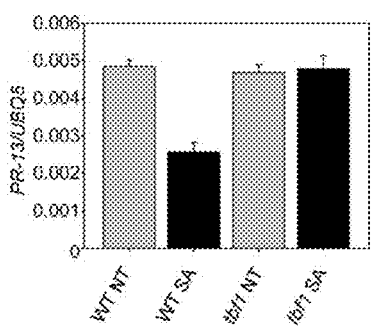
Pathogenesis-related 13, thionin
(AT1G66100)
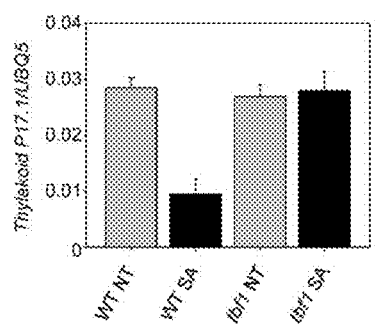
Thylakoid lumenal P17.1 protein
(AT3G44020)
Fig. 8, related to Fig. 5D

Validation of the microarray data using qRT-PCR analysis of selected genes
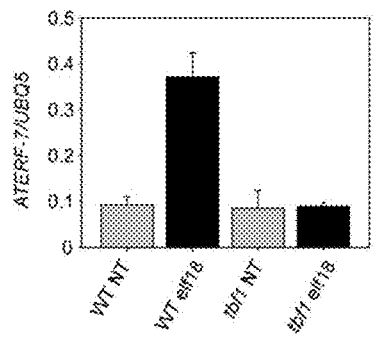
Ethylene response factor 7
(AT3G20310)
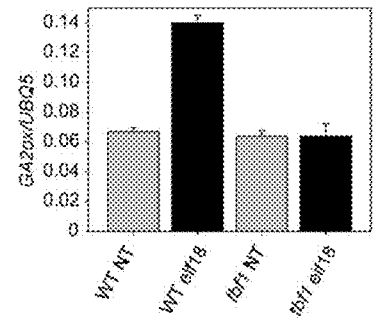
Gibberellin 2-oxidase
(AT4G21200)
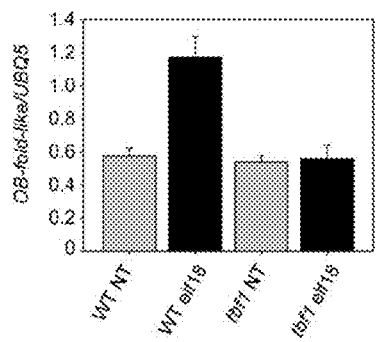
OB-fold-like ribosomal protein
(AT2G07715)
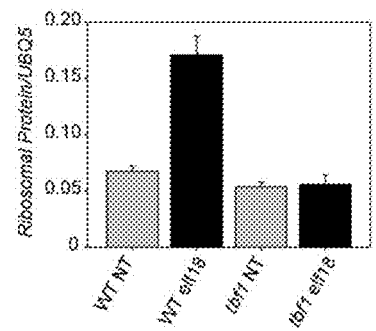
Ribosome small subunit precursor
(AT5G20600)
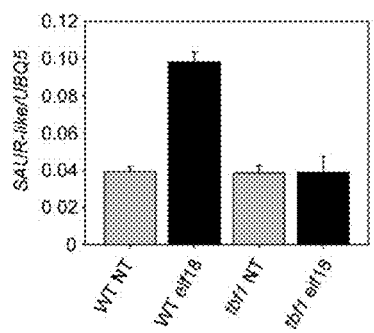
Auxin responsive SAUR-like protein
(AT3G61900)
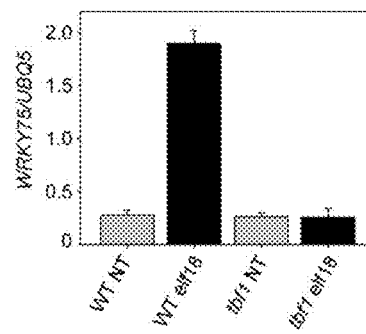
WRKY75 transcription factor
(AT5G13080)
Fig. 9, related to Fig. 5E

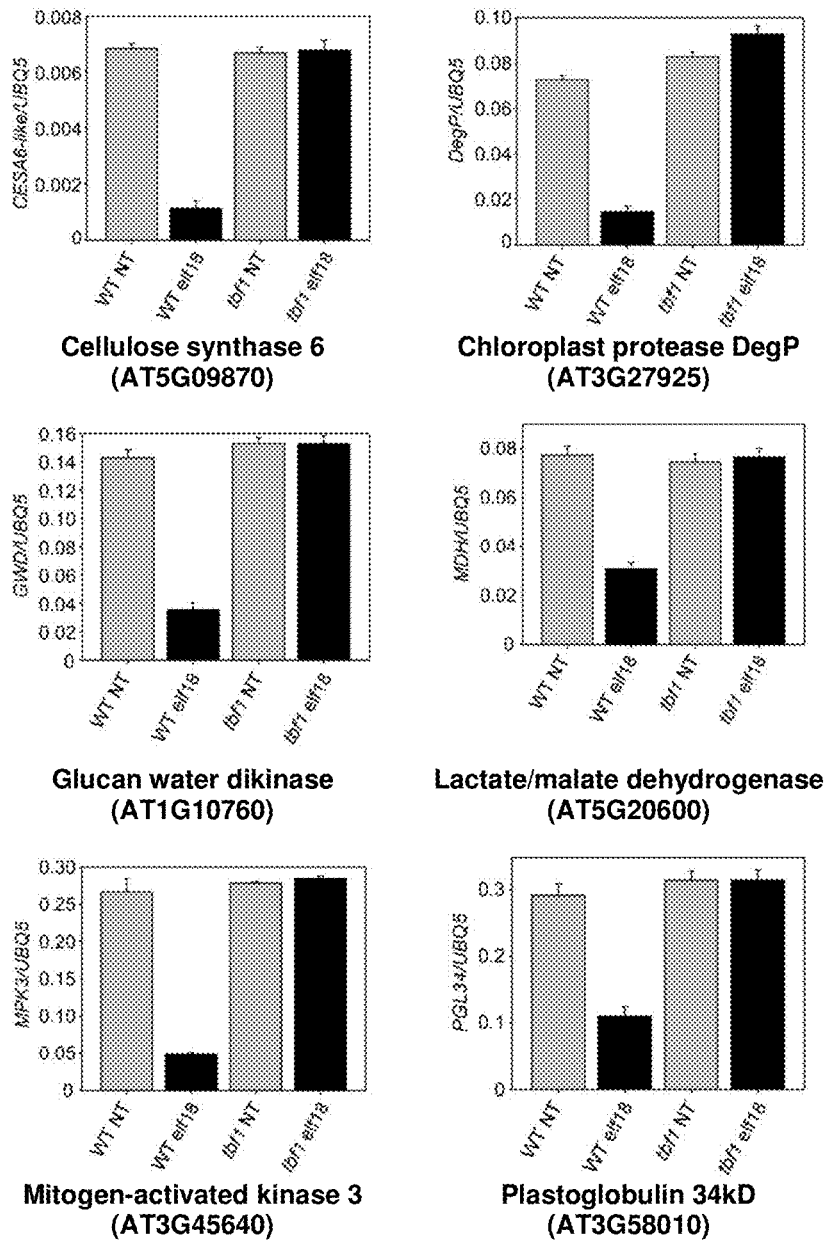
Fig. 10, related to Fig. 5E

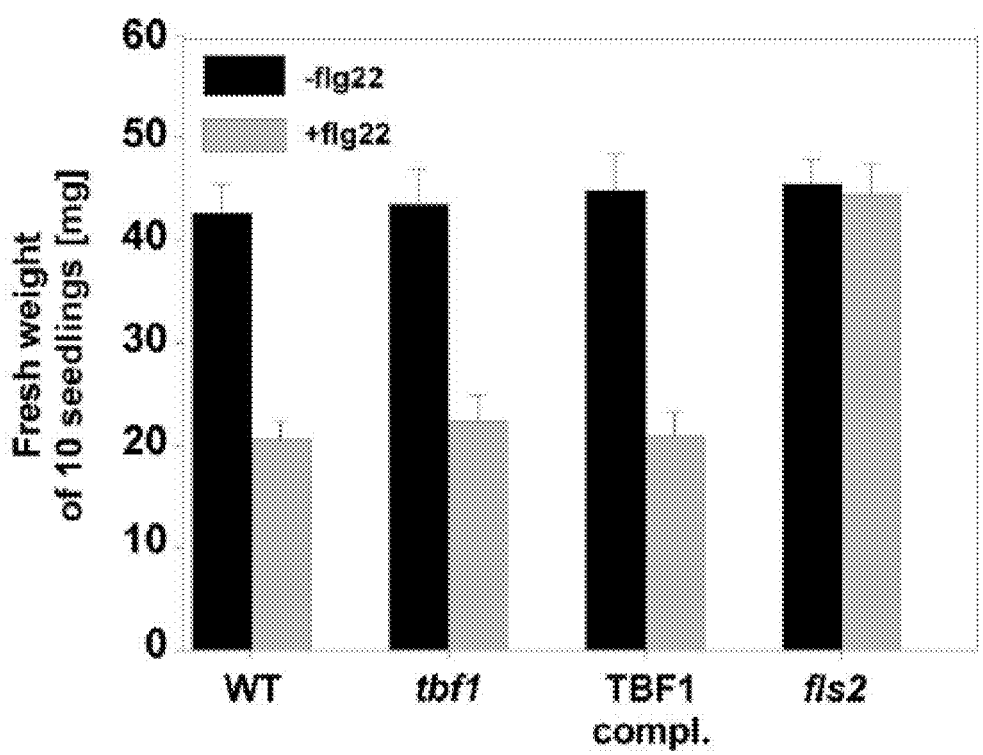
Fig. 12, related to Fig. 11

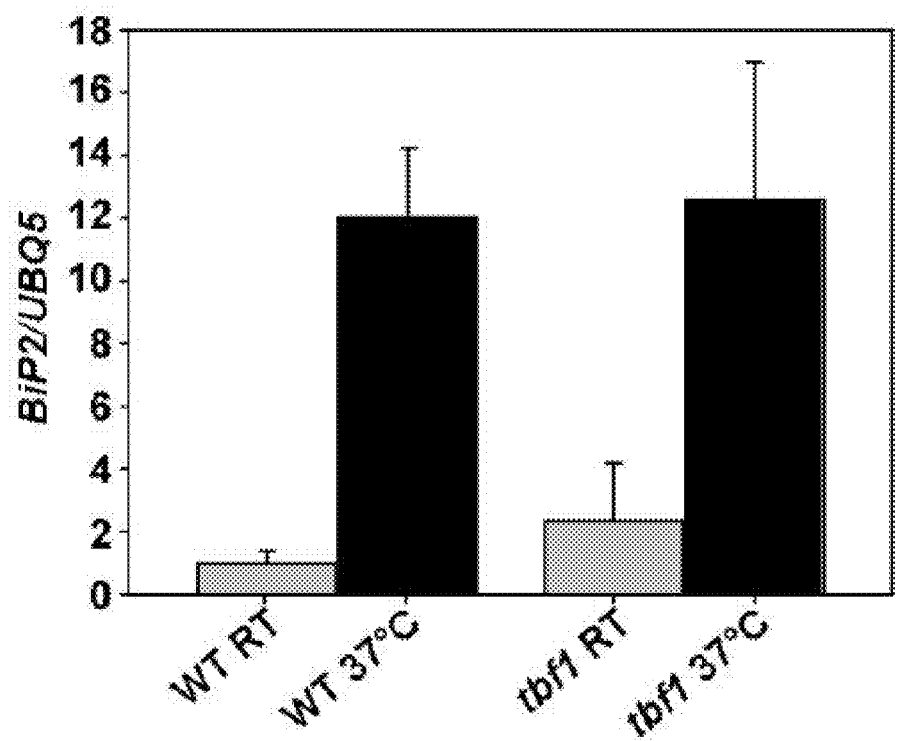
Fig. 13, related to Fig. 11

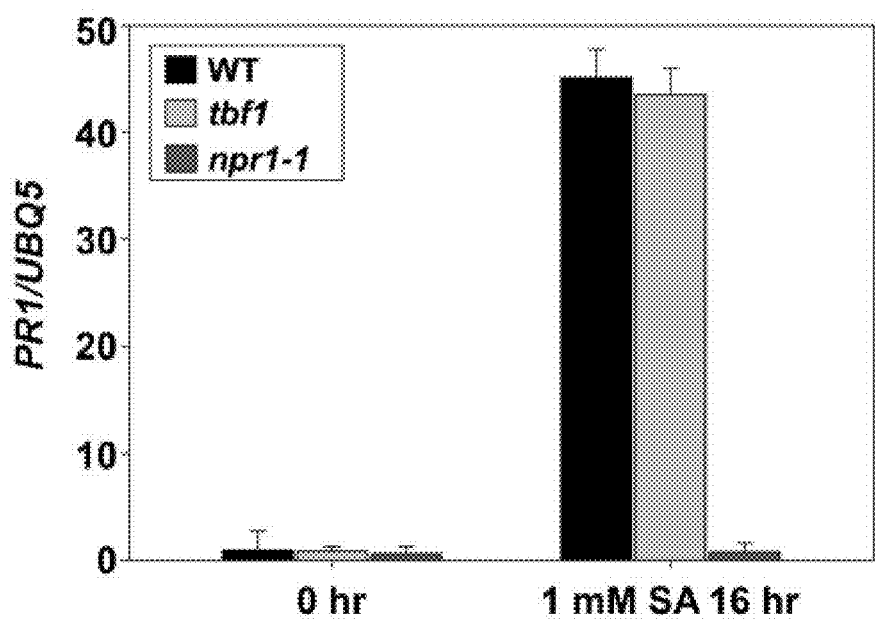
Fig. 14, related to Fig. 11C

**The *tbf1* mutant has normal flg22-induced resistance to *Psm* ES4326**
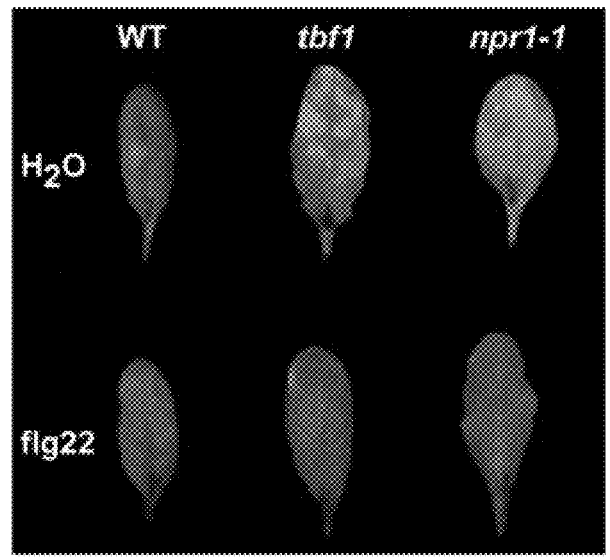
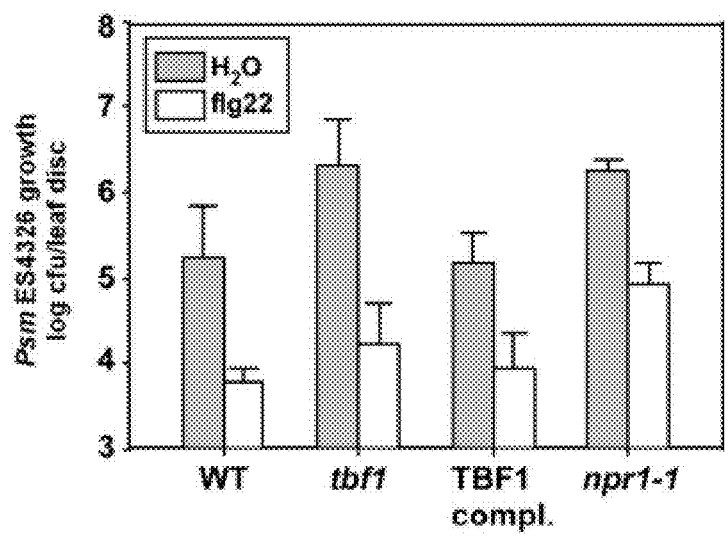
Fig. 15, related to Fig 11F

TBF1 translation is regulated in response to pathogen-induced changes in phenylalanine metabolism
A
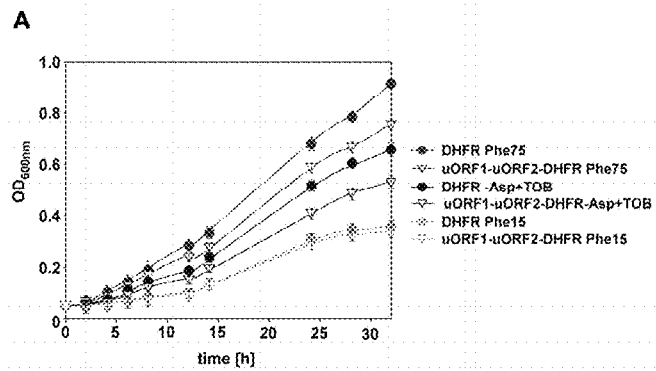
B
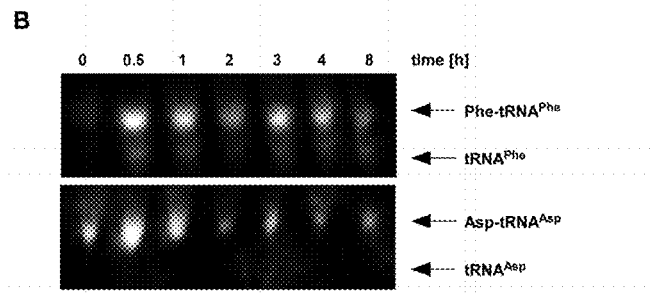
C
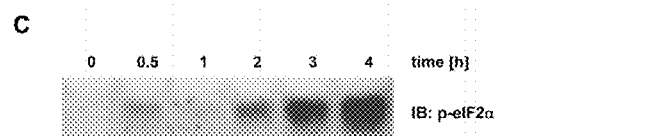
D
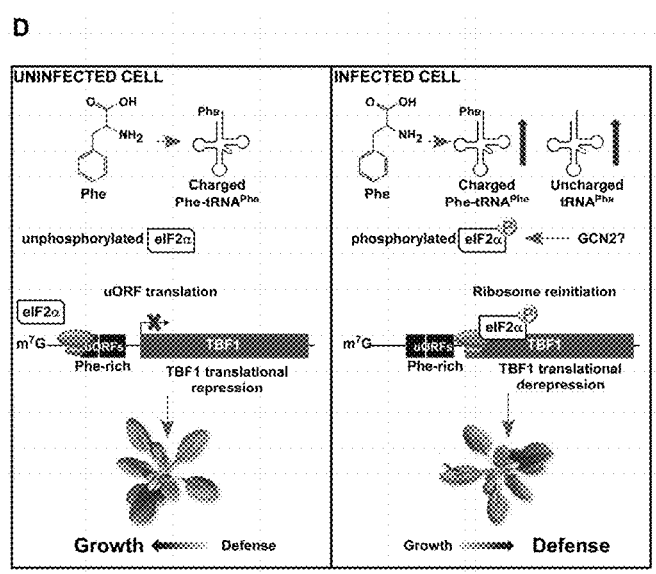
Fig. 17

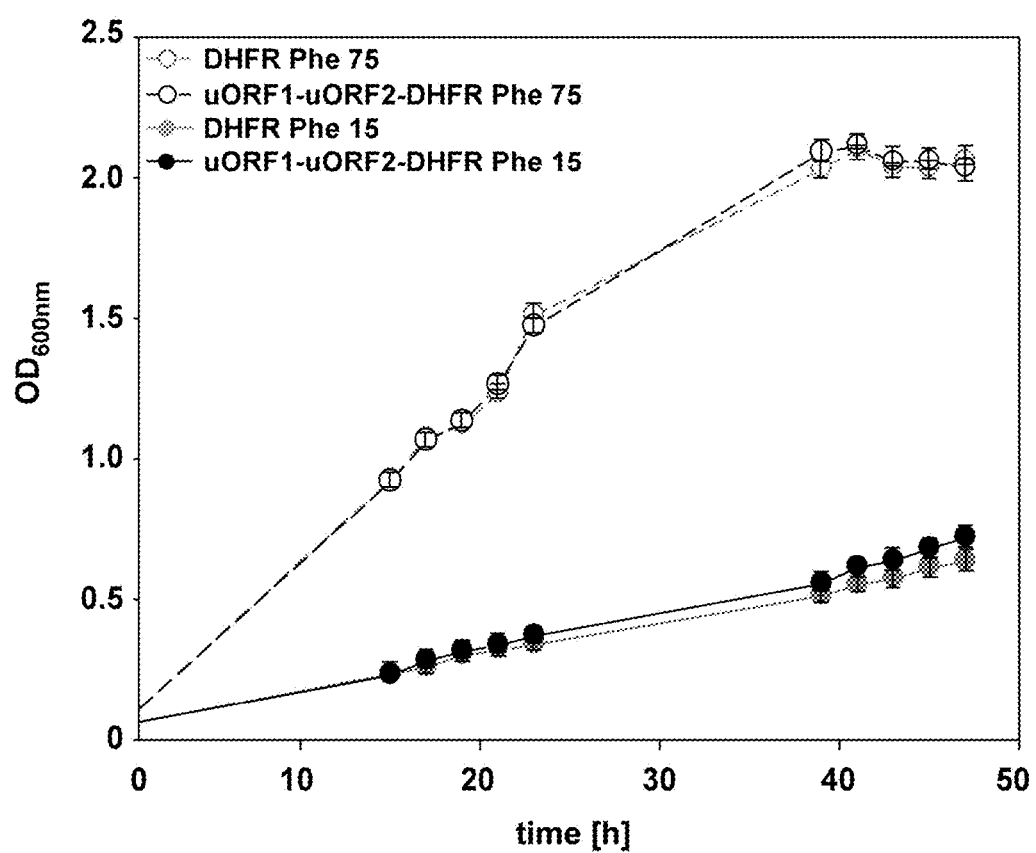
Fig. 18, related to Fig. 17A

Compact Display of TBF1 genomic region (SEQ ID NO: 101)

```
aaaattttcaggcgaattttggcgataatttttatatttccgacgactagtttacagagaatttggaccgtccgatgtaaagcgaaaataga
tctaggttttccacgtgtccoctattttaatgaaaccttctgattcatgtagaagttttactcaatttaatattttttagtatgtagtttt
gtgtgtgtgtgtgtgtgtttttatggctccacaccaacttttaaaatggtagaagcatgttgcatgtgatcgagtaaaaagccaataat
gagattcagaaaaataaaaattacttatatagttttttagagaaaaaattgtatttgtttaaagccttaatccggttgttgaaagagctg
tgtcacgagttaaaaatattttcttttcattttttaagtaattagtttataatgcaaaaatggtttttattttattttgtcttcgcttataga
actgcaaattgagagagaaaaaaatgaattagtggtggtgaccaaacattcaggaagctgtgattgatcatttgttttttgaggtgagtgta
gtggcaacgtatgacgttaacatatggcgtacataataattacatgaacttaatcataataatcatattgcatttaattcatatatcatat
cccattagttggaccacttgatttgaggtcatgagaagaacatttatgtttttttagtttgaatcggagtgatcactaaaaactagatac
tgaaaattttcaaactaaaatcatattaatcttcaaaaaatgtgaaatctaaaaaaaaaaaaaatttaacgcgttcattgtagccaagta
gccaagtattgttaaagtagtagtaaaagaagtttagctttaagtgatataatttgacacaaatcctacttagatatggataataggatat
agcttcatgtatatttttatcgttgcttctgtaaccccaaaatgtgttgatataagcatttgaatattcgtatgtataatgttttcttttc
accgtaaaacatattacaatgttagtttatattggatttgaatgtgtttatgaacagttttgtcgactcaaaagttaagatgagaatat
ggaagaaagtaaagtttaaaagtcatgatgggaacaaggaatggaactcaaacattctaatactcaacaaacgcaattatattattaccat
gactcatctttcaagttccatcaaaaagattcgtggaaaataatagacttacgtttcaaatccatgtttctttctttataacaaaaaaaat
ggatgttcttgacgcgtgtcgagagtactcaccattactctgacttcagtgagtttggtcaagtggtcttttttttctcatgtcaccaa
aggtccaaaccctagaaattagttcgaactttccatagaagaactgaataaatggtccaaaattgttaaaaggacctaagccattagt
tcattgaattcgagttaatgggtgaagattttatgataacgaaagtcggagtaattatgcttttggtccgatagttttctaatttgtttt
ctttccattttttttttttcaaatactacatactatataagatagtggtttgtgttaatgtcatcgatgtgttaccatccgcattatatta
attatttatcccaacataaagtcagaatctgtaatttcttgttataaaatacagtaaatggtccgtttaagctgttagatgattttga
gtaaaaactaatgtaaaaaaaacaaaaaaaaacaatgtagttcataatacatgcatgttttaaagaagtttcttgtttactatcaacttg
aatagtatttcacgaagtcaaaattgttcattccgacttttctatgtggagaaaaaaaattctatcattgtgcacaatttaacagaatgta
atttcttgtaaagaagaggaaacaattcgctgttagtaaatgtgaagtatagaagtctaaatgagatacctcaactagcttgaattaag
aaaaaaaacaaaaactctatcgacatgaaaaaggtcgcaaatatttatcatttatcaatgccaaaggagtatttggttcacaaaatactga
atcatttatatagatataattagctctaaattctactataacttgcaaaataagtatactgactcaattatatagcgtttaaaaataga
cgatttgtatgatgaggtccatatatatggagatgtgcatgcaactatcgacattttcacacgttgatatcgtctttctccaatggagact
tgaatttgtgtaaactatgaatactcgtctctctaagacctttttttcttcaaccatgccaactatttaggtaagattttactgtctttgat
tgatattaaatacttagccgtggcgttatcaatgaatgataataaaaatgcggataaaagccaaaggtgttggaaataaatccaagaatga
agacgtagatgtcgatgggtatttaagaacttgaatttgtcacgactcacacgttaaaatatattatccgaattgtttagtctaaagaca
cacatatattgaaaagaaaaggtaaatgaagctcattggtgcctaaatgtgaaatgaagccgaaatgtgttaggtgaacacatttaaata
tacaaaagaaatataatagaaacaaaactaattaacaaagtcgcaatttgtattgtataaaatatctttccgtctcccgtcatatttgaa
aaaaaaaaattacaaatctgttaattttaaaactttctagaaaaacacaagtatataattttctcttttcgtgcgtgtttgttttaaaat
aacattgtttttgattggcgactcaacatatttagcatttacatatttctgcatatattaaatgattatcaactcaactatagattaaaa
tataatttgacatctaataatttttaacaataatataaaatatgagatttataaattacgaatataaatattcaagggagagaaaagtaga
acataattcaaaagataagacttttttagactttttttaacaatattttttgatggataaaaattattcaaaagagaagaaagtaagaagaaaa
gatgtttctg (Continued . . .)
```

Fig. 19, continued as 20

Compact Display of TBF1 genomic region (SEQ ID NO: 101) (continued)

```
        Start of untranslated region ->
agaatttctagaaacagcatccgttttataatttaatttcttacaaaggtaggaccaacatttgtgatctataaatcttcctactacgttatata gagacccttcgacataacacttaactcgtttatatatttgttttacttgttttgcacatacacacaaaaataaaaaagactttatatttatttactt uORF1--------------------------------------->***uORF2-----------
tttaatcacacggattagctccggcgaagtATGGTCGTCGTCTTCATCTTCTTCCTCCATCATCAGATTTTTCCTTAAATGGAAGAAACCAAAC ---------------------------------------------------------------------------------------->***-
GAAACTCCGATCTTCTCCGTTCTCGTGTTTTCCTCTCTGGCTTTTATTGCTGGGATTGGGAATTCTCACCGCTCTCTTGCTTTTTAGTTGCTGAt Tcttttttccttcgactttctatttccaatctttcttcttctctttgtgtattagattattttttagttttattttttctgtggtaaaataaaaaaagtt TBF1 EXON----------------------------------------------------------------------------
cgccggagATGACGGCTGTGACGGCGGCGCAAAGATCAGTTCCGGCGCCGTTTTTAAGCAAAACGTATCAGCTAGTTGATGATCATAGCACAGACG -------------------------------------------------------------------------------------------
ACGTCGTTTCATGGAACGAAGAAGGAACAGCTTTTGTCGTGTGGAAAACAGCAGAGTTTGCTAAAGATCTTCTTCCTCAATACTTCAAGCATAATAA ---------------------------------->TBF1 intron---------------------------------------------
TTTCTCAAGCTTCATTCGTCAGCTCAACACTTACgtgagtttcactctaacgaaaactcatttactctcaatttaatgcttcatttaattcgtttgg Tgaattgaatcattcttttgtagttggttagccaatttcgtaattttctcataatttggggttggtgagaaaaccttctagaagctgagaatgttc -------------------------->TBF1 EXON-------------------------------------------------------
ttgttcttttttttttttttttggttagGGATTTCGTAAAACTGTACCGGATAAATGGGAATTTGCAAACGATTATTTCCGGAGAGGCGGGGA GGATCTGTTGACGGACATACGACGGCGTAAATCGGTGATTGCTTCAACGGCGGGGAAATGTGTTGTTGTTGGTTCGCCTTCTGAGTCTAATTCTGGT GGTGGTGATGATCACGGTTCAAGCTCCACGTCATCACCCGGTTCGTCGAAGAATCCTGGTTCGGTGGAGAACATGGTTGCTGATTTATCAGGAGAGA ACGAGAAGCTTAAACGTGAAAACAATAACTTGAGCTCGGAGCTCGCGGCGGCGAAGAAGCAGCGCGATGAGCTAGTGACGTTCTTGACGGGTCATCT GAAAGTAAGACCGGAACAAATCGATAAAATGATCAAAGGAGGGAAATTTAAACCGGTGGAGTCTGACGAAGAGAGTGAGTGCGAAGGTTGCGACGGC GGCGGAGGAGCAGAGGAGGGGGTAGGTGAAGGATTGAAATTGTTTGGGGTGTGGTTGAAAGGAGAGAGAAAAAAGAGGGACCGGGATGAAAAGAATT -------------------------------------------------------------------------------***
ATGTGGTGAGTGGGTCCCGTATGACGGAAATAAAGAACGTGGACTTTCACGCGCCGTTGTGGAAAAGCAGCAAAGTCTGCAACTAAaaaaagagta Gaagactgttcaaaccagcgtgtgacacgtcatcgacgacgacgaaaaaaatgatttaaaaaactattttttttccgtaaggaagaaaagttatttt Atgttttaaaaaggtgaagaaggtccagaaggatcaacgcaaatatataaatggatttcatgtattatataatttaattagtgtattaagaaaata Aaacagatgttgaagttttattgttgcttaatttatgtcttcataatgtaaaaaagcatgtgaaatacttggtctaaggtcatctacttagttgaaa Acttgtgaaagaggaagaaatttacttttatgtttgattgatttctttgcaagtagtagtaggtggtttccgtgtttttacgtaatccgttgaat atttttccctcgaaattgtctttataaaagtcacagaaacatttttct Key:
Promoter UTRs UORF1 uORF2 TBF1 EXONS TBF1 intron
```

Fig. 20

Schematic diagram of TBF1 mRNA encoding uORF1 and uORF2 uORF1 (SEQ ID NO: 102) and uORF2 (SEQ ID NO: 103)

TBF1 uORF suppresses both cytosol-synthesized and ER (endoplasmic reticulum) synthesized proteins
24A
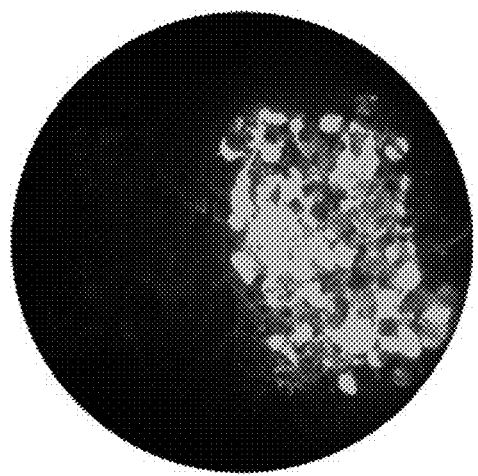
24B
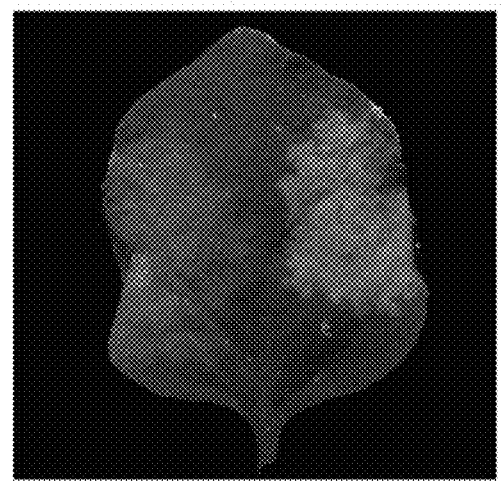
Fig. 24 (Panels 24A and 24B)

HSF-LIKE TRANSCRIPTION FACTOR, TBF1, IS A MAJOR MOLECULAR SWITCH FOR GROWTH-TO-DEFENSE TRANSITION IN PLANTS

CROSS REFERENCE TO RELATED APPLICATIONS

This application is a continuation of U.S. patent application Ser. No. 14/576,304, filed Dec. 19, 2014, which is a continuation of U.S. patent application Ser. No. 14/310,320, filed 2014 Jun. 20, which is a continuation-in-part of PCT/US2012/070838, filed 2012 Dec. 20, published as WO 2013/096567 A2 on 2013-06-27, claiming benefit under 35 U.S.C. § 119(e) to U.S. Provisional Application No. 61/578,632, filed 2011 Dec. 21, each of which is incorporated herein by reference in their entirety.

STATEMENT REGARDING FEDERALLY-SPONSORED RESEARCH OR DEVELOPMENT

This invention was made with U.S. Government Support under Federal Grant Numbers MCB-0519898 and 10S-0929226, both awarded by the National Science Foundation, to X. Dong. The U.S. Government has certain rights in the invention.

INCORPORATION-BY-REFERENCE OF A SEQUENCE LISTING

The sequence listing contained in the file "761_183_008_US_ST25.txt", created on 2014 Dec. 18, modified on 2014 Dec. 18, file size 235,438 bytes, is incorporated by reference in its entirety herein. The sequence listing contained in the file "127183_0007_US_ST25.txt", created on 2014 Jun. 20, modified on 2014 Jun. 20, file size 235,395 bytes, is also incorporated by reference in its entirety herein. The originally-filed and amended sequence listings, if any, of PCT/US2012/070838, filed 2012 Dec. 20, U.S. Ser. No. 61/578,632, filed 2011 Dec. 21, are also incorporated by reference in their entireties.

INCORPORATION-BY-REFERENCE IN NON-PROVISIONAL APPLICATION UNDER 37 CFR 1.58 TO LARGE TABLES, INCLUDING SUPPLEMENTAL TABLES OF INFORMATION INCLUDED IN EARLIER PRIORITY APPLICATIONS

Table S1, which collectively refers to eight Supplemental Tables S1A-S1H, in the subsection labeled "Statistical Analysis" of the "Detailed Description of the Invention", provides a summary of the complete lists of TBF1-dependent SA- and elf18-regulated genes set forth in tables formatted in Microsoft Word, extracted from eight worksheets of an Excel file.

The data in the eight Supplemental Tables S1A-S1H, which would occupy more than 580 pages if submitted on paper, are incorporated by reference in their entirety, herein, under 37 CFR 1.58. The data in these Supplemental Tables are contained in the following file: "DULV_D946US_Table_S1A-S1H_Supplemental_Tables.pdf", modified on 2011 Dec. 21, file size 3,473,862 bytes, which was co-filed with and incorporated by reference in U.S. Provisional Application No. 61/578,632, filed 2011 Dec. 21. These tables were also incorporated by reference in the international application as PCT/US12/078038, filed 2012 Dec. 20, under Rule 20.6 to Supplemental Tables of Information Included In Earlier Priority Applications, and in Non-Provisional U.S. application Ser. No. 14/310,320, filed 2014 Jun. 20.

FIELD OF THE INVENTION

The present invention relates to new methods to study and control the expression of plant genes, particularly genes located downstream from regions comprising binding sites for transcription factors, such as the cis-element translocon 1 (TL1) comprising GAAGAAGAA (SEQ ID NO: 99) and similar sequences. The invention relates to isolated nucleotide sequences comprising a regulatory region comprising a promoter operably-linked to one or more upstream open reading frames (uORFs) and one or more downstream open reading frames (dORFs) encoding one or more functional polypeptides, including transcription factors such as TBF1, reporter polypeptides, and polypeptides conferring resistance to drugs, resistance of plants viral, bacterial, or fungal pathogens, and polypeptides involved in the growth of plants. Another aspect of the invention relates to the use of a translational regulatory region wherein said uORFs encode polypeptides designated uORF1 and uORF2 from *Arabidopsis* plants, natural and synthetic variants of these polypeptides, and their homologues and orthologues isolated from other plant species, including crop plants. This regulatory region allows translation of dORFs in response to pathogen challenge. The invention is also directed to vectors, cells, plant propagation material, transgenic plants, and seeds comprising nucleic acids comprising said regulatory region. Other aspects relate to methods of using these regulatory elements to generate and screen for transgenic plants having improved resistance to disease, particularly microbial and viral plant pathogens. The invention is also directed to plants comprising said ORFs to facilitate the controlled production of one or more recombinant proteins in plant-based expression systems. Measurement of the amount or activity of a recombinant protein in this system can reflect the actions of one or more factors involved in the transcriptional and/or translational control signals, including promoters and uORFS upstream from the coding sequence for a polypeptide. The invention is also directed to engineered cells and plants comprising these genetic elements to facilitate the production of proteins for use in structure/function studies, in industrial, agricultural, and medical applications, and particularly in the understanding and development of disease-resistant plants.

BACKGROUND OF THE INVENTION

The sessile nature of plants subjects them to a constant exposure of biotic and abiotic stresses. Although plants do not have specialized immune cells, they can mount local and systemic immune responses, which require extensive cross-talk between plant defense and other physiological processes [1]. Induction of local defense responses involves recognition of microbe-associated molecular patterns (MAMPs) by membrane-associated receptors, leading to MAMP-triggered immunity (MTI), and recognition of pathogen-delivered effectors by cytosolic receptors, resulting in effector-triggered immunity (ETI) [2]. Salicylic acid (SA) that is produced during local infection events can lead to systemic acquired resistance (SAR). In *Arabidopsis*, SA signals through a key immune regulator, designated NPR1 (Nonexpressor of PR genes), which is involved in regulating changes at the transcriptional level of as many as ~10% of all genes [3]. Systemic acquired resistance is broad-spectrum and long lasting, compared to the signal-specific MAMP- and effector-triggered immunity responses [4].

SAR-associated transcriptional reprogramming re-directs cellular resources, normally dedicated to growth-related activities, towards de novo synthesis of anti-microbial proteins, such as the pathogenesis-related (PR) proteins. Before PR proteins can accumulate, endoplasmic reticulum (ER)-resident genes encoding the secretory pathway components are coordinately up-regulated to ensure efficient post-translational modification and secretion of the antimicrobial PR peptides [3, 5]. The enhancement of ER components is not restricted to SAR, however, as ER-resident genes have been shown to be involved in MTI. In studies directed to the biogenesis of EFR, a membrane-bound receptor for the MAMP signal elf18 (the N terminal 18 amino acids of the bacterial translation elongation factor Tu, EF-Tu), TBF1 was found to regulate glycosylation pathway genes, including calreticulin 3 (CRT3), and UDP-glucose:glycoprotein glycosyltransferase, STT3A, involved in the ER quality control mechanism (ERQC) required for EFR function [6, 7].

In earlier studies, we demonstrated that induction of both PR and ER-resident genes requires NPR1, a transcription cofactor. Upon induction by SA, NPR1 is translocated to the nucleus [8] inducing PR genes through its interaction with TGA transcription factors (TFs) at the promoters of PR genes [9, 10]. It is not known how NPR1 regulates the ER-resident genes. TGA TFs are not likely candidates, because expression of ER-resident genes is unaltered following induction in tga mutants [3]. Significant enrichment of a novel cis-element TL1 (translocon 1; GAAGAAGAA) in the promoter regions of these NPR1-dependent ER-resident genes suggests the involvement of an unknown TF [3]. Point mutations in the TL1 elements in the BiP2 (Lumenal Binding Protein 2) promoter abolished the inducibility of this gene upon SA treatment, supporting this hypothesis [3]. Identification of the TL1-binding TF is important to our understanding of the mechanism controlling the transition from growth- to defense-responses, as the secretory pathway is required for a wide variety of other cellular functions.

In this study, we report the identification of a heat shock factor-like protein (HSF4/HsfB1) that binds to the TL1 cis-element, which transcriptionally-regulates the expression of genes containing this motif in their promoter regions. We renamed it TL1-Binding Transcription Factor 1, TBF1, since mutants of this transcription factor have normal heat shock responses, but are compromised in the growth-to-defense transition upon challenge by pathogens. The translation of TBF1 is also tightly-regulated through two upstream open reading frames (uORFs) enriched in aromatic amino acids, which are precursors of a large array of plant secondary metabolites involved in defense. Taken together, these observations suggest that TBF1 plays a key role in the general control of events at the transcriptional level in plants.

BRIEF SUMMARY OF THE INVENTION

The present invention relates to an isolated nucleic acid molecule comprising a regulatory region used to modulate the expression of one or more polypeptides in a cell, wherein said regulatory region comprises a promoter, functional in said cell, operably-linked to at least one upstream open reading frame (uORF) that encodes a polypeptide selected from the group consisting of: (a) (i) a polypeptide represented by uORF1 (SEQ ID NO: 102); (ii) a variant polypeptide thereof that contains one or more conservative substitutions in which one or more uORF1 functions are conserved; or (iii) a variant polypeptide thereof that contains one or more substitutions, fusions, or truncations in which one or more uORF1 functions are conserved; and (b) (i) a polypeptide represented by uORF2 (SEQ ID NO: 103); (ii) a variant polypeptide thereof that contains one or more conservative substitutions in which one or more uORF2 functions are conserved; or (iii) a variant polypeptide thereof that contains one or more substitutions, fusions, or truncations in which one or more uORF2 functions are conserved.

Separate aspects of the invention relate to a vector, cell, or a transgenic plant comprising a regulatory region used to modulate the expression of one or more polypeptides in a cell, wherein said regulatory region comprises a promoter, functional in said cell, operably-linked to at least one upstream open reading frame (uORF) that encodes a polypeptide selected from the group consisting of: (a) (i) a polypeptide represented by uORF1 (SEQ ID NO: 102); (ii) a variant polypeptide thereof that contains one or more conservative substitutions in which one or more uORF1 functions are conserved; or (iii) a variant polypeptide thereof that contains one or more substitutions, fusions, or truncations in which one or more uORF1 functions are conserved; and (b) (i) a polypeptide represented by uORF2 (SEQ ID NO: 103); (ii) a variant polypeptide thereof that contains one or more conservative substitutions in which one or more uORF2 functions are conserved; or (iii) a variant polypeptide thereof that contains one or more substitutions, fusions, or truncations in which one or more uORF2 functions are conserved.

Still another aspect of the invention relates to a method of using a regulatory region to modulate the expression of one or more polypeptides in a cell, wherein said regulatory region comprises a promoter, functional in said cell, operably-linked to one or more upstream ORFs and one or more downstream ORFs encoding said one or more polypeptides, comprising the steps of: (a) introducing one or more nucleic acids comprising said regulatory region into a cell; (b) expressing one or more upstream ORFs and one or more downstream ORFs encoding one or more polypeptides for a period sufficient to modulate the amount or level of activity of at least one of the one or more polypeptides within the cell or in the cell culture medium obtained from said cell. Another aspect relates to a method, further comprising the step (c) of purifying at least one of said polypeptides from the cell comprising said regulatory region or from the cell culture medium obtained from said cell.

A better understanding of the invention will be obtained from the following detailed descriptions and accompanying drawings, which set forth illustrative embodiments that are indicative of the various ways in which the principals of the invention may be employed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

(Panels 1A and 1B) TBF1 (HSF4) binding to the TL1 cis-elements in the BiP2 promoter was detected in Y1H.

Strain 1 carries the WT BiP2 promoter upstream of both the HIS3 and LacZ reporters and Strain 2 contains a mutant BiP2 promoter in the TL1 elements upstream of LacZ [3]. Strain 1 and Strain 2 were both transformed with either pDEST-AD TBF1 encoding TBF1-AD, or the empty vector, pDEST-AD. Yeast growth assays for the HIS3 locus were performed on selective media (SD-His-Ura-Trp) supplemented with increasing concentrations of 3-AT, and photographed four days later (Panel 1A). β-galactosidase reporter activity was measured using ONPG as the substrate (Panel 1B). Error bars represent standard deviation from three different technical replications. The experiments were repeated three times with similar results.

(Panel 1C) Electrophoretic mobility shift assays were performed using plant extracts from wild-type (WT) and the tbf1 mutant, with (+) and without (−) 6 hr-treatment with 1 mM SA. 40,000 cpm of the radioactive probe containing the TL1 element was mixed with 10 μg of protein extract in the presence (+) or absence (−) of the unlabeled WT (cold) or the mutant TL1 (mTL1) oligo (5 pmol/μL). The autoradiograph was developed 24 hrs after electrophoresis. The arrow marks the TBF-TL1 complex. Asterisks indicate non-specific binding. The experiment was repeated three times with similar results.

(Panel 1D) TBF1-GFP binding to the TL1 elements in the BiP2 promoter was measured by ChIP analysis after treatment with $H_2O$ or 1 mM SA. The PCR amplicons designated 1 to 6 (gray boxes in the upper panel) used in the ChIP analysis are shown, with TL1 elements highlighted in white. The arrow represents the translational start site of BiP2. After ChIP analysis using an antibody directed against GFP, the fold-enrichment for each amplicon was calculated from the real-time PCR results, which were normalized to input, and represented by the ratio between TBF1p:TBF1-GFP (in tbf1) and untransformed control plants (lower panel). Error bars represent the standard deviation from three different replicates. The experiment was repeated five times with similar results.

Figure 1:
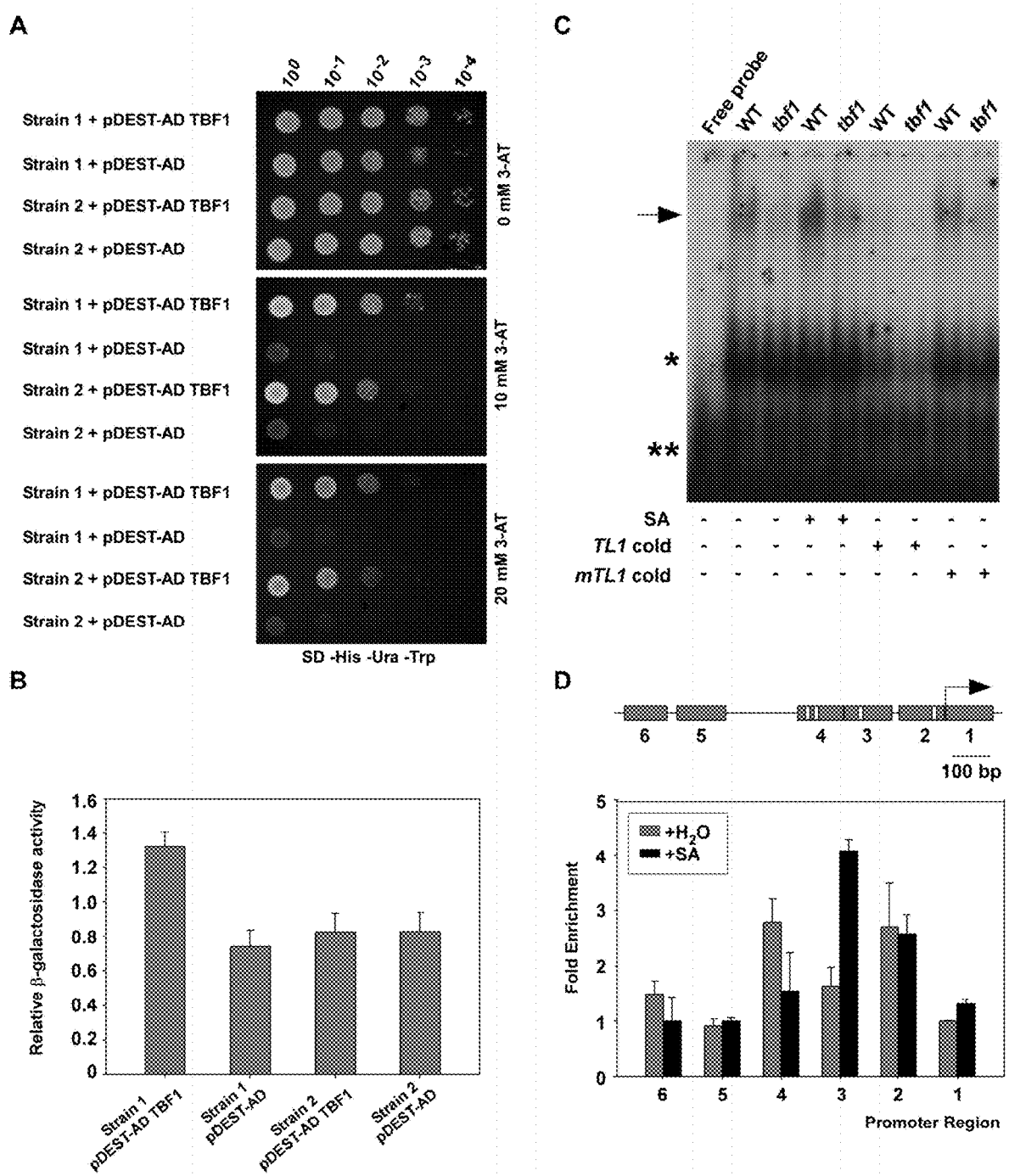
FIG. 1 sets forth an illustration showing that HSF4 is the TL1-Binding TF, TBF1.

FIG. 2, related to FIGS. 1A and 1B, sets forth an illustration showing the yeast strains used in the Y1H assay.

(Panel 2A) BiP2 promoter containing multiple functional TL1 cis-elements (top) (SEQ ID NO: 95) and mutated TL1 (mTL1; bottom) (SEQ ID NO: 96) are shown.

(Panel 2B) Strain 1 contains the WT BiP2 promoter fragment upstream of the HIS3 and the LacZ reporters. Strain 2 contains the WT BiP2 promoter upstream of HIS3, but mTL1 upstream of LacZ.

FIG. 3, related to FIG. 1C, sets forth an illustration showing that TBF1 transcript levels in the tbf1 T-DNA insertion mutant.

(Panel 3A) Schematic representation of the T-DNA insertion site in the tbf1 mutant. The genomic organization of TBF1 encompassing exon 1, intron 1 and exon 2 is shown. The position and direction of the T-DNA insertion within TBF1 are indicated. Disruption of TBF1 leads to the loss-of-function mutant, designated as SALK_104713, also referred to as tbf1.

(Panel 3B) Expression of TBF1 in WT and the tbf1 mutant. Relative TBF1 transcript levels were determined by quantitative RT-PCR using cDNA generated from leaves of 3-week-old WT and tbf1 plants. The expression values were normalized using those of UBQ5 as internal standards. Error bars represent the standard deviation among three technical replications. The experiment was repeated three times with similar results.

FIG. 4, related to FIG. 1D, sets forth an illustration showing that TBF1p:TBF1-GFP can complement the tbf1 mutation.

Bacterial growth was quantified 3 days after infection with Psm ES4326 ($OD_{600nm}$=0.0001). Error bars represent the 95% confidence intervals determined from six replicates. The experiment was performed three times with similar results.

Figure 5:
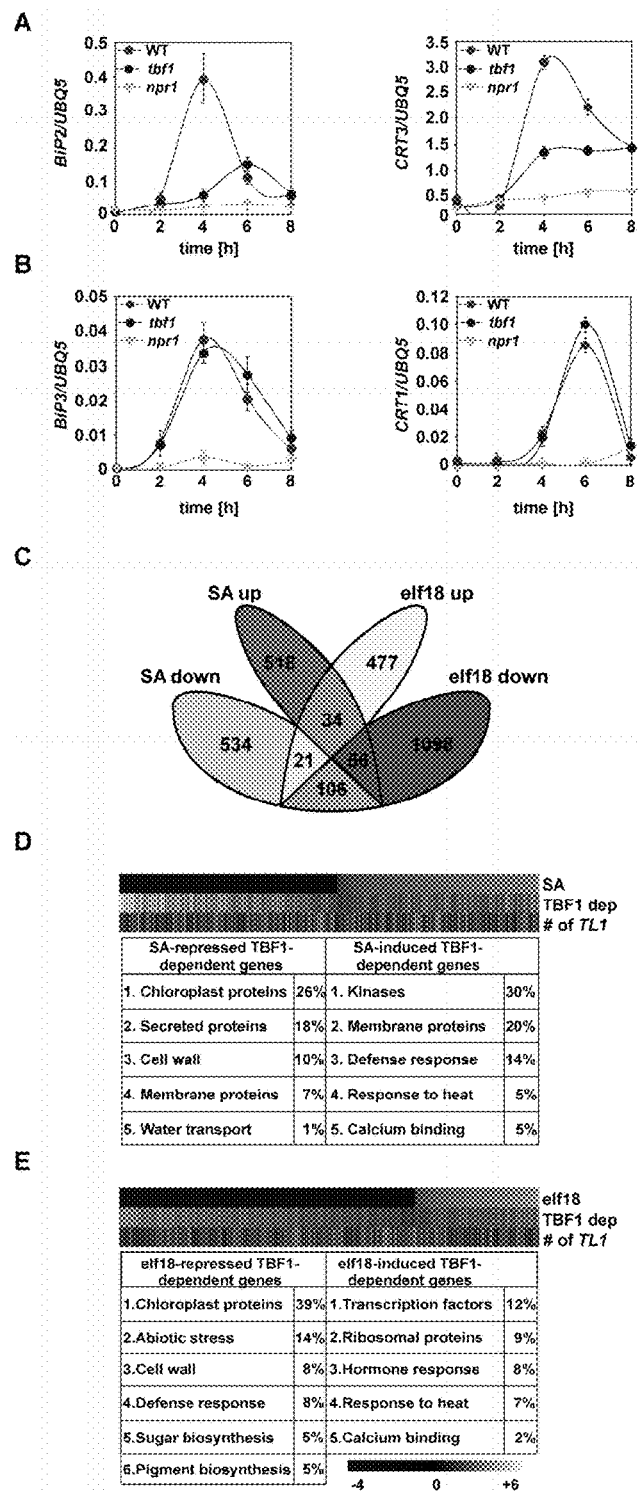

FIG. 5 sets forth an illustration showing that TBF1 plays a Major Role in Transcriptional Reprogramming during MTI and SAR (Panels 5A and 5B) Relative transcript levels of secretory pathway genes were determined by qRT-PCR using cDNA generated from WT, tbf1 and npr1-1 plants treated with 1 mM SA. The expression levels of BiP2 and CRT3 carrying TL1 in their promoters (2A) and BiP3 and CRT1 without TL1 in their promoters (2B) were normalized to the transcript levels of the constitutively-expressed UBQ5. Error bars represent the standard deviation from nine technical replicates derived from three independent experiments.

(Panel 5C) The Venn diagram shows the numbers of TBF1-dependent SA down-regulated (SA down), SA up-regulated (SA up), elf18 up-regulated (elf18 up) and elf18 down-regulated (elf18 down) genes (p-value<0.05).

(Panels 5D and 5E) Heatmaps of TBF1-regulated genes in total numbers (top), degrees of TBF1 dependency (middle), and numbers of TL1 cis-elements in the gene promoters (bottom), in response to SA (2D) and elf18 (2E) treatments. Top-ranked functional groups were determined using DAVID Gene Ontology (GO) analysis for TBF1-dependent, SA-repressed or induced genes (2D), and elf18-repressed or induced genes (2E). The scale indicates the log-transformed p-values of down-(blue) and up-(yellow) regulated genes (top). Yellow lines indicate TBF1-dependency (middle), and yellow lines correspond to the numbers of TL1 cis-elements in the gene promoters (bottom).

FIG. 6, related to FIG. 5A, sets forth an illustration showing that SA-induced accumulation of ER chaperones BiP1/2 is affected in the tbf1 mutant.

Total protein extract was obtained from six leaves derived from three plants per genotype 6 hours after treatment with 1 mM SA. An accumulation of highly sequence-similar BiP1/2 proteins was detected on Western blots with an antibody directed against BiP (α-BiP). Ponceau S stain was used to verify equal loading amounts. The experiment was repeated three times with similar results.

FIG. 7, related to FIG. 5D, sets forth an illustration showing validation of the microarray data using qRT-PCR analysis of selected genes.

qRT-PCR analysis of selected TBF1-dependent SA-induced genes, identified in the microarray analysis. Leaves of 3-week-old *Arabidopsis* plants were sprayed with 1 mM SA or water (NT) and tissues collected 6 hrs later. The expression values were normalized using those of UBQ5 as the internal standards. The error bars represent the standard deviation among three technical replications. The experiment was repeated three times with similar results.

FIG. 8, related to FIG. 5D, sets forth an illustration showing validation of the microarray data using qRT-PCR analysis of selected genes.

qRT-PCR analysis of selected TBF1-dependent SA-repressed genes, identified in the microarray analysis. Leaves of 3-week-old *Arabidopsis* plants were sprayed with 1 mM SA or water (NT) and tissues collected 6 hrs later. The expression values were normalized using those of UBQ5 as the internal standards. Error bars represent the standard deviation among three technical replications. The experiment was repeated three times with similar results.

FIG. 9, related to FIG. 5E, sets forth an illustration showing validation of the microarray data using qRT-PCR analysis of selected genes.

qRT-PCR analysis of selected TBF1-dependent elf18-induced genes, identified in the microarray analysis. Leaves of 3-week-old *Arabidopsis* plants were infiltrated with 10 µM elf18 or water (NT) and tissues collected 2 hrs later. The expression values were normalized using those of UBQ5 as the internal standards. Error bars represent the standard deviation among three technical replications. The experiment was repeated three times with similar results.

FIG. 10, related to FIG. 5E, sets forth an illustration showing validation of the microarray data using qRT-PCR analysis of selected genes.

qRT-PCR analysis of selected TBF1-dependent elf18-repressed genes, identified in the microarray analysis. Leaves of 3-week-old *Arabidopsis* plants were infiltrated with 10 µM elf18 or water (NT) and tissues collected 2 hrs later. The expression values were normalized using those of UBQ5 as the internal standards. Error bars represent the standard deviation among three technical replications. The experiment was repeated three times with similar results.

Figure 11:
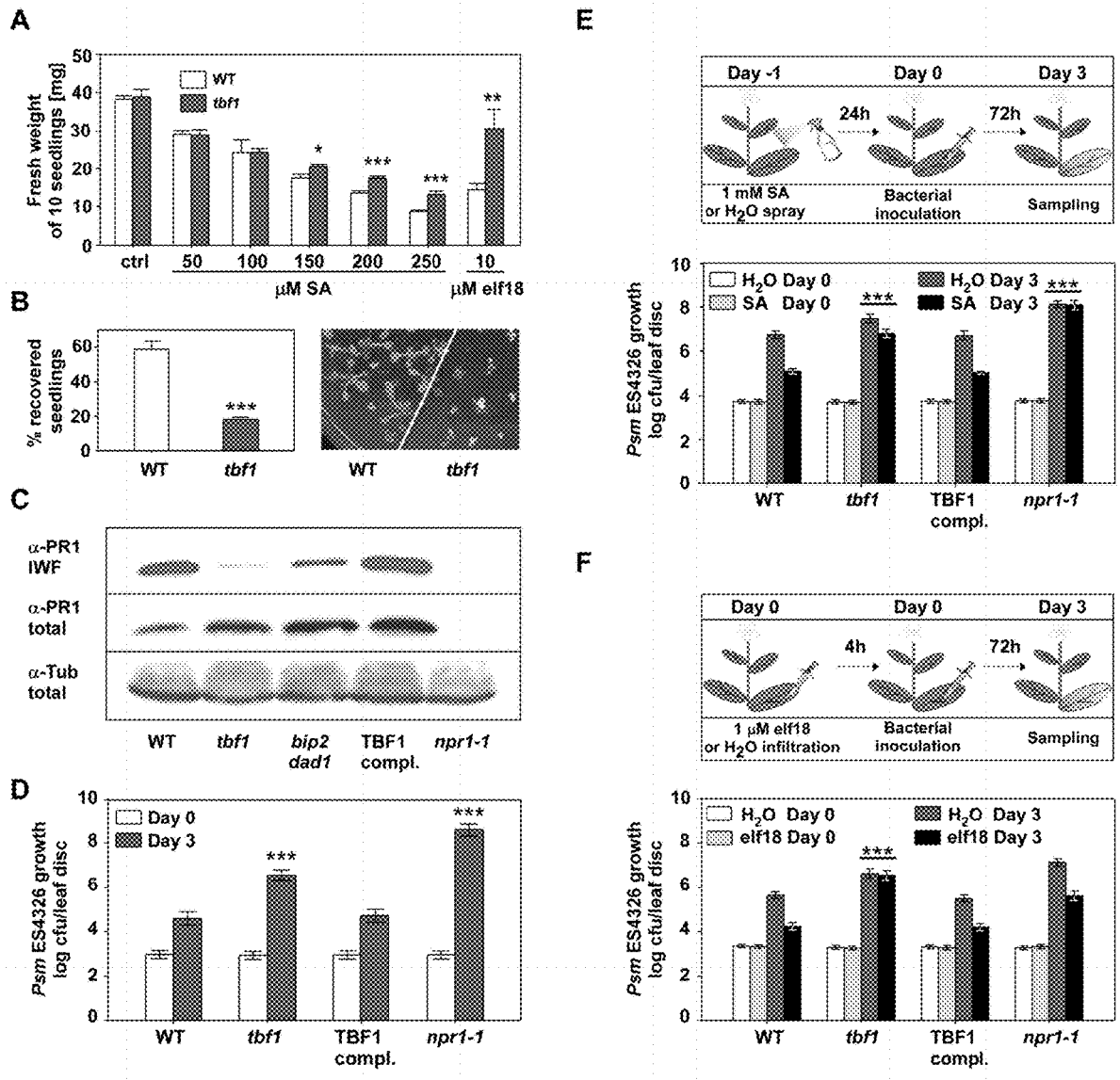

FIG. 11 sets forth an illustration showing that TBF1 is a Major Molecular Switch for the Growth-to-Defense Transition (Panel 11A) Fresh weight of ten seedlings grown for 10 days on plates with MS growth media (Ctrl), MS supplemented with increasing concentrations of SA or 10 µM elf18. Error bars represent the standard deviation of three replicates. This experiment was repeated three times with similar results. Statistical analysis was performed using the Student's t-test, *, p-value<0.05, , p-value<0.01, *, p-value≤0.001.

(Panel 11B) Seedling recovery after a two-day treatment with the UPR inducer tunicamycin at 300 µg/L was measured 10 days later by counting the percentage of surviving seedlings (left), and by phenotype observations (right). Error bars represent standard deviation of three replicates. This experiment was repeated five times with similar results. Statistical analysis was performed using the Student's t-test, ***, p-value≤0.001.

(Panel 11C) Intracellular wash fluid (IWF) and total protein extracts from leaves of three-week-old WT, tbf1, tbf1 transformed with the WT TBF1 gene (TBF1 comp.), npr1-1, and bip2 dad2 were collected 24 hrs after 1 mM SA treatment and subsequently subjected to Western blotting using an antibody directed against PR1 (α-PR1). For loading controls, an antibody against tubulin (α-Tub) was used to probe the total protein blot.

(Panel 11D) Enhanced disease susceptibility was measured in 3-week-old WT, tbf1, TBF1 comp. and npr1-1 plants three days after infiltration with a bacterial suspension of Psm ES4326 ($OD_{600nm}$=0.0001). Error bars represent the 95% confidence intervals of twenty-four replicates derived from three independent experiments. This experiment was repeated at least five times with similar results. Statistical analysis was performed using the Bonferroni post-test, ***, p-value<0.0001.

(Panel 11E) SA-induced resistance was determined according to the schematic representation (upper panel) and the growth of Psm ES4326 was plotted as in (D) but with a higher initial inoculum ($OD_{600nm}$=0.001) (lower panel). Error bars represent 95% confidence intervals of twenty-four replicates derived from three independent experiments. Statistical analysis was performed using Bonferroni post-test, ***, p-value<0.0001.

(Panel 11F) elf18-induced resistance was measured according to the schematic representation (upper panel) and with the initial Psm ES4326 inoculum of $OD_{600nm}$=0.001 (lower panel). Error bars represent 95% confidence intervals of twenty-four replicates derived from three independent experiments. Statistical analysis was performed using Bonferroni post-test,***, p-value<0.0001.

FIG. 12, related to FIG. 11A, sets forth an illustration showing that the tbf1 mutant displays wild type levels of sensitivity to flg22.

Fresh weight of ten seedlings grown for 10 days on plates with regular MS growth media (−flg22) or MS supplemented with 10 µM flg22 (+flg22). Error bars represent standard deviation of three replicates. The experiment was repeated three times with similar results.

FIG. 13, related to FIG. 11, sets forth an illustration showing that the tbf1 mutant shows normal heat shock response.

Relative BiP2 transcript levels were determined by quantitative RT-PCR using cDNA generated from leaf tissue of room temperature (RT)-incubated and heat-shocked (at 37° C. for 2 hrs)) 3-week-old WT and tbf1 plants. The expression values were normalized using those of UBQ5 as the internal standards. Error bars represent the standard deviation among three technical replications. Experiment was repeated three times with similar results.

FIG. 14, related to FIG. 11C, sets forth an illustration showing that PR1 transcript levels are not altered in the tbf1 mutant.

Relative PR1 transcript levels were determined by quantitative RT-PCR using cDNA generated from leaf tissue of 3-week-old WT, tbf1 and npr1-1 plants. Samples were harvested at 0 and 16 hrs after 1 mM salicylic acid (SA) application. The expression values were normalized using those of UBQ5 as the internal standards. Error bars represent the standard deviation among three technical replications. The experiment was repeated three times with similar results.

FIG. 15, related to FIG. 11F, sets forth an illustration showing that the tbf1 mutant has normal flg22-induced resistance to Psm ES4326.

(Panel 15A) Leaves were first injected with $H_2O$ or 10 µM flg22 4 hrs prior to bacterial infection. Disease symptoms upon infection with Psm ES4326 ($OD_{600nm}$=0.001) were observed at 3.5 days post inoculation.

(Panel 15B) Leaves were first treated with $H_2O$ or 10 µM flg22 for 4 hrs followed by infection with Psm ES4326 ($OD_{600nm}$=0.001). Bacterial growth was quantified at 3.5 days post inoculation. Error bars represent the 95% confidence interval of eight replicates. The experiment was performed three times with similar results.

Figure 16:
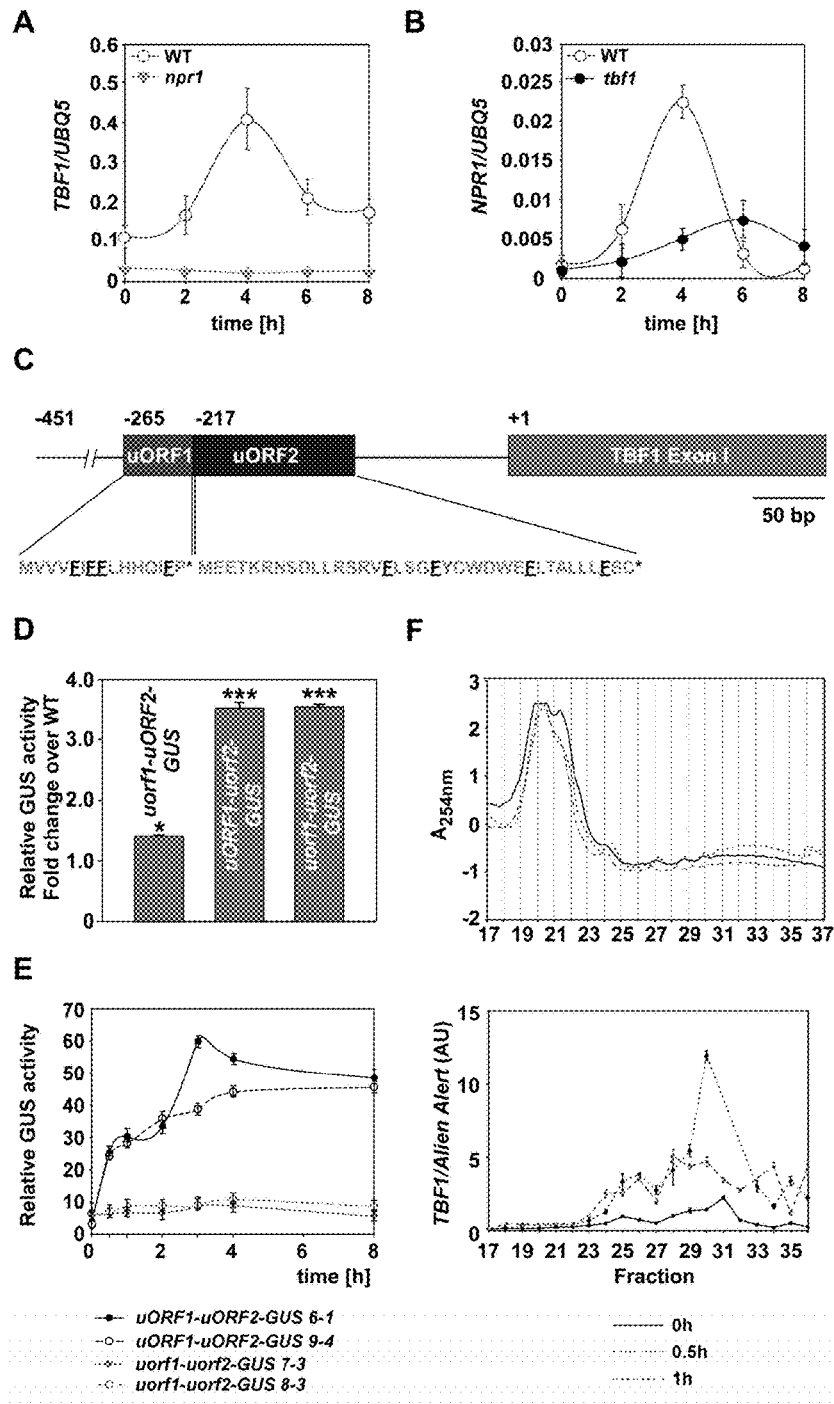

FIG. 16 sets forth an illustration showing that TBF1 Expression is Regulated at both the Transcriptional and Translational Levels.

(Panels 16A and 16B) Relative transcript levels of TBF1 (16A) and NPR1 (16B) genes in response to 1 mM SA treatment were determined by qRT-PCR using cDNA generated from WT, tbf1 and npr1-1 plants. The expression values were normalized using the transcript levels of UBQ5. Error bars represent standard deviation from nine technical replicates derived from three independent experiments.

(Panel 16C) Schematic representation of uORF1 and uORF2 and exon I of TBF1. The phenylalanines (F) in uORF1 and uORF2 are highlighted in red and the stop codons are shown as asterisks. "+1" represents the translational start of TBF1 and −451, −266, and −217 represent the upstream positions of the 5' end of the transcript, the start codon for uORF1 and the start codon for uORF2, respectively.

(Panel 16D) The effects of uORFs on TBF1 translation were determined by transiently expressing uORF1-uORF2-GUS (WT), uorf1-uORF2-GUS, uORF1-uorf2-GUS and uorf1-uorf2-GUS constructs under the control of the 35S promoter in Nicotiana benthamiana leaves, followed by GUS activity quantification 3 days later. GUS activities from mutant constructs were normalized to that of the WT construct. This experiment was repeated three times with similar results.

(Panel 16E) Quantification of translational inhibitory effect exerted by uORFs in transgenic $T_3$ plants expressing uORF1-uORF2-GUS (two independent transformants 6-1 and 9-4) or uorf1-uorf2 GUS (two independent transformants 7-3 and 8-3) at various time points after inoculation with Psm ES4326/avrRpt2 ($OD_{600nm}$=0.02). Error bars represent the standard deviation from three different replicates. The experiment was repeated at least three times with similar results.

(Panel 16F) Polysome profiles (upper panel) and TBF1 expression (lower panel) in samples obtained from WT plants at 0, 0.5 and 1 hr after inoculation with Psm ES4326/avrRpt2 ($OD_{600nm}$=0.02). The fractions containing monosome and polysome were identified based on the absorbance at 254 nm ($A_{254nm}$). The TBF1 transcript abundance normalized against Alien Alert® control transcript is expressed in arbitrary units (AU). Error bars represent standard error. This experiment was repeated using two biological replicates (each with three technical replicates) with similar results.

FIG. 17 sets forth an illustration showing that TBF1 Translation is Regulated in Response to Pathogen-Induced Changes in Phenylalanine Metabolism.

(Panel 17A) The effects of phenylalanine and aspartate starvation on the translational inhibitory function of uORFs were measured by growth of the yeast strain aro7 (phe-, tyr-) transformed with the uORF1-uORF2-DHFR or DHFR reporter. 80 µM methotrexate was added to the media so that yeast growth became dependent on the DHFR reporter expression. Optical densities for cultures containing two different concentrations of phenylalanine (Phe; 15 and 75 mg/L) and for cultures lacking Asp, but supplemented with 15 mM tobramycin (TOB), an inhibitor of yeast $tRNA^{Asp}$ aspartylation, were recorded over the course of 32 hrs. Error bars represent the standard deviation from nine technical replicates derived from three independent experiments.

(Panel 17B) tRNA analysis of wild type plants 0, 0.5, 1, 2, 3, 4, and 8 hrs after inoculation with Psm ES4326/avrRpt2 ($OD_{600nm}$=0.02). tRNA was extracted from leaf samples, and a Northern blot experiment using DIG-labeled probes (Roche Applied Science) against $tRNA^{Phe}$ or $tRNA^{Asp}$ was performed to detect charged and uncharged $tRNA^{Phe}$ or $tRNA^{Asp}$. This experiment was repeated using three biological replicates with similar results.

(Panel 17C) Total protein extracts from leaves of three-week-old WT plants were collected at various time points after inoculation with Psm ES4326/avrRpt2 ($OD_{600nm}$=0.02) and subsequently subjected to Western blotting analysis using an antibody directed against a phosphorylated form of elF2α (pelF2α, Epitomics). Ponceau S stain was used to determine the sample amounts needed for equal loading.

(Panel 17D) A model illustrating the molecular mechanism by which the translation initiation of TBF1 is regulated through rapid increases in uncharged and charged $tRNA^{Phe}$, phosphorylation of elF2α, and ribosomal read-through of uORFs.

FIG. 18, related to FIG. 17A, sets forth an illustration showing that the uORF1-uORF2-DHFR and DHFR recombinant proteins do not affect yeast growth in the absence of methotrexate.

The growth of yeast aro7 strains (Phe⁻, Tyr⁻) carrying uORF1-uORF2-TBF1$_{1st\ exon}$-DHFR (uORF1-uORF2-DHFR) or DHFR in the absence of methotrexate was measured over the course of ~47 hrs by optical density ($OD_{600nm}$). The selective media (SD-Leu-Phe) was supplemented with 15 mg/L (Phe 15) and 75 mg/L (Phe 75) of phenylalanine, respectively. Error bars represent the standard deviation from three technical replicates. This experiment was repeated three times with similar results.

FIGS. 19 and 20 display the sequence and genetic elements of the TBF1 region in compact form FIG. 19, continued as FIG. 20, displaying the sequence and genetic elements of the TBF1 region set forth in SEQ ID NO: 101 in compact form.

Figure 21:
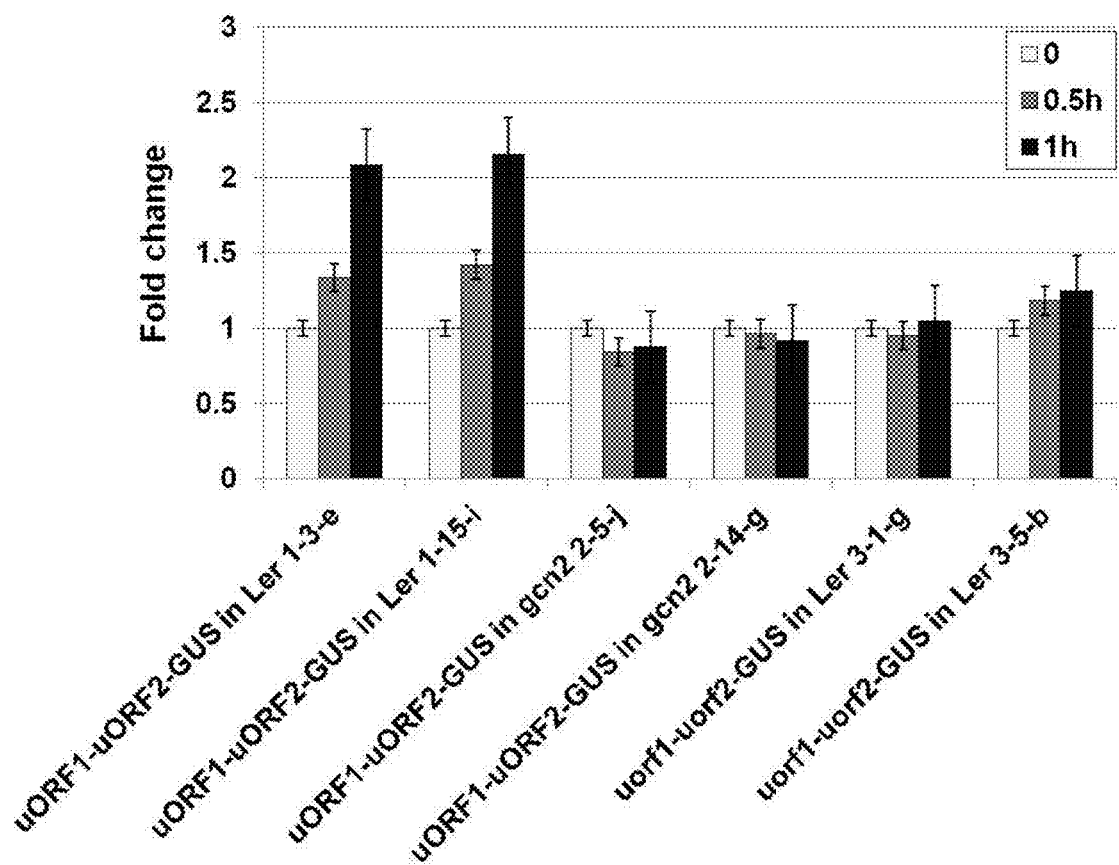

FIG. 21 presents quantification of translational inhibitory effect exerted by uORFs in transgenic $T_3$ plants FIG. 21 presents quantification of translational inhibitory effect exerted by uORFs in transgenic $T_3$ plants expressing uORF1-uORF2-GUS or uorf1-uorf2-GUS in Ler or gcn2 backgrounds (two independent lines per construct per genotype) at indicated time points after inoculation with Psm ES4326/avrRpt2. Error bars represent the standard deviation from three technical replicates.

Figure 22:
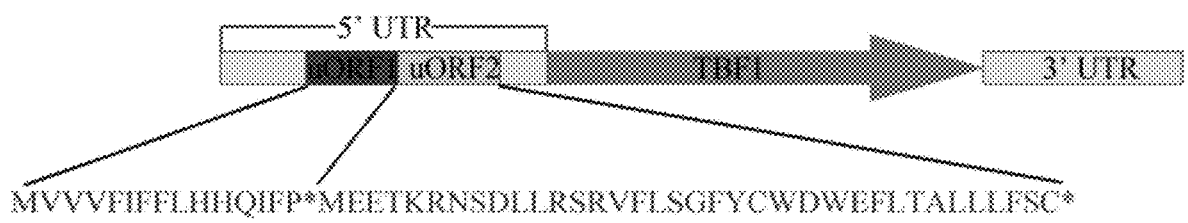

FIG. 22 sets forth a schematic diagram of TBF1 mRNA encoding uORF1 and uORF1.

The potential peptides encoded by uORF1 (SEQ ID NO: 102) and uORF2 (SEQ ID NO: 103) are shown at the bottom of the illustration.

Figure 23:
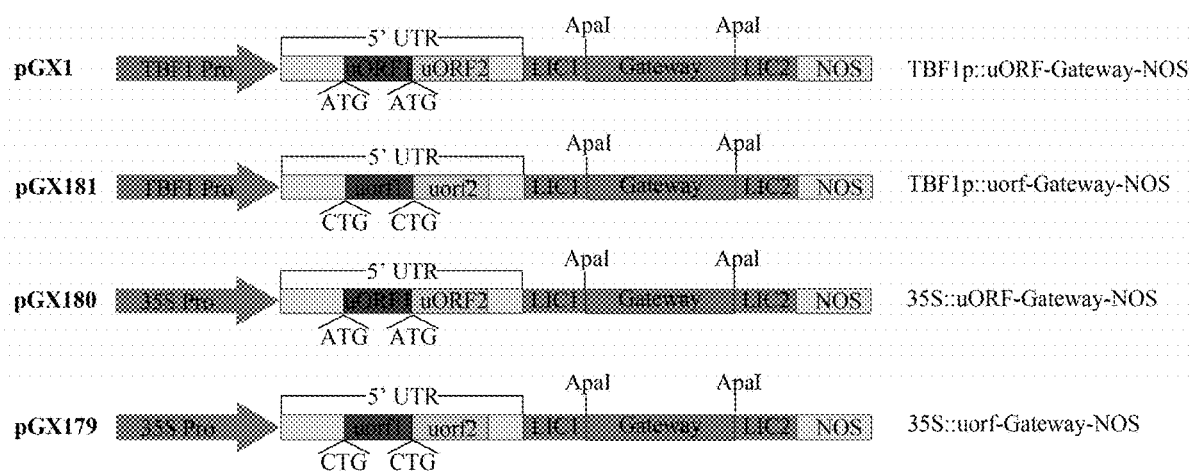

FIG. 23 sets forth a schematic diagram of the expression cassettes.

Target genes can be inserted to replace the Gateway cassette using the adapters LIC1 (SEQ ID NO: 130) and LIC2 (SEQ ID NO: 131). The 5'UTR of TBF1 with native uORFs (starting with an ATG codon, pGX1 (SEQ ID NO: 132)/pGX180 (SEQ ID NO: 135)) or mutant uorfs (starting with a CTG codon, pGX181 (SEQ ID NO: 133)/pGX179 SEQ ID NO: (134)) are placed upstream of the Gateway cassette. The 35S promoter with duplicated enhancers (pGX179 (SEQ ID NO: 134)/pGX180 (SEQ ID NO: 135)) or the TBF1 promoter (pGX1 (SEQ ID NO: (132)/pGX181 (SEQ ID NO: 133)) is used to drive expression of downstream sequences. The genetic elements are as follows: TBF1 pro: TBF1 promoter; 35S Pro: 35S promoter with duplicated enhancers; uORF1/2: upstream open reading frame; uorf1/2: mutant form of uORF1/2 respectively; LIC1/2: ligation-independent cloning sequences; NOS; NOS terminator.

FIG. 24 sets forth an illustration demonstrating that TBF1 uORF suppresses both cytosol-synthesized andER (endoplasmic reticulum)-synthesized proteins.

Genes encoding luciferase (synthesized in the cytosol) and mGFP5 (synthesized in the ER) are cloned into pGX179 (SEQ ID NO: 134) and pGX180 (SEQ ID NO: 135) as 35S::uORF-Luciferase/35S::uorf-Luciferase and 35S::uORF-mGFP5/35S::uorf-mGFP5, respectively. Luciferase activity of transgenic Arabidopsis seedlings harboring the 35S::uORF-Luciferase cassette (left) or the 35S::uorf-Luciferase cassette (right) are detected by CCD camera after the application of luciferin substrate. Agrobacteria containing the 35S::uORF-mGFP5 cassette (left) or the 35S::uorf-mGFP5 cassette (right) were injected into *N. benthamiana*. *N. benthamiana* leaves were observed under UV at two days post-injection. Red fluorescence is observed in chloroplasts. These results demonstrate that the uORF region can suppress both the activity of luciferase and the level of mGFP in the transformed plant cells.

TERMS AND ABBREVIATIONS

The following is a list of terms and their definitions used throughout the specification and the claims:

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as an unmodified or a transgenic plant or animal.

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; ug, µg=micro gram(s); ul, µl=micro liter(s); uM, µM=micromolar; HPLC, high-performance liquid chromatography; ORF=open reading frame; PCR=polymerase chain reaction; SDS-PAGE=sodium dodecyl sulfate-polyacrylamide gel electrophoresis; RT=reverse transcriptase.

DETAILED DESCRIPTION OF THE INVENTION

Induction of plant immune responses involves significant reprogramming of transcription that prioritizes defense-over growth-related cellular functions. Despite intensive efforts involving forward genetic screens and genome-wide expression-profiling experiments, only a limited number of transcription factors have been found that are involved in regulating the growth-to-defense transition. Using endoplasmic reticulum (ER)-resident genes required for antimicrobial protein secretion as markers, we identified a heat shock factor-like transcription factor that specifically binds to the TL1 (GAAGAAGAA) cis-element required for the induction of these genes. Plants lacking this TL1-binding factor (TBF1) respond normally to heat stress, but were shown to be compromised in their immune responses induced by salicylic acid (SA), and by microbe-associated molecular pattern (MAMP), elf18. Genome-wide expression profiling indicated that TBF1 plays a key role in the growth-to-defense transition. The expression of TBF1 itself was shown to be tightly regulated at both the transcriptional and translational levels. Two small upstream open reading frames (uORFs) encoding multiple aromatic amino acids were found 5' to the translation initiation codon of TBF1 and shown to affect its translation. Through this unique regulatory mechanism, TBF1 can sense metabolic changes upon invasion by pathogens, triggering specific transcriptional reprogramming by modifying the expression of its target genes. Key aspects of this study can be summarized as follows: (1) the plant transcription factor, TBF1, binds to the TL1 element in vitro and in vivo; (2) TBF1 controls the expression of nearly 3,000 genes involved in development and immunity; (3) TBF1 is required for effective SA- and MAMP-induced defense responses; and (4) translation of TBF1 is regulated by uORFs in 5' UTR and is sensitive to metabolic changes.

The present invention relates to an isolated nucleic acid molecule comprising a regulatory region used to modulate the expression of one or more polypeptides in a cell, wherein said regulatory region comprises a promoter, functional in said cell, operably-linked to at least one upstream open reading frame (uORF) that encodes a polypeptide selected from the group consisting of: (a) (i) a polypeptide represented by uORF1 (SEQ ID NO: 102); (ii) a variant polypeptide thereof that contains one or more conservative substitutions in which one or more uORF1 functions are conserved; or (iii) a variant polypeptide thereof that contains one or more substitutions, fusions, or truncations in which one or more uORF1 functions are conserved; and (b) (i) a polypeptide represented by uORF2 (SEQ ID NO: 103); (ii) a variant polypeptide thereof that contains one or more conservative substitutions in which one or more uORF2 functions are conserved; or (iii) a variant polypeptide thereof that contains one or more substitutions, fusions, or truncations in which one or more uORF2 functions are conserved.

An aspect of the invention relates to an isolated nucleic acid, as described above, wherein said molecule comprises uORF1, or a functional variant thereof, and uORF2, or a functional variant thereof. Another aspect, relates to an isolated nucleic acid, further comprising one or more downstream ORFs (dORFs) encoding one or more polypeptides. In another aspect, at least one dORF encodes a polypeptide selected from the group consisting of: (i) a polypeptide that is functionally-active as a transcription factor; (ii) a reporter polypeptide; (iii) a polypeptide that confers resistance to drugs or agrichemicals; (iv) a polypeptide involved in in resistance of plants to viral, bacterial, fungal pathogens, oomycete pathogens, phytoplasmas, and nematodes; and (v) a polypeptide involved in the growth or development of plants.

A variety of polypeptides encoded by a downstream ORF are contemplated by the invention. In one aspect, the polypeptide is a transcription factor selected from the group consisting of: (i) a polypeptide represented by TBF1 (SEQ ID NO: 106); (ii) a variant polypeptide thereof, that contains one or more conservative substitutions in which one or more TBF1 functions are conserved; or (iii) a variant polypeptide thereof, that contains one or more substitutions, fusions, or truncations in which one or more TBF1 functions are conserved. In another aspect, the polypeptide is a reporter polypeptide selected from the group consisting of: (i) β-galactosidase (β-gal), β-glucuronidase (β-gluc), chloramphenicol acetyltransferase (CAT), *Renilla*-luciferase (ruc), *Photinus* luciferase (luc), secreted alkaline phosphatase (SAP), and green fluorescent protein (GFP); (ii) a variant of the reporter polypeptide specified in (i) that contains one or more conservative substitutions in which one or more reporter functions are conserved; or (iii) a variant of the reporter polypeptide specified in (i) that contains one or more substitutions, fusions, or truncations in which one or more reporter functions are conserved.

The invention is not limited by the specific nature of the polypeptide encoded by the downstream ORF, provided it is functional in the cellular or organismal environment being evaluated. In some cases, it may be desirable to express a partially-functional or non-functional polypeptide, compared to a fully-functional polypeptide to study its properties with respect to its biological activity, including its binding affinity to, or influence on the properties of, other cellular molecules. In this respect, polypeptides being studied, including those encoded by upstream or downstream ORFS (uORFs and dORFs), may contain a variety of alterations, such as conservative substitutions, in which amino acids having similar structural or chemical properties (e.g., size, charge, or polarity) are substituted for amino acids in the unmodified polypeptide. A variety of polypeptides can tolerate insertions of other polypeptide segments, at the amino terminus, carboxy terminus, or at internal positions, permitting the evaluation of protein fusions, which may retain or interfere with the activity of the unmodified polypeptide. Many polypeptides can also tolerate internal deletions, or truncations of amino acids at the amino terminus or carboxy terminus, which may retain or interfere with the activity of the unmodified polypeptide. Polypeptides may also contain one or more alterations, such as substitutions, insertions/fusions, deletions/truncations, in a variety of combinations, which alter the structure, and in some cases function, of the polypeptide being studied.

The types of alterations that are tolerated depend on the nature of the polypeptide being studied. For example, for polypeptides having more than one function, alterations may be tolerated in specific structural domains, if the system being evaluated is not sensitive to the function carried out by polypeptide domain. Reporter polypeptides, for example, may more easily tolerate alterations at either end of the polypeptide, permitting the construction of fused or truncated polypeptides, that retain the catalytic activity responsible for the reporter function (e.g., enzymatic activity, or fluorescence), than alterations located in the middle of the molecule. Transcriptional factors, like TBF1, may tolerate alterations in regions that are not involved in the binding of the polypeptide to nucleic acids, other polypeptides, or other types of regulatory co-factors.

The promoters used with the invention may comprise a variety of genetic elements that regulate their properties, including level of transcription at different times, generally in response to different concentrations of general or specific transcriptional components, including regulatory molecules, polymerase complexes, typically be small molecules, nucleic acids, peptides, or polypeptides, or conjugates between these and other cellular molecules or macromolecules. In one aspect of the invention, the promoter is constitutive, and in another aspect, the promoter is inducible.

In one aspect, the promoter is active in plant cells. In one aspect, the promoter is selected from the group consisting of: (a) a plant promoter; (b) a plant virus promoter; (c) a promoter from a non-viral plant pathogen; (d) a mammalian cell promoter; and (e) a mammalian virus promoter. In one aspect, the promoter is a plant promoter. In another aspect, the plant promoter is selected from the group consisting of: (a) the TBF1 promoter as set forth in SEQ ID NO: 113; (b) a variant sequence thereof, that contains one or more substitutions, insertions, or deletions, in which one or more TBF1 promoter functions are preserved; or (c) a nucleotide sequence which is 50% or more identical to the TBF1 promoter set forth in (a) in which one or more promoter functions are preserved. In another aspect, the plant promoter is selected from the group consisting of: (a) the BiP2 promoter as set forth in SEQ ID NO: 109; (b) a variant sequence thereof, that contains one or more substitutions, insertions, or deletions, in which one or more TBF1 promoter functions are preserved. In another aspect, the plant promoter is a nucleotide sequence comprising a binding site for the TBF1 polypeptide in which one or more promoter functions are preserved. In a specific aspect, the plant promoter is a nucleotide sequence comprising a functionally-active pathogen-inducible or constitutive promoter. In more specific aspect, the promoter is derived from an *Arabidopsis* locus selected from the group consisting of AT1G48850, AT1G62300, AT4G34230, AT4G34180, AT4G35110, AT2G30490, AT5G38900, AT5G24430, AT1G63720, AT4G39270.

In one aspect, the promoter is a plant promoter which is inducible. In another aspect, the plant promoter is inducible upon challenge by a plant pathogen or a chemical inducer. In another aspect, the inducer is selected from the group consisting of salicylic acid, jasmonic acid, methyl ester of jasmonic acid, abscisic acid, ethylene, AgNO$_3$, cycloheximide, mannitol, NaCl, flg22, elf18 and LPS. This non-limiting list of inducers have all been tested and shown to induce the TBF1 promoter. Other stimuli, which trigger a similar induction response in TBF1-like genes could be used to test their ability to modulate expression mediated the regulatory region described above.

Other aspects of the invention include cells and vectors comprising nucleic acids comprising the regulatory regions described above, and organisms, particularly plant propagation material, plants, and seeds derived from plants comprising said cells or vectors. One aspect, for example, is a cell comprising a nucleic acid with a regulatory region comprising a promoter operable in said cell, and one or more upstream ORFs, optionally linked to one or more downstream ORFS, as described above. In another aspect, the cell is a plant cell and said promoter is active in plant cells. Another aspect is plant propagation material comprising said cell. Other aspects include a transgenic plant comprising said cell, and a seed derived from said transgenic plant.

Related aspects include a vector comprising a nucleic acid with a regulatory region comprising a promoter operable in a cell, and one or more upstream ORFs, optionally linked to one or more downstream ORFS, as described above. Another aspect is a cell comprising a vector comprising the regulatory region as noted above, and a plant cell comprising the vector, wherein the promoter is active in plant cells. Other aspects include a transgenic plant comprising the vector, and the seed of a transgenic plant comprising the vector described above.

It should be noted that vectors may carry genetic elements, such as those that confer resistance to drugs, that are not essential to the function of the nucleic acids of the invention that comprise the regulatory region (e.g., promoter, one or more uORFs, optionally one or more dORFs) described above. The vectors may be plasmids, propagated in bacteria or plants, or viruses. Plasmids are typically propagated as double-stranded DNA circles, while viruses may carry genetic information as single- or double-stranded RNA or DNA molecules. The nucleic acids that comprise the regulatory region noted above may be introduced into cells as part of a larger molecule, such as a vector, or introduced directly into a cell not covalently linked to other nucleic acids, although other nucleic acids or vectors may be used to facilitate the introduction of genetic material, such as selectable or screenable genetic markers, into the cell. The nucleic acids of the invention, therefore, may not be stably-propagated, after introduction into a cell, or may be stably-propagated, either by replication of a vector comprising the regulatory region noted above, or by stable integration of the nucleic acid at one or more regions within the genome of the cell.

One aspect of the invention relates to a transgenic plant comprising a regulatory region used to modulate the expression of one or more polypeptides in a cell, wherein said regulatory region comprises a promoter, functional in said cell, operably-linked to at least one upstream open reading frame (uORF) that encodes a polypeptide selected from the group consisting of: (a) (i) a polypeptide represented by uORF1 (SEQ ID NO: 102); (ii) a variant polypeptide thereof that contains one or more conservative substitutions in which one or more uORF1 functions are conserved; or (iii) a variant polypeptide thereof that contains one or more substitutions, fusions, or truncations in which one or more uORF1 functions are conserved; and (b) (i) a polypeptide represented by uORF2 (SEQ ID NO: 103); (ii) a variant polypeptide thereof that contains one or more conservative substitutions in which one or more uORF2 functions are conserved; or (iii) a variant polypeptide thereof that contains one or more substitutions, fusions, or truncations in which one or more uORF2 functions are conserved. A related aspect includes a transgenic plant, wherein said molecule comprises uORF1, or a functional variant thereof, and uORF2, or a functional variant thereof.

Another aspect includes a transgenic plant further comprising one or more downstream ORFs (dORFs) encoding one or more polypeptides. The invention also includes a transgenic plant, wherein at least one dORF encodes a polypeptide selected from the group consisting of: (i) a polypeptide that is functionally-active as a transcription factor; (ii) a reporter polypeptide; (iii) a polypeptide that confers resistance to drugs or agrichemicals; (iv) a polypeptide involved in in resistance of plants to viral, bacterial, fungal pathogens, oomycete pathogens, phytoplasmas, and nematodes; and (v) a polypeptide involved in the growth or development of plants.

Related aspects of the invention also include transgenic plants wherein downstream ORFs encode specific polypeptides, such as TBF1, and natural or synthetic variants, homologues, and orthologs, or reporter polypeptides, such as β-glucuronidase, β-galactosidase, luciferase, and fluorescent proteins, as noted above.

The invention also relates to a variety of methods of using the regulatory region described above to facilitate the expression (e.g., transcription of mRNA, and translation of the mRNA comprising one or more ORFs) of one or more peptides or polypeptides in a cell. A polypeptide may be also released from the cell into the extracellular environment, such as cell culture medium, after being processed for secretion, or by degradation of the cell membrane or cell wall, where it may be recovered and purified. It is not necessary for a polypeptide to be expressed at high levels to have an effect on other cellular functions. A transcriptional factor, for example, may have pleiotropic effects by modulating its expression only slightly, compared to the amount or level of activity in a parent cell that does not contain a regulatory region described above.

One aspect of the invention relates to a method of using a regulatory region to modulate the expression of one or more polypeptides in a cell, wherein said regulatory region comprises a promoter, functional in said cell, operably-linked to one or more upstream ORFs and one or more downstream ORFs encoding said one or more polypeptides, comprising the steps of: (a) introducing one or more nucleic acids comprising said regulatory region into a cell; (b) expressing one or more upstream ORFs and one or more downstream ORFs encoding one or more polypeptides for a period sufficient to modulate the amount or level of activity of at least one of the one or more polypeptides within the cell or in the cell culture medium obtained from said cell. Another aspect relates to a method, further comprising the step (c) of purifying at least one of said polypeptides from the cell comprising said regulatory region or from the cell culture medium obtained from said cell.

In any of these methods, the amount or level of activity at least one of said polypeptides may be enhanced above, or reduced below, the endogenous amount or level of activity in a parent cell lacking an introduced nucleic acid comprising said regulatory region.

Another aspect relates to a method wherein said regulatory region contains a nucleic acid comprising at least one upstream open reading frame (uORF) that encodes a polypeptide selected from the group consisting of: (a) (i) a polypeptide represented by uORF1 (SEQ ID NO: 102); (ii) a variant polypeptide thereof that contains one or more conservative substitutions in which one or more uORF1 functions are conserved; or (iii) a variant polypeptide thereof that contains one or more substitutions, fusions, or truncations in which one or more uORF1 functions are conserved; (b) (i) a polypeptide represented by uORF2 (SEQ ID NO: 103); (ii) a variant polypeptide thereof that contains one or more conservative substitutions in which one or more uORF2 functions are conserved; or (iii) a variant polypeptide thereof that contains one or more substitutions, fusions, or truncations in which one or more uORF2 functions are conserved.

Related aspects include methods wherein said nucleic acid molecule comprises uORF1, or a functional variant thereof, and uORF2, or a functional variant thereof, and also methods wherein said nucleic acid molecule further comprises one or more downstream ORFs (dORFs) encoding one or more polypeptides.

Another aspect includes a method wherein the regulatory region further comprises one or more downstream ORFs (dORFs) encoding one or more polypeptides. The invention also includes a method wherein at least one dORF encodes a polypeptide selected from the group consisting of: (i) a polypeptide that is functionally-active as a transcription factor; (ii) a reporter polypeptide; (iii) a polypeptide that confers resistance to drugs or agrichemicals; (iv) a polypeptide involved in in resistance of plants to viral, bacterial, fungal pathogens, oomycete pathogens, phytoplasmas, and nematodes; and (v) a polypeptide involved in the growth or development of plants. Related aspects include methods where the downstream ORFs encode specific polypeptides, such as TBF1, and natural or synthetic variants, homologues, and orthologs, or reporter polypeptides, such as β-glucuronidase, β-galactosidase, luciferase, and fluorescent proteins, as noted above.

Other aspects also relate to methods wherein the regulatory region comprises a specific promoter, such as those described above, which may be constitutive or inducible, or derived from different sources, provided they are functionally active in the cell or organism being evaluated.

The invention is also directed to any of the methods described above that include introducing the nucleic acid comprising the regulatory region comprising a promoter, one or more uORFs, and one or more dORFs, into a cell, expressing a polypeptide under the control of the regulatory region, and purifying the polypeptide from a cell, tissue, or plants, or its extracellular environment.

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

EXAMPLES

The foregoing discussion may be better understood in connection with the following representative examples which are presented for purposes of illustrating the principle methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods and Sources of Materials

All parts are by weight (e.g., % w/w), and temperatures are in degrees centigrade (° C.), unless otherwise indicated. Table 1 presents a summary of the PCR primers and nucleotide and amino acid sequences described in this application.

TABLE 1

PCR Primers, Nucleotide and Amino Acid Sequences and SEQ ID NOS Used In This Study

| Name | Description | Length | Type | SEQ ID NO: |
|---|---|---|---|---|
| A. primers used in the ChIP experiment | | | | |
| BiP2-ChIP-F1 | ATGGCTCGGCTCGCT | 15 | ssDNA | 1 |
| BiP2-ChIP-R1 | GAGATCAAGCAACAATGCAGA | 21 | ssDNA | 2 |
| BiP2-ChIP-F2 | TCGGGCACTGGACCTATTTA | 20 | ssDNA | 3 |
| BiP2-ChIP-R2 | CGGAAACTTTTGCGTACGAT | 20 | ssDNA | 4 |
| BiP2-ChIP-F3 | GGCCACGATTACTCCAACAC | 20 | ssDNA | 5 |
| BiP2-ChIP-R3 | TCGCTTTTTATGGAAGACGAA | 21 | ssDNA | 6 |
| BiP2-ChIP-F4 | GGTTCCGGTTCTTTTCCACT | 20 | ssDNA | 7 |
| BiP2-ChIP-R4 | TGTGTTGGAGTAATCGTGGC | 20 | ssDNA | 8 |
| BiP2-ChIP-F5 | GGTACGCAGATCGGATTCGAGTAAAAC | 27 | ssDNA | 9 |
| BiP2-ChIP-R5 | TTATAGCCAATTGATCCGAACCAAAACCG | 29 | ssDNA | 10 |
| BiP2-ChIP-F6 | CATCCAAAAATATATTAGTACGAGCC | 26 | ssDNA | 11 |
| BiP2-ChIP-R6 | CCATCACCGTTAACAAAGAAA | 21 | ssDNA | 12 |
| B. Primers used for real-time PCR | | | | |
| UBQ5-qPCR-F | GACGCTTCATCTCGTCC | 17 | ssDNA | 13 |
| UBQ5-qPCR-R | GTAAACGTAGGTGAGTCCA | 19 | ssDNA | 14 |
| TBF1-qPCR-F | GTTGGTTCGCCTTCTG | 16 | ssDNA | 15 |
| TBF1-qPCR-R | CCACACCCCAAACAAT | 16 | ssDNA | 16 |
| BiP2-qPCR-F | GACGCCAACGGTATTC | 16 | ssDNA | 17 |
| BiP2-qPCR-R | TGTCTCCAGGGCATTC | 16 | ssDNA | 18 |
| CRT3-qPCR-F | ATGACCCCAACGATGT | 16 | ssDNA | 19 |
| CRT3-qPCR-R | CCTTGTAGTTCGGGTTCT | 18 | ssDNA | 20 |
| PR1-qPCR-F | CTCATACACTCTGGTGGG | 18 | ssDNA | 21 |
| PR1-qPCR-R | TTGGCACATCCGAGTC | 16 | ssDNA | 22 |
| BiP3-qPCR-F | AGCACTCGAATCCCAA | 16 | ssDNA | 23 |
| BiP3-qPCR-R | GCCTCCGACAGTTTCA | 16 | ssDNA | 24 |
| CRT1-qPCR-F | CTGTGGTGGTGGCTAC | 16 | ssDNA | 25 |
| CRT1-qPCR-R | GTCTCACATGGGACCT | 16 | ssDNA | 26 |
| NPR1-qPCR-F | AAACATGTCTCGAATGT | 17 | ssDNA | 27 |
| NPR1-qPCR-R | GATTCCTATGGTTGACA | 17 | ssDNA | 28 |
| CNX1-qPCR-F | CCCATGTCTACACCGC | 16 | ssDNA | 29 |

TABLE 1-continued

PCR Primers, Nucleotide and Amino Acid Sequences and SEQ ID NOS Used In This Study

| Name | Description | Length | Type | SEQ ID NO: |
|---|---|---|---|---|
| CNX1-qPCR-R | CACGGCATTTGGATCAG | 17 | ssDNA | 30 |
| MPK11-qPCR-F | ACCCAAACAGACGCATTACAG | 21 | ssDNA | 31 |
| MPK11-qPCR-R | CTCCTTGATGTTCTCTTCCGTC | 22 | ssDNA | 32 |
| GWD-qPCR-F | ATCGCAGATTTGGAGAGTGAG | 21 | ssDNA | 33 |
| GWD-qPCR-R | TGTAGCCATAAACCTCATCCAG | 22 | ssDNA | 34 |
| TGA3-qPCR-F | TCTTGATGTCGGGAATGTGG | 20 | ssDNA | 35 |
| TGA3-qPCR-R | AGTTGCTGATCGGTTAAGGG | 20 | ssDNA | 36 |
| SecY-qPCR-F | TTCTACACCTCCAACATGCC | 20 | ssDNA | 37 |
| SecY-qPCR-R | CTCTGATTCTTTCCACTGTCCC | 22 | ssDNA | 38 |
| PR-13-qPCR-F | TGTGTATCCTCTGTTTGCGG | 20 | ssDNA | 39 |
| PR-13-qPCR-R | TGCATTCATAGAGCCCTTGG | 20 | ssDNA | 40 |
| CRR23-qPCR-F | ACATCTCACACCAAACCCAAC | 21 | ssDNA | 41 |
| CRR23-qPCR-R | TAAGGCTGGATGGTCAATCG | 20 | ssDNA | 42 |
| OB-fold-like-qPCR-F | AACCTACCACGAACACCATC | 20 | ssDNA | 43 |
| OB-fold-like-qPCR-R | ACTACATAAGCGGCCATCAG | 20 | ssDNA | 44 |
| ANNAT4-qPCR-F | CAAACCAAGAGCCGGAAATC | 20 | ssDNA | 45 |
| ANNAT4-qPCR-R | TCCCCAGTGTGCTTATCAATG | 21 | ssDNA | 46 |
| FLA8-qPCR-F | TGCTCCACACTGACACTTG | 19 | ssDNA | 47 |
| FLA8-qPCR-R | GCGAGGATTTGAGTGATGTTG | 21 | ssDNA | 48 |
| HSP70-qPCR-F | AATGGCTGGTAAAGGAGAAGG | 21 | ssDNA | 49 |
| HSP70-qPCR-R | CTATCAGTGAAGGCGACGTAAG | 22 | ssDNA | 50 |
| ATERF-7-qPCR-F | AAATCTCGTGTCTGGCTCG | 19 | ssDNA | 51 |
| ATERF-7-qPCR-R | AGGTGAGAGGTTGGAGAGG | 19 | ssDNA | 52 |
| DegP-qPCR-F | AAGAGAACACTCCTTCCGTTG | 21 | ssDNA | 53 |
| DegP-qPCR-R | TGACCTTGCTTATCCCACAC | 20 | ssDNA | 54 |
| Thylakoid P17-qPCR-F | GAGATCCAGTTCCTTGTGAGAG | 22 | ssDNA | 55 |
| Thylakoid P17-qPCR-R | ATTCCACCTTCATCTTCCCTTC | 22 | ssDNA | 56 |
| MPK3-qPCR-F | CGAAAAGATACATCCGGCAAC | 21 | ssDNA | 57 |
| MPK3-qPCR-R | GATTCAGAGCTTGTTCAACAGTG | 23 | ssDNA | 58 |
| Clathrin-qPCR-F | CCTCGTGAAGTGCCAGTTATAG | 22 | ssDNA | 59 |
| Clathrin-qPCR-R | GGATTGTGCTTGAGTTTCGTG | 21 | ssDNA | 60 |
| PAD4-qPCR-F | AAGATCCATGACATCGCCG | 19 | ssDNA | 61 |
| PAD4-qPCR-R | AGGTAGAGGTTCATCGGAGG | 20 | ssDNA | 62 |
| PDIL-qPCR-F | GTGGATGTTGACCGTACAGTAG | 22 | ssDNA | 63 |
| PDIL-qPCR-R | CTTGGAACTATCACCCTCGATC | 22 | ssDNA | 64 |
| PGL34-qPCR-F | GCTTCTCATCCTCTGTATCACC | 22 | ssDNA | 65 |
| PGL34-qPCR-R | AACCGAGTCTTGAACCATAGC | 21 | ssDNA | 66 |

TABLE 1-continued

PCR Primers, Nucleotide and Amino Acid Sequences and SEQ ID NOS Used In This Study

| Name | Description | Length | Type | SEQ ID NO: |
|---|---|---|---|---|
| SAUR-like-qPCR-F | TGGATTCGAGCAGAAAGGTAC | 21 | ssDNA | 67 |
| SAUR-like-qPCR-R | TGGGTTAGGCCGTGTTTG | 18 | ssDNA | 68 |
| GA2ox-qPCR-F | GAACCGATATCCACCTTGTCC | 21 | ssDNA | 69 |
| GA2ox-qPCR-R | TGAGGAAATCACTGTCCGTG | 20 | ssDNA | 70 |
| EXLA2-qPCR-F | TGACAAAGTACCCAACGGAG | 20 | ssDNA | 71 |
| EXLA2-qPCR-R | ATGTCTGTGATCTGAACGCC | 20 | ssDNA | 72 |
| CESA6-qPCR-F | TCCTTCTCGCCTCTATCCTTAC | 22 | ssDNA | 73 |
| CESA6-qPCR-R | CAGTCCAAGCCACATATCTCG | 21 | ssDNA | 74 |
| WRKY75-qPCR-F | GGAGGGATATGATAATGGGTCG | 22 | ssDNA | 75 |
| WRKY75-qPCR-R | ACCTTCTGATCTAACCTTTGAGC | 23 | ssDNA | 76 |
| Ribosomal Protein-qPCR-F | TTGCCTCTGAAATGAGTCCG | 20 | ssDNA | 77 |
| Ribosomal Protein-qPCR-R | TGCTCTTCCCCTTTGTTCTC | 20 | ssDNA | 78 |
| MDH-qPCR-F | TTGCCTCTGAAATGAGTCCG | 20 | ssDNA | 79 |
| MDH-qPCR-R | TGCTCTTCCCCTTTGTTCTC | 20 | ssDNA | 80 |
| C. Primers used for cloning BiP2 promoter, TBF1 genomic fragment and 5'UTR of TBF1 | | | | |
| TBF1-cDNA-GW-F | GGGGACAAGTTTGTACAAAAAAGCAGGCTTAATGACGGCTGTGACGGCGGCGCAAAG | 57 | ssDNA | 81 |
| TBF1-cDNA-GW-R (STOP) | GGGGACCACTTTGTACAAGAAAGCTGGGTCTTAGTTGCAGACTTTGCTGCTTTTC | 55 | ssDNA | 82 |
| TBF1-cDNA-GW-R (NON_STOP) | GGGGACCACTTTGTACAAGAAAGCTGGGTCGTTGCAGACTTTGCTGCTTTTCCTC | 55 | ssDNA | 83 |
| TBF1-promoter-GW-F | GGGGACAAGTTTGTACAAAAAAGCAGGCTTACGACGACTAGTTTACAGAGAATTTGGAC | 60 | ssDNA | 84 |
| BiP2-promoter-GW-F | GGGGACAAGTTTGTACAAAAAAGCAGGCTTATTCCGGTTCTTTTCCACTCCTAATG | 56 | ssDNA | 85 |
| BiP2-promoter-GW-R | GGGGACCACTTTGTACAAGAAAGCTGGGTCATCGGAAACTTTTGCGTACGATC | 53 | ssDNA | 86 |
| TBF1 5'UTR-GW-F | GGGGACAAGTTTGTACAAAAAAGCAGGCTTATTTCTTACAAAGGTAGGACCAAC | 54 | ssDNA | 87 |
| TBF1 5'UTR-GW-R | GGGGACCACTTTGTACAAGAAAGCTGGGTCGTAAGTGTTGAGCTGACGAATG | 52 | ssDNA | 88 |
| uORF1 Phe->Leu-F | GCTCCGGCGAAGTCTGGTCGTCGTCTTCATC | 31 | ssDNA | 89 |
| uORF1 Phe->Leu-R | GATGAAGACGACGACCAGACTTCGCCGGAGC | 31 | ssDNA | 90 |
| uORF2 Phe->Leu-F | GATTTTTCCTTAACTGGAAGAAACCAAACG | 30 | ssDNA | 91 |
| uORF2 Phe->Leu-R | CGTTTGGTTTCTTCCAGTTAAGGAAAAATC | 30 | ssDNA | 92 |
| pTB3-dhAGT-TBF1 5'UTR-F | GAGAAATTGAAGAGCGCAACGAACTACGAGCGGATCCTTTCTTACAAAGGTAGGACC | 58 | ssDNA | 93 |
| pTB3-dhAGT-TBF1 5'UTR-R | GGACACGGCGACGATGCAGTTCAATGGTCGAACGTAAGTGTTGAGCTGACGAATG | 55 | ssDNA | 94 |

TABLE 1-continued

PCR Primers, Nucleotide and Amino Acid Sequences and SEQ ID NOS Used In This Study

| Name | Description | Length | Type | SEQ ID NO: |
| --- | --- | --- | --- | --- |
| D. Oligos used for EMSA | | | | |
| TL1 oligo (EMSA) | TCCAGTGCTGAAGAAGAATTCTACG | 25 | ssDNA | 95 |
| mTL1 oligo (EMSA) | TCCAGTGTCATCACGTGTTTCTACG | 25 | ssDNA | 96 |
| E. tRNA Probe Sequences | | | | |
| tRNA-Phe | AGCGTGGATCGAACACGCGACCTTCAGATCTTCAGTCTGACGCT CTCCCAACTGAGCTA | 59 | ssDNA | 97 |
| tRNA-Asp | GCCGGGGATCGAACCCGGGTCACCCGCGTGACAGGCGGGAAT ACTTACCACTATACTAC | 59 | ssDNA | 98 |
| F. TBF1 region | | | | |
| Exact TL1 motif | GAAGAAGAA | 9 | DNA | 99 |
| Degenerate TL1 motif | GXXXGXXXX, approximating degenerate motif, G-(A/G)-(AGT)-G-(ACG)-(ACG)-(ACG)-(AC)-(ACGT) as noted in the frequencies specified in the weight matrix of Table 6. | 9 | Synthetic | 100 |
| Genomic TBF1 region | Genomic TBF1 region from *Arabidopsis thaliana* including TBF1 promoter, and regions encoding uORF1, uORF1, and TBF1 polypeptides (in exons 1 and 2, separated by TBF1 intron) See FIGS. 19 and 20 displaying the sequence and genetic elements of the TBF1 region in compact form. Beginning with Aaaattttca . . . Ending with . . . acagaaacat tttct 5085 | 5085 | DNA | 101 |
| uORF1 aa | MVVVFIFFLHHQIFP | 15 | AA | 102 |
| uORF2 aa | MEETKRNSDLLRSRVFLSGFYCWDWEFLTALLLFSC | 36 | AA | 103 |
| TBF1 aa (1$^{st}$ Exon) | MTAVTAAQRSVPAPFLSKTYQLVDDHSTDDVVSWNEEGTAFVV WKTAEFAKDLLPQYFKH NNFSSFIRQLNTY | 73 | AA | 104 |
| TBF1 aa (2$^{nd}$ Exon) | GFRKTVPDKWEFANDYFRRGGEDLLTDIRRRKSVIASTAGKCVVVGS PSESNSGGGDDHGSSSTSSPGSSKNPGSVENMVADLSGENEKLKRENN NLSSELAAAKKQ RDELVTFLTGHLKVRPEQIDKMIKGGKFKPVESDEESECEGCDGGGGAE EGVGEGLKLFG VWLKGERKKRDRDEKNYVVSGSRMTEIKNVDFHAPLWKSSKVCN | 211 | AA | 105 |
| TBF1 aa (1$^{st}$ and 2$^{nd}$ Exons) | MTAVTAAQRSVPAPFLSKTYQLVDDHSTDDVVSWNEEGTAFVVWKT AEFAKDLLPQYFKH NNFSSFIRQLNTY GFRKTVPDKWEFANDYFRRGGEDLLTDIRRRKSVIASTAGKCVVVGS PSESNSGGGDDHGSSSTSSPGSSKNPGSVENMVADLSGENEKLKRENN NLSSELAAAKKQ RDELVTFLTGHLKVRPEQIDKMIKGGKFKPVESDEESECEGCDGGGGAE EGVGEGLKLFG VWLKGERKKRDRDEKNYVVSGSRMTEIKNVDFHAPLWKSSKVCN | 284 | AA | 106 |
| TBF1 genomic region with STOP codon used for complementation | The 4601-bp genomic DNA containing the TBF1 promoter and the coding region (SEQ ID NO: 107) with the TBF1 intron was amplified using primers TBF1-promoter-GW-F (SEQ ID NO: 84) and TBF1-cDNA-GW-R (SEQ ID NO: 82) Beginning with cgacgactag... Ending with ...tctgcaacta a 4601 | 4601 | DNA | 107 |
| TBF1 UTR through first exon of TBF1 ORF | The DNA fragment containing the 5' untranslated region (UTR) and the first exon of TBF1 was amplified by polymerase chain reaction (PCR) using primers TBF1 5'UTR-GW-F (SEQ ID NO: 87) and TBF1 5'UTR-GW-R (SEQ ID NO: | 670 | DNA | 108 |

TABLE 1-continued

PCR Primers, Nucleotide and Amino Acid Sequences and SEQ ID NOS Used In This Study

| Name | Description | Length | Type | SEQ ID NO: |
|---|---|---|---|---|
| | 88), designated uORF1-uORF2-TBF1 1st exon<br>tttcttacaa aggtaggacc aacatttgtg atctataaat cttcctacta cgttatatag 60<br>agaccccttcg acataacact taactcgttt atatatttgt tttacttgtt ttgcacatac 120<br>acacaaaaat aaaaaagact ttatatttat ttacttttta atcacacgga ttagctccgg 180<br>cgaagtatgg tcgtcgtctt catcttcttc ctccatcatc agatttttcc ttaaatggaa 240<br>gaaaccaaac gaaactccga tcttctccgt tctcgtgttt tcctctctgg cttttattgc 300<br>tgggattggg aatttctcac cgctctcttg cttttttagtt gctgattctt tttccttcga 360<br>cttctctattt ccaatctttc ttcttctctt tgtgtattag attattttta gttttatttt 420<br>tctgtggtaa aataaaaaaa gttcgccgga gatgacggct gtgacggcgg cgcaaagatc 480<br>agttccggcg ccgttttttaa gcaaaacgta tcagctagtt gatgatcata gcacagacga 540<br>cgtcgtttca tggaacgaag aaggaacagc ttttgtcgtg tggaaaacag cagagtttgc 600<br>taaagatctt cttcctcaat acttcaagca taataatttc tcaagcttca ttcgtcagct 660<br>caacacttac 670 | | | |
| BiP2 promoter fragment | A 352-bp long fragment of the BiP2 promoter containing four TL1 motifs was PCR-amplified using primers BiP2-promoter-GW-F (SEQ ID NO: 85) and BiP2-promoter-GW-R (SEQ ID NO: 86), cloned into the pDONR207 Gateway Entry vector and subsequently recombined into yeast one hybrid bait destination vectors pMW2 and pMW3.<br>Ttccggttcttttccactcctaatgatgtaatagaagaagactggcccaacaaaagctc attgtctaattaagaagaagaaacgaagtaaccaacggccacgattactccaacacaa gaccaaatctgattggttgacattatagatcgtcgtaagataattggtccacgtcatctcc gatgacatagttaaatttcttcgtcttccataaaaagcgactacttcaccatcaccttcgg gcactggacctatttaagcatcctaacttcttcttcaaagcttaaaaaccagaaaacaaa aggaagctctctgttcaaatcaaaaagagagatcgtacgcaaaagtttccgat | 352 | DNA | 109 |
| Genomic TBF1 region NON_STOP | The 4,598-bp genomic DNA containing the TBF1 promoter and the coding region (SEQ ID NO: 107) was amplified using primers TBF1-promoter-GW-F (SEQ ID NO: 84) and TBF1-cDNA-GW-R (NON_STOP) (SEQ ID NO: 83). The resulting fragment was cloned into pDONR207, subsequently recombined into pMDC107 and used to generate a genomic TBF1-GFP fusion.<br><u>cgacgactagtttacagagaatttggaccgtccgatgtaaa</u><br>gcgaaaatagatctaggttttccacgtgtcccctatttttaa tgaaaccttctgattcatgtagaagttttactcaatttaat attttttagtatgtagttttgtgtgtgtgtgtgtgtgtt tttatggctccacaccaactttttaaaatggtagaagcatgt tgcatgtgatcgagtaaaaagccaataatgagattcagaaa aataaaaattacttatatagtttttttagagaaaaaattgta ttttgtttaaagccttaatccggttgttgaaagagctgtgt cacgagttaaaaatattttcttttcattttttaagtaatta gtttataatgcaaaaatggttttatttatttgtcttcgct tatagaactgcaaattgagagagaaaaaatgaattagtgg tggtgaccaaacattcaggaagctgtgattgatcatttgtt tttgaggtgagtgtagtggcaacgtatgacgttaacatatg gcgtacataataattacatgaacttaatcataataatcata ttgcatttaattcatatatcatatcccattagttggaccac ttgatttgaggtcatgagaagaacatttatgttttttttag tttgaatcggagtgatcactaaaaactagatactgaaaatt ttcaaactaaaatcatattaatcttcaaaaaatgtgaaatc taaaaaaaaaaaatttttaacgcgttcattgtagccaagt agccaagtattgttaaagtagtagtaaaagaagtttagctt taagtgatataatttgacacaaatcctacttagatatggat aataggatatagcttcatgtatattttttatcgttgcttctg taaccccaaaatgtgttgatataagcatttgaatattcgta tgtataatgttttcttttcaccgtaaaacatattacaatgt tagtttatattggattttgaatgtgtttatgaacagttttt gtcgactcaaaagttaagatgagaatacggaagaaagtaaa gtttaaaagtcatgatgggaacaaggaatggaactcaaaca ttctaatactcaacaaacgcaattatattattaccatgact catctctttcaagttccatcaaaaagattcgtggaaaataata | 4598 | DNA | 110 |

TABLE 1-continued

PCR Primers, Nucleotide and Amino Acid Sequences and SEQ ID NOS Used In This Study

| Name | Description | Length | Type | SEQ ID NO: |
|------|-------------|--------|------|------------| gacttacgtttcaaatccatgtttctttctttataacaaaa
aaaatggatgtttcttgacgcgtgtcgagagtactcaccat
tactctgacttcagtgagtttggtcaagtggtcttttttt
tctcatgtcaccaaaggtccaaaccctagaaattagttcga
actttccatagaagaactgaataaatggtccaaaattgttt
taaaaaggacctaagccattagttcattgaattcgagttaa
tgggtgaagattttttatgataacgaaagtcggagtaattat
gcttttggtccgatagttttctaatttgttttctttccatt
ttttttttttcaaatactacatactatataagatagtggtt
tgtgttaatgtcatcgatgtgttaccatccgcattatatta
attatttatcccaacataaagtcagaatctgtaatttcttt
gttataaaatacagtaaatggttccgtttaagctgttagat
gattttttgagtaaaaactaatgtaaaaaaaacaaaaaaaa
acaatgtagttcataatacatgcatgtttaaagaagtttc
ttgtttactatcaacttgaatagtatttcacgaagtcaaaa
ttgttcattccgacttttctatgtggagaaaaaaaattcta
tcattgtgcacaatttaacagaatgtaatttcttgtaaaag
aagaggaaacaattcgctgttagtaaatgtgaagtatagaa
gtctaaaatgagatacctcaactagcttgaattaagaaaaa
aaacaaaaactctatcgacatgaaaaaggtcgcaaatattt
atcatttatcaatgccaaggagtatttggttcacaaaata
ctgaatcatttatatagatatataattagctctaaattcta
ctataacttgcaaaataagtatactgactcaattatatagc
gtttaaaaatagacgatttgtatgatgaggtccatatatat
ggagatgtgcatgcaactatcgacattttcacacgttgata
tcgtctttctccaatggagacttgaatttgtgtaaactatg
aatactcgtctctctaagaccttttttcttcaaccatgcca
actatttaggtaagattttactgtctttgattgatattaaa
tacttagccgtggcgttatcaatgaatgataataaaaatgc
ggataaaagccaaaggtgttggaaataaatccaagaatgaa
gacgtagatgtcgatgggtattttaagaacttgaatttgtc
acgactcacacgttaaaatatattatccgaattgtttagtc
taaagacacacatatattgaaaagaaaaggtaaatgaagc
tcattggtgcctaaatgtgaaatgaagccgaaatgtgttag
gtgaacacatttaaatatacaaaaagaaatataatagaaac
aaaactaattaacaaagtcgcaatttgtattgtataaaata
tctttccgtctcccgtcatatttgaaaaaaaaaaaattaca
aatctgttaattttaaaactttctagaaaaacacaagtata
taattttctcttttcgtgcgtgtttgtttaaaataacatt
gttttgattggcgactcaacatatttagcatttacatatt
tctgcatatattaaatgatttataaactcaactatagatta
aaatataatttgacatctaataattttaacaataatatataaa
atatgagatttataaattacgaatataaatattcagggag
agaaaaagtagaacataattcaaaagataagacttttttaga
cttttttaacaatattttttgatggataaaaattattcaaaa
gagaagaaagtaagaagaaaagatgtttctgagaatt
tctagaaacagcatccgttttttataatttaattttcttaca
aaggtaggaccaacatttgtgatctataaatcttcctacta
cgttatatagagaccttcgacataacacttaactcgttta
tatatttgttttacttgtttgcacatacacacaaaaataa
aaaagactttatatttatttactttttaatcacacggatta
gctccggcgaagt
ATGGTCGTCGTCTTCATCTTCTTCCTCCATCATCAGATTTT
TCCTTAA
ATGGAAGAAACCAAACGAAACTCCGATCTTCTCCGTTCTCG
TGTTTTCCTCTCTGGCTTTTATTGCTGGGATTGGGAATTTC
TCACCGCTCTCTTGCTTTTTAGTTGCTGA
ttcttttccttcgactttctatttccaatctttcttcttc
tctttgtgtattagattattttttagttttattttctgtgg
taaaataaaaaagttcgccggag
ATGACGGCTGTGACGGCGGCGCAAAGATCAGTTCCGGCGCC
GTTTTTAAGCAAAACGTATCAGCTAGTTGATGATCATAGCA
CAGACGACGTCGTTTCATGGAACGAAGAAGGAACAGCTTTT
GTCGTGTGGAAAACAGCAGAGTTTGCTAAAGATCTTCTTCC
TCAATACTTCAAGCATAATAATTTCTCAAGCTTCATTCGTC
AGCTCAACACTTAC
gtgagtttcactctaacgaaaactcatttactctcaattta
atgcttcatttaattcgtttggtgaattgaatcattctttt
gtagttggttagccaatttcgtaattttctcataatttggg
ggttggtgagaaaaccttctagaagctgagaatgttcttgt
tctttttttttttttttttttggtttag
GGATTTCGTAAAACTGTACCGGATAAATGGGAATTTGCAAA
CGATTATTTCCGGAGAGGCGGGGAGGATCTGTTGACGGACA
TACGACGGCGTAAATCGGTGATTGCTTCAACGGCGGGGAAA

TABLE 1-continued

PCR Primers, Nucleotide and Amino Acid Sequences and SEQ ID NOS Used In This Study

| Name | Description | Length Type | SEQ ID NO: |
|---|---|---|---|
| | TGTGTTGTTGTTGGTTCGCCTTCTGAGTCTAATTCTGGTGG<br>TGGTGATGATCACGGTTCAAGCTCCACGTCATCACCCGGTT<br>CGTCGAAGAATCCTGGTTCGGTGGAGAACATGGTTGCTGAT<br>TTATCAGGAGAGAACGAGAAGCTTAAACGTGAAAACAATAA<br>CTTGAGCTCGGAGCTCGCGGCGGCGAAGAAGCAGCGCGATG<br>AGCTAGTGACGTTCTTGACGGGTCATCTGAAAGTAAGACCG<br>GAACAAATCGATAAAATGATCAAAGGAGGGAAATTTAAACC<br>GGTGGAGTCTGACGAAGAGAGTGAGTGCGAAGGTTGCGACG<br>GCGGCGGAGGAGCAGAGGAGGGGGTAGGTGAAGGATTGAAA<br>TTGTTTGGGGTGTGGTTGAAAGGAGAGAGAAAAAAGAGGGA<br>CCGGGATGAAAAGAATTATGTGGTGAGTGGGTCCCGTATGA<br>CGGAAATAAAGAACGTGGACTTTCACGCGCCGTTGTGGAAA<br>AGCAGCAAAGTCTGCAAC | | |
| uORF1 nucleotide seq | ATGGTCGTCGTCTTCATCTTCTTCCTCCATCATCAGATTTT<br>TCCTTAA | 48 | 111 |
| uORF2 nucleotide seq | ATGGAAGAAACCAAACGAAACTCCGATCTTCTCCGTTCTCG<br>TGTTTTCCTCTCTGGCTTTTATTGCTGGGATTGGGAATTTC<br>TCACCGCTCTCTTGCTTTTTAGTTGCTGA | 111 | 112 |
| TBF1 promoter | <u>cgacgactagtttacagagaatttggac</u><br>cgtccgatgtaaagcgaaaatagatctaggttttccacgtg<br>tccctattttaatgaaaccttctgattcatgtagaagttt<br>tactcaatttaatatttttagtatgtagttttgtgtgtgt<br>gtgtgtgtgtgttttatggctccacaccaacttttaaaat<br>ggtagaagcatgttgcatgtgatcgagtaaaaagccaataa<br>tgagattcagaaaaataaaaattacttatatagttttttag<br>agaaaaaattgtatttgtttaaagccttaatccggttgtt<br>gaaagagctgtgtcacgagttaaaaatattttcttttcatt<br>ttttaagtaattagtttataatgcaaaaatggttttattt<br>atttgtcttcgcttatagaactgcaaattgagagagaaaaa<br>aatgaattagtggtggtgaccaaacattcaggaagctgtga<br>ttgatcatttgtttttgaggtgagtgtagtggcaacgtatg<br>acgttaacatatggcgtacataataattacatgaacttaat<br>cataataatcatattgcatttaattcatatatcatatccca<br>ttagtggaccacttgatttgaggtcatgagaagaacattt<br>atgttttttttagtttgaatcggagtgatcactaaaaacta<br>gatactgaaaattttcaaactaaaatcatattaatcttcaa<br>aaaatgtgaaatctaaaaaaaaaaaaaaatttaacgcgttc<br>attgtagccaagtagccaagtattgttaaagtagtagtaaa<br>agaagtttagctttaagtgatataatttgacacaaatccta<br>cttagatatggataataggatatagcttcatgtatatttt<br>atcgttgcttctgtaaccccaaaatgtgttgatataagcat<br>ttgaatattcgtatgtataatgttttcttttcaccgtaaaa<br>catattacaatgttagtttatattggattttgaatgtgttt<br>atgaacagttttgtcgactcaaaagttaagatgagaatat<br>ggaagaaagtaaagtttaaaagtcatgatgggaacaaggaa<br>tggaactcaaacattctaatactcaacaaacgcaattatat<br>tattaccatgactcatctttcaagttccatcaaaaagattc<br>gtggaaaataatagacttacgtttcaaatccatgtttcttt<br>ctttataacaaaaaaaatggatgtttcttgacgcgtgtcga<br>gagtactcaccattactctgacttcagtgagtttggtcaag<br>tggtctttttttttctcatgtcaccaaaggtccaaaccta<br>gaaattagttcgaactttccatagaagaactgaataaatgg<br>tccaaaattgttttaaaaaggacctaagccattagttcatt<br>gaattcgagttaatgggtgaagattttatgataacgaaag<br>tcggagtaattatgcttttggtccgatagttttctaatttg<br>ttttcttttccatttttttttttcaaatactacatactata<br>taagatagtggtttgtgttaatgtcatcgatgtgttaccat<br>ccgcattatattaattatttatcccaacataaagtcagaat<br>ctgtaatttcttttgttataaaatacagtaaatggttccgtt<br>taagctgttagatgattttgagtaaaaactaatgtaaaaa<br>aaacaaaaaaaacaatgtagttcataatacatgcatgtt<br>ttaaagaagtttcttgtttactatcaacttgaatagtattt<br>cacgaagtcaaaattgttcattccgacttttctatgtggag<br>aaaaaaaattctatcattgtgcacaatttaacagaatgtaa<br>tttcttgtaaaagaagagggaaacaattcgctgttagtaaat<br>gtgaagtatagaagtctaaaatgagatacctcaactagctt<br>gaattaagaaaaaaacaaaaactctatcgacatgaaaaag<br>gtcgcaaatatttatcatttatcaatgccaaaggagtattt<br>ggttcacaaaatactgaatcatttatatagatatataatta<br>gctctaaattctactataacttgcaaaataagtatactgac<br>tcaattatatagcgttaaaaatagacgatttgtatgatga | 3354 | 113 |

TABLE 1-continued

PCR Primers, Nucleotide and Amino Acid Sequences and SEQ ID NOS Used In This Study

| Name | Description | Length | Type | SEQ ID NO: |
|---|---|---|---|---|
| | ggtccatatatatggagatgtgcatgcaactatcgacattt<br>tcacacgttgatatcgtctttctccaatggagacttgaatt<br>tgtgtaaactatgaatactcgtctctctaagaccttttttc<br>ttcaaccatgccaactatttaggtaagattttactgtcttt<br>gattgatattaaatacttagccgtggcgttatcaatgaatg<br>ataataaaaatgcggataaaagccaaaggtgttggaaataa<br>atccaagaatgaagacgtagatgtcgatgggtattttaaga<br>acttgaatttgtcacgactcacacgttaaaatatattatcc<br>gaattgtttagtctaaagacacacatatattgaaaaagaaa<br>aggtaaatgaagctcattggtgcctaaatgtgaaatgaagc<br>cgaaatgtgttaggtgaacacatttaaatatacaaaaagaa<br>atataatagaaacaaaactaattaacaaagtcgcaatttgt<br>attgtataaaatatctttccgtctcccgtcatatttgaaaa<br>aaaaaaaattacaaatctgttaattttaaaactttctagaa<br>aaacacaagtatataattttctcttttcgtgcgtgtttgtt<br>ttaaaataacattgttttgattggcgactcaacatatttta<br>gcatttacatatttctgcatatattaaatgatttataaact<br>caactatagattaaaatataatttgacatctaataatttta<br>acaataatataaaatatgagatttataaattacgaatataa<br>atattcaagggagagaaaaagtagaacataattcaaaagat<br>aagacttttagactttttaacaatatttttgatggataa<br>aaattattcaaaagagaagaaagtaagaagaaaagatgttt<br>ctgagaatt<br>tctagaaacagcatccgttttataatttaattttcttaca<br>aaggtaggaccaacatttgtgatctataaatcttcctacta<br>cgttatatagagaccccttcgacataacacttaactcgttta<br>tatatttgttttacttgttttgcacatacacacaaaaataa<br>aaaaagactttatatttatttactttttaatcacacggatta<br>gctccggcgaagt<br>ATGGTCGTCGTCTTCATCTTCTTCCTCCATCATCAGATTTT<br>TCCTTAA<br>ATGGAAGAAACCAAACGAAACTCCGATCTTCTCCGTTCTCG<br>TGTTTTCCTCTCTGGCTTTTATTGCTGGGATTGGGAATTTC<br>TCACCGCTCTCTTGCTTTTTAGTTGCTGA<br>ttcttttttccttcgactttctatttccaatctttcttcttc<br>tctttgtgtattagattattttttagttttattttctgtgg<br>taaaataaaaaaagttcgccggag | | | |
| TBF1 genomic seq | ATGACGGCTGTGACGGCGGCGCAAAGATCAGTTCCGGCGCC<br>GTTTTTAAGCAAAACGTATCAGCTAGTTGATGATCATAGCA<br>CAGACGACGTCGTTTCATGGAACGAAGAAGGAACAGCTTTT<br>GTCGTGTGGAAAACAGCAGAGTTTGCTAAAGATCTTCTTCC<br>TCAATACTTCAAGCATAATAATTTCTCAAGCTTCATTCGTC<br>AGCTCAACACTTAC<br>gtgagtttcactctaacgaaaactcatttactctcaattta<br>atgcttcatttaattcgtttggtgaattgaatcattctttt<br>gtagttggttagccaatttcgtaattttctcataatttggg<br>ggttggtgagaaaaccttctagaagctgagaatgttcttgt<br>tctttttttttttttttttttggtttag<br>GGATTTCGTAAAACTGTACCGGATAAATGGGAATTTGCAAA<br>CGATTATTTCCGGAGAGGCGGGGAGGATCTGTTGACGGACA<br>TACGACGGCGTAAATCGGTGATTGCTTCAACGGCGGGGAAA<br>TGTGTTGTTGTTGGTTCGCCTTCTGAGTCTAATTCTGGTGG<br>TGGTGATGATCACGGTTCAAGCTCCACGTCATCACCCGGTT<br>CGTCGAAGAATCCTGGTTCGGTGGAGAACATGGTTGCTGAT<br>TTATCAGGAGAGAACGAGAAGCTTAAACGTGAAAACAATAA<br>CTTGAGCTCGGAGCTCGCGGCGGCGAAGAAGCAGCGCGATG<br>AGCTAGTGACGTTCTTGACGGGTCATCTGAAAGTAAGACCG<br>GAACAAATCGATAAAATGATCAAAGGAGGGAAATTTAAACC<br>GGTGGAGTCTGACGAAGAGAGTGAGTGCGAAGGTTGCGACG<br>GCGGCGGAGGAGCAGAGGAGGGGTAGGTGAAGGATTGAAA<br>TTGTTTGGGGTGTGGTTGAAAGGAGAGAGAAAAAGAGGGA<br>CCGGGATGAAAAGAATTATGTGGTGAGTGGGTCCCGTATGA<br>CGGAAATAAAGAACGTGGACTTTCACGCGCCGTTGTGGAAA<br>AGCAGCAAAGTCTGCAACTAA | 1047 | | 114 |

TABLE 2

Host strains

| Designation | Organism | Relevant Genotype | Reference/Source |
|---|---|---|---|
| Psm ES4326 | Pseudomonas syringae pv. maculicola (Psm) | ES4326 | [60] |
| Psm ES4326/avrRpt2 | Pseudomonas syringae pv. maculicola (Psm) carrying an avirulent effector avrRpt2 | ES4326 avrRpt2 | [82] |
| YM4271 | Saccharomyces cerevisiae | Yeast strain used in yeast-one-hybrid experiments, MATa, ura3-52, his3-200, ade2-101, ade5, lys2-801, leu2-3, 112, trp1-901, tyr1-501, gal4D, gal8D, ade5::hisG | [71] Clontech |
| BY4742 | Saccharomyces cerevisiae | yeast strain BY4742 MATαhis3Δ1 leu2Δ0 lys2Δ0 ura3Δ0 pep4Δ::KAN$^R$ | [72] International Yeast Deletion Consortium |
| Strain 1 | Saccharomyces cerevisiae | Strain 1 derived from YM4271 that has the WT BiP2 promoter driving both HIS3 and URA3 genes. | This study |
| Strain 2 | Saccharomyces cerevisiae | Strain 2 derived from YM4271 that has the WT BiP2 promoter for HIS3 and the mutated BiP2 promoter [61] for URA3 (FIG 2). | This study |
| GV3101 | Agrobacterium tumefaciens | Bacterial strain for floral-dip based plant transformation, rifampicin-resistant | [73] |

TABLE 3

Plasmids

| Designation | Markers | Description | Reference/Source |
|---|---|---|---|
| pMDC140 | Kan$^R$, Hygro$^R$ | Gateway plant expression vector carrying a Gateway cassette cloned downstream of the 35S promoter and upstream of the GUS reporter gene; vector confers kanamycin resistance in E. coli and hygromycin resistance in transgenic plants. | [56] |
| pMDC140-uORF1-uORF2 | Kan$^R$, Hygro$^R$ | WT region | |
| pMDC140-mORF1-uORF2 | Kan$^R$, Hygro$^R$ | One A-to-C point mutation was introduced into the start codons (ATG) of uORF1. The mutant mORF1-uORF2 sequence was inserted downstream of the constitutive 35S promoter and upstream of the coding region of the GUS reporter in pMDC140 through recombination [56]. | This study |
| pMDC140-uORF1-mORF2 | Kan$^R$, Hygro$^R$ | One A-to-C point mutation was introduced into the start codons (ATG) of uORF2. The mutant uORF1-mORF2 sequence was inserted downstream of the constitutive 35S promoter and upstream of the coding region of the GUS reporter in pMDC140 through recombination [56]. | This study |
| pMDC140-mORF1-mORF2 | Kan$^R$, Hygro$^R$ | Two A-to-C point mutations were introduced into the start codons (ATG) of uORF1 and uORF2. The mutant mORF1-mORF2 sequences were inserted downstream of the constitutive 35S promoter and upstream of the coding region of the GUS reporter in pMDC140 through recombination [56]. | This study |
| pTB3 | | Plasmid comprising S. cerevisiae DHFR promoter and reporter gene | Chandra Tucker |
| pTB3-unstable DHFR&MTX resistance L22F/F31S | MTX$^R$ | The DHFR reporter gene carried by plasmid pTB3 was engineered to make an unstable enzyme [37] and to contain the L22F/F31S mutations that confer resistance to methotrexate (MTX) [58]. | This study |

TABLE 3-continued

Plasmids

| Designation | Markers | Description | Reference/Source |
|---|---|---|---|
| pDONR207 | Gent$^R$, Cat$^R$ | Gateway Entry vector | Invitrogen |
| pMDC123 | Kan$^R$, Cat$^R$, Hph$^R$ | Gateway plant expression vector that confers kanamycin and chloramphenicol resistance in *E. coli* and hygromycin resistance in transgenic plants. | [56] |
| pMW2 | Amp$^R$, Cat$^R$, HIS3 | Yeast one hybrid destination vector, HIS3 reporter | [83] |
| pMW3 | Amp$^R$, Cat$^R$, URA3 | Yeast one hybrid destination vector, LacZ reporter | [83] |
| pENTR207-BiP2 | Gent$^R$ | A 352-bp long fragment of the BiP2 promoter cloned into the pDONR207 Gateway Entry vector | This study |
| pMW2-BiP2 | Amp$^R$, HIS3 | pMW2 plasmid containing a 352-bp long fragment of the BiP2 promoter | This study |
| pMW3-BiP2 | Amp$^R$, URA3 | pMW3 plasmid containing a 352-bp long fragment of the BiP2 promoter | This study |
| pMDC123 TBF1p:TBF1 | Kan$^R$ | To perform genetic complementation of tbf1, the 4,601-bp genomic DNA containing the TBF1 promoter and the coding region (SEQ ID NO: 107) was amplified using primers TBF1-promoter-GW-F (SEQ ID NO: 84) and TBF1-cDNA-GW-R (SEQ ID NO: 82) cloned into the vector pDONR207 using the Gateway technology (Invitrogen), and inserted by recombination into the destination vector pMDC123 [6]. | This study |
| pMDC107 | Kan$^R$, Hygro$^R$ | Gateway plant expression vector carrying a Gateway cassette cloned upstream of the GFP reporter gene; vector confers kanamycin resistance in *E. coli* and hygromycin resistance in transgenic plants. | [56] |
| pMDC107 TBF1p:TBF1-GFP | Kan$^R$, Hygro$^R$ | The genomic TBF1 to GFP fusion was also generated by recombining pENTR207 TBF1p:TBF1 NON_STOP (amplified using primers TBF1-promoter-GW-F (SEQ ID NO: 84) and TBF1-cDNA-GW-R (NON_STOP) (SEQ ID NO: 83) into the destination vector pMDC107 [66]. The resulting destination clone pMDC107 TBF1p:TBF1-GFP, was transformed into *Agrobacterium tumefaciens* strain GV3101 and introduced into tbf1 mutant plants. A homozygous T3 line was selected for additional analysis. | This study |

TABLE 4

Description and sources of cloned genes

| Designation | Full Name | Origin | GenBank Accession Number | Reference/Source |
|---|---|---|---|---|
| TBF1 | 4,601-bp genomic DNA containing the TBF1 promoter and the coding region | *Arabidopsis thaliana* | At4g36990/ NM_119862 | *Arabidopsis* genomic DNA (gDNA), This study |
| GUS (uidA) | 1809 bp long gene encoding beta-glucuronidase | *Escherichia coli* | NP_416134 | [75] [76] [76] Invitrogen |
| LacZ | 3072 bp long gene encoding beta-galactosidase | *Escherichia coli* | ABI99820 | [78] [79] [80] Invitrogen |
| GFP | 714 bp long gene encoding green fluorescent protein | *Aequorea victoria* | AAA27722 | [81] Invitrogen |
| BiP2 promoter fragment | | *Arabidopsis thaliana* | At4g42020/ NM_123567 | *Arabidopsis* genomic DNA (gDNA), This study |

TABLE 5

Features of Engineered Cell Lines or Plants

| Cell line | Description | Reference/Source |
|---|---|---|
| Strain 1/ pDESTAD-TBF1 | pMW2 BiP2 WT, pMW3 BiP2 WT, pDESTAD-TBF1 | This study |
| Strain 1/ pDEST-AD | pMW2 BiP2 WT, pMW3 BiP2 WT, pDEST-AD | This study |
| Strain 2/ pDESTAD-TBF1 | pMW2 BiP2 WT, pMW3 mBiP2, pDESTAD-TBF1 | This study |
| Strain 2/ pDESTAD-AD | pMW2 BiP2 WT, pMW3 mBiP2, pDEST-AD | This study |
| GV3101/ pMDC123 TBF1p:TBF1 | The resulting destination clone pMDC123 TBF1p:TBF1, was transformed into *Agrobacterium tumefaciens* strain GV3101. Constructs were introduced into tbf1 mutant plants by the floral dipping method [67]. | This study |
| GV3101/ pMDC107 TBF1p:TBF1-GFP | The genomic TBF1 to GFP fusion was generated by recombining pENTR207 TBF1p:TBF1 into the destination vector pMDC107 [66]. The resulting destination clone pMDC107 TBF1p:TBF1-GFP, was transformed into *Agrobacterium tumefaciens* strain GV3101 and introduced into tbf1 mutant plants. A homozygous T3 line was selected for additional analysis. | This study |
| GV3101/ pMDC140-uORF1-uORF2 | Transiently expressed in *Nicotiana benthamiana* using *Agrobacterium tumefaciens* | This study |
| GV3101/ pMDC140-uorf1-uORF2 | Transiently expressed in *Nicotiana benthamiana* using *Agrobacterium tumefaciens* | This study |
| GV3101/ pMDC140-uORF1-uorf2 | Transiently expressed in *Nicotiana benthamiana* using *Agrobacterium tumefaciens* | This study |
| GV3101/ pMDC140-uorf1-uorf2 | Transiently expressed in *Nicotiana benthamiana* using *Agrobacterium tumefaciens* | This study |
| GV3101/ pMDC140-uORF1-uORF2 | Constructs were transformed into *Arabidopsis* wild-type Col-0 plants. Two stable transgenic $T_3$ lines homozygous for each construct were chosen for quantitative GUS assay [3] at 0, 0.5, 1, 2, 3, 4 and 8 hours after Psm E54326/avrRpt2 infiltration ($OD_{600\ nm}$ = 0.02). | This study |
| GV3101/ pMDC140-uorf1-uorf2 | Same as above except that the mutant construct was used here (wild-type construct above) | This study |
| *Arabidopsis* plants (Columbia-0) | Control genotype | ABRC* |
| *Arabidopsis* plants (tbf1 mutant) | SALK_104713 | ABRC* |
| *Arabidopsis* plants (tbf1 background) pMDC123 TBF1p:TBF1 | Homozygous $T_3$ *Arabidopsis* line used for complementation assays | This study |
| *Arabidopsis* plants (tbf1 background) pMDC107 TBF1p:TBF1-GFP | Homozygous $T_3$ *Arabidopsis* line used for ChIP experiments | This study |

*Arabidopsis* Biological Resource Center (ABRC, abrc.osu.edu).

EXPERIMENTAL PROCEDURES

Translational Analysis of uORF1-uORF2-GUS

The DNA fragment containing the 5' untranslated region (UTR) and the first exon of TBF1 (designated uORF1-uORF2-TBF1 $1^{st}$ exon) was amplified by polymerase chain reaction (PCR) using primers TBF1 5'UTR-GW-F (SEQ ID NO: 87) and TBF1 5'UTR-GW-R (SEQ ID NO: 88), wherein the DNA fragment is represented by the nucleic acid set forth as SEQ ID NO: 108 and cloned into the Gateway vector pDONR207 (Invitrogen). Two A-to-C point mutations were introduced, either separately or together, into the start codons (ATG) of uORF1 and uORF2. The WT and mutant uORF1-uORF2 sequences were inserted downstream of the constitutive 35S promoter and upstream of the coding region of the GUS reporter in pMDC140 through recombination [56]. The resulting translational reporter plasmids (designated pMDC140-uORF1-uORF2-GUS and its mutant variants pMDC140-uorf1-uORF2-GUS, pMDC140-uORF1-uorf2-GUS and pMDC140-uorf1-uorf2-GUS (Table E3) were transformed into Col-0 WT plants or transiently-expressed in *Nicotiana benthamiana* using *Agrobacterium tumefaciens* [57]. For *Arabidopsis* stable transgenic lines, two independent $T_3$ lines homozygous for each construct (as set forth in Table 5) were chosen for quantitative GUS assay [3] at 0, 0.5, 1, 2, 3, 4 and 8 hours after Psm ES4326/avrRpt2 infiltration ($OD_{600nm}$=0.02).

Yeast Growth Assay Using the DHFR Reporter

The DHFR reporter gene carried by plasmid pTB3 was engineered to make an unstable enzyme [37] and to contain the L22F/F31S mutations that confer resistance to methotrexate (MTX) [58]. The uORF1-uORF2 of TBF1 was translationally-fused to the coding region of the DHFR reporter and integrated into the genome of yeast strain BY4742 by homologous recombination. Equal amounts of yeast culture grown in liquid media (SD-Leu) were inoculated into SD-Leu-Phe double drop-out media supplemented with 15 mg/L or 75 mg/L phenylalanine. In other experiments, yeast cultures were also grown in Phe-rich, Asp-deficient media supplemented with 15 mM tobramycin (TOB) (Sigma, St. Louis, Mich., USA), a known inhibitor of yeast tRNA$^{Asp}$ aspartylation. MTX was added to all cultures at the final concentration of 80 µM to inhibit the endogenous DHFR activity. Yeast growth, which was dependent on the expression of the recombinant DHFR reporter in the presence of MTX, was measured using optical density ($OD_{600nm}$) over a 32-hour time course.

Genome-Wide Search of the TL1 cis-Element

To perform a genome-wide search for the TL1 cis-element, 1000-bp upstream sequences with a cutoff at the adjacent gene were fetched from the *Arabidopsis* Information Resource website (www.arabidopsis.org) and analyzed using the Athena website software (www.bioinformatics2.wsu.edu/cgi-bin/Athena/cgi/home.pl). The sequence GAAGAAGAA (SEQ ID NO: 99) was considered as the exact TL1 motif. Degeneracy of the TL1 element was based on Wang et al. [61] and shown in Table 6, below. To control the level of degeneracy, the total weight of the hit was restricted to be more than 664. The exact (SEQ ID NO: 99) and degenerate TL1 motifs (approximately represented by SEQ ID NO: 100) were searched for using the scan_for_matches software, available at (iubio.bio.indiana.edu/soft/molbio/pattern/scan_for_matches.readme).

TABLE 6

Weight matrix for degenerate TL1 element used in the genome-wide search for TL1

| Motif | G | A | A | G | A | A | G | A | A |
|---|---|---|---|---|---|---|---|---|---|
| Position | 1 | 2 | 3 | 4 | 5 | 6 | 7 | 8 | 9 |
| A | 0 | 88 | 85 | 0 | 91 | 91 | 12 | 62 | 65 |
| C | 0 | 0 | 0 | 0 | 3 | 6 | 6 | 38 | 26 |
| G | 100 | 12 | 3 | 100 | 6 | 3 | 82 | 0 | 6 |
| T | 0 | 0 | 12 | 0 | 0 | 0 | 0 | 0 | 3 |

Yeast One Hybrid Assays

Y1H assays were performed according to a previously-published protocol [62]. In brief, a 352-bp long fragment of the BiP2 promoter (SEQ ID NO: 109) was cloned into the pDONR207 Gateway Entry vector, recombined into pMW2 and pMW3 vectors, and then integrated into the HIS3 and URA3 loci in yeast, respectively. Strain 1 has the WT BiP2 promoter driving both HIS3 and URA3 genes, and Strain 2 has the WT BiP2 promoter for HIS3 and the mutated BiP2 promoter [61] for URA3 (Table 2, FIG. 2). Both strains were transformed with the construct pDESTAD-TBF1 or pDEST-AD, and the resulting yeast colonies were pooled and spotted on selection media (SD-Leu-Trp-Ura) (Clontech) supplemented with increasing concentrations of 3-AT (Sigma). Yeast growth was recorded 3 days later.

Quantitative β-Galactosidase Assay

The assay was modified from protocols described in earlier studies [63]. In brief, 0.1 ml of yeast transformant extract was added to 0.9 ml of Z buffer and warmed to 28° C. Reactions were initiated by addition of 0.2 ml of ONPG substrate (4 mg/ml) in Z buffer and terminated with 0.5 ml of 1 M $Na_2CO_3$. Reactions were terminated within the linear range of the assay ($OD_{420nm}$<1.0). The β-galactosidase activity in yeast supernatants was normalized to their protein concentrations. The data represent the average from three dilutions of extracts.

Electrophoretic Mobility Shift Assay

The assay was performed as described in earlier studies [61]. Briefly, 3-week-old plants were treated with 1 mM SA for 4 hrs before leaf tissues were harvested. 40,000 cpm of labeled probe was added to 10 µg of protein, incubated in a buffer containing 12 mM HEPES pH 8.0, 60 mM KCl, 2 mM $MgCl_2$, 0.1 mM EDTA, 12% glycerol, and 0.3 mM DTT for 20 min, and separated on a 5% polyacrylamide gel. DNA-protein interactions were detected using autoradiography.

Chromatin Immunoprecipitation (ChIP)

ChIP assays were performed as described in earlier studies [64]. For each sample, 1 g of leaves from 3-week-old *Arabidopsis* plants was crosslinked with 1% formaldehyde under vacuum for 15 min, followed by addition of glycine to a final concentration of 0.1 M. The leaves were washed with water and then ground in liquid nitrogen. *Arabidopsis* nuclei were isolated and sonicated in Bioruptor® sonicator (Diagenode). The TBF1-GFP-tagged protein was immunoprecipitated using 1 µl of an anti-GFP antibody ab-290 (Abcam) that was first coupled to the protein G Dynabeads (Invitrogen). The purified ChIP DNA samples were subject to real-time PCR analysis. The amount of each amplicon was normalized to the input. The relative amount (fold-enrichment) of each signal was determined by the ratio of normalized ChIP signals between samples. The primer sequences used for ChIP analysis are listed in Table 1}.

qRT-PCR

Total RNA was extracted from 3-week-old plants with and without 1 mM SA treatment at different time points. RNA extractions were performed using TRIzol Reagent (Ambion). RNA samples were reverse-transcribed into cDNA using SuperScript III Reverse Transcriptase (Invitrogen). The cDNA was quantified using gene specific primers (Table 1, above) and the POWER SYBR GREEN PCR Master Mix (Applied Biosystems) in a LightCycler (Roche) or RealPlex S (Eppendorf).

Microarray

*Arabidopsis* plants (Columbia-0 and tbf1 mutant) were grown on soil (Metro Mix 360) at 22° C. under a 16/8 hr light/dark cycle for 3 weeks and treated with 1 mM SA for 6 hrs (spray) or 10 µM elf18 for 2 hrs (infiltration into leaves). Mock treatments with water were included for both spray and infiltration. The RNA, extracted with TRIzol (Ambion) and labeled with MessageAmp Premier RNA Amplification Kit (Ambion), was hybridized with GeneChip *Arabidopsis* ATH1Genome Array (Affymetrix), and subsequently washed and scanned at the Duke Microarray Facility. Experiments were repeated three times using independently-grown and treated plants. The resulting data were normalized using Gene-Spring GX Software (RMA algorithm; Agilent). Two-way ANOVA with the Benjamini-Hochberg multiple comparison correction was used to identify TBF1-dependent genes (i.e., with significant interaction between genotypes and treatments, p-value<0.05). The SA- and elf18-responsive genes (fold change>2) were found through unpaired Student's t test with the Benjamini-Hochberg multiple comparison correction (p-value<0.05). The Venn diagram was adapted from Venny [5]. To generate the heatmaps of SA- or elf18-upregulated and down-regulated genes, -log 10p-values of induced genes and log 10p-values of repressed genes from Student's t test were used. Higher positive values represent greater induction, and lower negative values indicate greater repression. For TBF1 dependence, -log 10p-values from two-way ANOVA tests were used. The gene ontology analysis was performed using the Database for Annotation, Visualization and Integrated Discovery (DAVID) (available at david.abcc.ncifcrf.gov/).

Tunicamycin Sensitivity Assay

This assay was performed as described in earlier studies [61].

Genetic Complementation of tbf1

To perform genetic complementation of tbf1, the 4,601-bp genomic DNA containing the TBF1 promoter and the coding region (SEQ ID NO: 107) was amplified using primers TBF1-promoter-GW-F (SEQ ID NO: 84) and TBF1-cDNA-GW-R (SEQ ID NO: 82) (Table 1), cloned into the vector pDONR207 using the Gateway technology (Invitrogen), and inserted by recombination into the destination vector pMDC123 [6]. The resulting destination clone pMDC123 TBF1p:TBF1, was transformed into *Agrobacterium tumefaciens* strain GV3101. Constructs were introduced into tbf1 mutant plants by the floral dipping method [67]. $T_3$ transgenic plants homozygous for the transgene were further analyzed. The genomic TBF1 to GFP fusion was also generated by recombining pENTR207 TBF1p:TBF1 into the destination vector pMDC107 [66]. The resulting destination clone pMDC107 TBF1p:TBF1-GFP, was transformed into *Agrobacterium tumefaciens* strain GV3101 and introduced into tbf1 mutant plants. A homozygous $T_3$ line was selected for additional analysis.

Bacterial Infection Assay

Infection of *Arabidopsis* plants with *Pseudomonas syringae* pv. *maculicola* (Psm) ES4326 was performed as described previously [68]. To test for enhanced disease susceptibility, a bacterial suspension at $OD_{600nm}$=0.0001 was infiltrated into 2-3 leaves per plant and 12 plants/genotype. Bacterial growth was quantified 3 days later. To test for SAR and MAMP-induced resistance, plants were pre-treated with relevant compounds (1 mM SA, spray 24 hrs prior to infection; 10 µM elf18, infiltration 2 hrs prior to infection; 10 µM flg22, infiltration 2 hrs prior to infection), and subsequently inoculated with Psm ES4326 ($OD_{600nm}$=0.001) into 2-3 leaves per plant and 12 plants/genotype/treatment. Sampling was performed 3 days post inoculation.

PR1 Protein Secretion

Three-week-old plants were treated with 1 mM SA for 24 hrs before infiltration under vacuum in a 20 mM phosphate buffer ($KH_2PO_4$ and $K_2HPO_4$, pH=7.4). Intercellular wash fluid was collected from equal amounts of tissue by centrifuging the infiltrated leaf samples, which were packed in a syringe, for 5 min at 1500 g. As a control, total protein was also extracted from 50 mg of leaf tissue (from 3-4 independent plants) using a buffer described previously [61]. Secreted and total protein were run on 15% SDS-PAGE gels, transferred to a nitrocellulose membrane, and probed with a polyclonal rabbit antibody raised against a synthetic peptide matching the carboxy terminus of the *Arabidopsis* PR1 protein (1:4000 dilution, 2 hrs) followed by a goat anti-rabbit secondary antibody (Santa Cruz Biotechnology) (1:2000 dilution, 1.5 hrs). To confirm equal loading of total protein, an anti-α-tubulin antibody (Sigma) was used subsequently to probe the total protein concentration on the blot.

Western Blotting

The anti-BiP Western blotting experiment was performed as described previously [61], using leaf tissue sprayed with 1 mM SA 6 hrs prior to collection. The primary antibody was α-BiP (Santa Cruz Biotechnology, aC-19, 1:4000 dilution, overnight at 4° C.), followed by the secondary antibody (bovine anti-goat, Santa Cruz Biotechnology, 1:2000 dilution, 2 hrs, RT). The anti-phospho elF2α Western blotting experiment was performed as described previously [69], using leaf tissue infected with Psm ES4326 expressing avrRpt2 ($OD_{600nm}$=0.02) over the indicated time periods. The protein extraction was carried out in presence of a phosphatase inhibitor PhosSTOP (Roche), Protease Inhibitor Cocktail (Sigma Aldrich) and proteasome inhibitor MG-115 (Sigma Aldrich). The primary antibody was α-p-elF2α (pS51) (Epitomics, Burlingame, Calif., 1090-1), (1:1000 dilution, overnight at 4° C.), followed by the secondary antibody (goat anti-rabbit, Bio-Rad, 1:4000 dilution, 1 hr, RT).

Rapid Amplification of cDNA Ends (RACE)-PCR

RACE-PCR analyses were performed as described in manufacturer's protocol (SMART™ RACE cDNA Amplification Kit, Clontech, Mountain View, Calif., USA).

tRNA Analysis

Total RNA was extracted using TRIzol reagent (Invitrogen) according to the instructions provided by the manufacturer. Total RNA was then dissolved in 0.1 M sodium acetate (pH 5.0). mRNA was precipitated using 2 M LiCl overnight. 2 volumes of isopropanol were added to the supernatant to precipitate the tRNA. After washing with 100% ethanol, the tRNA was dissolved in 0.1 M sodium acetate. 1 µg tRNA was separated by acid urea PAGE, and transferred to NEF 976 GeneScreen Plus Hybridization Transfer Membrane (PerkinElmer) according to procedures established in earlier studies [70].

Specific tRNA species were detected by hybridization using digoxigenin-labeled DNA probes (shown in Table 1} as tRNA$^{Phe}$ represented by SEQ ID NO: 97, and tRNA$^{Asp}$ represented by SEQ ID NO: 98) according to the manufacturer's instructions (DIG High Prime DNA Labeling and Detection Starter Kit II, Roche Applied Science). The signal was visualized using a low-light CCD camera.

Polysome Profiling

Before extraction, a spike-in control was added into the pulverized leaf tissue at a concentration of $10^7$ copies of Alien qRT-PCR Inhibitor Alert (Agilent Technologies, USA) per mg of fresh weight. 500 mg of pulverized leaf tissue was hydrated on ice for 10 min with occasional vortexing in 3 ml of extraction buffer, containing 0.2 M Tris (pH=9.0), 0.2 M KCl, 0.025 M EGTA, 0.035 M $MgCl_2$, 1% (w/v) Brij-35, 1% (v/v) Triton X-100, 1% (v/v) Igepal CA 630, 1% (v/v) Tween 20, 1% (w/v) sodium deoxycholate, 1% (v/v) polyoxyethylene 10 tridecyl ether, 5 mM dithiothreitol, 1 mM phenylmethylsulfonyl fluoride, 50 µg/mL cycloheximide, 50 µg/mL chloramphenicol. The hydrated tissue was centrifuged at 16,000 g for 15 min. The supernatant was then separated in a 10 ml continuous (15-60% w/v) sucrose gradient containing 400 mM potassium acetate, 25 mM potassium HEPES (pH=7.2), 15 mM magnesium acetate, 200 µM cycloheximide by ultracentrifugation at 35,000 rpm using SW 41Ti rotor (Beckman Coulter, Germany) for 10 hrs at 4° C. The gradients were fractionated into 36 fractions of about 330 µL each using automated Density Gradient Fractionation System (Teledyne Isco Inc., USA) with a simultaneous $A_{254nm}$ trace. Total RNA was extracted from the fractions containing ribosomes using TRIzol reagent (Invitrogen) according to instructions provided by the manufacturer. mRNA was further precipitated using 2 M LiCl overnight. cDNA was prepared and qRT-PCR analyses performed as described above.

Statistical Analyses

For gene expression data, expression values were used for linear models. Effects of genotype, treatment, time, biological replicate and interactions between genotype and time, and genotype and treatment were included in the linear model where appropriate. For bacterial infection data, logarithmic transformed colony forming units (cfu) were used for linear models. Effects of genotype, treatment, time, biological replicate and interactions between genotype and time, and genotype and treatment were included in the linear model where appropriate. Bonferroni post-tests were applied to address the significant difference at individual time points between WT and mutant samples. All statistical analyses were performed using R software programs (CRAN).

Table S1 summarizes the complete list of TBF1-dependent SA- and elf18-regulated genes which are set forth supplementary data tables extracted from eight worksheets in an Excel file, herein specifically incorporated by reference, as noted above in the section entitled "Incorporation-By-Reference Under 37 CFR 1.58 to Large Tables Including Supplemental Tables of Information Included In Earlier Priority Applications".

TABLE S1

Tables S1A-S1H, incorporated by reference,
listing TBF1-dependent SA- and elf18-regulated genes

| Table # | Excel Sheet # | Description | SA | elf18 | # Data Rows |
|---|---|---|---|---|---|
| S1A | 1 | SA induced only | + | | 528 |
| S1B | 2 | SA repressed only | − | | 534 |
| S1C | 3 | elf18 induced only | | + | 477 |
| S1D | 4 | elf18 repressed only | | − | 1098 |
| S1E | 5 | SA and elf18 induced | + | + | 37 |
| S1F | 6 | SA and elf18 repressed | − | − | 110 |
| S1G | 7 | SA induced elf18 repressed | + | − | 60 |
| S1H | 8 | SA repressed elf18 induced | − | + | 22 |

Example 1

Results

TBF1 is a TF that Binds to the TL1 cis-Element Enriched in Defense-Related Gene Promoters The TL1 cis-element (consensus sequence GAAGAAGAA) in the ER-resident genes is essential for their activation in response to SA induction [3]. To determine whether this cis element is important only for the ER-resident genes or also for induction of other defense-related functions, we examined the promoter regions (1000 bp upstream of the ATG start codon) of genes regulated by the SA analog BTH (benzothiadiazole) (available at affy.arabidopsis.info/narrays/experimentbrowse.pl, experiment ID:NASCARRAYS-392) [11] and by the MAMP signals flg22 and elf26 (the first 26 amino acids of EF-Tu) (available at www.ebi.ac.uk/arrayexpress/, experiment ID: E-MEXP-547) [12] using the Athena program (www.bioinformatics2.wsu.edu/Athena). We found that the TL1 cis-element is enriched in the promoter regions of genes regulated by elf26 (p-value<0.001) and flg22 (p-value<0.01), indicating that this novel element may play a role in MTI. No significant enrichment of TL1 was detected when all of the BTH-affected promoters were analyzed, even though the element was first discovered in the SA-induced, NPR1-dependent ER-resident genes [3].

To search for the TF that regulates the TL1 cis-element (i.e., TBF1), we submitted the TL1 core sequence GAAGAAGAA to the TFSEARCH database (www.cbrc.jp/research/db/TFSEARCH.html) and found several HSFs of *Saccharomyces cerevisiae* and *Drosophila melanogaster* as potential candidates. The *Arabidopsis* genome contains 21 HSF-like genes. Several reports have indicated the involvement of the HSFs in immediate heat response, acquired thermotolerance, sensing of reactive oxygen species (ROS), and seed development [13, 14]. To identify a candidate gene for TBF1, we first examined the expression profiles of the *Arabidopsis* HSF family members using available microarray data in response to BTH induction (affy.arabidopsis.info/narrays/experimentbrowse.pl, experiment ID: NASCARRAYS-392) [11] and to the virulent and avirulent *Pseudomonas syringae* pv. *maculicola* (Psm) ES4326 bacteria (affy.arabidopsis.info/narrays/experimentbrowse.pl, experiment ID: NASCARRAYS-168). Only one gene family member, HSF4 (also known as HsfB1; AT4G36990), was strongly induced by these treatments. Because *Arabidopsis* HSF4 and its tomato homolog do not functionally complement the yeast hsf1 mutant strain [15] (Daniel Neef and Dennis Thiele, personal communication), and its overexpression has little effect on heat shock protein expression or thermotolerance [16, 17], we thought that HSF4 does not encode a typical heat shock factor. Its pathogen-inducible expression pattern suggests that it has a novel function related to plant immunity, and is a candidate for TBF1.

We carried out additional studies to demonstrate that HSF4 is the TL1 cis-element TBF1 involving a yeast one-hybrid (Y1H) vector system, in which the promoter fragment of BiP2, containing multiple functional TL1 cis-elements, was used as bait [3]. Two yeast bait strains containing the WT and the mutant (mTL1) BiP2 promoters, respectively, were constructed (FIG. 2). Expression of TBF1-AD (containing the activation domain) in Strain 1, activated both HIS3 and LacZ reporters driven by the WT BiP2 promoter (FIGS. 1A and 1B). The binding specificity of TBF1 to TL1 was confirmed in Strain 2, where the two single-nucleotide substitutions in the mTL1 core binding sequence blocked the induction of LacZ, while the control HIS3 reporter with the WT TL1 was induced normally (FIG. 1B).

TBF1 binding to the TL1 cis-element was further demonstrated using electrophoretic mobility shift assays with protein extracts from both WT and an insertional knock-out TBF1 mutant, tbf1 (FIG. 3). As shown in FIG. 1C, WT displayed an up-shifted band, whose intensity was further enhanced in the extract made from plants treated with SA. This band was diminished in the tbf1 mutant extract, indicating that TBF1 is required for the DNA-protein complex formation. Competition assays, using non-radioactive TL1 and mutant mTL1 probes, indicated that the observed TBF1 binding was specific to the TL1 consensus sequence.

To test TBF1 DNA-binding activity in vivo, we generated transgenic tbf1 plants expressing a translational fusion between TBF1 and GFP driven by the endogenous TBF1 promoter (TBF1p:TBF1-GFP). Because the fusion protein was proven to be biologically-active through genetic complementation of the tbf1 mutant phenotype (FIG. 4), we used it for chromatin immunoprecipitation (ChIP). As shown in FIG. 1D, using six pairs of primers spanning different regions of the BiP2 promoter (SEQ ID NOS: 1-12), we detected sequence enrichment corresponding to the TL1-containing region 2 in both uninduced and SA-treated samples, region 3 in the SA-treated sample, and region 4 in the uninduced sample. No enrichment was found in regions 1, 5 and 6 that do not contain the TL1 element.

TBF1 is a Major Molecular Switch Involved in Transcriptional Reprogramming Induced by SA and Elf18

In earlier studies, we showed that the TL1 cis-element is present in many ER-resident genes [3]. In this study, we tested if SA-mediated induction of these genes is dependent on TBF1. We found that the induction of BiP2 and CRT3, containing multiple copies of TL1 elements in their promoters, was compromised in the tbf1 mutant and in npr1-1 (FIG. 5A). BiP2 protein accumulation was not induced in the SA-treated tbf1 mutant plants (FIG. 6). In contrast to BiP2 and CRT3, induction of two other ER-resident genes, BiP3 and CRT1, which do not have TL1 in their promoters, was not affected in tbf1 (FIG. 5B), confirming the specificity of TBF1 to TL1.

Enrichment of the TL1 cis-element in immune-induced ER-resident gene promoters, as well as promoters responsive to diverse immune signals [3, 18, 19], prompted us to perform a genome-wide transcriptional profiling experiment to determine the global effect of TBF1. WT and tbf1 plants challenged with SA for 6 hours or elf18 for 2 hours, were used to generate probes for the Affymetrix ATH1 GeneChip (Affymetrix, Santa Clara, Calif.). We noted that 1269 and 1792 TBF1-dependent genes were differentially-regulated by SA and elf18, respectively (fold change>2, p-values<0.05), but only a small number of genes (~8%) were regulated by both signals (FIG. 5C, Table S1, incorporated as a large table by reference), indicating that TBF1 controls distinct output genes in SAR and MTI. The total numbers of significantly-induced and repressed genes (the top heatmaps in FIGS. 5D and 5E), the degrees of TBF1 dependency (the middle heatmaps), and the numbers of TL1 cis-elements present in the gene promoters (the bottom heatmaps) indicate that TBF1 plays a greater role in SA- and elf18-mediated transcription repression, than in induction. These results are in agreement with earlier studies indicating that class B-Hsfs mainly act as repressors of target gene expression [20, 21].

To identify the biological functions induced and repressed by TBF1, we performed gene ontology (GO) analyses and selected functional categories that were significant at p≤0.001. We identified a significantly-enriched cluster of SA-induced secretory pathway genes (FIG. 5D "membrane proteins", Table S1, incorporated as a large table by reference), which were in agreement with our earlier findings [3].

We also identified several major functional categories comprising genes known to encode defense-related proteins (FIGS. 5D and 5E), such as the master regulator of SA pathway NPR1, a TGA-class TF, several WRKY family members, EDSS, ADR1, metacaspase 2, membrane-associated proteins like SNAP33 and members of the MLO family, and several kinases including RLKs, MAPKKs and WAKs (Table S1) [22]. These genes appear to be directly controlled by TBF1, since their regulatory regions contain the TL1 element (Table S1). A strong enrichment of ribosomal proteins was also noted among the elf18-induced TBF1-dependent genes, suggesting that significant translation events occur after MAMP induction.

Upon SA treatment, TBF1 down-regulates genes encoding chloroplast proteins (FIG. 5D), an effect that is known to be associated with SA [23]. Chloroplast function-related genes were even more profoundly repressed by elf18 (FIG. 5E). These genes encode several structural and regulatory proteins of the chloroplast (e.g., PsbR subunit of photosystem II, chloroplast o-succinylbenzoyl-CoA ligase, plastid ribosomal protein, a subunit of the chloroplast NAD(P)H dehydrogenase complex and components involved in thylakoid membrane biogenesis) (Table S1). Loss-of-function mutants involving these genes display a variety of developmental defects, such as decreased photosynthesis rate, reduced chloroplast number, pale pigmentation, dwarfism and lethality [24]. These metabolic and chloroplast-related genes are likely direct targets of TBF1, since their regulatory regions contain the TL1 element. Taken together, these results suggest that TBF1 is used in plants to rapidly reprogram cellular transcription after an infection, diverting energy resources from growth and development functions to cope with pathogenic responses.

The GO analyses indicated that elf18 treatment had a significant inhibitory effect on both abiotic stress and defense responses through TBF1, which was unexpected (FIG. 5E). These repressed genes are involved in jasmonate (JA), ethylene and auxin biosynthesis or signaling pathways (e.g., lipoxygenases, JAZ2, WRKY33, CEV1, and SAUR and IAA families) (Table S1), which are known to be down-regulated during SA-mediated defense [25-27].

The expression changes observed in the microarray experiment were also confirmed through qRT-PCR experiments of independent biological samples on 26 selected genes representing several GO categories, which are illustrated in FIGS. 5D, 5E, and FIGS. 7-10.

TBF1 Plays a Key Role in the Growth-to-Defense Transition

To determine if TBF1 is a major molecular switch involved in the transition from growth to defense functions, we first measured the growth of both WT and the tbf1 mutant plants. As shown in FIG. 11A, in the absence of SA or elf18, the tbf1 mutant grew at a similar rate as the WT plant. In the presence of elf18 or increasing concentrations of SA, however, growth of the WT plants was significantly inhibited. The inhibitory effect was partially-alleviated in the tbf1 mutant. In contrast, another MAMP signal, flg22, exerted a similar growth-suppressing effect on WT and tbf1 seedlings (FIG. 12).

We also performed a series of tests to determine the stress responses mediated by TBF1. Although the tbf1 mutant has been shown to have a normal heat-induced marker gene expression profile (FIG. 13), and plays no detectable role in the heat shock response [28], its defect in the induction of multiple chaperone genes prompted us to examine the unfolded protein response (UPR). In mutant plants treated with the UPR inducer tunicamycin, seedling survival rate for tbf1 was only ~20% compared to ~60% for WT (FIG. 11B), indicating that TBF1 plays a role in UPR. In earlier studies, SA-inducible ER-resident genes are required for efficient secretion of antimicrobial PR proteins [3]. Because TBF1 was shown to control SA-mediated induction of these genes (FIGS. 5A and 5D, Table S1, incorporated as a large table by reference), we tested the secretion of PR1 in the tbf1 plants. While the PR1 transcript induction and total PR1 protein levels were unchanged in tbf1 (FIG. 11C and FIG. 14), secreted PR1 in the intercellular wash fluid was dramatically reduced in the tbf1 mutant, compared to the WT sample. This phenotype was complemented in the transgenic line carrying a genomic fragment comprising upstream regulatory sequences (3,554 bp) (SEQ ID NO: 113) and the coding region (1,047 bp) of TBF1 (TBF1 Compl.) (SEQ ID NO: 114). The bip2 dad1 double mutant, which was previously shown to be defective in PR1 secretion [3], was used as a control. The defect in secretion of antimicrobial proteins in the tbf1 mutant correlated with the 1 log higher growth of the bacterial pathogen, Psm ES4326, compared to WT and the complementation lines (FIG. 11D). In response to induction by SA, less than 1 log reduction in Psm ES4326 growth was observed in the tbf1 mutant, compared to the ~2 log reduction detected in WT plants (FIG. 11E). SA-inducible defenses were restored in the TBF1 complementation line, while the npr1-1 line was completely deficient in establishing resistance.

We also examined elf18-triggered immunity in the tbf1 mutant, because expression profiling data demonstrated that TBF1 was responsible for significant genome-wide transcriptional changes induced by elf18 (FIG. 5C). Leaves were infiltrated with elf18 or another MAMP signal, flg22, and infected with Psm ES4326 4 hours later. WT pre-treated with the MAMP signals showed a 1-log reduction in Psm ES4326 growth, compared to mock-treated samples (FIG. 11F and FIG. 15). The tbf1 mutant, however, completely failed to establish the resistance induced by elf18. This defect was specific to elf18, as flg22-induced resistance was intact in the tbf1 mutant, resembling the trend observed for the growth inhibition phenotype (FIG. 11A and FIG. 15). Since earlier studies demonstrated that flg22 and elf18 induce largely overlapping sets of genes [12], different levels of responsiveness to elf18 and flg22 in tbf1 were unexpected. Our current results are consistent with the genetic data showing that the recognition of elf18, but not flg22, specifically requires the ERQC mechanism [6, 7, 29, 30], and with observations demonstrating that TBF1 controls the induction of these ERQC genes (FIG. 5A). The molecular mechanism underlying the TBF1-requirement has not been determined. TBF1 may affect the biogenesis of EFR, downstream signaling functions, or elf18-triggered secretion of antimicrobial compounds.

A near normal response to elf18 was also observed in the SA-insensitive npr1-1 mutant in the Psm ES4326 infection experiment (FIG. 11F). Although there was an overall increase in Psm ES4326 growth in npr1-1, elf18 could still induce a 1-log reduction in pathogen growth, which was similar to that observed in the WT sample. These results are in agreement with expression profiling data demonstrating that elf18 and SA induce distinct sets of genes (FIG. 5C). Recent studies have also demonstrated that MTI induced by flg22 and elf18, is largely intact in a sid2 mutant, which is deficient in SA synthesis [31]. MTI and SAR, therefore, are two temporally and spatially separate immune responses. MTI occurs locally and immediately upon challenge by a pathogen, while SAR is a systemic response induced after the local response.

Translation of TBF1 is Controlled by uORFs Sensitive to Cellular Metabolic Changes The genome-wide expression profiling data and the genetic data in the Examples set forth herein demonstrate that TBF1 is a major molecular switch, that upon challenge by a pathogen, turns on multiple defense responses and inhibits primary growth and development (FIGS. 5 and 11). To understand how TBF1 is regulated, we analyzed its expression patterns upon treatment with SA, detecting maximum levels of transcript at 4 hours (FIG. 16A). The SA-dependent induction was abolished in the npr1-1 mutant, demonstrating that NPR1 is required for SA-mediated TBF1 transcription. TBF1 also plays a role in regulating NPR1, as the NPR1 transcript levels were diminished in tbf1 (FIG. 16B), suggesting that a feedback mechanism exists involving these two key immune system regulatory factors.

Analysis of the TBF1 mRNA through the 5' and 3' rapid amplification of cDNA ends (RACE) experiments demonstrated that the transcript which encodes TBF1, also comprises two upstream open reading frames (uORFs) (SEQ ID NOS: 108 and 109) (FIG. 16C). The second of these, uORF2 (also known as conserved peptide upstream open reading frame 49, CPUORF49, *Arabidopsis* gene model AT4G36988) (SEQ ID NO: 103) is well-conserved among TBF1 homologs in other plant species [32]. Translation in eukaryotes normally starts at the first 5' AUG codon. The presence of two uORFs upstream from (5' to) the TBF1 start codon, suggests that they may influence the initiation of translation of TBF1. To test this, we made a vector comprising a translational fusion between the 5' UTR of TBF1 containing both uORFs, the first exon of TBF1, and the GUS reporter gene (abbreviated as uORF1-uORF2-GUS). We also constructed three other vectors which have the start codon mutated (from ATG to CTG) for uORF1 (uorf1-uORF2-GUS), uORF2 (uORF1-uorf2-GUS), and both uORFs (uorf1-uorf2-GUS). To ensure equal levels of transcription in these vectors, we used the constitutive 35S promoter to drive the expression of these reporter genes. The vectors were used in transient-expression experiments carried out in Nicotiana benthamiana leaves, measuring the GUS activity in each sample (FIG. 16D). Using activity of the WT construct as a control, we detected 1.5- and 3.5-fold increases in the GUS activities in uorf1-uORF2-GUS and uORF1-uorf2-GUS samples, respectively. Mutating both uORFs in uorf1-uorf2-GUS resulted in a 3.5-fold elevation in GUS activity over WT, which was similar to the result observed for the uorf2 mutant. These results suggest that both uORFs can function to inhibit TBF1 translation, with uORF2 likely to play a more important role than uORF1 in this matter.

To better understand the regulatory mechanisms involved in TBF1 translation during plant defense events, we measured the GUS activities of the translational fusion vectors in stable transgenic *Arabidopsis* lines when challenged by Psm ES4326 carrying the avirulent effector, avrRpt2. We found that introduction and recognition of this avirulent bacterial strain, which can induce MTI, ETI, and SAR in plants, caused a rapid increase in the activity of GUS translated from the TBF1 start codon downstream of the uORFs (FIG. 16E). This increase was not observed in the uorf1-uorf2-GUS transgenic lines. These results suggest that the Psm ES4326/avrRpt2 challenge could rapidly alleviate the inhibitory effect of the uORFs on translation of the downstream gene.

To determine whether the endogenous TBF1 was translated in the plant cell upon pathogen challenge, we conducted a polysome profiling experiment shown in FIG. 16F. There was a significant increase in TBF1 transcript 30 minutes after Psm ES4326/avrRpt2 inoculation in the polysomal fractions of the gradient. This rapid association with polysome samples correlates well with the GUS reporter activities observed in the transgenic plants, noted above (FIG. 16E). The association of TBF1 within polysome samples appeared to be transient, as the TBF1 transcript decreased at 1 hour post inoculation. This pathogen-induced derepression of TBF1 translation occurs earlier than the transcription activation of the TBF1 gene (FIG. 16A).

Both uORFs are enriched in aromatic amino acids, particularly in phenylalanine (Phe) (uORF1—27%, and uORF2—19%), as compared to the average frequency of aromatic amino acids reported for species sequenced so far (7.63-7.86%) ([33]; ExPASy proteomics server expasy.ordsprot/relnotes/relstat.html). The enrichment in Phe is evolutionarily-conserved for uORF2 among the TBF1 homologs in other plant species [32]. This suggests that translation of the two uORFs and the downstream TBF1 may be influenced by the cellular availability of Phe for translation, caused by the pathogen challenge. Amino acid starvation has previously been shown to de-repress uORF-mediated translation inhibition on the yeast General Control Nondepressible 4 (GCN4) and the mammalian Activating Transcription Factor 4 (ATF4) genes [34, 35].

To determine if pathogenic infections can trigger changes in amino acid concentrations, we carried out the studies involving the measurement of amino acids in a large number of biological replicates. We could occasionally detect a rapid decrease in the level of Phe that occurred 15 to 45 minutes after Psm ES4326/avrRpt2 inoculation, followed by an increase in the level of Phe that was observed consistently (data not shown). These results suggest that Phe concentrations may change dramatically during early time points after infection, and that it is difficult to measure transient metabolic changes following pathogen challenge using methods that are currently available.

To improve our method of examining whether Phe levels affect the TBF1 translation rate, we used a yeast-based reporter system. Since a Phe-deficient *Arabidopsis* mutant that has not been identified to date, a yeast chorismate mutase deletion strain, aro7, which is auxotrophic for Phe and tyrosine (Tyr) [36]. A reporter vector was generated by fusing uORF1-uORF2-TBF1$_{1st\ exon}$ to the coding region of the mouse DHFR (dihydrofolate reductase), which has been engineered to be less stable [37] and resistant to methotrexate (MTX) [38]. DHFR is an enzyme that regulates levels of tetrahydrofolate essential for growth. In the presence of 80 μM of MTX that abolishes the endogenous DHFR enzymatic activity, yeast growth becomes dependent on the recombinant DHFR reporter expression. Since both uORF1-uORF2-TBF1$_{1st\ exon}$-DHFR (abbreviated as uORF1-uORF2-DHFR), and the DHFR control, are driven by the endogenous yeast DHFR promoter, growth of these yeast strains reflect the translational rate of DHFR. We cultured the aro7 strain containing either uORF1-uORF2-DHFR or DHFR in presence of MTX. As shown in FIG. 17A, under the Phe-rich conditions (75 mg/L; standard Phe concentration in synthetic yeast growth media), the yeast strain carrying the DHFR displayed a much higher growth rate than the strain carrying the uORF1-uORF2-DHFR, showing the inhibitory effects of the uORFs on DHFR translation. Both strains grew at similar rates under Phe-restricting conditions (15 mg/L), suggesting that low Phe level released the inhibitory effects of uORFs on DHFR translation (FIG. 17A). To ensure that the TBF1$_{1st\ exon}$-DHFR fusion protein was not toxic to yeast cells, we grew the strains in the absence of MTX and observed no significant difference in their growth rates (FIG. 18). The uORFs of TBF1 appear to be specifically sensitive to Phe starvation, because aspartic acid starvation caused by addition of 15 mM tobramycin (TOB), a known inhibitor of yeast tRNA$^{Asp}$ aspartylation [39], did not eliminate the difference in the growth rate between the strain carrying uORF1-uORF2-DHFR, and the strain carrying DHFR.

To understand the molecular mechanism by which uORFs control TBF1 translation, we carried out additional experiments. In yeast, amino acid starvation leads to accumulation of uncharged tRNAs, which in turn bind to the HisRS domain of the GCN2 serine/threonine protein kinase, activating it, and causing structural rearrangements within the GCN2 dimer [40, 41]. The activated GCN2 undergoes autophosphorylation, and activating its kinase function involved in phosphorylation of its sole target, eukaryotic initiation factor 2α (elF2α) [42]. The phosphorylated elF2α allows initiation of translation, such as GCN4, downstream of uORFs [35]. To determine whether a similar mechanism controls the translation of TBF1 after pathogen infection in plants, we first performed Northern blot analyses to measure the levels of charged and uncharged tRNA after inoculation with Psm ES4326/avrRpt2. As shown in FIG. 17B, a dramatic increase in both charged and uncharged tRNA$^{Phe}$, was measured, appearing as early as 30 minutes after bacterial inoculation, and persisting for 8 hours, compared to only a moderate increase in the level of charged tRNA$^{Asp}$ level under the same conditions. No uncharged tRNA$^{Asp}$ was detected. These results are consistent with observations suggesting that pathogen challenges in plants can lead to dramatic changes in Phe metabolism.

We then investigated whether the pathogen-induced accumulation of uncharged tRNA$^{Phe}$ can lead to phosphorylation of elF2α, since a functional and stress-inducible GCN2-elF2α pathway has been found in *Arabidopsis* [43]. As shown in FIG. 17C, in leaf samples infected with Psm ES4326/avrRpt2, a rapid accumulation of the phosphorylated elF2α was detected, supporting observations which suggest that it may facilitate re-attachment of the ribosome to the TBF1 translation start codon downstream of uORFs to initiate TBF1 translation.

Taken together, these observations strongly suggest that TBF1 expression is tightly controlled in the plant cell at not only the transcriptional level by NPR1, but also at the translational level through uORFs. Pathogen challenges, which cause a temporary increase in uncharged tRNA$^{Phe}$ accumulation, trigger elF2α phosphorylation, resulting in de-repression of the translation of TBF1.

Discussion

The presence of TL1 in a wide array of defense-related gene promoters suggests that it plays a critical role as a transcription factor (TF) involved in immune responses in plants [3, 18, 19] (FIGS. 5D and 5E). In these studies, we also demonstrated that the tbf1 mutant plants are impaired in UPR, elf18-induced MTI and SA-mediated SAR, but not in the heat shock response (FIG. 11 and FIG. 13). The evolution of transcriptional factors with novel functions may explain the greater expansion of HSF-like genes in plants compared to other organisms (one each in yeast and Drosophila, and three in vertebrates) [44].

Activation of the immune system consumes a significant amount of metabolic activity. Mutant plants with constitutively-activated defense responses often have stunted growth and retarded development [45]. Our studies demonstrate that TBF1 is a master molecular switch for this growth-to-defense reprogramming that involves activation and repression of nearly 3,000 genes during SAR and MTI. About 46% of these contain at least one copy of the TL1 element in their promoters. TBF1 is involved not only in the control of immune response genes, but also the control of genes relating to primary metabolism, growth, and photosynthesis.

Our analysis revealed seven members of the alpha-expansin gene family in the SA-repressed, TBF1-dependent category. Expansins are cell wall-loosening proteins that mediate pH-dependent extensions of the plant cell wall and growth of the cell [46]. Cell hypertrophy (enlargement) is a common virulence strategy used by bacteria to promote pathogenicity [47-49]. A bacterial effector AvrBs3 from *Xanthomonas* spp. activates a plant bHLH TF gene, UPA20, which in turn induces multiple alpha-expansin genes [47]. Our study reveals that upon SA signal perception, TBF1 down-regulates expansin that may inhibit this virulence strategy. The presence of TL1 elements in alpha-expansin promoter regions, as shown in Table S1, incorporated as a large table by reference, suggests that they are direct transcriptional targets of TBF1.

The pivotal role that TBF1 plays in the growth-to-defense transition underscores the importance for the need to understand how it regulates other cellular functions and how its expression and activity are regulated. The expression of TBF1 is tightly controlled at both transcriptional and translational levels. Transcription of TBF1 and NPR1 appears to be interdependent, as mutations in either gene affect the transcription of the other gene (FIG. 5A). TBF1 may directly regulate NPR1 expression through the TL1 elements in the NPR1 promoter. Since the NPR1 promoter also contains W-boxes [50], TBF1 may regulate NPR1 indirectly through its transcriptional targets, WRKY TFs (Table S1). NPR1 may also regulate TBF1 expression through either TGA or WRKY TFs, as the TBF1 promoter contains five W-boxes and three TGA binding sites, also known as as-1 elements [51].

The two uORFs upstream of TBF1 ORF link translation of TBF1 with the availability of specific amino acids within the cell. About 10% of all eukaryotic mRNAs contain uORFs, and a high percentage of them encode critical cellular regulators, such as protooncogenes, TFs, receptors, and other proteins involved in immune responses [52]. Expression of these genes is highly-regulated, as their protein products are essential for controlled cell growth and proliferation. TBF1 appears to be a key regulator, as transgenic lines overexpressing TBF1 cDNA under the constitutive 35S promoter were not viable (Pajerowska-Mukhtar and Dong, personal observation).

Pathogen challenges, resulting in increases in uncharged tRNA$^{Phe}$ and the phosphorylation of elF2α, release the inhibitory effect of uORFs on the translation of TBF1 (FIG. 17D). These results appear to be similar to the regulatory mechanisms described for the well-studied yeast GCN4 and mammalian ATF4 gene products (reviewed in [35]). The yeast GCN4 transcript contains four uORFs in its 5' regulatory region [53]. Under normal conditions, ribosomes bind to the 5' cap of GCN4 mRNA and initiate translation at the first uORF. They are unable to reinitiate translation at the start codon of GCN4. During amino-acid starvation, uncharged tRNAs induce phosphorylation of elF2α mediated by GCN2, which hinders reassembly of the 80S ribosome after translation of uORF1. This allows the 40S ribosomal subunit to continue scanning the mRNA and reinitiate translation at the start codon for GCN4 [53].

While derepression of GCN4 translation can be triggered by starvation of any amino acid, the uORF-mediated regulation of TBF1 in plants appears to be controlled by the metabolic levels of specific amino acids, such as Phe. It is note clear, yet, if an infection by a pathogen causes a transient reduction in the levels of Phe. The rapid increase in the uncharged tRNA$^{Phe}$ after pathogen challenge coincided with the increase of the total tRNA$^{Phe}$ (FIG. 17B). These results suggest that infection by a pathogen affects the availability of Phe required for translation, as aromatic amino acids are known precursors for a large array of plant metabolites, including the growth hormone auxin, the SAR signal SA, cell wall components, and pigments such as anthocyanins [4, 54, 55]. In a manner similar to that observed for GCN4, the accumulation of uncharged tRNA$^{Phe}$ triggers phosphorylation of elF2α, ribosomal movement through uORFs, and the translation of TBF1. The translational mechanisms involved in the regulation of TBF1 allow the cell to quickly detect pathogen-triggered metabolic changes, and produce sufficient amounts of TBF1 protein to activate cellular and systemic immune responses.

Example 2

Plant disease is a large threat to crop yield and security of the food supply around the world. A variety of approaches have been used to minimize plant disease. NLR (Nucleotide-binding leucine-rich repeat) proteins, PRRs (pattern-recognition receptors), and mutant alleles of host disease-susceptibility genes, for example, have all been used to engineer disease-resistant transgenic plants [85]. Immune responses are energy-consuming processes, adversely affecting plant growth and development. Approaches which stringently control the expression of genes of interest, may minimize the impact of these costly processes. The transcriptional control factor known as TBF1 (TL1 binding factor 1) affects transcriptional reprogramming induced by two important immune signals, elf18 and SA (Salicylic acid) [88]. The level of TBF1 mRNA is rapidly induced by treatment with SA, suggesting that its promoter (TBF1p) is a good candidate for experiments designed to control the transcription of genes of interest in cells infected by a pathogen. The two upstream open reading frames (uORFs) residing in the 5'UTR (5' untranslated region) of TBF1 mRNA (FIG. 22) appear to suppress the translation of the TBF1 polypeptide. This suppression can be alleviated by infection with a pathogen, suggesting that the uORFs can be used to control translation of genes of interest in pathogen-infected cells. Use of a nucleotide sequence comprising the TBF1 promoter with sequences encoding uORFs may facilitate the control over the level of transcription and translation of disease-related genes and their products. Tissues infected with pathogens have increased accumulation of plant defensive proteins to execute immune response in a spatial and temporal manner. Since the amount of plant defensive proteins are limited in plants, and most of them are specific to particular strains of pathogens, we can exploit target genes from other species, such as toxic or cell death-promoting genes, to locally induce cell death to restrict the growth of a variety of pathogens (exemplified by the list in Table 7).

Recently, the *Arabidopsis* GCN2 (general control nonrepressed 2; a serine/threonine-protein kinase) protein was shown to directly phosphorylate elF2α [59]. We previously noted a rapid accumulation of the phosphorylated elF2α in leaf samples infected with Psm ES4326/avrRpt2 (FIG. 17C). This accumulation temporally correlated with translational de-repression of the uORF1-uORF2-GUS reporter in planta (FIG. 16E). These results suggested that TBF1 might be controlled by a pathogen-mediated induction of the GCN2-elF2α pathway.

TABLE 7

Characteristics of target genes

| Protein name | Synthetic location | Major function | Reference/Source |
| --- | --- | --- | --- |
| Luciferase | Cytosol | Positive control for cytosol-synthesized proteins, to facilitate monitoring of both the response of TBF1 promoter and the uORF genetic elements during biotic and abiotic stresses. | Promega |
| HA-mBax | Cytosol | Mammalian apoptosis-promoting protein which causes cell death in plants. | [86] |
| NPR1-EGFP | Cytosol | Master regulator of plant resistance. | [84] |
| snc1 | Cytosol | Constitutively-active resistance protein. | [87] |
| snc1-cMyc | Cytosol | Constitutive active resistance protein with cMyc tag to facilitate the detection of changes in protein accumulation. | [87] |
| mGFP5 | ER | Positive control for polypeptides synthesized in the ER and to monitor the responses of the TBF1 promoter and the uORF genetic elements during biotic and abiotic stresses. | [90] |
| Bax-inhibitor 1-HA (BI-1-HA) | ER | Polypeptide conferring broad-spectrum resistance to both biotic and abiotic stress. | [89] |

Materials and Methods

A variety of primers used in the construction of various plasmid vectors comprising genetic elements including promoters and sequences encoding polypeptides of interest are listed in Table 8. Key features of plasmid vectors used in this study are listed in Table 9.

TABLE 8

Primers used in plasmid construction

| Name | Sequence | Length | Description | Reference | SEQ ID NO: |
| --- | --- | --- | --- | --- | --- |
| P1 | cggCTGCAGgtcaacatggtggagcacga | 29 | PstI-35S 5' | This study | 115 |
| P2 | cggTCTAGAccggcctctccaaatgaaatgaac | 33 | XbaI-35S-3' | This study | 116 |
| P3 | cggGGTACCgatcgttcaaacatttggcaata | 32 | KpnI-NOS 5' | This study | 117 |
| P4 | cggGAATTCcccgatctagtaacatagatg | 30 | EcoRI-NOS 3' | This study | 118 |
| P5 | cggGGTACCttcgacgacaagaccgggcccacaagttTgtacaaaaaagctgaac | 55 | KpnI-Gateway 5' | This study | 119 |
| P6 | ggaaattcgagcggctcgagtgaggagaagagccgggcccctaccactttgtacaagaaag | 61 | Gateway 3' | This study | 120 |
| P7 | cggCTTAAGaaactttattgccaaatgtttgaacgatcggggaaattcgagcggctcg | 58 | AflII-Gateway 3' | This study | 121 |
| P8 | cggGGTACCctccggcgaacttttttattt | 31 | KpnI-TBF1 5'UTR 3' | This study | 122 |
| P9 | aattTCTAGAaacagcatccg | 21 | XbaI-TBF1 5'UTR with native uORFs5' | This study | 123 |
| P10 | cggTCTAGAaacagcatccgttttTataatttaatttTcttacaaaggtaggacc | 55 | XbaI-TBF1 5'UTR With Mutant uORFs 5' | This study | 124 |
| P11 | cggAAGCTTcgacgactagtttacagagaa | 30 | HindIII-TBF1 promoter 5' | This study | 125 |
| P12 | cggGGCGCGCCctagaaattctcagaaacatcttttcttc | 40 | AscI-TBF1 promoter 3' | This study | 126 |
| P13 | cggGGCGCGCCttcttacaaaggtaggaccaac | 33 | AscI-TBF1 5'UTR 5' | This study | 127 |
| P14 | cggAAGCTTtacagagaatttggaccgtc | 29 | HindIII-TBF1 promoter 5' | This study | 128 |

TABLE 8-continued

Primers used in plasmid construction

| Name | Sequence | Length | Description | Reference | SEQ ID NO: |
|---|---|---|---|---|---|
| P15 | cggACTAGTaattctcagaaacatcttttcttc | 33 | SpeI-TBF1 promoter 3' | This study | 129 |
| LIC1 | tcgacgacaagacc | 14 | Gateway LIC adapter sequence 1 | This study | 130 |
| LIC2 | tgaggagaagagcc | 14 | Gateway LIC adapter sequence 2 | This study | 131 |

The 35S promoter, with duplicated enhancer elements, was amplified from pRNAi-LIC (GenBank: GQ870263.1) using primers P1 (SEQ ID NO: 115)/P2 (SEQ ID NO: 116) and was flanked with PstI and XbaI sites. The NOS terminator was amplified from pRNAi-LIC (GenBank: GQ870263.1) using primers P3 (SEQ ID NO: 117)/P4 (SEQ ID NO: 118) to produce a DNA sequence which is flanked with KpnI and EcoRI sites. The Gateway cassette with LIC adapter sequences LIC1:
(SEQ ID NO: 130)
tcgacgacaagacc LIC2:
(SEQ ID NO: 131)
tgaggagaagagcc were amplified using primers P5 (SED ID NO: 119)/P6 (SED ID NO: 120)/P7 (SED ID NO: 121) (the PCR fragment by P5/P6 was used as template for P5/P7) from pDEST375 (GenBank: KC614689.1) and was flanked with KpnI and AflII sites. The NOS terminator, 35S promoter, and Gateway cassette were sequentially ligated into pCAMBIA1300 (GenBank: AF234296.1) via KpnI/EcoRI, PstI/XbaI and KpnI/AflII. The resulting plasmid (designated pGX0 (SEQ ID NO: 136) was used as an intermediate plasmid.

The 5'UTR of TBF1 with native or mutant uORFs were amplified with P8 (SEQ ID NO: 122)/P9 (SEQ ID NO: 123) and P8 (SEQ ID NO: 122)/P10 (SEQ ID NO: 124) from uORF1-uORF2-GUS and uorf1-uorf2-GUS plasmids as previously published [88] respectively, and were cloned into the intermediate plasmid via XbaI/KpnI. The resulting plasmids were designated as pGX180 (35S-uORF-Gateway-NOS) (SEQ ID NO:135) and pGX179 (35S-uorf-Gateway-NOS) (SEQ ID NO: 134), respectively.

The TBF1 promoter was amplified from *Arabidopsis* Genomic DNA using primers P11 (SED ID NO: 125)/P12 (SED ID NO: 126) and was flanked with HindIII/AscI. The TBF1 SUTR was amplified from pGX180 using primers P8(SED ID NO: 123)/P13(SED ID NO: 127) and was flanked with AscI/KpnI. The TBF1 promoter (P11(SED ID NO: 125)/P12(SED ID NO: 126)) and TBF1 SUTR (P8 (SED ID NO: 122)/P13 (SED ID NO: 127)) were digested with AscI and ligated together. The ligation product was used as template for amplifying the TBF1 promoter-5'UTR fusion PCR product with primer pair P11 (SED ID NO: 125)/P8 (SED ID NO: 122), which produced a DNA fragment that was flanked with HindIII/KpnI sites. The 35S promoter-uORF region on pGX179 was also replaced by the TBF1 promoter-5'UTR, and the resulting plasmid was designated as pGX1 (TBF1p-uORF-Gateway-NOS) (SEQ ID NO: 132).

The TBF1 promoter was amplified from *Arabidopsis* genomic DNA using primers P14 (SEQ ID NO: 128)/P15 (SEQ ID NO: 129) and was flanked with HindIII/SpeI and was ligated into pGX179 (SEQ ID NO: 134) which was cut with HindIII/XbaI (generating SpeI-compatible sticky ends). The resulting plasmid was designated pGX181 (TBF1p-uorf-Gateway-NOS) (SEQ ID NO: 133).

TABLE 9

Plasmids

| Designation | Markers | Description | Length (nt/aa) | Reference/ Source | SEQ ID NO |
|---|---|---|---|---|---|
| pGX1 | Kan$^R$, Hygro$^R$ | pGX1 (TBF1p-uORF-Gateway-NOS) Gateway plant expression vector carrying a Gateway cassette cloned downstream of uORF1 and uORF2. Target genes can be cloned via Ligation independent cloning method [91] to replace Gateway cassette. The target gene with uORFs on its 5' is driven by TBF1 promoter; vector confers kanamycin resistance in *E. coli* and hygromycin resistance in transgenic plants. | 14478 | This study | 132 |
| pGX181 | Kan$^R$, Hygro$^R$ | pGX181 (TBF1p-uorf-Gateway-NOS) A-to-C point mutation was introduced into the start codons (ATG) of uORF1 and uORF2, designated as uorf1-uorf2. Gateway plant | 14488 | This study | 133 |

TABLE 9-continued

Plasmids

| Designation | Markers | Description | Length (nt/aa) | Reference/ Source | SEQ ID NO |
|---|---|---|---|---|---|
| pGX179 | Kan$^R$, Hygro$^R$ | expression vector carrying a Gateway cassette cloned downstream of uorf1 and uorf2. Target genes can be cloned via Ligation independent cloning method [91] to replace Gateway cassette. The target gene with uorfs on its 5' is driven by TBF1 promoter; vector confers kanamycin resistance in *E. coli* and hygromycin resistance in transgenic plants. pGX179 (35S-uORF-Gateway-NOS) A-to-C point mutation was introduced into the start codons (ATG) of uORF1 and uORF2, designated as uorf1-uorf2. Gateway plant expression vector carrying a Gateway cassette cloned downstream of uorf1 and uorf2. Target genes can be cloned via Ligation independent cloning method [91] to replace Gateway cassette. Expression of the target gene with uorfs on its 5' end is driven by 35S promoter. The vector confers kanamycin resistance in *E. coli* and hygromycin resistance in transgenic plants. | 12194 | This study | 134 |
| pGX180 | Kan$^R$, Hygro$^R$ | pGX180 (35S-uorf-Gateway-NOS) Gateway plant expression vector carrying a Gateway cassette cloned downstream of uORF1 and uORF2. Target genes can be cloned via Ligation independent cloning method [91] to replace Gateway cassette. Expression of the target gene with uORFs on its 5' end is driven by 35S promoter. The vector confers kanamycin resistance in *E. coli* and hygromycin resistance in transgenic plants. | 12187 | This study | 135 |
| pGX0 | Kan$^R$, Hygro$^R$ | pGX0 Intermediate plasmid Gateway plant expression vector carrying a Gateway cassette cloned downstream of 35S promoter. The vector confers kanamycin resistance in *E. coli* and hygromycin resistance in transgenic plants. This intermediate vector was used in the construction of pGX1, pGX181, pGX179, and pGX180. | 11726 | This study | 136 |
| Luciferase | | Positive control for cytosol-synthesized proteins, to facilitate monitoring of both the response of TBF1 promoter and the uORF genetic elements during biotic and abiotic stresses. | 1653 | Promega | 137 |
| Luciferase | | Luciferase polypeptide | 550 aa | Promega | 138 |
| NPR1-EGFP | | *Arabidopsis* NPR1 gene that controls systemic acquired resistance encodes a novel protein containing ankyrin repeats [84]. | 2532 | This study PCR amplify from *Arabidopsis* cDNA and PCR fuse with EGFP | 139 |
| NPR1-EGFP | | NPR1-EGFP fusion polypeptide | 84 aa | This study | 140 |
| HA-mBax | | Mammalian apoptosis-promoting protein which causes cell death in plants [86]. | 780 | This study PCR amplify from Mouse cDNA and PCR fuse with HA tag, | 141 |
| HA-mBax | | HA-mBax fusion polypeptide | 259 aa | This study | 142 |
| mGFP5 | | ER localized GFP used as positive control for polypeptides synthesized in the ER and to monitor the responses of the TBF1 promoter and the uORF genetic elements during biotic and abiotic stresses [90]. | 792 | [90] | 143 |
| mGFP5 | | mGFP5 polypeptide | 263 aa | [90] | 144 |
| BI-1-HA | | Polypeptide conferring broad-spectrum resistance to both biotic and abiotic stress [89]. Amplify PCR fragment from *Arabidopsis* cDNA and fuse with HA fragment. | 936 | [89] | 145 |

TABLE 9-continued

Plasmids

| Designation | Markers | Description | Length (nt/aa) | Reference/ Source | SEQ ID NO |
|---|---|---|---|---|---|
| BI-1-HA | | BI-1-HA fusion polypeptide | 311 aa | [89] | 146 |
| snc1 | | Genomic fragment of *Arabidopsis* snc1 mutant plant encoding constitutively-active form of SNC1 resistance protein (suppressor of NPR1) [87] having 6 exons and 5 introns. | 4950 | This study PCR amplify from genomic DNA of snc1 mutant plant. | 147 |
| snc1-cMyc | | Nucleotide sequence encoding constitutively-active resistance protein [87] fused via linker sequence to cMyc on its C terminal end. Snc1 portion is encoded by nucleotide sequence having 6 exons and 5 introns, where the snc1-related exons encode a polypeptide fused via linker to a cMyc polypeptide. | 5244 | This study | 148 |
| | | Linker portion of snc1-linker-cMyc fusion polypeptide. | 11 aa | | 149 |
| | | cMyc portion of snc1-linker-cMyc fusion polypeptide | 78 aa | | 150 |

Results

Four different versatile vectors were generated using the Gateway system and ligation-independent cloning strategy as illustrated in FIG. 23. A variety of genes were cloned into the four expression cassettes using a ligation independent cloning method [91].

Use of the uORF elements to control expression of luciferase (cytosol-synthesized protein) and mGFP5 (ER-synthesized protein) demonstrated that TBF1 uORF can suppress both cytosol- and ER-synthesized proteins (FIG. 24), which enables the secreted proteins and membrane proteins as the potential targets.

In this example, we transformed the uORF1-uORF2-GUS construct into the *Arabidopsis* gcn2 knock-out mutant and the corresponding *Landsberg erecta* (Ler) wild-type plants. To test whether GCN2 controls TBF1 translation via uORFs, we also created an additional set of transgenic lines in the Ler background that express a derivative construct in which the start codons for both uORFs (uorf1-uorf2-GUS) were mutated (from ATG to CTG). GUS activities of these translational fusions were quantified in $T_3$ stable transgenic *Arabidopsis* lines in response to Psm ES4326/avrRpt2.

We observed a rapid increase in the GUS activities only in the wild-type Ler plants expressing uORF1-uORF2-GUS (FIG. 21). This increase was not observed in the gcn2 mutant carrying uORF1-uORF2-GUS or wild-type expressing uorf1-uorf2-GUS. These data demonstrate that TBF1 translation is mediated by the GCN2/eIF2α pathway upon pathogen infection. Since GCN2 kinase homologs have been found across kingdoms from yeast to animals to plants, the uORF-mediated translation regulatory mechanism discovered for the *Arabidopsis* TBF1 mRNA is likely to function in a heterologous genetic background. Based on this observation, we replaced the GUS reporter gene with several functional "cargo" genes and transformed them into *Arabidopsis*. Transgenic plants will be characterized with regard to levels of disease resistance as well as plant fitness.

Transgenic *Arabidopsis* plants generated by the floral dip method [92] are being assessed for fitness and disease resistance.

While the preferred embodiments of the invention have been illustrated and described in detail, it will be appreciated by those skilled in the art that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

REFERENCES

All references, patents, or applications cited herein are incorporated by reference in their entirety, as if written herein.

1. Nishimura, M. T., and Dangl, J. L. (2010). *Arabidopsis* and the plant immune system. *Plant J* 61, 1053-1066.
2. Jones, J. D., and Dangl, J. L. (2006). The plant immune system. *Nature* 444, 323-329.
3. Wang, D., Weaver, N. D., Kesarwani, M., and Dong, X. (2005). Induction of protein secretory pathway is required for systemic acquired resistance. *Science* 308, 1036-1040.
4. Durrant, W. E., and Dong, X. (2004). Systemic acquired resistance. *Annu Rev Phytopathol* 42, 185-209.
5. Kwon, C., Bednarek, P., and Schulze-Lefert, P. (2008). Secretory pathways in plant immune responses. *Plant Physiol* 147, 1575-1583.
6. Nekrasov, V., Li, J., Batoux, M., Roux, M., Chu, Z. H., Lacombe, S., Rougon, A., Bittel, P., Kiss-Papp, M., Chinchilla, D., et al. (2009). Control of the pattern-recognition receptor EFR by an ER protein complex in plant immunity. *EMBO J* 28, 3428-3438.
7. Saijo, Y., Tintor, N., Lu, X., Rauf, P., Pajerowska-Mukhtar, K., Haweker, H., Dong, X., Robatzek, S., and Schulze-Lefert, P. (2009). Receptor quality control in the endoplasmic reticulum for plant innate immunity. *EMBO J* 28, 3439-3449.
8. Kinkema, M., Fan, W., and Dong, X. (2000). Nuclear localization of NPR1 is required for activation of PR gene expression. *Plant Cell* 12, 2339-2350.
9. Song, J., Durrant, W. E., Wang, S., Yan, S., Tan, E. H., and Dong, X. (2011). DNA Repair Proteins Are Directly Involved in Regulation of Gene Expression during Plant Immune Response. *Cell Host Microbe* 9, 115-124.
10. Zhang, Y., Fan, W., Kinkema, M., Li, X., and Dong, X. (1999). Interaction of NPR1 with basic leucine zipper protein transcription factors that bind sequences required for salicylic acid induction of the PR-1 gene. *Proc Natl Acad Sci USA* 96, 6523-6528.
11. Wang, D., Amornsiripanitch, N., and Dong, X. (2006). A genomic approach to identify regulatory nodes in the transcriptional network of systemic acquired resistance in plants. *PLoS Pathog* 2, e123.
12. Zipfel, C., Kunze, G., Chinchilla, D., Caniard, A., Jones, J. D., Boller, T., and Felix, G. (2006). Perception of the bacterial PAMP EF-Tu by the receptor EFR restricts *Agrobacterium*-mediated transformation. *Cell* 125, 749-760.
13. Kotak, S., Larkindale, J., Lee, U., von Koskull-Doring, P., Vierling, E., and Scharf, K. D. (2007). Complexity of the heat stress response in plants. *Curr Opin Plant Biol* 10, 310-316.
14. Baniwal, S. K., Bharti, K., Chan, K. Y., Fauth, M., Ganguli, A., Kotak, S., Mishra, S. K., Nover, L., Port, M., Scharf, K. D., et al. (2004). Heat stress response in plants: a complex game with chaperones and more than twenty heat stress transcription factors. *J Biosci* 29, 471-487.
15. Boscheinen, O., Lyck, R., Queitsch, C., Treuter, E., Zimarino, V., and Scharf, K. D. (1997). Heat stress transcription factors from tomato can functionally replace HSF1 in the yeast *Saccharomyces cerevisiae*. *Mol Gen Genet* 255, 322-331.
16. Busch, W., Wunderlich, M., and Schoffl, F. (2005). Identification of novel heat shock factor-dependent genes and biochemical pathways in *Arabidopsis thaliana*. *Plant J* 41, 1-14.
17. Prandl, R., Hinderhofer, K., Eggers-Schumacher, G., and Schoffl, F. (1998). HSF3, a new heat shock factor from *Arabidopsis thaliana*, derepresses the heat shock response and confers thermotolerance when overexpressed in transgenic plants. *Mol Gen Genet* 258, 269-278.
18. Fabro, G., Di Rienzo, J. A., Voigt, C. A., Savchenko, T., Dehesh, K., Somerville, S., and Alvarez, M. E. (2008). Genome-wide expression profiling *Arabidopsis* at the stage of *Golovinomyces cichoracearum* haustorium formation. *Plant Physiol* 146, 1421-1439.
19. Humphry, M., Bednarek, P., Kemmerling, B., Koh, S., Stein, M., Gobel, U., Stuber, K., Pislewska-Bednarek, M., Loraine, A., Schulze-Lefert, P., et al. (2010). A regulon conserved in monocot and dicot plants defines a functional module in antifungal plant immunity. *Proc Natl Acad Sci USA*.
20. Czarnecka-Verner, E., Pan, S., Salem, T., and Gurley, W. B. (2004). Plant class B HSFs inhibit transcription and exhibit affinity for TFIIB and TBP. *Plant Mol Biol* 56, 57-75.
21. Czarnecka-Verner, E., Yuan, C. X., Scharf, K. D., Englich, G., and Gurley, W. B. (2000). Plants contain a novel multi-member class of heat shock factors without transcriptional activator potential. *Plant Mol Biol* 43, 459-471.
22. Panstruga, R., Parker, J. E., and Schulze-Lefert, P. (2009). SnapShot: Plant immune response pathways. *Cell* 136, 978 e971-973.
23. Sugano, S., Jiang, C. J., Miyazawa, S., Masumoto, C., Yazawa, K., Hayashi, N., Shimono, M., Nakayama, A., Miyao, M., and Takatsuji, H. (2010). Role of OsNPR1 in rice defense program as revealed by genome-wide expression analysis. *Plant Mol Biol* 74, 549-562.
24. Leister, D., and Schneider, A. (2003). From genes to photosynthesis in *Arabidopsis thaliana*. *Int Rev Cytol* 228, 31-83.
25. Wang, D., Pajerowska-Mukhtar, K., Culler, A. H., and Dong, X. (2007). Salicylic Acid Inhibits Pathogen Growth in Plants through Repression of the Auxin Signaling Pathway. *Curr Biol* 17, 1784-1790.
26. Gfeller, A., Liechti, R., and Farmer, E. E. (2010). *Arabidopsis jasmonate* signaling pathway. *Sci Signal* 3, cm4.
27. Zheng, Z., Qamar, S. A., Chen, Z., and Mengiste, T. (2006). *Arabidopsis* WRKY33 transcription factor is required for resistance to necrotrophic fungal pathogens. *Plant J* 48, 592-605.
28. Kumar, M., Busch, W., Birke, H., Kemmerling, B., Nurnberger, T., and Schoffl, F. (2009). Heat shock factors HsfB1 and HsfB2b are involved in the regulation of Pdf1.2 expression and pathogen resistance in *Arabidopsis*. *Mol Plant* 2, 152-165.
29. Li, J., Zhao-Hui, C., Batoux, M., Nekrasov, V., Roux, M., Chinchilla, D., Zipfel, C., and Jones, J. D. (2009). Specific ER quality control components required for biogenesis of the plant innate immune receptor EFR. *Proc Natl Acad Sci USA* 106, 15973-15978.
30. Lu, X., Tintor, N., Mentzel, T., Kombrink, E., Boller, T., Robatzek, S., Schulze-Lefert, P., and Saijo, Y. (2009). Uncoupling of sustained MAMP receptor signaling from early outputs in an *Arabidopsis* endoplasmic reticulum glucosidase II allele. *Proc Natl Acad Sci USA* 106, 22522-22527.
31. Tsuda, K., Sato, M., Stoddard, T., Glazebrook, J., and Katagiri, F. (2009). Network properties of robust immunity in plants. *PLoS Genet* 5, e1000772.
32. Hayden, C. A., and Jorgensen, R. A. (2007). Identification of novel conserved peptide uORF homology groups in *Arabidopsis* and rice reveals ancient eukaryotic origin of select groups and preferential association with transcription factor-encoding genes. *BMC Biol* 5, 32.
33. Brooks, D. J., Fresco, J. R., Lesk, A. M., and Singh, M. (2002). Evolution of amino acid frequencies in proteins over deep time: inferred order of introduction of amino acids into the genetic code. *Mol Biol Evol* 19, 1645-1655.
34. Harding, H. P., Novoa, I., Zhang, Y., Zeng, H., Wek, R., Schapira, M., and Ron, D. (2000). Regulated translation initiation controls stress-induced gene expression in mammalian cells. *Mol Cell* 6, 1099-1108.
35. Hinnebusch, A. G. (2005). Translational regulation of GCN4 and the general amino acid control of yeast. *Annu Rev Microbiol* 59, 407-450.
36. Ball, S. G., Wickner, R. B., Cottarel, G., Schaus, M., and Tirtiaux, C. (1986). Molecular cloning and characterization of ARO7-OSM2, a single yeast gene necessary for chorismate mutase activity and growth in hypertonic medium. *Mol Gen Genet* 205, 326-330.
37. Tucker, C. L., and Fields, S. (2001). A yeast sensor of ligand binding. *Nat Biotechnol* 19, 1042-1046.
38. Ercikan-Abali, E. A., Waltham, M. C., Dicker, A. P., Schweitzer, B. I., Gritsman, H., Banerjee, D., and Bertino, J. R. (1996). Variants of human dihydrofolate reductase with substitutions at leucine-22: effect on catalytic and inhibitor binding properties. *Mol Pharmacol* 49, 430-437.
39. Walter, F., Putz, J., Giege, R., and Westhof, E. (2002). Binding of tobramycin leads to conformational changes in yeast tRNA(Asp) and inhibition of aminoacylation. *EMBO J* 21, 760-768.
40. Dey, M., Cao, C., Sicheri, F., and Dever, T. E. (2007). Conserved intermolecular salt bridge required for activation of protein kinases PKR, GCN2, and PERK. *J Biol Chem* 282, 6653-6660.
41. Dong, J., Qiu, H., Garcia-Barrio, M., Anderson, J., and Hinnebusch, A. G. (2000). Uncharged tRNA activates 41. GCN2 by displacing the protein kinase moiety from a bipartite tRNA-binding domain. *Mol Cell* 6, 269-279.
42. Padyana, A. K., Qiu, H., Roll-Mecak, A., Hinnebusch, A. G., and Burley, S. K. (2005). Structural basis for autoinhibition and mutational activation of eukaryotic initiation factor 2alpha protein kinase GCN2. *J Biol Chem* 280, 29289-29299.
43. Lageix, S., Lanet, E., Pouch-Pelissier, M. N., Espagnol, M. C., Robaglia, C., Deragon, J. M., and Pelissier, T. (2008). *Arabidopsis* eIF2alpha kinase GCN2 is essential for growth in stress conditions and is activated by wounding. *BMC Plant Biol* 8, 134.
44. Nover, L., Bharti, K., Doring, P., Mishra, S. K., Ganguli, A., and Scharf, K. D. (2001). *Arabidopsis* and the heat stress transcription factor world: how many heat stress transcription factors do we need? *Cell Stress Chaperones* 6, 177-189.
45. Heidel, A. J., Clarke, J. D., Antonovics, J., and Dong, X. (2004). Fitness Costs of Mutations Affecting the Systemic Acquired Resistance Pathway in *Arabidopsis thaliana*. *Genetics* 168, 2197-2206.
46. Li, Y., Darley, C. P., Ongaro, V., Fleming, A., Schipper, O., Baldauf, S. L., and McQueen-Mason, S. J. (2002). Plant expansins are a complex multigene family with an ancient evolutionary origin. *Plant Physiol* 128, 854-864.
47. Kay, S., Hahn, S., Marois, E., Hause, G., and Bonas, U. (2007). A bacterial effector acts as a plant transcription factor and induces a cell size regulator. *Science* 318, 648-651.
48. Marois, E., Van den Ackerveken, G., and Bonas, U. (2002). The *Xanthomonas* type III effector protein AvrBs3 modulates plant gene expression and induces cell hypertrophy in the susceptible host. *Mol Plant Microbe Interact* 15, 637-646.
49. Wichmann, G., and Bergelson, J. (2004). Effector genes of *Xanthomonas axonopodis* pv. *vesicatoria* promote transmission and enhance other fitness traits in the field. *Genetics* 166, 693-706.
50. Eulgem, T., Rushton, P. J., Robatzek, S., and Somssich, I. E. (2000). The WRKY superfamily of plant transcription factors. *Trends Plant Sci* 5, 199-206.
51. Lebel, E., Heifetz, P., Thorne, L., Uknes, S., Ryals, J., and Ward, E. (1998). Functional analysis of regulatory sequences controlling PR-1 gene expression in *Arabidopsis*. *Plant Journal* 16, 223-233.
52. Kozak, M. (1991). An analysis of vertebrate mRNA sequences: intimations of translational control. *J Cell Biol* 115, 887-903.
53. Miller, P. F., and Hinnebusch, A. G. (1990). cis-acting sequences involved in the translational control of GCN4 expression. *Biochim Biophys Acta* 1050, 151-154.
54. Holton, T. A., and Cornish, E. C. (1995). Genetics and Biochemistry of Anthocyanin Biosynthesis. *Plant Cell* 7, 1071-1083.
55. Zhao, Y. (2010). Auxin biosynthesis and its role in plant development. *Annu Rev Plant Biol* 61, 49-64.
56. Curtis, M. D., and Grossniklaus, U. (2003). A gateway cloning vector set for high-throughput functional analysis of genes in planta. *Plant Physiol* 133, 462-469.
57. Pajerowska-Mukhtar, K. M., Mukhtar, M. S., Guex, N., Halim, V. A., Rosahl, S., Somssich, I. E., and Gebhardt, C. (2008). Natural variation of potato allene oxide synthase 2 causes differential levels of jasmonates and pathogen resistance in *Arabidopsis*. *Planta* 228, 293-306.
58. Ercikan-Abali, E. A., Mineishi, S., Tong, Y., Nakahara, S., Waltham, M. C., Banerjee, D., Chen, W., Sadelain, M., and Bertino, J. R. (1996). Active site-directed double mutants of dihydrofolate reductase. *Cancer Res* 56, 4142-4145.
59. Li, M. W., Auyeung, W. K., Lam, H. M. (2013, January) The GCN2 homologue in *Arabidopsis thaliana* interacts with uncharged tRNA and uses *Arabidopsis* eIF2alpha molecules as direct substrates. *Plant Biol (Stuttg)* 15(1): 13-8. doi: 10.1111/j.1438-8677.2012.00606.x. Epub 2012 Jun. 5.
60. Dong, X., Mindrinos, M., Davis, K. R., and Ausubel, F. M. (1991) Induction of *Arabidopsis* Defense Genes by Virulent and Avirulent *Pseudomonas syringae* Strains and by a Cloned Avirulence Gene. *The Plant Cell*, 3(1), 61-72.
61. Wang, D., Weaver, N. D., Kesarwani, M., and Dong, X. (2005). Induction of protein secretory pathway is required for systemic acquired resistance. *Science* 308, 1036-1040.
62. Deplancke, B., Vermeirssen, V., Arda, H. E., Martinez, N. J., and Walhout, A. J. M. (2006). Gateway-compatible yeast one-hybrid screens. *Cold Spring Harb Protoc*, doi: 10.1101/pdb.prot4590.
63. Zhang, X., and Bremer, H. (1996). Effects of Fis on ribosome synthesis and activity and on rRNA promoter activities in *Escherichia coli*. *J Mol Biol* 259, 27-40.
64. Song, J., Durrant, W. E., Wang, S., Yan, S., Tan, E. H., and Dong, X. (2011). DNA Repair Proteins Are Directly Involved in Regulation of Gene Expression during Plant Immune Response. *Cell Host Microbe* 9, 115-124.
65. Oliveros, J. C. (2007). VENNY. An interactive tool for comparing lists with Venn Diagrams. bioinfogp.cnb.csic.es/tools/venny/index.html.
66. Curtis, M. D., and Grossniklaus, U. (2003). A gateway cloning vector set for high-throughput functional analysis of genes in planta. *PlantPhysiol* 133, 462-469.
67. Clough, S. J., and Bent, A. F. (1998). Floral dip: a simplified method for *Agrobacterium*-mediated transformation of *Arabidopsis thaliana*. *Plant Journal* 16, 735-743.
68. Durrant, W. E., Wang, S., and Dong, X. N. (2007). *Arabidopsis* SNI1 and RAD51D regulate both gene transcription and DNA recombination during the defense response. *Proc Natl Acad Sci USA* 104, 4223-4227.
69. Lageix, S., Lanet, E., Pouch-Pelissier, M. N., Espagnol, M. C., Robaglia, C., Deragon, J. M., and Pelissier, T. (2008). *Arabidopsis* eIF2alpha kinase GCN2 is essential for growth in stress conditions and is activated by wounding. *BMC Plant Biol* 8, 134.
70. Kohrer, C., and Rajbhandary, U. L. (2008). The many applications of acid urea polyacrylamide gel electrophoresis to studies of tRNAs and aminoacyl-tRNA synthetases. *Methods* 44, 129-138.
71. Deplancke, B., Dupuy, D., Vidal, M., and Walhout, A. J. M. (2004) A Gateway-Compatible Yeast One-Hybrid *System Genome Res.* 14: 2093-2101.
72. Winzeler, E. A. et al. (1999) Functional characterization of the *S. cerevisiae* genome by gene deletion and parallel analysis. *Science* 285, 901-906.
73. Holsters, M., Silva, B., Van Vliet, F., Genetello, C., De Block, M., Dhaese, P., Depicker, A., lnze, D., Engler, G., Villarroel, R., Van Montagu, M. Schell, J. (1980) The functional organization of the nopaline *A. tumefaciens* plasmid pTiC58. *Plasmid*, 3, 212-230.
74. Deplancke, B., Mukhopadhyay, A., Ao, W., Elewa, A. E., Grove, C. A., Martinez, N. J., Sequerra, R., Doucette-Stamm, L., Reece-Hoyes, J. S., Hope, I. A., Tissenbaum, H. A., Mango S. E., and Walhout, A. J. (2006). A gene-centered *C. elegans* protein-DNA interaction network. *Cell*, 125: 1192-1205

75. Riley, M., Abe, T., Arnaud, M. B., Berlyn, M. K. B., Blattner, F. R., Chaudhuri, R. R., Glasner, J. D., Horiuchi, T., Keseler, I. M., Kosuge, T., Mori, H., Perna, N. T., Plunkett III, G., Rudd, K. E., Serresm, M. H., Thomas, G. H., Thomson, N. R., Wishart, D. and Wanner, B. L. (2006) *Escherichia coli* K-12: a cooperatively developed annotation snapshot—2005. *Nucleic Acids Res.* 34 (1), 1-9

76. Jefferson, R. A. (1987). Assaying chimeric genes in plants: The GUS gene fusion system. *Plant Mol. Biol. Rep.* 5, 387-405.

77. Jefferson, R. A., Kavanagh, T. A., and Bevan, M. W. (1987). GUS fusion: β-Glucuronidase as a sensitive and versatile gene fusion marker in higher plants. *EMBO J.* 6, 3901-3907.

78. Miller, J. H. (1972) Experiments in molecular genetics. [Cold Spring Harbor, N.Y.] Cold Spring Harbor Laboratory.

79. Johnson, T. J., Kariyawasam, S., Wannemuehler, Y., Mangiamele, P.,Johnson, S. J., Doetkott, C., Skyberg, J. A., Lynne, A. M., Johnson, J. R., and Nolan, L. K. (2007) The genome sequence of avian pathogenic *Escherichia coli* strain O1:K1:H7 shares strong similarities with human extraintestinal pathogenic *E. coli* genomes. *J. Bacteriol.* 189 (8), 3228-3236.

80. Hall C. V., Jacob P. E., Ringold G. M., and Lee F. J. (1983) Expression and regulation of *Escherichia coli* lacZ gene fusions in mammalian cells. *Mol Appl Genet.* 2(1), 101-109.

81. Prasher, D. C., Eckenrode, V. K., Ward, W. W., Prendergast, F. G., and Cormier, M. J. (1992) Primary structure of the *Aequorea victoria* green-fluorescent protein. *Gene* 111 (2), 229-233.

82. Whalen, M. C., Innes, R. W., Bent, A. F., and Staskawicz, B. J. (1991) Identification of *Pseudomonas syringae* Pathogens of *Arabidopsis* and a Bacterial Locus Determining Avirulence on Both *Arabidopsis* and Soybean. *The Plant Cell*, 3, 49-59.

83. Deplancke B, Dupuy D, Vidal M, Walhout A J. (2004) A gateway-compatible yeast one-hybrid system. *Genome Res.* 14(10B):2093-101.

84. Cao, H., Glazebrook, J., Clarke, J. D., Volko, S., and Dong, X. N. (1997). The *Arabidopsis* NPR1 gene that controls systemic acquired resistance encodes a novel protein containing ankyrin repeats. *Cell* 88, 57-63.

85. Dangl, J. L., Horvath, D. M., and Staskawicz, B. J. (2013). Pivoting the plant immune system from dissection to deployment. Science 341, 746-751.

86. Kawai-Yamada, M., Jin, L., Yoshinaga, K., Hirata, A., and Uchimiya, H. (2001). Mammalian Bax-induced plant cell death can be down-regulated by overexpression of *Arabidopsis* Bax Inhibitor-1 (AtBI-1). *Proc Nati Acad Sci USA* 98, 12295-12300.

87. Li, X., Clarke, J. D., Zhang, Y. L., and Dong, X. N. (2001). Activation of an EDS1-mediated R-gene pathway in the snc1 mutant leads to constitutive, NPR1-independent pathogen resistance. *Mol Plant Microbe In* 14, 1131-1139.

88. Pajerowska-Mukhtar, K. M., Wang, W., Tada, Y., Oka, N., Tucker, C. L., Fonseca, J. P., and Dong, X. N. (2012). The HSF-like Transcription Factor TBF1 is a Major Molecular Switch for Plant Growth-to-Defense Transition. *Curr Biol* 22, 103-112.

89. Watanabe, N., and Lam, E. (2009). Bax Inhibitor-1, a conserved cell death suppressor, is a key molecular switch downstream from a variety of biotic and abiotic stress signals in plants. *Intl J Molec Sci* 10, 3149-3167.

90. Xu, G., Li, S., Xie, K., Zhang, Q., Wang, Y., Tang, Y., Liu, D., Hong, Y., He, C., and Liu, Y. (2012). Plant ERD2-like proteins function as endoplasmic reticulum luminal protein receptors and participate in programmed cell death during innate immunity. *The Plant Journal: Cell Molec Biol* 72, 57-69.

91. Xu, G., Sui, N., Tang, Y., Xie, K., Lai, Y., Liu, Y. (2010) One-step, zero-background ligation-independent cloning intron-containing hairpin RNA constructs for RNAi in plants. *New Phytologist* 187, 240-250

92. Zhang, X., Henriques, R., Lin, S. S. Niu, Q. W., Chua N. H. (2012) *Agrobacterium*-mediated transformation of *Arabidopsis thaliana* using the floral dip method. *Nature Protocol* 1, 641-646

What is claimed is:

1. A nucleic acid comprising, in a 5' to 3' direction, a promoter, at least one upstream open reading frame (uORF), and a heterologous sequence, wherein the promoter is operably linked to the uORF and the heterologous sequence, wherein the uORF encodes a polypeptide selected from the group consisting of SEQ ID NO: 102, a variant of SEQ ID NO: 102 comprising one or two substitutions and having the translation control function of SEQ ID NO: 102, SEQ ID NO: 103, and a variant of SEQ ID NO: 103 comprising one or two substitutions and having the translation control function of SEQ ID NO: 103, and wherein the heterologous sequence comprises a synthetic polylinker, a ligation independent cloning sequence, or a downstream open reading frame (dORF), wherein the dORF does not encode a TBF1 open reading frame.

2. The nucleic acid of claim 1, wherein the nucleic acid comprises both a sequence encoding a polypeptide selected from the group consisting of SEQ ID NO: 102 and the variant of SEQ ID NO: 102 and a sequence encoding a polypeptide selected from the group consisting of SEQ ID NO: 103 and the variant of SEQ ID NO: 103.

3. The nucleic acid of claim 1, wherein the heterologous sequence comprises a synthetic polylinker or a ligation independent cloning sequence.

4. The nucleic acid of claim 1, wherein the heterologous sequence comprises the dORF, wherein the dORF encodes a polypeptide.

5. The nucleic acid of claim 4, wherein the dORF encodes a transcription factor, a reporter polypeptide, a polypeptide that confers resistance to drugs or agrichemicals, a polypeptide involved in resistance of plants to viral, bacterial, fungal pathogens, oomycete pathogens, phytoplasmas, or nematodes, or a polypeptide involved in the growth or development of plants.

6. The nucleic acid of claim 4, wherein the dORF encodes a NPR1 polypeptide.

7. The nucleic acid of claim 1, wherein the promoter is a plant promoter.

8. The nucleic acid of claim 7, wherein the plant promoter comprises a TBF1 promoter.

9. The nucleic acid of claim 7, wherein the plant promoter comprises a 35S promoter.

10. The nucleic acid of claim 7, wherein the plant promoter is inducible upon challenge by a plant pathogen or a chemical inducer.

11. The nucleic acid of claim 10, wherein the chemical inducer comprises salicylic acid, jasmonic acid, methyl ester of jasmonic acid, abscisic acid, ethylene, AgNO3, cycloheximide, mannitol, NaCl, flg22, elf18, or LPS.

12. A vector comprising the nucleic acid of claim 1.

13. The vector of claim 12, wherein the vector is selected from the group consisting of pGX1 of SEQ ID NO: 132, pGX179 of SEQ ID NO: 133, pGX180 of SEQ ID NO: 134, and pGX181 of SEQ ID NO: 135.

14. A modified cell comprising the nucleic acid of claim 1.

15. A modified cell comprising the vector of claim 12.

16. A transgenic plant comprising the nucleic acid of claim 1.

17. The nucleic acid of claim 3, wherein the uORF modulates expression of an open reading frame cloned into the synthetic polylinker or the ligation independent cloning sequence.

18. The nucleic acid of claim 4, wherein the uORF modulates expression of the dORF.

* * * * *

SEQUENCE LISTING

<160> NUMBER OF SEQ ID NOS: 160

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
atggctcggc tcgct                                                    15

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gagatcaagc aacaatgcag a                                             21

<210> SEQ ID NO 3

```
<211> LENGTH: 20
<212> TYPE: DNA
<213> ORGANISM: Artificial Sequence
<220> FEATURE:
<223> OTHER INFORMATION: Synthetic

<400> SEQUENCE: 3
tcgggcactg gacctattta                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cggaaacttt tgcgtacgat                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggccacgatt actccaacac                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tcgcttttta tggaagacga a                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ggttccggtt cttttccact                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tgtgttggag taatcgtggc                                                   20

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
```
ggtacgcaga tcggattcga gtaaaac                           27

<210> SEQ ID NO 10
<211> LENGTH: 29
<212> TYPE: DNA
<213> ORGANISM: Artificial Sequence
<220> FEATURE:
<223> OTHER INFORMATION: Synthetic

<400> SEQUENCE: 10
ttatagccaa ttgatccgaa ccaaaaccg                         29

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
catccaaaaa tatattagta cgagcc                            26

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
ccatcaccgt taacaaagaa a                                 21

<210> SEQ ID NO 13
<211> LENGTH: 17
<212> TYPE: DNA
<213> ORGANISM: Artificial Sequence
<220> FEATURE:
<223> OTHER INFORMATION: Synthetic

<400> SEQUENCE: 13
gacgcttcat ctcgtcc                                      17

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
gtaaacgtag gtgagtcca                                    19

<210> SEQ ID NO 15
<211> LENGTH: 16
<212> TYPE: DNA
<213> ORGANISM: Artificial Sequence
<220> FEATURE:
<223> OTHER INFORMATION: Synthetic

<400> SEQUENCE: 15
gttggttcgc cttctg                                       16

<210> SEQ ID NO 16
<211> LENGTH: 16
<212> TYPE: DNA

```
<213> ORGANISM: Artificial Sequence
<220> FEATURE:
<223> OTHER INFORMATION: Synthetic

<400> SEQUENCE: 16
ccacacccca aacaat                                                   16

<210> SEQ ID NO 17
<211> LENGTH: 16
<212> TYPE: DNA
<213> ORGANISM: Artificial Sequence
<220> FEATURE:
<223> OTHER INFORMATION: Synthetic

<400> SEQUENCE: 17
gacgccaacg gtattc                                                   16

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
tgtctccagg gcattc                                                   16

<210> SEQ ID NO 19
<211> LENGTH: 16
<212> TYPE: DNA
<213> ORGANISM: Artificial Sequence
<220> FEATURE:
<223> OTHER INFORMATION: Synthetic

<400> SEQUENCE: 19
atgaccccaa cgatgt                                                   16

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
ccttgtagtt cgggttct                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
ctcatacact ctggtggg                                                 18

<210> SEQ ID NO 22
<211> LENGTH: 16
<212> TYPE: DNA
<213> ORGANISM: Artificial Sequence
<220> FEATURE:
<223> OTHER INFORMATION: Synthetic

<400> SEQUENCE: 22
ttggcacatc cgagtc                                                   16
```

<210> SEQ ID NO 23
<211> LENGTH: 16
<212> TYPE: DNA
<213> ORGANISM: Artificial Sequence
<220> FEATURE:
<223> OTHER INFORMATION: Synthetic

<400> SEQUENCE: 23
agcactcgaa tcccaa                                                       16

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
gcctccgaca gtttca                                                       16

<210> SEQ ID NO 25
<211> LENGTH: 16
<212> TYPE: DNA
<213> ORGANISM: Artificial Sequence
<220> FEATURE:
<223> OTHER INFORMATION: Synthetic

<400> SEQUENCE: 25
ctgtggtggt ggctac                                                       16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
gtctcacatg ggacct                                                       16

<210> SEQ ID NO 27
<211> LENGTH: 17
<212> TYPE: DNA
<213> ORGANISM: Artificial Sequence
<220> FEATURE:
<223> OTHER INFORMATION: Synthetic

<400> SEQUENCE: 27
aaacatgtct cgaatgt                                                      17

<210> SEQ ID NO 28
<211> LENGTH: 17
<212> TYPE: DNA
<213> ORGANISM: Artificial Sequence
<220> FEATURE:
<223> OTHER INFORMATION: Synthetic

<400> SEQUENCE: 28
gattcctatg gttgaca                                                      17

<210> SEQ ID NO 29
<211> LENGTH: 16
<212> TYPE: DNA
<213> ORGANISM: Artificial Sequence
<220> FEATURE:

<223> OTHER INFORMATION: Synthetic

<400> SEQUENCE: 29
cccatgtcta caccgc                                                    16

<210> SEQ ID NO 30
<211> LENGTH: 17
<212> TYPE: DNA
<213> ORGANISM: Artificial Sequence
<220> FEATURE:
<223> OTHER INFORMATION: Synthetic

<400> SEQUENCE: 30
cacggcattt ggatcag                                                   17

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
acccaaacag acgcattaca g                                              21

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
ctccttgatg ttctcttccg tc                                             22

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
atcgcagatt tggagagtga g                                              21

<210> SEQ ID NO 34
<211> LENGTH: 22
<212> TYPE: DNA
<213> ORGANISM: Artificial Sequence
<220> FEATURE:
<223> OTHER INFORMATION: Synthetic

<400> SEQUENCE: 34
tgtagccata aacctcatcc ag                                             22

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tcttgatgtc gggaatgtgg                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
agttgctgat cggttaaggg                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ttctacacct ccaacatgcc                                               20

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
ctctgattct ttccactgtc cc                                            22

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tgtgtatcct ctgtttgcgg                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
tgcattcata gagcccttgg                                               20

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
acatctcaca ccaaacccaa c                                             21

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
taaggctgga tggtcaatcg                                           20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
aacctaccac gaacaccatc                                           20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
actacataag cggccatcag                                           20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
caaaccaaga gccggaaatc                                           20

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
tccccagtgt gcttatcaat g                                         21

<210> SEQ ID NO 47
<211> LENGTH: 19
<212> TYPE: DNA
<213> ORGANISM: Artificial Sequence
<220> FEATURE:
<223> OTHER INFORMATION: Synthetic

<400> SEQUENCE: 47
tgctccacac tgacacttg                                            19

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gcgaggattt gagtgatgtt g                                         21

<210> SEQ ID NO 49
<211> LENGTH: 21

```
<212> TYPE: DNA
<213> ORGANISM: Artificial Sequence
<220> FEATURE:
<223> OTHER INFORMATION: Synthetic

<400> SEQUENCE: 49
aatggctggt aaaggagaag g                                              21

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
ctatcagtga aggcgacgta ag                                             22

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
aaatctcgtg tctggctcg                                                 19

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
aggtgagagg ttggagagg                                                 19

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
aagagaacac tccttccgtt g                                              21

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
tgaccttgct tatcccacac                                                20

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
```

-continued gagatccagt tccttgtgag ag                                                      22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
attccacctt catcttccct tc                                                      22

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
cgaaaagata catccggcaa c                                                       21

<210> SEQ ID NO 58
<211> LENGTH: 23
<212> TYPE: DNA
<213> ORGANISM: Artificial Sequence
<220> FEATURE:
<223> OTHER INFORMATION: Synthetic

<400> SEQUENCE: 58
gattcagagc ttgttcaaca gtg                                                     23

<210> SEQ ID NO 59
<211> LENGTH: 22
<212> TYPE: DNA
<213> ORGANISM: Artificial Sequence
<220> FEATURE:
<223> OTHER INFORMATION: Synthetic

<400> SEQUENCE: 59
cctcgtgaag tgccagttat ag                                                      22

<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
ggattgtgct tgagtttcgt g                                                       21

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
aagatccatg acatcgccg                                                          19

<210> SEQ ID NO 62
<211> LENGTH: 20
<212> TYPE: DNA
<213> ORGANISM: Artificial Sequence

```
<220> FEATURE:
<223> OTHER INFORMATION: Synthetic

<400> SEQUENCE: 62
aggtagaggt tcatcggagg                                                   20

<210> SEQ ID NO 63
<211> LENGTH: 22
<212> TYPE: DNA
<213> ORGANISM: Artificial Sequence
<220> FEATURE:
<223> OTHER INFORMATION: Synthetic

<400> SEQUENCE: 63
gtggatgttg accgtacagt ag                                                22

<210> SEQ ID NO 64
<211> LENGTH: 22
<212> TYPE: DNA
<213> ORGANISM: Artificial Sequence
<220> FEATURE:
<223> OTHER INFORMATION: Synthetic

<400> SEQUENCE: 64
cttggaacta tcaccctcga tc                                                22

<210> SEQ ID NO 65
<211> LENGTH: 22
<212> TYPE: DNA
<213> ORGANISM: Artificial Sequence
<220> FEATURE:
<223> OTHER INFORMATION: Synthetic

<400> SEQUENCE: 65
gcttctcatc ctctgtatca cc                                                22

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
aaccgagtct tgaaccatag c                                                 21

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
tggattcgag cagaaaggta c                                                 21

<210> SEQ ID NO 68
<211> LENGTH: 18
<212> TYPE: DNA
<213> ORGANISM: Artificial Sequence
<220> FEATURE:
<223> OTHER INFORMATION: Synthetic

<400> SEQUENCE: 68
tgggttaggc cgtgtttg                                                     18
```

```
<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
gaaccgatat ccaccttgtc c                                           21

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
tgaggaaatc actgtccgtg                                             20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
tgacaaagta cccaacggag                                             20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
atgtctgtga tctgaacgcc                                             20

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
tccttctcgc ctctatcctt ac                                          22

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
cagtccaagc cacatatctc g                                           21

<210> SEQ ID NO 75
<211> LENGTH: 22
<212> TYPE: DNA
<213> ORGANISM: Artificial Sequence
<220> FEATURE:
<223> OTHER INFORMATION: Synthetic
```

-continued

<400> SEQUENCE: 75
ggagggatat gataatgggt cg					22

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
accttctgat ctaacctttg agc					23

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
ttgcctctga aatgagtccg					20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
tgctcttccc ctttgttctc					20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
ttgcctctga aatgagtccg					20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
tgctcttccc ctttgttctc					20

<210> SEQ ID NO 81
<211> LENGTH: 57
<212> TYPE: DNA
<213> ORGANISM: Artificial Sequence
<220> FEATURE:
<223> OTHER INFORMATION: Synthetic

<400> SEQUENCE: 81
ggggacaagt ttgtacaaaa aagcaggctt aatgacggct gtgacggcgg cgcaaag					57

<210> SEQ ID NO 82

<211> LENGTH: 55
<212> TYPE: DNA
<213> ORGANISM: Artificial Sequence
<220> FEATURE:
<223> OTHER INFORMATION: Synthetic

<400> SEQUENCE: 82
ggggaccact tgtacaaga aagctgggtc ttagttgcag actttgctgc ttttc          55

<210> SEQ ID NO 83
<211> LENGTH: 55
<212> TYPE: DNA
<213> ORGANISM: Artificial Sequence
<220> FEATURE:
<223> OTHER INFORMATION: Synthetic

<400> SEQUENCE: 83
ggggaccact tgtacaaga aagctgggtc gttgcagact tgctgctttt cctc           55

<210> SEQ ID NO 84
<211> LENGTH: 59
<212> TYPE: DNA
<213> ORGANISM: Artificial Sequence
<220> FEATURE:
<223> OTHER INFORMATION: Synthetic

<400> SEQUENCE: 84
ggggacaagt tgtacaaaa aagcaggctt acgacgacta gtttacagag aatttggac      59

<210> SEQ ID NO 85
<211> LENGTH: 56
<212> TYPE: DNA
<213> ORGANISM: Artificial Sequence
<220> FEATURE:
<223> OTHER INFORMATION: Synthetic

<400> SEQUENCE: 85
ggggacaagt tgtacaaaa aagcaggctt attccggttc ttttccactc ctaatg         56

<210> SEQ ID NO 86
<211> LENGTH: 53
<212> TYPE: DNA
<213> ORGANISM: Artificial Sequence
<220> FEATURE:
<223> OTHER INFORMATION: Synthetic

<400> SEQUENCE: 86
ggggaccact tgtacaaga aagctgggtc atcggaaact tttgcgtacg atc            53

<210> SEQ ID NO 87
<211> LENGTH: 54
<212> TYPE: DNA
<213> ORGANISM: Artificial Sequence
<220> FEATURE:
<223> OTHER INFORMATION: Synthetic

<400> SEQUENCE: 87
ggggacaagt tgtacaaaa aagcaggctt atttcttaca aaggtaggac caac           54

<210> SEQ ID NO 88
<211> LENGTH: 52
<212> TYPE: DNA
<213> ORGANISM: Artificial Sequence
<220> FEATURE:
<223> OTHER INFORMATION: Synthetic

<400> SEQUENCE: 88

```
ggggaccact tgtacaaga aagctgggtc gtaagtgttg agctgacgaa tg        52
```

<210> SEQ ID NO 89
<211> LENGTH: 31
<212> TYPE: DNA
<213> ORGANISM: Artificial Sequence
<220> FEATURE:
<223> OTHER INFORMATION: Synthetic

<400> SEQUENCE: 89

```
gctccggcga agtctggtcg tcgtcttcat c                              31
```

<210> SEQ ID NO 90
<211> LENGTH: 31
<212> TYPE: DNA
<213> ORGANISM: Artificial Sequence
<220> FEATURE:
<223> OTHER INFORMATION: Synthetic

<400> SEQUENCE: 90

```
gatgaagacg acgaccagac ttcgccggag c                              31
```

<210> SEQ ID NO 91
<211> LENGTH: 30
<212> TYPE: DNA
<213> ORGANISM: Artificial Sequence
<220> FEATURE:
<223> OTHER INFORMATION: Synthetic

<400> SEQUENCE: 91

```
gatttttcct taactggaag aaaccaaacg                                30
```

<210> SEQ ID NO 92
<211> LENGTH: 30
<212> TYPE: DNA
<213> ORGANISM: Artificial Sequence
<220> FEATURE:
<223> OTHER INFORMATION: Synthetic

<400> SEQUENCE: 92

```
cgtttggttt cttccagtta aggaaaaatc                                30
```

<210> SEQ ID NO 93
<211> LENGTH: 57
<212> TYPE: DNA
<213> ORGANISM: Artificial Sequence
<220> FEATURE:
<223> OTHER INFORMATION: Synthetic

<400> SEQUENCE: 93

```
gagaaattga agagcgcaac gaactacgag cggatccttt cttacaaagg taggacc   57
```

<210> SEQ ID NO 94
<211> LENGTH: 55
<212> TYPE: DNA
<213> ORGANISM: Artificial Sequence
<220> FEATURE:
<223> OTHER INFORMATION: Synthetic

<400> SEQUENCE: 94

```
ggacacggcg acgatgcagt tcaatggtcg aacgtaagtg ttgagctgac gaatg     55
```

<210> SEQ ID NO 95
<211> LENGTH: 25
<212> TYPE: DNA

```
<213> ORGANISM: Artificial Sequence
<220> FEATURE:
<223> OTHER INFORMATION: Synthetic

<400> SEQUENCE: 95
tccagtgctg aagaagaatt ctacg                                          25

<210> SEQ ID NO 96
<211> LENGTH: 25
<212> TYPE: DNA
<213> ORGANISM: Artificial Sequence
<220> FEATURE:
<223> OTHER INFORMATION: Synthetic

<400> SEQUENCE: 96
tccagtgtca tcacgtgttt ctacg                                          25

<210> SEQ ID NO 97
<211> LENGTH: 59
<212> TYPE: DNA
<213> ORGANISM: Artificial Sequence
<220> FEATURE:
<223> OTHER INFORMATION: Synthetic

<400> SEQUENCE: 97
agcgtggatc gaacacgcga ccttcagatc ttcagtctga cgctctccca actgagcta     59

<210> SEQ ID NO 98
<211> LENGTH: 59
<212> TYPE: DNA
<213> ORGANISM: Artificial Sequence
<220> FEATURE:
<223> OTHER INFORMATION: Synthetic

<400> SEQUENCE: 98
gccggggatc gaacccgggt cacccgcgtg acaggcggga atacttacca ctatactac     59

<210> SEQ ID NO 99
<211> LENGTH: 9
<212> TYPE: DNA
<213> ORGANISM: Arabidopsis thaliana
<220> FEATURE:
<221> NAME/KEY: protein_bind
<222> LOCATION: (1)..(9)
<223> OTHER INFORMATION: Exact (non-degenerate) TL1 transcriptional
      protein binding motif

<400> SEQUENCE: 99 gaagaagaa                                                             9

<210> SEQ ID NO 100
<211> LENGTH: 9
<212> TYPE: DNA
<213> ORGANISM: Arabidopsis thaliana
<220> FEATURE:
<221> NAME/KEY: protein_bind
<222> LOCATION: (1)..(9)
<223> OTHER INFORMATION: GnnnGnnnn, approximating degenerate motifs,
      G-(A/G)-(AGT)-G-(ACG)-(ACG)-(ACG)-(AC)-(ACGT)-n as noted in the
      frequencies specified in the weight matrix of Table S2
<220> FEATURE:
<221> NAME/KEY: protein_bind
<222> LOCATION: (1)..(9)
<223> OTHER INFORMATION: GnnnGnnnn, approximating degenerate motifs,
      G-(A/G)-(AGT)-G-(ACG)-(ACG)-(ACG)-(AC)-(ACGT) as noted in the
      frequencies specified in the weight matrix of Table S2
<220> FEATURE:
<221> NAME/KEY: misc_feature
<222> LOCATION: (2)..(4)
```

<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t

<400> SEQUENCE: 100 gnnngnnnn                                                                9

<210> SEQ ID NO 101
<211> LENGTH: 5085
<212> TYPE: DNA
<213> ORGANISM: Arabidopsis thaliana
<220> FEATURE:
<221> NAME/KEY: promoter
<222> LOCATION: (1)..(3110)
<223> OTHER INFORMATION: TBF1 promoter region
<220> FEATURE:
<221> NAME/KEY: 5'UTR
<222> LOCATION: (3111)..(3328)
<220> FEATURE:
<221> NAME/KEY: CDS
<222> LOCATION: (3329)..(3376)
<223> OTHER INFORMATION: uORF1 CDS
<220> FEATURE:
<221> NAME/KEY: CDS
<222> LOCATION: (3377)..(3487)
<223> OTHER INFORMATION: uORF2 CDS
<220> FEATURE:
<221> NAME/KEY: CDS
<222> LOCATION: (3594)..(3812)
<223> OTHER INFORMATION: TBF1 exon 1
<220> FEATURE:
<221> NAME/KEY: Intron
<222> LOCATION: (3813)..(4004)
<223> OTHER INFORMATION: TBF1 intron
<220> FEATURE:
<221> NAME/KEY: CDS
<222> LOCATION: (4005)..(4640)
<223> OTHER INFORMATION: TBF1 exon 2
<220> FEATURE:
<221> NAME/KEY: 3'UTR
<222> LOCATION: (4641)..(5085)

<400> SEQUENCE: 101
aaaattttca ggcgaatttt ggcgataatt ttatatttcc gacgactagt ttacagagaa      60
tttggaccgt ccgatgtaaa gcgaaaatag atctaggttt tccacgtgtc ccctatttta     120
atgaaacctt ctgattcatg tagaagtttt actcaattta atatttttta gtatgtagtt     180
ttgtgtgtgt gtgtgtgtgt gttttatgg ctccacacca acttttaaaa tggtagaagc     240
atgttgcatg tgatcgagta aaaagccaat aatgagattc agaaaaataa aaattactta     300
tatagttttt tagagaaaaa attgtatttt gtttaaagcc ttaatccggt tgttgaaaga     360
gctgtgtcac gagttaaaaa tattttcttt tcattttta agtaattagt ttataatgca     420
aaaatggttt ttatttattt gtcttcgctt atagaactgc aaattgagag agaaaaaat     480 gaattagtgg tggtgaccaa acattcagga agctgtgatt gatcatttgt ttttgaggtg     540
agtgtagtgg caacgtatga cgttaacata tggcgtacat aataattaca tgaacttaat     600
cataataatc atattgcatt taattcatat atcatatccc attagttgga ccacttgatt     660
tgaggtcatg agaagaacat ttatgttttt tttagtttga atcggagtga tcactaaaaa     720
ctagatactg aaaattttca aactaaaatc atattaatct tcaaaaaatg tgaaatctaa     780
aaaaaaaaaa aattttaacg cgttcattgt agccaagtag ccaagtattg ttaaagtagt     840
agtaaaagaa gtttagcttt aagtgatata atttgacaca aatcctactt agatatggat     900
aataggatat agcttcatgt atattttat cgttgcttct gtaaccccaa aatgtgttga     960

```
tataagcatt tgaatattcg tatgtataat gttttctttt caccgtaaaa catattacaa       1020
tgttagttta tattggattt tgaatgtgtt tatgaacagt ttttgtcgac tcaaaagtta       1080
agatgagaat atggaagaaa gtaaagttta aaagtcatga tgggaacaag gaatggaact       1140
caaacattct aatactcaac aaacgcaatt atattattac catgactcat ctttcaagtt       1200
ccatcaaaaa gattcgtgga aataatagsa cttacgtttc aaatccatgt ttctttcttt       1260
ataacaaaaa aaatggatgt ttcttgacgc gtgtcgagag tactcaccat tactctgact       1320
tcagtgagtt tggtcaagtg gtctttttt ttctcatgtc accaaaggtc caaaccctag        1380
aaattagttc gaactttcca tagaagaact gaataaatgg tccaaaattg ttttaaaaag       1440
gacctaagcc attagttcat tgaattcgag ttaatgggtg aagatttta tgataacgaa        1500 agtcggagta attatgcttt tggtccgata gttttctaat ttgttttctt tccatttttt       1560
ttttttcaaa tactacatac tatataagat agtggtttgt gttaatgtca tcgatgtgtt      1620
accatccgca ttatattaat tatttatccc aacataaagt cagaatctgt aatttctttg       1680
ttataaaata cagtaaatgg ttccgtttaa gctgttagat gatttttgag taaaaactaa       1740
tgtaaaaaaa acaaaaaaaa aacaatgtag ttcataatac atgcatgttt taagaagtt        1800 tcttgtttac tatcaacttg aatagtattt cacgaagtca aaattgttca ttccgacttt       1860
tctatgtgga gaaaaaaat tctatcattg tgcacaattt aacagaatgt aatttcttgt        1920 aaagaagag gaaacaattc gctgttagta aatgtgaagt atagaagtct aaaatgagat        1980
acctcaacta gcttgaatta agaaaaaaaa caaaaactct atcgacatga aaaggtcgc        2040 aaatatttat catttatcaa tgccaaagga gtatttggtt cacaaaatac tgaatcattt      2100
atatagatat ataattagct ctaaattcta ctataacttg caaaataagt atactgactc       2160
aattatatag cgtttaaaaa tagacgattt gtatgatgag gtccatatat atggagatgt       2220
gcatgcaact atcgacattt tcacacgttg atatcgtctt tctccaatgg agacttgaat       2280
ttgtgtaaac tatgaatact cgtctctcta agaccttttt tcttcaacca tgccaactat      2340
ttaggtaaga ttttactgtc tttgattgat attaaatact tagccgtggc gttatcaatg       2400
aatgataata aaaatgcgga taaaagccaa aggtgttgga aataaatcca agaatgaaga       2460
cgtagatgtc gatgggtatt ttaagaactt gaatttgtca cgactcacac gttaaaatat       2520
attatccgaa ttgtttagtc taaagacaca catatattga aaaagaaaag gtaaatgaag       2580
ctcattggtg cctaaatgtg aaatgaagcc gaaatgtgtt aggtgaacac atttaaatat       2640 acaaaagaa atataataga aacaaaacta attaacaaag tcgcaatttg tattgtataa       2700
aatatctttc cgtctcccgt catatttgaa aaaaaaaaa ttacaaatct gttaattta        2760 aaactttcta gaaaaacaca agtatataat tttctctttt cgtgcgtgtt tgttttaaaa      2820
taacattgtt ttgattggcg actcaacata ttttagcatt tacatatttc tgcatatatt      2880
aaatgattta taaactcaac tatagattaa aatataattt gacatctaat aattttaaca      2940
ataatataaa atatgagatt tataaattac gaatataaat attcaaggga gagaaaaagt      3000
agaacataat tcaaaagata agactttta gactttttta acaatatttt tgatggataa       3060
aaattattca aaagagaaga aagtaagaag aaaagatgtt tctgagaatt tctagaaaca     3120
gcatccgttt ttataattta attttcttac aaaggtagga ccaacatttg tgatctataa     3180
atcttcctac tacgttatat agagacccctt cgacataaca cttaactcgt ttatatattt    3240
gttttacttg ttttgcacat acacacaaaa ataaaaaaga ctttatattt atttactttt    3300
```

-continued

```
taatcacacg gattagctcc ggcgaagt atg gtc gtc gtc ttc atc ttc ttc    3352
                              Met Val Val Val Phe Ile Phe Phe
                              1               5 ctc cat cat cag att ttt cct taa atg gaa gaa acc aaa cga aac tcc    3400
Leu His His Gln Ile Phe Pro     Met Glu Glu Thr Lys Arg Asn Ser
10              15                              20 gat ctt ctc cgt tct cgt gtt ttc ctc tct ggc ttt tat tgc tgg gat    3448
Asp Leu Leu Arg Ser Arg Val Phe Leu Ser Gly Phe Tyr Cys Trp Asp
    25              30                  35 tgg gaa ttt ctc acc gct ctc ttg ctt ttt agt tgc tga ttcttttttcc    3497
Trp Glu Phe Leu Thr Ala Leu Leu Leu Phe Ser Cys
40              45              50 ttcgactttc tatttccaat ctttcttctt ctctttgtgt attagattat ttttagtttt    3557
atttttctgt ggtaaaataa aaaaagttcg ccggag atg acg gct gtg acg gcg    3611
                                        Met Thr Ala Val Thr Ala
                                                            55 gcg caa aga tca gtt ccg gcg ccg ttt tta agc aaa acg tat cag cta    3659
Ala Gln Arg Ser Val Pro Ala Pro Phe Leu Ser Lys Thr Tyr Gln Leu
        60                  65                  70 gtt gat gat cat agc aca gac gtc gtt tca tgg aac gaa gaa gga        3707
Val Asp Asp His Ser Thr Asp Val Val Ser Trp Asn Glu Glu Gly
75              80                  85 aca gct ttt gtc gtg tgg aaa aca gca gag ttt gct aaa gat ctt ctt    3755
Thr Ala Phe Val Val Trp Lys Thr Ala Glu Phe Ala Lys Asp Leu Leu
90              95                  100                 105 cct caa tac ttc aag cat aat aat ttc tca agc ttc att cgt cag ctc    3803
Pro Gln Tyr Phe Lys His Asn Asn Phe Ser Ser Phe Ile Arg Gln Leu
            110                 115                 120 aac act tac gtgagtttca ctctaacgaa aactcattta ctctcaattt            3852
Asn Thr Tyr aatgcttcat ttaattcgtt tggtgaattg aatcattctt ttgtagttgg ttagccaatt   3912
tcgtaatttt ctcataattt gggggttggt gagaaaacct tctagaagct gagaatgttc   3972
ttgttctttt tttttttttt ttttggtttt ag gga ttt cgt aaa act gta ccg    4025
                                 Gly Phe Arg Lys Thr Val Pro
                                 125             130 gat aaa tgg gaa ttt gca aac gat tat ttc cgg aga ggc ggg gag gat    4073
Asp Lys Trp Glu Phe Ala Asn Asp Tyr Phe Arg Arg Gly Gly Glu Asp
    135                 140                 145 ctg ttg acg gac ata cga cgg cgt aaa tcg gtg att gct tca acg gcg    4121
Leu Leu Thr Asp Ile Arg Arg Arg Lys Ser Val Ile Ala Ser Thr Ala
        150                 155                 160 ggg aaa tgt gtt gtt gtt ggt tcg cct tct gag tct aat tct ggt ggt    4169
Gly Lys Cys Val Val Val Gly Ser Pro Ser Glu Ser Asn Ser Gly Gly
165             170                 175 ggt gat gat cac ggt tca agc tcc acg tca tca ccc ggt tcg tcg aag    4217
Gly Asp Asp His Gly Ser Ser Ser Thr Ser Ser Pro Gly Ser Ser Lys
180             185                 190                 195 aat cct ggt tcg gtg gag aac atg gtt gct gat tta tca gga gag aac    4265
Asn Pro Gly Ser Val Glu Asn Met Val Ala Asp Leu Ser Gly Glu Asn
            200                 205                 210 gag aag ctt aaa cgt gaa aac aat aac ttg agc tcg gag ctc gcg gcg    4313
Glu Lys Leu Lys Arg Glu Asn Asn Asn Leu Ser Ser Glu Leu Ala Ala
            215                 220                 225 gcg aag aag cag cgc gat gag cta gtg acg ttc ttg acg ggt cat ctg    4361
Ala Lys Lys Gln Arg Asp Glu Leu Val Thr Phe Leu Thr Gly His Leu
        230                 235                 240 aaa gta aga ccg gaa caa atc gat aaa atg atc aaa gga ggg aaa ttt    4409
Lys Val Arg Pro Glu Gln Ile Asp Lys Met Ile Lys Gly Gly Lys Phe
```

```
                245                 250                 255
aaa ccg gtg gag tct gac gaa gag agt gag tgc gaa ggt tgc gac ggc       4457
Lys Pro Val Glu Ser Asp Glu Glu Ser Glu Cys Glu Gly Cys Asp Gly
260                 265                 270                 275 ggc gga gga gca gag gag ggg gta ggt gaa gga ttg aaa ttg ttt ggg       4505
Gly Gly Gly Ala Glu Glu Gly Val Gly Glu Gly Leu Lys Leu Phe Gly
                280                 285                 290 gtg tgg ttg aaa gga gag aga aaa aag agg gac cgg gat gaa aag aat       4553
Val Trp Leu Lys Gly Glu Arg Lys Lys Arg Asp Arg Asp Glu Lys Asn
            295                 300                 305 tat gtg gtg agt ggg tcc cgt atg acg gaa ata aag aac gtg gac ttt       4601
Tyr Val Val Ser Gly Ser Arg Met Thr Glu Ile Lys Asn Val Asp Phe
        310                 315                 320 cac gcg ccg ttg tgg aaa agc agc aaa gtc tgc aac taa aaaaagagta        4650
His Ala Pro Leu Trp Lys Ser Ser Lys Val Cys Asn
    325                 330                 335 gaagactgtt caaaccagcg tgtgacacgt catcgacgac gacgaaaaaa atgatttaaa     4710
aaactatttt tttccgtaag gaagaaaagt tattttatg ttttaaaaag gtgaagaagg      4770
tccagaagga tcaacgcaaa tatataaatg gattttcatg tattatataa tttaattagt    4830
gtattaagaa aataaaacag atgttgaagt tttattgttg cttaatttat gtcttcataa    4890
tgtaaaaaag catgtgaaat acttggtcta aggtcatcta cttagttgaa aacttgtgaa    4950
agaggaagaa attttacttt tatgtttgat tgattttctt tgcaagtagt agtaggtggt    5010
ttccgtgttt ttacgtaatc cgttgaatat ttttccctcg aaattgtctt tataaaagtc    5070
acagaaacat tttct                                                     5085

<210> SEQ ID NO 102
<211> LENGTH: 15
<212> TYPE: PRT
<213> ORGANISM: Arabidopsis thaliana

<400> SEQUENCE: 102

Met Val Val Val Phe Ile Phe Phe Leu His His Gln Ile Phe Pro
1               5                   10                  15

<210> SEQ ID NO 103
<211> LENGTH: 36
<212> TYPE: PRT
<213> ORGANISM: Arabidopsis thaliana

<400> SEQUENCE: 103

Met Glu Glu Thr Lys Arg Asn Ser Asp Leu Leu Arg Ser Arg Val Phe
1               5                   10                  15

Leu Ser Gly Phe Tyr Cys Trp Asp Trp Glu Phe Leu Thr Ala Leu Leu
            20                  25                  30

Leu Phe Ser Cys
        35

<210> SEQ ID NO 104
<211> LENGTH: 73
<212> TYPE: PRT
<213> ORGANISM: Arabidopsis thaliana

<400> SEQUENCE: 104

Met Thr Ala Val Thr Ala Ala Gln Arg Ser Val Pro Ala Pro Phe Leu
1               5                   10                  15

Ser Lys Thr Tyr Gln Leu Val Asp Asp His Ser Thr Asp Asp Val Val
            20                  25                  30
```

```
Ser Trp Asn Glu Glu Gly Thr Ala Phe Val Val Trp Lys Thr Ala Glu
            35                  40                  45

Phe Ala Lys Asp Leu Leu Pro Gln Tyr Phe Lys His Asn Asn Phe Ser
 50                  55                  60

Ser Phe Ile Arg Gln Leu Asn Thr Tyr
 65                  70

<210> SEQ ID NO 105
<211> LENGTH: 211
<212> TYPE: PRT
<213> ORGANISM: Arabidopsis thaliana

<400> SEQUENCE: 105

Gly Phe Arg Lys Thr Val Pro Asp Lys Trp Glu Phe Ala Asn Asp Tyr
 1               5                  10                  15

Phe Arg Arg Gly Gly Glu Asp Leu Leu Thr Asp Ile Arg Arg Arg Lys
                20                  25                  30

Ser Val Ile Ala Ser Thr Ala Gly Lys Cys Val Val Gly Ser Pro
            35                  40                  45

Ser Glu Ser Asn Ser Gly Gly Gly Asp Asp His Gly Ser Ser Ser Thr
 50                  55                  60

Ser Ser Pro Gly Ser Ser Lys Asn Pro Gly Ser Val Glu Asn Met Val
 65                  70                  75                  80

Ala Asp Leu Ser Gly Glu Asn Glu Lys Leu Lys Arg Glu Asn Asn Asn
                85                  90                  95

Leu Ser Ser Glu Leu Ala Ala Ala Lys Lys Gln Arg Asp Glu Leu Val
            100                 105                 110

Thr Phe Leu Thr Gly His Leu Lys Val Arg Pro Glu Gln Ile Asp Lys
        115                 120                 125

Met Ile Lys Gly Gly Lys Phe Lys Pro Val Glu Ser Asp Glu Glu Ser
    130                 135                 140

Glu Cys Glu Gly Cys Asp Gly Gly Gly Ala Glu Glu Gly Val Gly
145                 150                 155                 160

Glu Gly Leu Lys Leu Phe Gly Val Trp Leu Lys Gly Glu Arg Lys Lys
                165                 170                 175

Arg Asp Arg Asp Glu Lys Asn Tyr Val Val Ser Gly Ser Arg Met Thr
            180                 185                 190

Glu Ile Lys Asn Val Asp Phe His Ala Pro Leu Trp Lys Ser Ser Lys
        195                 200                 205

Val Cys Asn
    210

<210> SEQ ID NO 106
<211> LENGTH: 284
<212> TYPE: PRT
<213> ORGANISM: Arabidopsis thaliana
<220> FEATURE:
<221> NAME/KEY: MISC_FEATURE
<222> LOCATION: (1)..(284)
<223> OTHER INFORMATION: Entire sequence of TBF1 polypeptide (fusing
      domains from first and second exons.

<400> SEQUENCE: 106

Met Thr Ala Val Thr Ala Ala Gln Arg Ser Val Pro Ala Pro Phe Leu
 1               5                  10                  15

Ser Lys Thr Tyr Gln Leu Val Asp Asp His Ser Thr Asp Asp Val Val
                20                  25                  30
```

Ser Trp Asn Glu Glu Gly Thr Ala Phe Val Val Trp Lys Thr Ala Glu
         35                  40                  45

Phe Ala Lys Asp Leu Leu Pro Gln Tyr Phe Lys His Asn Asn Phe Ser
 50                  55                  60

Ser Phe Ile Arg Gln Leu Asn Thr Tyr Gly Phe Arg Lys Thr Val Pro
 65                  70                  75                  80

Asp Lys Trp Glu Phe Ala Asn Asp Tyr Phe Arg Arg Gly Gly Glu Asp
                 85                  90                  95

Leu Leu Thr Asp Ile Arg Arg Arg Lys Ser Val Ile Ala Ser Thr Ala
                100                 105                 110

Gly Lys Cys Val Val Val Gly Ser Pro Ser Glu Ser Asn Ser Gly Gly
            115                 120                 125

Gly Asp Asp His Gly Ser Ser Ser Thr Ser Ser Pro Gly Ser Ser Lys
130                 135                 140

Asn Pro Gly Ser Val Glu Asn Met Val Ala Asp Leu Ser Gly Glu Asn
145                 150                 155                 160

Glu Lys Leu Lys Arg Glu Asn Asn Asn Leu Ser Ser Glu Leu Ala Ala
                165                 170                 175

Ala Lys Lys Gln Arg Asp Glu Leu Val Thr Phe Leu Thr Gly His Leu
                180                 185                 190

Lys Val Arg Pro Glu Gln Ile Asp Lys Met Ile Lys Gly Gly Lys Phe
            195                 200                 205

Lys Pro Val Glu Ser Asp Glu Glu Ser Glu Cys Glu Gly Cys Asp Gly
        210                 215                 220

Gly Gly Gly Ala Glu Glu Gly Val Gly Glu Gly Leu Lys Leu Phe Gly
225                 230                 235                 240

Val Trp Leu Lys Gly Glu Arg Lys Lys Arg Asp Arg Asp Glu Lys Asn
                245                 250                 255

Tyr Val Val Ser Gly Ser Arg Met Thr Glu Ile Lys Asn Val Asp Phe
                260                 265                 270

His Ala Pro Leu Trp Lys Ser Ser Lys Val Cys Asn
            275                 280

<210> SEQ ID NO 107
<211> LENGTH: 4601
<212> TYPE: DNA
<213> ORGANISM: Arabidopsis thaliana
<220> FEATURE:
<221> NAME/KEY: misc_feature
<222> LOCATION: (1)..(4601)
<223> OTHER INFORMATION: TBF1 genomic region with stop codon used for
      complementation experiments

<400> SEQUENCE: 107
cgacgactag tttacagaga atttggaccg tccgatgtaa agcgaaaata gatctaggtt      60
ttccacgtgt cccctatttt aatgaaacct tctgattcat gtagaagttt tactcaattt    120 aatattttt agtatgtagt tttgtgtgtg tgtgtgtgtg tgtttttatg gctccacacc     180
aacttttaaa atggtagaag catgttgcat gtgatcgagt aaaaagccaa taatgagatt    240
cagaaaaata aaaattactt atatagtttt ttagagaaaa aattgtattt tgtttaaagc    300
cttaatccgg ttgttgaaag agctgtgtca cgagttaaaa atatttttctt ttcattttt    360 aagtaattag tttataatgc aaaaatggtt tttattttatt tgtcttcgct tatagaactg    420
caaattgaga gagaaaaaaa tgaattagtg gtggtgacca acattcagg aagctgtgat     480 tgatcatttg ttttttgaggt gagtgtagtg gcaacgtatg acgttaacat atggcgtaca    540

```
taataattac atgaacttaa tcataataat catattgcat ttaattcata tatcatatcc      600
cattagttgg accacttgat ttgaggtcat gagaagaaca tttatgtttt ttttagtttg      660
aatcggagtg atcactaaaa actagatact gaaaattttc aaactaaaat catattaatc      720
ttcaaaaaat gtgaaatcta aaaaaaaaaa aaattttaac gcgttcattg tagccaagta      780
gccaagtatt gttaaagtag tagtaaaaga agtttagctt taagtgatat aatttgacac      840
aaatcctact tagatatgga taataggata tagcttcatg tatatttta tcgttgcttc      900
tgtaacccca aaatgtgttg ataaagcat ttgaatattc gtatgtataa tgttttcttt      960
tcaccgtaaa acatattaca atgttagttt atattggatt ttgaatgtgt ttatgaacag     1020
tttttgtcga ctcaaaagtt aagatgagaa tatggaagaa agtaaagttt aaaagtcatg     1080
atgggaacaa ggaatggaac tcaaacattc taatactcaa caaacgcaat tatattatta     1140
ccatgactca tctttcaagt tccatcaaaa agattcgtgg aaaataatag acttacgttt     1200
caaatccatg tttctttctt tataacaaaa aaatggatg tttcttgacg cgtgtcgaga     1260
gtactcacca ttactctgac ttcagtgagt ttggtcaagt ggtctttttt tttctcatgt     1320
caccaaaggt ccaaacccta gaaattagtt cgaactttcc atagaagaac tgaataaatg     1380
gtccaaaatt gttttaaaaa ggacctaagc cattagttca ttgaattcga gttaatgggt     1440
gaagatttt atgataacga aagtcggagt aattatgctt ttggtccgat agttttctaa     1500
tttgttttct ttccattttt ttttttttcaa atactacata ctatataaga tagtggtttg     1560
tgttaatgtc atcgatgtgt taccatccgc attatattaa ttatttatcc caacataaag     1620
tcagaatctg taatttcttt gttataaaat acagtaaatg gttccgttta agctgttaga     1680
tgatttttga gtaaaaacta atgtaaaaaa aacaaaaaaa aaacaatgta gttcataata     1740
catgcatgtt ttaaagaagt ttcttgttta ctatcaactt gaatagtatt tcacgaagtc     1800
aaaattgttc attccgactt ttctatgtgg agaaaaaaaa ttctatcatt gtgcacaatt     1860
taacagaatg taatttcttg taaaagaaga ggaaacaatt cgctgttagt aaatgtgaag     1920
tatagaagtc taaaatgaga tacctcaact agcttgaatt aagaaaaaaa acaaaaactc     1980
tatcgacatg aaaaggtcg caaatattta tcatttatca atgccaaagg agtatttggt     2040
tcacaaaata ctgaatcatt tatatagata tataattagc tctaaattct actataactt     2100
gcaaaataag tatactgact caattatata gcgtttaaaa atagacgatt tgtatgatga     2160
ggtccatata tatggagatg tgcatgcaac tatcgacatt ttcacacgtt gatatcgtct     2220
ttctccaatg gagacttgaa tttgtgtaaa ctatgaatac tcgtctctct aagacctttt     2280
tcttcaacc atgccaacta tttaggtaag attttactgt ctttgattga tattaaatac     2340
ttagccgtgg cgttatcaat gaatgataat aaaaatgcgg ataaaagcca aggtgttgg     2400
aaataaatcc aagaatgaag acgtagatgt cgatgggtat tttaagaact tgaatttgtc     2460
acgactcaca cgttaaaata tattatccga attgttagt ctaaagacac acatatattg     2520
aaaagaaaa ggtaaatgaa gctcattggt gcctaaatgt gaaatgaagc cgaaatgtgt     2580
taggtgaaca catttaaata tacaaaaga aatataatag aaacaaaact aattaacaaa     2640
gtcgcaattt gtattgtata aaatatcttt ccgtctcccg tcatatttga aaaaaaaaa     2700
attacaaatc tgttaatttt aaaactttct agaaaacac aagtatataa ttttctcttt     2760
tcgtgcgtgt ttgttttaaa ataacattgt tttgattggc gactcaacat attttagcat     2820
ttacatattt ctgcatatat taaatgattt ataaactcaa ctagattaa aaatataatt     2880
tgacatctaa taatttaac aataatataa aatatgagat ttataaatta cgaatataaa     2940
```

```
tattcaaggg agagaaaaag tagaacataa ttcaaaagat aagacttttt agactttttt    3000
aacaatattt ttgatggata aaaattattc aaaagagaag aaagtaagaa gaaaagatgt    3060
ttctgagaat ttctagaaac agcatccgtt tttataattt aattttctta caaaggtagg    3120
accaacattt gtgatctata aatcttccta ctacgttata tagagaccct tcgacataac    3180
acttaactcg tttatatatt tgttttactt gttttgcaca tacacacaaa aataaaaaag    3240
actttatatt tatttacttt ttaatcacac ggattagctc cggcgaagta tggtcgtcgt    3300
cttcatcttc ttcctccatc atcagatttt tccttaaatg gaagaaacca aacgaaactc    3360
cgatcttctc cgttctcgtg ttttcctctc tggcttttat tgctgggatt gggaatttct    3420
caccgctctc ttgcttttta gttgctgatt cttttccctt cgactttcta tttccaatct    3480
ttcttcttct ctttgtgtat tagattattt ttagttttat ttttctgtgg taaaataaaa    3540
aaagttcgcc ggagatgacg gctgtgacgg cggcgcaaag atcagttccg cgccgtttt    3600 taagcaaaac gtatcagcta gttgatgatc atagcacaga cgacgtcgtt tcatggaacg    3660
aagaaggaac agcttttgtc gtgtggaaaa cagcagagtt tgctaaagat cttcttcctc    3720
aatacttcaa gcataataat ttctcaagct tcattcgtca gctcaacact tacgtgagtt    3780
tcactctaac gaaaactcat ttactctcaa tttaatgctt catttaattc gtttggtgaa    3840
ttgaatcatt cttttgtagt tggttagcca atttcgtaat tttctcataa tttgggggtt    3900
ggtgagaaaa ccttctagaa gctgagaatg ttcttgttct tttttttttt tttttttttgg    3960 tttagggatt tcgtaaaact gtaccggata aatgggaatt tgcaaacgat tatttccgga    4020
gaggcgggga ggatctgttg acggacatac gacggcgtaa atcggtgatt gcttcaacgg    4080
cggggaaatg tgttgttgtt ggttcgcctt ctgagtctaa ttctggtggt ggtgatgatc    4140
acggttcaag ctccacgtca tcacccggtt cgtcgaagaa tcctggttcg gtggagaaca    4200
tggttgctga tttatcagga gagaacgaga agcttaaacg tgaaaacaat aacttgagct    4260
cggagctcgc ggcggcgaag aagcagcgcg atgagctagt gacgttcttg acgggtcatc    4320
tgaaagtaag accggaacaa atcgataaaa tgatcaaagg agggaaattt aaaccggtgg    4380
agtctgacga agagagtgag tgcgaaggtt gcgacggcgg cggaggagca gaggagggg    4440 taggtgaagg attgaaattg tttggggtgt ggttgaaagg agagagaaaa aagagggacc    4500
gggatgaaaa gaattatgtg gtgagtgggt cccgtatgac ggaaataaag aacgtggact    4560
ttcacgcgcc gttgtggaaa agcagcaaag tctgcaacta a                       4601

<210> SEQ ID NO 108
<211> LENGTH: 670
<212> TYPE: DNA
<213> ORGANISM: Arabidopsis thaliana
<220> FEATURE:
<221> NAME/KEY: misc_feature
<222> LOCATION: (1)..(670)
<223> OTHER INFORMATION: uORF1-uORF2-TBF1 1st exon region

<400> SEQUENCE: 108
tttcttacaa aggtaggacc aacatttgtg atctataaat cttcctacta cgttatatag      60
agacccttcg acataacact taactcgttt atatatttgt tttacttgtt ttgcacatac     120
acacaaaaat aaaaaagact ttatatttat ttactttttta atcacacgga ttagctccgg    180
cgaagtatgg tcgtcgtctt catcttcttc ctccatcatc agattttttcc ttaaatggaa    240 gaaaccaaac gaaactccga tcttctccgt tctcgtgttt tcctctctgg cttttattgc     300
```

```
tgggattggg aatttctcac cgctctcttg cttttagtt gctgattctt tttccttcga    360
ctttctattt ccaatctttc ttcttctctt tgtgtattag attatttta gttttatttt    420 tctgtggtaa aataaaaaaa gttcgccgga gatgacggct gtgacggcgg cgcaaagatc   480
agttccggcg ccgtttttaa gcaaaacgta tcagctagtt gatgatcata gcacagacga   540
cgtcgtttca tggaacgaag aaggaacagc ttttgtcgtg tggaaaacag cagagtttgc   600
taaagatctt cttcctcaat acttcaagca taataatttc tcaagcttca ttcgtcagct   660
caacacttac                                                          670

<210> SEQ ID NO 109
<211> LENGTH: 352
<212> TYPE: DNA
<213> ORGANISM: Saccharomyces cerevisiae
<220> FEATURE:
<221> NAME/KEY: promoter
<222> LOCATION: (1)..(352)
<223> OTHER INFORMATION: 352 bp BIP2 promoter region used in yeast 2
      hybrid studies

<400> SEQUENCE: 109
ttccggttct tttccactcc taatgatgta atagaagaag actggcccaa caaaagctca    60
ttgtctaatt aagaagaaga acgaagtaa ccaacggcca cgattactcc aacacaagac    120
caaatctgat tggttgacat tatagatcgt cgtaagataa ttggtccacg tcatctccga   180
tgacatagtt aaatttcttc gtcttccata aaaagcgact acttcaccat caccttcggg   240
cactggacct atttaagcat cctaacttct tcttcaaagc ttaaaaacca gaaaacaaaa   300
ggaagctctc tgttcaaatc aaaaagagag atcgtacgca aaagtttccg at           352

<210> SEQ ID NO 110
<211> LENGTH: 4598
<212> TYPE: DNA
<213> ORGANISM: Arabidopsis thaliana
<220> FEATURE:
<221> NAME/KEY: misc_feature
<222> LOCATION: (1)..(4598)
<223> OTHER INFORMATION: Genomic region including TBF1 promoter, uORF
      regions, and TBF1 ORF, but lacking a stop codon that was used to
      generate a TBF1-GFP gene fusion.

<400> SEQUENCE: 110
cgacgactag tttacagaga atttggaccg tccgatgtaa agcgaaaata gatctaggtt    60
ttccacgtgt cccctatttt aatgaaacct tctgattcat gtagaagttt tactcaattt   120
aatatttttt agtatgtagt tttgtgtgtg tgtgtgtgtg tgtttttatg gctccacacc   180 aactttttaaa atggtagaag catgttgcat gtgatcgagt aaaaagccaa taatgagatt   240
cagaaaaata aaaattactt atatagtttt ttagagaaaa aattgtattt tgtttaaagc   300
cttaatccgg ttgttgaaag agctgtgtca cgagttaaaa atatttcctt ttcatttttt   360
aagtaattag tttataatgc aaaaatggtt tttatttatt tgtcttcgct tatagaactg   420
caaattgaga gagaaaaaaa tgaattagtg gtggtgacca acattcagg aagctgtgat    480 tgatcatttg ttttttgaggt gagtgtagtg gcaacgtatg acgttaacat atggcgtaca   540
taataattac atgaacttaa tcataatatt catattgcat ttaattcata tatcatatcc    600
cattagttgg accacttgat tgaggtcat gagaagaaca tttatgtttt ttttagtttg     660
aatcggagtg atcactaaaa actagatact gaaaatttc aaactaaaat catattaatc     720
ttcaaaaaat gtgaaatcta aaaaaaaaaa aaatttaac gcgttcattg tagccaagta     780
```

```
gccaagtatt gttaaagtag tagtaaaaga agtttagctt taagtgatat aatttgacac    840
aaatcctact tagatatgga taataggata tagcttcatg tatattttta tcgttgcttc    900 tgtaaccccca aaatgtgttg atataagcat ttgaatattc gtatgtataa tgttttcttt    960
tcaccgtaaa acatattaca atgttagttt atattggatt ttgaatgtgt ttatgaacag   1020 ttttttgtcga ctcaaaagtt aagatgagaa tatggaagaa agtaaagttt aaaagtcatg  1080
atgggaacaa ggaatggaac tcaaacattc taatactcaa caaacgcaat tatattatta   1140
ccatgactca tctttcaagt tccatcaaaa agattcgtgg aaaataatag acttacgttt   1200
caaatccatg tttctttctt tataacaaaa aaatggatg tttcttgacg cgtgtcgaga   1260
gtactcacca ttactctgac ttcagtgagt ttggtcaagt ggtctttttt tttctcatgt   1320
caccaaaggt ccaaaccta gaaattagtt cgaactttcc atagaagaac tgaataaatg    1380
gtccaaaatt gttttaaaaa ggacctaagc cattagttca ttgaattcga gttaatgggt   1440
gaagattttt atgataacga aagtcggagt aattatgctt ttggtccgat agttttctaa   1500
tttgttttct ttccattttt tttttttcaa atactcacata ctatataaga tagtggtttg  1560
tgttaatgtc atcgatgtgt taccatccgc attatattaa ttatttatcc caacataaag   1620
tcagaatctg taatttcttt gttataaaat acagtaaatg gttccgttta agctgttaga   1680 tgattttttga gtaaaaacta atgtaaaaaa aacaaaaaaa aaacaatgta gttcataata  1740
catgcatgtt ttaaagaagt ttcttgttta ctatcaactt gaatagtatt tcacgaagtc   1800
aaaattgttc attccgactt ttctatgtgg agaaaaaaa ttctatcatt gtgcacaatt    1860
taacagaatg taatttcttg taaaagaaga ggaaacaatt cgctgttagt aaatgtgaag   1920
tatagaagtc taaatgaga tacctcaact agcttgaatt aagaaaaaaa acaaaaactc    1980
tatcgacatg aaaaaggtcg caaatattta tcatttatca atgccaaagg agtatttggt   2040
tcacaaaata ctgaatcatt tatatagata tataattagc tctaaattct actataactt   2100
gcaaaataag tatactgact caattatata gcgtttaaaa atagacgatt tgtatgatga   2160
ggtccatata tatggagatg tgcatgcaac tatcgacatt tcacacgtt gatatcgtct    2220 ttctccaatg gagacttgaa tttgtgtaaa ctatgaatac tcgtctctct aagacctttt   2280
ttcttcaacc atgccaacta tttaggtaag attttactgt ctttgattga tattaaatac   2340
ttagccgtgg cgttatcaat gaatgataat aaaaatgcgg ataaaagcca aaggtgttgg   2400
aaataaatcc aagaatgaag acgtagatgt cgatgggtat tttaagaact tgaatttgtc   2460
acgactcaca cgttaaaata tattatccga attgttagt ctaaagacac acatatattg    2520
aaaaagaaaa ggtaaatgaa gctcattggt gcctaaatgt gaaatgaagc cgaaatgtgt   2580
taggtgaaca catttaaata tacaaaaaga aatataatag aaacaaaact aattaacaaa   2640
gtcgcaattt gtattgtata aaatatcttt ccgtctcccg tcatatttga aaaaaaaaa    2700 attacaaatc tgttaatttt aaaactttct agaaaacac aagtatataa ttttctcttt    2760
tcgtgcgtgt ttgtttaaa ataacattgt tttgattggc gactcaacat attttagcat    2820
ttacatattt ctgcatatat taaatgattt ataaactcaa ctatagatta aaatataatt   2880
tgacatctaa taattttaac aataatataa aatatgagat ttataaatta cgaatataaa   2940
tattcaaggg agagaaaaag tagaacataa ttcaaaagat aagcttttt agactttttt    3000 aacaatatttt ttgatggata aaaattattc aaaagagaag aaagtaagaa gaaaagatgt  3060
ttctgagaat ttctagaaac agcatccgtt tttataattt aattttctta caaaggtagg   3120 accaacatttt gtgatctata aatcttccta ctacgttata tagagaccct tcgacataac  3180
```

-continued

```
acttaactcg tttatatatt tgttttactt gttttgcaca tacacacaaa aataaaaaag    3240
actttatatt tatttacttt ttaatcacac ggattagctc cggcgaagta tggtcgtcgt    3300
cttcatcttc ttcctccatc atcagatttt tccttaaatg aagaaaacca aacgaaactc    3360
cgatcttctc cgttctcgtg ttttcctctc tggcttttat tgctgggatt gggaatttct    3420
caccgctctc ttgcttttta gttgctgatt cttttccctt cgactttcta tttccaatct    3480
ttcttcttct ctttgtgtat tagattattt ttagttttat ttttctgtgg taaaataaaa    3540
aaagttcgcc ggagatgacg gctgtgacgg cggcgcaaag atcagttccg cgccgtttt    3600 taagcaaaac gtatcagcta gttgatgatc atagcacaga cgacgtcgtt tcatggaacg    3660
aagaaggaac agcttttgtc gtgtggaaaa cagcagagtt tgctaaagat cttcttcctc    3720
aatacttcaa gcataataat ttctcaagct tcattcgtca gctcaacact tacgtgagtt    3780
tcactctaac gaaaactcat ttactctcaa tttaatgctt catttaattc gtttggtgaa    3840
ttgaatcatt cttttgtagt tggttagcca atttcgtaat tttctcataa tttgggggtt    3900
ggtgagaaaa ccttctagaa gctgagaatg ttcttgttct ttttttttt ttttttttgg    3960 tttagggatt tcgtaaaact gtaccggata aatgggaatt tgcaaacgat tatttccgga    4020
gaggcgggga ggatctgttg acggacatac gacggcgtaa atcggtgatt gcttcaacgg    4080
cggggaaatg tgttgttgtt ggttcgcctt ctgagtctaa ttctggtggt ggtgatgatc    4140
acggttcaag ctccacgtca tcacccggtt cgtcgaagaa tcctggttcg gtggagaaca    4200
tggttgctga tttatcagga gagaacgaga agcttaaacg tgaaaacaat aacttgagct    4260
cggagctcgc ggcggcgaag aagcagcgcg atgagctagt gacgttcttg acgggtcatc    4320
tgaaagtaag accggaacaa atcgataaaa tgatcaaagg agggaaattt aaaccggtgg    4380
agtctgacga agagagtgag tgcgaaggtt gcgacggcgg cggaggagca gaggaggggg    4440
taggtgaagg attgaaattg tttggggtgt ggttgaaagg agagagaaaa aagagggacc    4500
gggatgaaaa gaattatgtg gtgagtgggt cccgtatgac ggaaataaag aacgtggact    4560
ttcacgcgcc gttgtggaaa agcagcaaag tctgcaac                           4598
```

<210> SEQ ID NO 111
<211> LENGTH: 48
<212> TYPE: DNA
<213> ORGANISM: Arabidopsis thaliana
<220> FEATURE:
<221> NAME/KEY: misc_feature
<222> LOCATION: (1)..(48)
<223> OTHER INFORMATION: nucleotide sequence encoding upstream ORF1
      (uORF1) polypeptide

<400> SEQUENCE: 111

```
atggtcgtcg tcttcatctt cttcctccat catcagattt ttccttaa              48
```

<210> SEQ ID NO 112
<211> LENGTH: 111
<212> TYPE: DNA
<213> ORGANISM: Arabidopsis thaliana
<220> FEATURE:
<221> NAME/KEY: misc_feature
<222> LOCATION: (1)..(111)
<223> OTHER INFORMATION: nucleotide sequence encoding upstream ORF2
      (uORF2) polypeptide

<400> SEQUENCE: 112

```
atggaagaaa ccaaacgaaa ctccgatctt ctccgttctc gtgttttcct ctctggcttt    60
```
tattgctggg attgggaatt tctcaccgct ctcttgcttt ttagttgctg a           111

<210> SEQ ID NO 113
<211> LENGTH: 3554
<212> TYPE: DNA
<213> ORGANISM: Arabidopsis thaliana
<220> FEATURE:
<221> NAME/KEY: promoter
<222> LOCATION: (1)..(3554)
<223> OTHER INFORMATION: TBF1 promoter region

<400> SEQUENCE: 113

```
cgacgactag tttacagaga atttggaccg tccgatgtaa agcgaaaata gatctaggtt     60
ttccacgtgt cccctatttt aatgaaacct tctgattcat gtagaagttt tactcaattt    120
aatattttt agtatgtagt tttgtgtgtg tgtgtgtgtg tgtttttatg gctccacacc    180
aactttaaa atggtagaag catgttgcat gtgatcgagt aaaaagccaa taatgagatt    240
cagaaaata aaaattactt atatagtttt ttagagaaaa aattgtattt tgtttaaagc    300
cttaatccgg ttgttgaaag agctgtgtca cgagttaaaa atattttctt ttcattttt    360
aagtaattag tttataatgc aaaaatggtt tttatttatt tgtcttcgct tatagaactg    420
caaattgaga gagaaaaaaa tgaattagtg gtggtgacca acattcagg aagctgtgat    480
tgatcatttg tttttgaggt gagtgtagtg gcaacgtatg acgttaacat atggcgtaca    540
taataattac atgaacttaa tcataataat catattgcat ttaattcata tatcatatcc    600
cattagttgg accacttgat ttgaggtcat gagaagaaca tttatgtttt ttttagtttg    660
aatcggagtg atcactaaaa actagatact gaaaattttc aaactaaaat catattaatc    720
ttcaaaaaat gtgaaatcta aaaaaaaaaa aattttaac gcgttcattg tagccaagta    780
gccaagtatt gttaaagtag tagtaaaaga agttagctt taagtgatat aatttgacac    840
aaatcctact tagatatgga aataggata tagcttcatg tatatttta tcgttgcttc    900
tgtaaccca aaatgtgttg atataagcat ttgaatattc gtatgtataa tgttttcttt    960
tcaccgtaaa acatattaca atgttagttt atattggatt ttgaatgtgt ttatgaacag   1020
tttttgtcga ctcaaaagtt aagatgagaa tatggaagaa agtaaagttt aaaagtcatg   1080
atgggaacaa ggaatggaac tcaaacattc taatactcaa caaacgcaat tatattatta   1140
ccatgactca tctttcaagt tccatcaaaa agattcgtgg aaaataatag acttacgttt   1200
caaatccatg tttctttctt tataacaaaa aaaatggatg tttcttgacg cgtgtcgaga   1260
gtactcacca ttactctgac ttcagtgagt ttggtcaagt ggtcttttt ttctcatgt    1320
caccaaaggt ccaaacccta gaaattagtt cgaactttcc atagaagaac tgaataaatg   1380
gtccaaaatt gttttaaaaa ggacctaagc cattagttca ttgaattcga gttaatgggt   1440
gaagattttt atgataacga agtcggagt aattatgctt ttggtccgat agttttctaa   1500
tttgttttct ttccattttt tttttttcaa atactacata ctatataaga tagtggtttg   1560
tgttaatgtc atcgatgtgt taccatccgc attatattaa ttatttatcc caacataaag   1620
tcagaatctg taatttcttt gttataaaat acagtaaatg gttccgttta agctgttaga   1680
tgattttga gtaaaacta atgtaaaaa aacaaaaaaa aaacaatgta gttcataata   1740
catgcatgtt ttaaagaagt ttcttgttta ctatcaactt gaatagtatt tcacgaagtc   1800
aaaattgttc attccgactt ttctatgtgg agaaaaaaaa ttctatcatt gtgcacaatt   1860
taacagaatg taatttcttg taaaagaaga ggaaacaatt cgctgttagt aaatgtgaag   1920
tatagaagtc taaaatgaga tacctcaact agcttgaatt aagaaaaaaa acaaaaactc   1980
```

```
tatcgacatg aaaaaggtcg caaatattta tcatttatca atgccaaagg agtatttggt    2040
tcacaaaata ctgaatcatt tatatagata tataattagc tctaaattct actataactt    2100
gcaaaataag tatactgact caattatata gcgtttaaaa atagacgatt tgtatgatga    2160
ggtccatata tatggagatg tgcatgcaac tatcgacatt ttcacacgtt gatatcgtct    2220
ttctccaatg gagacttgaa tttgtgtaaa ctatgaatac tcgtctctct aagaccttt     2280 ttcttcaacc atgccaacta tttaggtaag attttactgt ctttgattga tattaaatac    2340
ttagccgtgg cgttatcaat gaatgataat aaaaatgcgg ataaaagcca aggtgttgg     2400 aaataaatcc aagaatgaag acgtagatgt cgatgggtat tttaagaact tgaatttgtc    2460
acgactcaca cgttaaaata tattatccga attgtttagt ctaaagacac acatatattg    2520
aaaaagaaaa ggtaaatgaa gctcattggt gcctaaatgt gaaatgaagc cgaaatgtgt    2580
taggtgaaca catttaaata tacaaaaga aatataatag aaacaaaact aattaacaaa    2640
gtcgcaattt gtattgtata aaatatcttt ccgtctcccg tcatatttga aaaaaaaaa    2700 attacaaatc tgttaatttt aaaactttct agaaaaacac aagtatataa ttttctcttt    2760
tcgtgcgtgt ttgttttaaa ataacattgt tttgattggc gactcaacat attttagcat    2820
ttacatattt ctgcatatat taaatgattt ataaactcaa ctatagatta aaatataatt    2880
tgacatctaa taatttaac aataataaa aatatgagat ttataaatta cgaatataaa    2940
tattcaaggg agagaaaaag tagaacataa ttcaaaagat aagactttt agactttttt    3000 aacaatattt ttgatggata aaaattattc aaaagagaag aaagtaagaa gaaaagatgt    3060
ttctgagaat ttctagaaac agcatccgtt tttataattt aattttctta caaggtagg    3120 accaacattt gtgatctata aatcttccta ctacgttata tagagaccct tcgacataac    3180
acttaactcg tttatatatt tgttttactt gttttgcaca tacacacaaa aataaaaaag    3240
actttatatt tatttacttt ttaatcacac ggattagctc cggcgaagta tggtcgtcgt    3300
cttcatcttc ttcctccatc atcagatttt tccttaaatg gaagaaacca aacgaaactc    3360
cgatcttctc cgttctcgtg ttttcctctc tggcttttat tgctgggatt gggaatttct    3420
caccgctctc ttgctttta gttgctgatt cttttttcctt cgactttcta tttccaatct    3480
ttcttcttct ctttgtgtat tagattattt ttagttttat ttttctgtgg taaaataaaa    3540
aaagttcgcc ggag                                                      3554
```

<210> SEQ ID NO 114
<211> LENGTH: 1047
<212> TYPE: DNA
<213> ORGANISM: Arabidopsis thaliana
<220> FEATURE:
<221> NAME/KEY: misc_feature
<222> LOCATION: (1)..(1047)
<223> OTHER INFORMATION: Coding sequence only for the Arabidopsis
      thaliana TBF1 open reading frame with exon 1, intron, and exon 2,
      starting with an ATG codon and terminating with a TAA stop codon.

<400> SEQUENCE: 114

```
atgacggctg tgacggcggc gcaaagatca gttccggcgc cgttttaag caaaacgtat     60 cagctagttg atgatcatag cacagacgac gtcgtttcat ggaacgaaga aggaacagct    120
tttgtcgtgt ggaaaacagc agagtttgct aaagatcttc ttcctcaata cttcaagcat    180
aataatttct caagcttcat tcgtcagctc aacacttacg tgagtttcac tctaacgaaa    240
actcatttac tctcaattta atgcttcatt taattcgttt ggtgaattga atcattcttt    300
```

-continued

```
tgtagttggt tagccaattt cgtaattttc tcataatttg ggggttggtg agaaaacctt    360
ctagaagctg agaatgttct tgttcttttt tttttttttt ttttggttta gggatttcgt    420
aaaactgtac cggataaatg ggaatttgca aacgattatt tccggagagg cggggaggat    480
ctgttgacgg acatacgacg gcgtaaatcg gtgattgctt caacggcggg gaaatgtgtt    540
gttgttggtt cgccttctga gtctaattct ggtggtggtg atgatcacgg ttcaagctcc    600
acgtcatcac ccggttcgtc gaagaatcct ggttcggtgg agaacatggt tgctgattta    660
tcaggagaga acgagaagct taaacgtgaa aacaataact tgagctcgga gctcgcggcg    720
gcgaagaagc agcgcgatga gctagtgacg ttcttgacgg gtcatctgaa agtaagaccg    780
gaacaaatcg ataaaatgat caaggaggg aaatttaaac cggtggagtc tgacgaagag    840
agtgagtgcg aaggttgcga cggcggcgga ggagcagagg aggggtagg tgaaggattg    900 aaattgtttg gggtgtggtt gaaggagag agaaaaaaga gggaccggga tgaaaagaat    960
tatgtggtga gtgggtcccg tatgacggaa ataaagaacg tggactttca cgcgccgttg    1020
tggaaaagca gcaaagtctg caactaa                                       1047
```

```
<210> SEQ ID NO 115
<211> LENGTH: 29
<212> TYPE: DNA
<213> ORGANISM: Artificial Sequence
<220> FEATURE:
<223> OTHER INFORMATION: Synthetic primer P1 PstI-35S 5'

<400> SEQUENCE: 115
cggctgcagg tcaacatggt ggagcacga                                     29

<210> SEQ ID NO 116
<211> LENGTH: 33
<212> TYPE: DNA
<213> ORGANISM: Artificial Sequence
<220> FEATURE:
<223> OTHER INFORMATION: Synthetic Primer P2

<400> SEQUENCE: 116
cggtctagac cggcctctcc aaatgaaatg aac                                33

<210> SEQ ID NO 117
<211> LENGTH: 32
<212> TYPE: DNA
<213> ORGANISM: Artificial Sequence
<220> FEATURE:
<223> OTHER INFORMATION: Synthetic Primer P3 KpiI-NOS 5'

<400> SEQUENCE: 117
cggggtaccg atcgttcaaa catttggcaa ta                                 32

<210> SEQ ID NO 118
<211> LENGTH: 30
<212> TYPE: DNA
<213> ORGANISM: Artificial Sequence
<220> FEATURE:
<223> OTHER INFORMATION: Synthetic Primer P4 EcoRI-NOS 3'

<400> SEQUENCE: 118
cgggaattcc ccgatctagt aacatagatg                                    30

<210> SEQ ID NO 119
<211> LENGTH: 55
<212> TYPE: DNA
<213> ORGANISM: Artificial Sequence
```

```
<220> FEATURE:
<223> OTHER INFORMATION: Synthetic Primer P5 KpnI-Gateway 5'

<400> SEQUENCE: 119
cggggtacct tcgacgacaa gaccgggccc acaagtttgt acaaaaaagc tgaac        55

<210> SEQ ID NO 120
<211> LENGTH: 61
<212> TYPE: DNA
<213> ORGANISM: Artificial Sequence
<220> FEATURE:
<223> OTHER INFORMATION: Synthetic Primer P6 Gateway 3'

<400> SEQUENCE: 120
ggaaattcga gcggctcgag tgaggagaag agccgggccc ctaccacttt gtacaagaaa   60
g                                                                  61

<210> SEQ ID NO 121
<211> LENGTH: 58
<212> TYPE: DNA
<213> ORGANISM: Artificial Sequence
<220> FEATURE:
<223> OTHER INFORMATION: Synthetic Primer P7 AflII-Gateway 3'

<400> SEQUENCE: 121
cggcttaaga aactttattg ccaaatgttt gaacgatcgg ggaaattcga gcggctcg     58

<210> SEQ ID NO 122
<211> LENGTH: 31
<212> TYPE: DNA
<213> ORGANISM: Artificial Sequence
<220> FEATURE:
<223> OTHER INFORMATION: Synthetic Primer P8 KpnI-TBF1 5'UTR 3'

<400> SEQUENCE: 122
cggggtaccc tccggcgaac ttttttatt t                                   31

<210> SEQ ID NO 123
<211> LENGTH: 21
<212> TYPE: DNA
<213> ORGANISM: Artificial Sequence
<220> FEATURE:
<223> OTHER INFORMATION: Synthetic Primer P9 XbaI-TBF1 5'UTR with native
      uORFs5'

<400> SEQUENCE: 123
aatttctaga aacagcatcc g                                             21

<210> SEQ ID NO 124
<211> LENGTH: 55
<212> TYPE: DNA
<213> ORGANISM: Artificial Sequence
<220> FEATURE:
<223> OTHER INFORMATION: Synthetic Primer P10 XbaI-TBF1 5'UTR with
      mutant uORFs 5'

<400> SEQUENCE: 124
cggtctagaa acagcatccg tttttataat ttaattttct tacaaaggta ggacc        55

<210> SEQ ID NO 125
<211> LENGTH: 30
<212> TYPE: DNA
<213> ORGANISM: Artificial Sequence
<220> FEATURE:
<223> OTHER INFORMATION: Synthetic Primer P11 HindIII-TBF1 promoter 5'
```

<400> SEQUENCE: 125
cggaagcttc gacgactagt ttacagagaa                                              30

<210> SEQ ID NO 126
<211> LENGTH: 40
<212> TYPE: DNA
<213> ORGANISM: Artificial Sequence
<220> FEATURE:
<223> OTHER INFORMATION: Synthetic Primer P12 AscI-TBF1 promoter 3'

<400> SEQUENCE: 126
cggggcgcgc cctagaaatt ctcagaaaca tcttttcttc                                   40

<210> SEQ ID NO 127
<211> LENGTH: 33
<212> TYPE: DNA
<213> ORGANISM: Artificial Sequence
<220> FEATURE:
<223> OTHER INFORMATION: Synthetic Primer P13 AscI-TBF1 5'UTR 5'

<400> SEQUENCE: 127
cggggcgcgc cttcttacaa aggtaggacc aac                                          33

<210> SEQ ID NO 128
<211> LENGTH: 29
<212> TYPE: DNA
<213> ORGANISM: Artificial Sequence
<220> FEATURE:
<223> OTHER INFORMATION: Synthetic Primer P14 HindIII-TBF1 promoter 5'

<400> SEQUENCE: 128
cggaagcttt acagagaatt tggaccgtc                                               29

<210> SEQ ID NO 129
<211> LENGTH: 33
<212> TYPE: DNA
<213> ORGANISM: Artificial Sequence
<220> FEATURE:
<223> OTHER INFORMATION: Synthetic Primer P15 SpeI-TBF1 promoter 3'

<400> SEQUENCE: 129
cggactagta attctcagaa acatcttttc ttc                                          33

<210> SEQ ID NO 130
<211> LENGTH: 14
<212> TYPE: DNA
<213> ORGANISM: Artificial Sequence
<220> FEATURE:
<223> OTHER INFORMATION: Synthetic Primer LIC1 Gateway LIC adapter
      sequence 1

<400> SEQUENCE: 130
tcgacgacaa gacc                                                               14

<210> SEQ ID NO 131
<211> LENGTH: 14
<212> TYPE: DNA
<213> ORGANISM: Artificial Sequence
<220> FEATURE:
<223> OTHER INFORMATION: Synthetic Primer LIC2 Gateway LIC adapter
      sequence 2

<400> SEQUENCE: 131
tgaggagaag agcc                                                               14

-continued

```
<210> SEQ ID NO 132
<211> LENGTH: 14478
<212> TYPE: DNA
<213> ORGANISM: Artificial Sequence
<220> FEATURE:
<223> OTHER INFORMATION: Plasmid pGX1
<220> FEATURE:
<221> NAME/KEY: misc_feature
<222> LOCATION: (8908)..(12273)
<223> OTHER INFORMATION: Expression cassette region in Figure 2
<220> FEATURE:
<221> NAME/KEY: promoter
<222> LOCATION: (11979)..(12177)
<223> OTHER INFORMATION: TBF1 promoter
<220> FEATURE:
<221> NAME/KEY: misc_feature
<222> LOCATION: (12178)..(12225)
<223> OTHER INFORMATION: uORF1 region
<220> FEATURE:
<221> NAME/KEY: misc_feature
<222> LOCATION: (12226)..(12336)
<223> OTHER INFORMATION: uORF2 region
<220> FEATURE:
<221> NAME/KEY: misc_feature
<222> LOCATION: (12464)..(12469)
<223> OTHER INFORMATION: LIC1
<220> FEATURE:
<221> NAME/KEY: misc_feature
<222> LOCATION: (14177)..(14181)
<223> OTHER INFORMATION: Gateway
<220> FEATURE:
<221> NAME/KEY: misc_feature
<222> LOCATION: (14196)..(14218)
<223> OTHER INFORMATION: LIC2
<220> FEATURE:
<221> NAME/KEY: misc_feature
<222> LOCATION: (14472)..(14473)
<223> OTHER INFORMATION: NOS

<400> SEQUENCE: 132
cgtaatcatg gtcatagctg tttcctgtgt gaaattgtta tccgctcaca attccacaca      60
acatacgagc cggaagcata agtgtaaag cctggggtgc ctaatgagtg agctaactca      120
cattaattgc gttgcgctca ctgcccgctt tccagtcggg aaacctgtcg tgccagctgc      180
attaatgaat cggccaacgc gcggggagag gcggtttgcg tattggctag agcagcttgc      240
caacatggtg gagcacgaca ctctcgtcta ctccaagaat atcaaagata cagtctcaga      300
agaccaaagg gctattgaga cttttcaaca aagggtaata tcgggaaacc tcctcggatt      360
ccattgccca gctatctgtc acttcatcaa aggacagta gaaaaggaag gtggaccta       420 caaatgccat cattgcgata aaggaaaggc tatcgttcaa gatgcctctg ccgacagtgg      480
tcccaaagat ggacccccac ccacgaggag catcgtggaa aagaagacg ttccaaccac      540 gtcttcaaag caagtggatt gatgtgataa catggtggag cacgacactc tcgtctactc      600
caagaatatc aaagatacag tctcagaaga ccaaagggct attgagactt tcaacaaag      660 ggtaatatcg ggaaacctcc tcggattcca ttgcccagct atctgtcact tcatcaaaag      720
gacagtagaa aaggaaggtg gcacctacaa atgccatcat tgcgataaag gaaaggctat      780
cgttcaagat gcctctgccg acagtggtcc caaagatgga cccccaccca cgaggagcat      840
cgtggaaaaa gaagacgttc caaccacgtc ttcaaagcaa gtggattgat gtgatatctc      900
cactgacgta agggatgacg cacaatccca ctatccttcg caagacccttc ctctatataa      960 ggaagttcat ttcatttgga ggacacgc tgaaatcacc agtctctctc tacaaatcta     1020
tctctctcga gctttcgcag atcccggggg gcaatgagat atgaaaaagc ctgaactcac     1080
cgcgacgtct gtcgagaagt ttctgatcga aaagttcgac agcgtctccg acctgatgca     1140
```

```
gctctcggag ggcgaagaat ctcgtgcttt cagcttcgat gtaggagggc gtggatatgt   1200
cctgcgggta aatagctgcg ccgatggttt ctacaaagat cgttatgttt atcggcactt   1260
tgcatcggcc gcgctcccga ttccggaagt gcttgacatt ggggagttta gcgagagcct   1320
gacctattgc atctcccgcc gtgcacaggg tgtcacgttg caagacctgc ctgaaaccga   1380
actgcccgct gttctacaac cggtcgcgga ggctatggat gcgatcgctg cggccgatct   1440
tagccagacg agcgggttcg gcccattcgg accgcaagga atcggtcaat acactacatg   1500
gcgtgatttc atatgcgcga ttgctgatcc ccatgtgtat cactggcaaa ctgtgatgga   1560
cgacaccgtc agtgcgtccg tcgcgcaggc tctcgatgag ctgatgcttt gggccgagga   1620
ctgccccgaa gtccggcacc tcgtgcacgc ggatttcggc tccaacaatg tcctgacgga   1680
caatggccgc ataacagcgg tcattgactg gagcgaggcg atgttcgggg attcccaata   1740
cgaggtcgcc aacatcttct tctggaggcc gtggttggct tgtatggagc agcagacgcg   1800
ctacttcgag cggaggcatc cggagcttgc aggatcgcca cgactccggg cgtatatgct   1860
ccgcattggt cttgaccaac tctatcagag cttggttgac ggcaatttcg atgatgcagc   1920
ttgggcgcag ggtcgatgcg acgcaatcgt ccgatccgga gccgggactg tcgggcgtac   1980
acaaatcgcc cgcagaagcg cggccgtctg gaccgatggc tgtgtagaag tactcgccga   2040
tagtggaaac cgacgcccca gcactcgtcc gagggcaaag aaatagagta gatgccgacc   2100
ggatctgtcg atcgacaagc tcgagtttct ccataataat gtgtgagtag ttccagata    2160 agggaattag ggttcctata gggtttcgct catgtgttga gcatataaga aacccttagt   2220
atgtatttgt atttgtaaaa tacttctatc aataaaattt ctaattccta aaaccaaaat   2280
ccagtactaa aatccagatc ccccgaatta attcggcgtt aattcagtac attaaaaacg   2340
tccgcaatgt gttattaagt tgtctaagcg tcaatttgtt tacaccacaa tatatcctgc   2400
caccagccag ccaacagctc cccgaccggc agctcggcac aaaatcacca ctcgatacag   2460
gcagcccatc agtccgggac ggcgtcagcg ggagagccgt tgtaaggcgg cagactttgc   2520
tcatgttacc gatgctattc ggaagaacgg caactaagct gccgggtttg aaacacggat   2580
gatctcgcgg agggtagcat gttgattgta acgatgacag agcgttgctg cctgtgatca   2640
ccgcggtttc aaaatcggct ccgtcgatac tatgttatac gccaactttg aaaacaactt   2700
tgaaaaagct gttttctggt atttaaggtt ttagaatgca aggaacagtg aattggagtt   2760
cgtcttgtta taattagctt cttggggtat ctttaaatac tgtagaaaag aggaaggaaa   2820
taataaatgg ctaaaatgag aatatcaccg gaattgaaaa aactgatcga aaaataccgc   2880
tgcgtaaaag atacggaagg aatgtctcct gctaaggtat ataagctggt gggagaaaat   2940
gaaaacctat atttaaaaat gacggacagc cggtataaag ggaccaccta tgatgtggaa   3000
cgggaaaagg acatgatgct atggctggaa ggaaagctgc ctgttccaaa ggtcctgcac   3060
tttgaacggc atgatggctg gagcaatctg ctcatgagtg aggccgatgg cgtcctttgc   3120
tcggaagagt atgaagatga acaaagccct gaaaagatta tcgagctgta tgcggagtgc   3180
atcaggctct ttcactccat cgacatatcg gattgtccct atacgaatag cttagacagc   3240
cgcttagccg aattggatta cttactgaat aacgatctgg ccgatgtgga ttgcgaaaac   3300
tgggaagaag acactccatt taaagatccg cgcgagctgt atgatttttt aaagacggaa   3360
aagcccgaag aggaacttgt ctttttcccac ggcgacctgg gagacagcaa catctttgtg   3420
aaagatggca agtaagtggc ttttattgat cttgggagaa gcgcagggc ggacaagtgg   3480 tatgacattg ccttctgcgt ccggtcgatc agggaggata tcggggaaga acagtatgtc   3540
```

```
gagctattttt ttgacttact ggggatcaag cctgattggg agaaaataaa atattatatt  3600
ttactggatg aattgtttta gtacctagaa tgcatgacca aaatccctta acgtgagttt  3660
tcgttccact gagcgtcaga ccccgtagaa aagatcaaag gatcttcttg agatcctttt  3720
tttctgcgcg taatctgctg cttgcaaaca aaaaaaccac cgctaccagc ggtggtttgt  3780
ttgccggatc aagagctacc aactcttttt ccgaaggtaa ctggcttcag cagagcgcag  3840
ataccaaata ctgtccttct agtgtagccg tagttaggcc accacttcaa gaactctgta  3900
gcaccgccta catacctcgc tctgctaatc ctgttaccag tggctgctgc cagtggcgat  3960
aagtcgtgtc ttaccgggtt ggactcaaga cgatagttac cggataaggc gcagcggtcg  4020
ggctgaacgg ggggttcgtg cacacagccc agcttggagc gaacgaccta caccgaactg  4080
agatacctac agcgtgagct atgagaaagc gccacgcttc ccgaagggag aaaggcggac  4140
aggtatccgg taagcggcag ggtcggaaca ggagagcgca cgagggagct tccagggggga  4200 aacgcctggt atctttatag tcctgtcggg tttcgccacc tctgacttga gcgtcgattt  4260
ttgtgatgct cgtcaggggg gcggagccta tggaaaaacg ccagcaacgc ggccttttta  4320
cggttcctgg ccttttgctg gccttttgct cacatgttct ttcctgcgtt atcccctgat  4380
tctgtggata accgtattac cgcctttgag tgagctgata ccgctcgccg cagccgaacg  4440
accgagcgca gcgagtcagt gagcgaggaa gcggaagagc gcctgatgcg gtattttctc  4500
cttacgcatc tgtgcggtat ttcacaccgc atatggtgca ctctcagtac aatctgctct  4560
gatgccgcat agttaagcca gtatacactc cgctatcgct acgtgactgg gtcatggctg  4620
cgccccgaca cccgccaaca cccgctgacg cgccctgacg ggcttgtctg ctcccggcat  4680
ccgcttacag acaagctgtg accgtctccg ggagctgcat gtgtcagagg ttttcaccgt  4740
catcaccgaa acgcgcgagg cagggtgcct tgatgtgggc gccggcggtc gagtggcgac  4800
ggcgcggctt gtccgcgccc tggtagattg cctggccgta ggccagccat ttttgagcgg  4860
ccagcggccg cgataggccg acgcgaagcg gcgggcgta gggagcgcag cgaccgaagg  4920
gtaggcgctt tttgcagctc ttcggctgtg cgctggccag acagttatgc acaggccagg  4980
cgggttttaa gagttttaat aagttttaaa gagttttagg cggaaaaatc gcctttttc  5040 tcttttatat cagtcactta catgtgtgac cggttcccaa tgtacggctt tgggttccca  5100
atgtacgggt tccggttccc aatgtacggc tttgggttcc caatgtacgt gctatccaca  5160
ggaaagagac cttttcgacc ttttttcccct gctagggcaa tttgccctag catctgctcc  5220
gtacattagg aaccggcgga tgcttcgccc tcgatcaggt tgcggtagcg catgactagg  5280
atcgggccag cctgccccgc ctcctccttc aaatcgtact ccggcaggtc atttgacccg  5340
atcagcttgc gcacggtgaa acagaacttc ttgaactctc cggcgctgcc actgcgttcg  5400
tagatcgtct tgaacaacca tctggcttct gccttgcctg cggcgcggcg tgccaggcgg  5460
tagagaaaac ggccgatgcc gggatcgatc aaaaagtaat cggggtgaac cgtcagcacg  5520
tccgggttct tgccttctgt gatctcgcgg tacatccaat cagctagctc gatctcgatg  5580
tactccggcc gccggtttc gctctttacg atcttgtagc ggctaatcaa ggcttcaccc  5640
tcggataccg tcaccaggcg gccgttcttg gccttcttcg tacgctgcat ggcaacgtgc  5700
gtggtgttta accgaatgca ggtttctacc aggtcgtctt tctgctttcc gccatcggct  5760
cgccggcaga acttgagtac gtccgcaacg tgtggacgga acacgcggcc gggcttgtct  5820 cccttcccctt cccggtatcg gttcatggat tcggttagat gggaaaccgc catcagtacc  5880
```

```
aggtcgtaat cccacacact ggccatgccg gccggccctg cggaaacctc tacgtgcccg    5940
tctggaagct cgtagcggat cacctcgcca gctcgtcggt cacgcttcga cagacggaaa    6000
acggccacgt ccatgatgct gcgactatcg cgggtgccca cgtcatagag catcggaacg    6060
aaaaaatctg gttgctcgtc gcccttgggc ggcttcctaa tcgacggcgc accggctgcc    6120
ggcggttgcc gggattcttt gcggattcga tcagcggccg cttgccacga ttcaccgggg    6180
cgtgcttctg cctcgatgcg ttgccgctgg gcggcctgcg cggccttcaa cttctccacc    6240
aggtcatcac ccagcgccgc gccgatttgt accgggccgg atggtttgcg accgtcacgc    6300
cgattcctcg ggcttggggg ttccagtgcc attgcagggc cggcagacaa cccagccgct    6360
tacgcctggc caaccgcccg ttcctccaca catgggggcat tccacggcgt cggtgcctgg   6420
ttgttcttga ttttccatgc cgcctccttt agccgctaaa attcatctac tcatttattc    6480
atttgctcat ttactctggt agctgcgcga tgtattcaga tagcagctcg gtaatggtct    6540
tgccttggcg taccgcgtac atcttcagct tggtgtgatc ctccgccggc aactgaaagt    6600
tgacccgctt catggctggc gtgtctgcca ggctggccaa cgttgcagcc ttgctgctgc    6660
gtgcgctcgg acggccggca cttagcgtgt ttgtgctttt gctcattttc tctttacctc    6720
attaactcaa atgagttttg atttaatttc agcggccagc gcctggacct cgcgggcagc    6780
gtcgccctcg ggttctgatt caagaacggt tgtgccggcg gcggcagtgc ctgggtagct    6840
cacgcgctgc gtgatacggg actcaagaat gggcagctcg tacccggcca cgcctcggc    6900
aacctcaccg ccgatgcgcg tgcctttgat cgccgcgac acgacaaagg ccgcttgtag    6960
ccttccatcc gtgacctcaa tgcgctgctt aaccagctcc accaggtcgg cggtggccca    7020
tatgtcgtaa gggcttggct gcaccggaat cagcacgaag tcggctgcct tgatcgcgga    7080
cacagccaag tccgccgcct ggggcgctcc gtcgatcact acgaagtcgc gccggccgat    7140
ggccttcacg tcgcggtcaa tcgtcgggcg gtcgatgccg acaacggtta gcggttgatc    7200
ttcccgcacg gccgcccaat cgcgggcact gccctgggga tcggaatcga ctaacagaac    7260
atcggccccg gcgagttgca gggcgcgggc tagatgggtt gcgatggtcg tcttgcctga    7320
cccgcctttc tggttaagta cagcgataac cttcatgcgt tccccttgcg tatttgttta    7380
tttactcatc gcatcatata cgcagcgacc gcatgacgca agctgtttta ctcaaataca    7440
catcaccttt ttagacggcg gcgctcggtt tcttcagcgg ccaagctggc cggccaggcc    7500
gccagcttgg catcagacaa accggccagg atttcatgca gccgcacggt tgagacgtgc    7560
gcgggcggct cgaacacgta cccggccgcg atcatctccg cctcgatctc ttcggtaatg    7620
aaaaacggtt cgtcctggcc gtcctggtgc ggtttcatgc ttgttcctct tggcgttcat    7680
tctcggcggc cgccagggcg tcggcctcgg tcaatgcgtc ctcacggaag gcaccgcgcc    7740
gcctggcctc ggtgggcgtc acttcctcgc tgcgctcaag tgcgcggtac agggtcgagc    7800
gatgcacgcc aagcagtgca gccgcctctt tcacggtgcg gccttcctgg tcgatcagct    7860
cgcgggcgtg cgcgatctgt gccggggtga gggtagggcg ggggccaaac ttcacgcctc    7920
gggccttggc ggcctcgcgc ccgctccggg tgcggtcgat gattagggaa cgctcgaact    7980
cggcaatgcc ggcgaacacg gtcaacacca tgccggcggc cggcgtggtg gtgtcggccc    8040
acggctctgc caggctacgc aggcccgcgc cggcctcctg gatgcgctcg gcaatgtcca    8100
gtaggtcgcg ggtgctgcgg gccaggcggt ctagcctggt cactgtcaca acgtcgccag    8160
ggcgtaggtg gtcaagcatc ctggccagct ccgggcggtc gcgcctggtg ccggtgatct    8220
tctcggaaaa cagcttggtg cagccggccg cgtgcagttc ggcccgttgg ttggtcaagt    8280
```

```
cctggtcgtc ggtgctgacg cgggcatagc ccagcaggcc agcggcggcg ctcttgttca    8340
tggcgtaatg tctccggttc tagtcgcaag tattctactt tatgcgacta aaacacgcga    8400
caagaaaacg ccaggaaaag ggcagggcgg cagcctgtcg cgtaacttag gacttgtgcg    8460
acatgtcgtt ttcagaagac ggctgcactg aacgtcagaa gccgactgca ctatagcagc    8520
ggaggggttg gatcaaagta ctttgatccc gaggggaacc ctgtggttgg catgcacata    8580
caaatggacg aacggataaa ccttttcacg ccctttaaa tatccgttat tctaataaac    8640
gctcttttct cttaggttta cccgccaata tatcctgtca aacactgata gtttaaactg    8700
aaggcgggaa acgacaatct gatccaagct caagctgctc tagcattcgc cattcaggct    8760
gcgcaactgt tgggaagggc gatcggtgcg ggcctcttcg ctattacgcc agctggcgaa    8820
agggggatgt gctgcaaggc gattaagttg ggtaacgcca gggttttccc agtcacgacg    8880
ttgtaaaacg acggccagtg ccaagcttcg acgactagtt tacagagaat ttggaccgtc    8940
cgatgtaaag cgaaaataga tctaggtttt ccacgtgtcc cctattttaa tgaaaccttc    9000
tgattcatgt agaagtttta ctcaatttaa tatttttag tatgtagttt tgtgtgtgtg    9060
tgtgtgtgtg tttttatggc tccacaccaa cttttaaaat ggtagaagca tgttgcatgt    9120
gatcgagtaa aaagccaata atgagattca gaaaaataaa aattacttat atagtttttt    9180
agagaaaaaa ttgtattttg tttaaagcct taatccggtt gttgaaagag ctgtgtcacg    9240
agttaaaaat attttctttt catttttttaa gtaattagtt tataatgcaa aaatggtttt    9300
tatttatttg tcttcgctta tagaactgca aattgagaga gaaaaaaatg aattagtggt    9360
ggtgaccaaa cattcaggaa gctgtgattg atcatttgtt tttgaggtga gtgtagtggc    9420
aacgtatgac gttaacatat ggcgtacata ataattacat gaacttaatc ataataatca    9480
tattgcattt aattcatata tcatatccca ttagttggac cacttgattt gaggtcatga    9540
gaagaacatt tatgtttttt ttagtttgaa tcggagtgat cactaaaaac tagatactga    9600
aaattttcaa actaaaatca tattaatctt caaaaaatgt gaaatctaaa aaaaaaaaa    9660
attttaacgc gttcattgta gccaagtagc caagtattgt taaagtagta gtaaagaag    9720
tttagcttta agtgatataa tttgacacaa atcctactta gatatggata ataggatata    9780
gcttcatgta tatttttatc gttgcttctg taaccccaaa atgtgttgat ataagcattt    9840
gaatattcgt atgtataatg ttttctttc accgtaaaac atattacaat gttagtttat    9900
attggatttt gaatgtgttt atgaacagtt tttgtcgact caaaagttaa gatgagaata    9960
tggaagaaag taaagtttaa aagtcatgat gggaacaagg aatggaactc aaacattcta    10020
atactcaaca aacgcaatta tattattacc atgactcatc tttcaagttc catcaaaaag    10080
attcgtggaa aataatagac ttacgtttca aatccatgtt tctttcttta taacaaaaaa    10140
aatggatgtt tcttgacgcg tgtcgagagt actcaccatt actctgactt cagtgagttt    10200
ggtcaagtgg tcttttttt tctcatgtca ccaaaggtcc aaaccctaga aattagttcg    10260
aactttccat agaagaactg aataaatggt ccaaaattgt tttaaaagg acctaagcca    10320
ttagttcatt gaattcgagt taatgggtga agatttttat gataacgaaa gtcggagtaa    10380
ttatgctttt ggtccgatag ttttctaatt tgttttcttt ccatttttt tttttcaaat    10440
actacatact atataagata gtggtttgtg ttaatgtcat cgatgtgtta ccatccgcat    10500
tatattaatt atttatccca acataaagtc agaatctga atttctttgt tataaaatac    10560
agtaaatggt tccgtttaag ctgttagatg atttttgagt aaaaactaat gtaaaaaaaa    10620
```

| | |
|---|---|
| caaaaaaaaa acaatgtagt tcataataca tgcatgtttt aaagaagttt cttgtttact | 10680 |
| atcaacttga atagtatttc acgaagtcaa aattgttcat tccgactttt ctatgtggag | 10740 |
| aaaaaaaatt ctatcattgt gcacaattta acagaatgta atttcttgta aaagaagagg | 10800 |
| aaacaattcg ctgttagtaa atgtgaagta tagaagtcta aaatgagata cctcaactag | 10860 |
| cttgaattaa gaaaaaaaac aaaaactcta tcgacatgaa aaaggtcgca aatatttatc | 10920 |
| atttatcaat gccaaaggag tatttggttc acaaaatact gaatcattta tatagatata | 10980 |
| taattagctc taaattctac tataacttgc aaaataagta tactgactca attatatagc | 11040 |
| gtttaaaaat agacgatttg tatgatgagg tccatatata tggagatgtg catgcaacta | 11100 |
| tcgacatttt cacacgttga tatcgtcttt ctccaatgga gacttgaatt tgtgtaaact | 11160 |
| atgaatactc gtctctctaa gacctttttt cttcaaccat gccaactatt taggtaagat | 11220 |
| tttactgtct ttgattgata ttaaatactt agccgtggcg ttatcaatga atgataataa | 11280 |
| aaatgcggat aaaagccaaa ggtgttggaa ataaatccaa gaatgaagac gtagatgtcg | 11340 |
| atgggtattt taagaacttg aatttgtcac gactcacacg ttaaaatata ttatccgaat | 11400 |
| tgtttagtct aaagacacac atatattgaa aaagaaaagg taaatgaagc tcattggtgc | 11460 |
| ctaaatgtga aatgaagccg aaatgtgtta ggtgaacaca tttaaatata caaaaagaaa | 11520 |
| tataatagaa acaaaactaa ttaacaaagt cgcaatttgt attgtataaa atatctttcc | 11580 |
| gtctcccgtc atatttgaaa aaaaaaaaat tacaaatctg ttaatttttaa aactttctag | 11640 |
| aaaaacacaa gtatataatt ttctcttttc gtgcgtgttt gttttaaaat aacattgttt | 11700 |
| tgattggcga ctcaacatat tttagcattt acatatttct gcatatatta aatgatttat | 11760 |
| aaactcaact atagattaaa atataatttg acatctaata attttaacaa taatataaaa | 11820 |
| tatgagattt ataaattacg aatataaata ttcaagggag agaaaaagta gaacataatt | 11880 |
| caaaagataa gacttttttag actttttttaa caatattttt gatggataaa aattattcaa | 11940 |
| aagagaagaa agtaagaaga aaagatgttt ctgagaattt ctagggcgcg ccttcttaca | 12000 |
| aaggtaggac caacatttgt gatctataaa tcttcctact acgttatata gagacccttc | 12060 |
| gacataaaac ttaactcgtt tatatatttg ttttacttgt tttgcacata cacacaaaaa | 12120 |
| taaaaaagac tttatattta tttactttttt aatcacacgg attagctccg gcgaagtatg | 12180 |
| gtcgtcgtct tcatcttctt cctccatcat cagatttttc cttaaatgga agaaaccaaa | 12240 |
| cgaaactccg atcttctccg ttctcgtgtt ttcctctctg gctttattg ctgggattgg | 12300 |
| gaatttctca ccgctctctt gcttttttagt tgctgattct ttttccttcg actttctatt | 12360 |
| tccaatcttt cttcttctct ttgtgtatta gattattttt agtttattt ttctgtggta | 12420 |
| aaataaaaaa agttcgccgg agggtacctt cgacgacaag accgggccca caagtttgta | 12480 |
| caaaaaagct gaacgagaaa cgtaaaatga tataaatatc aatatattaa attagatttt | 12540 |
| gcataaaaaa cagactacat aatactgtaa aacacaacat atccagtcac tatggcggcc | 12600 |
| gcattaggca ccccaggctt tacactttat gcttccggct cgtataatgt gtggattttg | 12660 |
| agttaggatc cgtcgagatt ttcaggagct aaggaagcta aaatggagaa aaaaatcact | 12720 |
| ggatatacca ccgttgatat atcccaatgg catcgtaaag aacattttga ggcatttcag | 12780 |
| tcagttgctc aatgtaccta taaccagacc gttcagctgg atattacggc ctttttaaag | 12840 |
| accgtaaaga aaaataagca caagttttat ccggccttta ttcacattct tgcccgcctg | 12900 |
| atgaatgctc atccggaatt ccgtatggca atgaaagacg gtgagctggt gatatgggat | 12960 |
| agtgttcacc cttgttacac cgttttccat gagcaaactg aaacgttttc atcgctctgg | 13020 |

```
agtgaatacc acgacgattt ccggcagttt ctacacatat attcgcaaga tgtggcgtgt   13080
tacggtgaaa acctggccta tttccctaaa gggtttattg agaatatgtt tttcgtctca   13140
gccaatccct gggtgagttt caccagtttt gatttaaacg tggccaatat ggacaacttc   13200
ttcgccccg ttttcaccat gggcaaatat tatacgcaag cgacaaggt gctgatgccg    13260
ctggcgattc aggttcatca tgccgtttgt gatggcttcc atgtcggcag aatgcttaat   13320
gaattacaac agtactgcga tgagtggcag ggcgggcgt aaagatctgg atccggctta   13380
ctaaaagcca gataacagta tgcgtatttg cgcgctgatt tttgcggtat aagaatatat   13440
actgatatgt atacccgaag tatgtcaaaa agaggtatgc tatgaagcag cgtattacag   13500
tgacagttga cagcgacagc tatcagttgc tcaaggcata tatgatgtca atatctccgg   13560
tctggtaagc acaaccatgc agaatgaagc ccgtcgtctg cgtgccgaac gctgaaaagc   13620
ggaaaatcag aagggatgg ctgaggtcgc ccggtttatt gaaatgaacg gctcttttgc    13680
tgacgagaac aggggctggt gaaatgcagt ttaaggttta cacctataaa agagagagcc   13740
gttatcgtct gtttgtggat gtacagagtg atattattga cacgcccggg cgacggatgg   13800
tgatccccct ggccagtgca cgtctgctgt cagataaagt ctcccgtgaa ctttacccgg   13860
tggtgcatat cggggatgaa agctggcgca tgatgaccac cgatatggcc agtgtgccgg   13920
tctccgttat cggggaagaa gtggctgatc tcagccaccg cgaaaatgac atcaaaaacg   13980
ccattaacct gatgttctgg ggaatataaa tgtcaggctc ccttatacac agccagtctg   14040
caggtcgacc atagtgactg gatatgttgt gttttacagt attatgtagt ctgtttttta   14100
tgcaaaatct aatttaatat attgatattt atatcatttt acgtttctcg ttcagctttc   14160
ttgtacaaag tggtaggggc ccggctcttc tcctcactcg agccgctcga atttccccga   14220
tcgttcaaac atttggcaat aaagtttctt aagattgaat cctgttgccg gtcttgcgat   14280
gattatcata taatttctgt tgaattacgt taagcatgta ataattaaca tgtaatgcat   14340
gacgttattt atgagatggg ttttatgat tagagtcccg caattataca tttaatacgc    14400
gatagaaaac aaaatatagc gcgcaaacta ggataaatta tcgcgcgcgg tgtcatctat   14460
gttactagat cgggaatt                                                 14478
```

<210> SEQ ID NO 133
<211> LENGTH: 14488
<212> TYPE: DNA
<213> ORGANISM: Artificial Sequence
<220> FEATURE:
<223> OTHER INFORMATION: Plasmid pGX181
<220> FEATURE:
<221> NAME/KEY: misc_feature
<222> LOCATION: (8909)..(14483)
<223> OTHER INFORMATION: Insert region

<400> SEQUENCE: 133

```
cgtaatcatg gtcatagctg tttcctgtgt gaaattgtta tccgctcaca attccacaca     60
acatacgagc cggaagcata aagtgtaaag cctggggtgc ctaatgagtg agctaactca    120
cattaattgc gttgcgctca ctgcccgctt tccagtcggg aaacctgtcg tgccagctgc    180
attaatgaat cggccaacgc gcggggagag cggtttgcg tattggctag agcagcttgc     240
caacatggtg gagcacgaca ctctcgtcta ctccaagaat atcaaagata cagtctcaga    300
agaccaaagg gctattgaga cttttcaaca aagggtaata tcgggaaacc tcctcggatt    360
ccattgccca gctatctgtc acttcatcaa aaggacagta gaaaggaag gtggcaccta     420
```

```
caaatgccat cattgcgata aaggaaaggc tatcgttcaa gatgcctctg ccgacagtgg      480
tcccaaagat ggaccccac ccacgaggag catcgtggaa aaagaagacg ttccaaccac       540
gtcttcaaag caagtggatt gatgtgataa catggtggag cacgacactc tcgtctactc      600
caagaatatc aaagatacag tctcagaaga ccaaagggct attgagactt ttcaacaaag      660
ggtaatatcg ggaaacctcc tcggattcca ttgcccagct atctgtcact tcatcaaaag     720
gacagtagaa aaggaaggtg gcacctacaa atgccatcat tgcgataaag gaaaggctat     780
cgttcaagat gcctctgccg acagtggtcc caaagatgga cccccaccca cgaggagcat    840
cgtggaaaaa gaagacgttc caaccacgtc ttcaaagcaa gtggattgat gtgatatctc     900
cactgacgta agggatgacg cacaatccca ctatccttcg caagaccttc ctctatataa    960
ggaagttcat ttcatttgga gaggacacgc tgaaatcacc agtctctctc tacaaatcta   1020
tctctctcga gctttcgcag atcccggggg gcaatgagat atgaaaaagc ctgaactcac   1080
cgcgacgtct gtcgagaagt ttctgatcga aaagttcgac agcgtctccg acctgatgca    1140
gctctcggag ggcgaagaat ctcgtgcttt cagcttcgat gtaggagggc gtggatatgt    1200
cctgcgggta aatagctgcg ccgatggttt ctacaaagat cgttatgttt atcggcactt    1260
tgcatcggcc gcgctcccga ttccggaagt gcttgacatt ggggagttta gcgagagcct   1320
gacctattgc atctcccgcc gtgcacaggg tgtcacgttg caagacctgc ctgaaaccga   1380
actgcccgct gttctacaac cggtcgcgga ggctatggat gcgatcgctg cggccgatct   1440
tagccagacg agcgggttcg gcccattcgg accgcaagga atcggtcaat acactacatg   1500
gcgtgatttc atatgcgcga ttgctgatcc ccatgtgtat cactggcaaa ctgtgatgga   1560
cgacaccgtc agtgcgtccg tcgcgcaggc tctcgatgag ctgatgcttt gggccgagga   1620
ctgccccgaa gtccggcacc tcgtgcacgc ggatttcggc tccaacaatg tcctgacgga   1680
caatggccgc ataacagcgg tcattgactg gagcgaggcg atgttcgggg attcccaata   1740
cgaggtcgcc aacatcttct tctggaggcc gtggttggct tgtatggagc agcagacgcg   1800
ctacttcgag cggaggcatc cggagcttgc aggatcgcca cgactccggg cgtatatgct   1860
ccgcattggt cttgaccaac tctatcagag cttggttgac ggcaatttcg atgatgcagc   1920
ttgggcgcag ggtcgatgcg acgcaatcgt ccgatccgga gccgggactg tcgggcgtac   1980
acaaatcgcc cgcagaagcg cggccgtctg gaccgatggc tgtgtagaag tactcgccga   2040
tagtggaaac cgacgcccca gcactcgtcc gagggcaaag aaatagagta gatgccgacc   2100
ggatctgtcg atcgacaagc tcgagttttct ccataataat gtgtgagtag ttcccagata   2160
agggaattag ggttcctata gggtttcgct catgtgttga gcatataaga aacccttagt   2220
atgtatttgt atttgtaaaa tacttctatc aataaaattt ctaattccta aaaccaaaat   2280
ccagtactaa aatccagatc ccccgaatta attcggcgtt aattcagtac attaaaaacg   2340
tccgcaatgt gttattaagt tgtctaagcg tcaatttgtt tacaccacaa tatatcctgc   2400
caccagccag ccaacagctc cccgaccggc agctcggcac aaaatcacca ctcgatacag   2460
gcagcccatc agtccgggac ggcgtcagcg ggagagccgt tgtaaggcgg cagactttgc   2520
tcatgttacc gatgctattc ggaagaacgg caactaagct gccgggtttg aaacacggat   2580
gatctcgcgg agggtagcat gttgattgta acgatgacag agcgttgctg cctgtgatca   2640
ccgcggtttc aaaatcggct ccgtcgatac tatgttatac gccaactttg aaacaacttt   2700
tgaaaaagct gttttctggt atttaaggtt ttagaatgca aggaacagtg aattggagtt   2760
cgtcttgtta taattagctt cttggggtat ctttaaatac tgtagaaaag aggaaggaaa   2820
```

```
taataaatgg ctaaaatgag aatatcaccg gaattgaaaa aactgatcga aaaataccgc    2880
tgcgtaaaag atacggaagg aatgtctcct gctaaggtat ataagctggt gggagaaaat    2940
gaaaacctat atttaaaaat gacggacagc cggtataaag ggaccaccta tgatgtggaa    3000
cgggaaaagg acatgatgct atggctggaa ggaaagctgc ctgttccaaa ggtcctgcac    3060
tttgaacggc atgatggctg gagcaatctg ctcatgagtg aggccgatgg cgtcctttgc    3120
tcggaagagt atgaagatga acaaagccct gaaaagatta tcgagctgta tgcggagtgc    3180
atcaggctct ttcactccat cgacatatcg gattgtccct atacgaatag cttagacagc    3240
cgcttagccg aattggatta cttactgaat aacgatctgg ccgatgtgga ttgcgaaaac    3300
tgggaagaag acactccatt taaagatccg cgcgagctgt atgatttttt aaagacggaa    3360
aagcccgaag aggaacttgt cttttcccac ggcgacctgg gagacagcaa catctttgtg    3420
aaagatggca agtaagtgg ctttattgat cttgggagaa gcggcagggc ggacaagtgg    3480
tatgacattg ccttctgcgt ccggtcgatc agggaggata tcggggaaga acagtatgtc    3540
gagctatttt ttgacttact ggggatcaag cctgattggg agaaaataaa atattatatt    3600
ttactggatg aattgtttta gtacctagaa tgcatgacca aaatccctta acgtgagttt    3660
tcgttccact gagcgtcaga ccccgtagaa aagatcaaag gatcttcttg agatccttt    3720 tttctgcgcg taatctgctg cttgcaaaca aaaaaaccac cgctaccagc ggtggtttgt    3780
ttgccggatc aagagctacc aactcttttt ccgaaggtaa ctggcttcag cagagcgcag    3840
ataccaaata ctgtccttct agtgtagccg tagttaggcc accacttcaa gaactctgta    3900
gcaccgccta catacctcgc tctgctaatc ctgttaccag tggctgctgc cagtggcgat    3960
aagtcgtgtc ttaccgggtt ggactcaaga cgatagttac cggataaggc gcagcggtcg    4020
ggctgaacgg ggggttcgtg cacacagccc agcttggagc gaacgaccta caccgaactg    4080
agatacctac agcgtgagct atgagaaagc gccacgcttc ccgaagggag aaaggcggac    4140
aggtatccgg taagcggcag ggtcggaaca ggagagcgca cgagggagct tccaggggga    4200
aacgcctggt atctttatag tcctgtcggg tttcgccacc tctgacttga gcgtcgattt    4260
ttgtgatgct cgtcaggggg gcggagccta tggaaaaacg ccagcaacgc ggccttttta    4320
cggttcctgg ccttttgctg gccttttgct cacatgttct ttcctgcgtt atcccctgat    4380
tctgtggata accgtattac cgcctttgag tgagctgata ccgctcgccg cagccgaacg    4440
accgagcgca gcgagtcagt gagcgaggaa gcggaagagc gcctgatgcg gtattttctc    4500
cttacgcatc tgtgcggtat ttcacaccgc atatggtgca ctctcagtac aatctgctct    4560
gatgccgcat agttaagcca gtatacactc cgctatcgct acgtgactgg gtcatggctg    4620
cgccccgaca cccgccaaca cccgctgacg cgccctgacg gcttgtctg ctcccggcat    4680 ccgcttacag acaagctgtg accgtctccg ggagctgcat gtgtcagagg ttttcaccgt    4740
catcaccgaa acgcgcgagg cagggtgcct tgatgtgggc gccggcggtc gagtggcgac    4800
ggcgcggctt gtccgcgccc tggtagattg cctggccgta ggccagccat ttttgagcgg    4860
ccagcggccg cgataggccg acgcgaagcg cggggcgta gggagcgcag cgaccgaagg    4920
gtaggcgctt tttgcagctc ttcggctgtg cgctggccag acagttatgc acaggccagg    4980
cgggttttaa gagttttaat aagttttaaa gagttttagg cggaaaaatc gccttttttc    5040
tcttttatat cagtcactta catgtgtgac cggttcccaa tgtacggctt tgggttccca    5100
atgtacgggt tccggttccc aatgtacggc tttgggttcc caatgtacgt gctatccaca    5160
```

```
ggaaagagac cttttcgacc ttttccccct gctagggcaa tttgccctag catctgctcc    5220
gtacattagg aaccggcgga tgcttcgccc tcgatcaggt tgcggtagcg catgactagg    5280
atcgggccag cctgccccgc ctcctccttc aaatcgtact ccggcaggtc atttgacccg    5340
atcagcttgc gcacggtgaa acagaacttc ttgaactctc cggcgctgcc actgcgttcg    5400
tagatcgtct tgaacaacca tctggcttct gccttgcctg cggcgcggcg tgccaggcgg    5460
tagagaaaac ggccgatgcc gggatcgatc aaaaagtaat cggggtgaac cgtcagcacg    5520
tccgggttct tgccttctgt gatctcgcgg tacatccaat cagctagctc gatctcgatg    5580
tactccggcc gcccggtttc gctctttacg atcttgtagc ggctaatcaa ggcttcaccc    5640
tcggataccg tcaccaggcg gccgttcttg gccttcttcg tacgctgcat ggcaacgtgc    5700
gtggtgttta accgaatgca ggtttctacc aggtcgtctt tctgctttcc gccatcggct    5760
cgccggcaga acttgagtac gtccgcaacg tgtggacgga acacgcggcc gggcttgtct    5820
cccttccctt cccggtatcg gttcatggat tcggttagat gggaaaccgc catcagtacc    5880
aggtcgtaat cccacacact ggccatgccg gccggccctg cggaaacctc tacgtgcccg    5940
tctggaagct cgtagcggat caccctcgcca gctcgtcggt cacgcttcga cagacggaaa    6000
acggccacgt ccatgatgct gcgactatcg cgggtgccca cgtcatagag catcggaacg    6060
aaaaaatctg gttgctcgtc gcccttgggc ggcttcctaa tcgacggcgc accggctgcc    6120
ggcggttgcc gggattcttt gcggattcga tcagcggccg cttgccacga ttcaccgggg    6180
cgtgcttctg cctcgatgcg ttgccgctgg gcggcctgcg cggccttcaa cttctccacc    6240
aggtcatcac ccagcgccgc gccgatttgt accgggccgg atggtttgcg accgtcacgc    6300
cgattcctcg ggcttggggg ttccagtgcc attgcagggc cggcagacaa cccagccgct    6360
tacgcctggc caaccgcccg ttcctccaca catgggggcat tccacggcgt cggtgcctgg    6420
ttgttcttga ttttccatgc cgcctccttt agccgctaaa attcatctac tcatttattc    6480
atttgctcat ttactctggt agctgcgcga tgtattcaga tagcagctcg gtaatggtct    6540
tgccttggcg taccgcgtac atcttcagct tggtgtgatc ctccgccggc aactgaaagt    6600
tgacccgctt catggctggc gtgtctgcca ggctggccaa cgttgcagcc ttgctgctgc    6660
gtgcgctcgg acggccggca cttagcgtgt ttgtgctttt gctcattttc tctttacctc    6720
attaactcaa atgagttttg atttaatttc agcggccagc gcctggacct cgcgggcagc    6780
gtcgccctcg ggttctgatt caagaacggt tgtgccggcg gcggcagtgc ctgggtagct    6840
cacgcgctgc gtgatacggg actcaagaat gggcagctcg taccggcca gcgcctcggc    6900
aacctcaccg ccgatgcgcg tgcctttgat cgcccgcgac acgacaaagg ccgcttgtag    6960
ccttccatcc gtgacctcaa tgcgctgctt aaccagctcc accaggtcgg cggtggccca    7020
tatgtcgtaa gggcttggct gcaccggaat cagcacgaag tcggctgcct tgatcgcgga    7080
cacagccaag tccgccgcct ggggcgctcc gtcgatcact acgaagtcgc gccggccgat    7140
ggccttcacg tcgcggtcaa tcgtcgggcg gtcgatgccg caacggtta gcggttgatc    7200
ttcccgcacg gccgcccaat cgcgggcact gccctgggga tcggaatcga ctaacagaac    7260
atcgccccg gcgagttgca gggcgcgggc tagatgggtt gcgatggtcg tcttgcctga    7320
cccgcctttc tggttaagta cagcgataac cttcatgcgt tcccttgcg tatttgttta    7380
tttactcatc gcatcatata cgcagcgacc gcatgacgca agctgtttta ctcaaataca    7440
catcacctt ttagacggcg gcgctcggtt tcttcagcgg ccaagctggc cggccaggcc    7500
gccagcttgg catcagacaa accggccagg atttcatgca gccgcacggt tgagacgtgc    7560
```

```
gcgggcggct cgaacacgta cccggccgcg atcatctccg cctcgatctc ttcggtaatg    7620
aaaaacggtt cgtcctggcc gtcctggtgc ggtttcatgc ttgttcctct tggcgttcat    7680
tctcggcggc cgccagggcg tcggcctcgg tcaatgcgtc ctcacggaag gcaccgcgcc    7740
gcctggcctc ggtgggcgtc acttcctcgc tgcgctcaag tgcgcggtac agggtcgagc    7800
gatgcacgcc aagcagtgca gccgcctctt tcacggtgcg gccttcctgg tcgatcagct    7860
cgcgggcgtg cgcgatctgt gccggggtga gggtagggcg ggggccaaac ttcacgcctc    7920
gggccttggc ggcctcgcgc ccgctccggg tgcggtcgat gattagggaa cgctcgaact    7980
cggcaatgcc ggcgaacacg gtcaacacca tgccgccggc cggcgtggtg gtgtcggccc    8040
acggctctgc caggctacgc aggcccgcgc cggcctcctg gatgcgctcg gcaatgtcca    8100
gtaggtcgcg ggtgctgcgg gccaggcggt ctagcctggt cactgtcaca acgtcgccag    8160
ggcgtaggtg gtcaagcatc ctggccagct ccggcggtc gcgcctggtg ccggtgatct    8220
tctcggaaaa cagcttggtg cagccggccg cgtgcagttc ggcccgttgg ttggtcaagt    8280
cctggtcgtc ggtgctgacg cgggcatagc ccagcaggcc agcggcggcg ctcttgttca    8340
tggcgtaatg tctccggttc tagtcgcaag tattctactt tatgcgacta aaacacgcga    8400
caagaaaacg ccaggaaaag ggcagggcgg cagcctgtcg cgtaacttag gacttgtgcg    8460
acatgtcgtt ttcagaagac ggctgcactg aacgtcagaa gccgactgca ctatagcagc    8520
ggaggggttg gatcaaagta cttttgatccc gaggggaacc ctgtggttgg catgcacata    8580
caaatggacg aacggataaa ccttttcacg ccctttttaaa tatccgttat tctaataaac    8640
gctcttttct cttaggttta cccgccaata tatcctgtca aacactgata gtttaaactg    8700
aaggcgggaa acgacaatct gatccaagct caagctgctc tagcattcgc cattcaggct    8760
gcgcaactgt tgggaagggc gatcggtgcg ggcctcttcg ctattacgcc agctggcgaa    8820
agggggatgt gctgcaaggc gattaagttg ggtaacgcca gggttttccc agtcacgacg    8880
ttgtaaaacg acggccagtg ccaagctttt tacagagaat ttggaccgtc cgatgtaaag    8940
cgaaaataga tctaggtttt ccacgtgtcc cctattttaa tgaaaccttc tgattcatgt    9000
agaagtttta ctcaatttaa tatttttttag tatgtagttt tgtgtgtgtg tgtgtgtgtg    9060
tttttatggc tccacaccaa cttttaaaat ggtagaagca tgttgcatgt gatcgagtaa    9120
aaagccaata atgagattca gaaaaataaa aattacttat atagtttttt agagaaaaaa    9180 ttgtatttg tttaaagcct taatccggtt gttgaaagag ctgtgtcacg agttaaaaat     9240
attttctttt catttttttaa gtaattagtt tataatgcaa aaatggtttt tatttatttg    9300
tcttcgctta tagaactgca aattgagaga gaaaaaatg aattagtggt ggtgaccaaa     9360
cattcaggaa gctgtgattg atcatttgtt tttgaggtga gtgtagtggc aacgtatgac    9420
gttaacatat ggcgtacata ataattacat gaacttaatc ataataatca tattgcattt    9480
aattcatata tcatatccca ttagttggac cacttgattt gaggtcatga gaagaacatt    9540
tatgtttttt ttagtttgaa tcggagtgat cactaaaaac tagatactga aattttcaa     9600 actaaaatca tattaatctt caaaaaatgt gaaatctaaa aaaaaaaaaa attttaacgc    9660
gttcattgta gccaagtagc caagtattgt taaagtagta gtaaagaag tttagcttta     9720 agtgatataa tttgacacaa atcctactta gatatggata ataggatata gcttcatgta    9780 tattttttatc gttgcttctg taaccccaaa atgtgttgat ataagcattt gaatattcgt    9840
atgtataatg ttttctttc accgtaaaac atattacaat gttagtttat attggatttt    9900
```

| | |
|---|---|
| gaatgtgttt atgaacagtt tttgtcgact caaaagttaa gatgagaata tggaagaaag | 9960 |
| taaagtttaa aagtcatgat gggaacaagg aatggaactc aaacattcta atactcaaca | 10020 |
| aacgcaatta tattattacc atgactcatc tttcaagttc catcaaaaag attcgtggaa | 10080 |
| aataatagac ttacgtttca aatccatgtt tctttcttta taacaaaaaa aatggatgtt | 10140 |
| tcttgacgcg tgtcgagagt actcaccatt actctgactt cagtgagttt ggtcaagtgg | 10200 |
| tcttttttt tctcatgtca ccaaaggtcc aaaccctaga aattagttcg aactttccat | 10260 |
| agaagaactg aataaatggt ccaaaattgt tttaaaaagg acctaagcca ttagttcatt | 10320 |
| gaattcgagt taatgggtga agatttttat gataacgaaa gtcggagtaa ttatgctttt | 10380 |
| ggtccgatag ttttctaatt tgttttcttt ccattttttt tttttcaaat actacatact | 10440 |
| atataagata gtggtttgtg ttaatgtcat cgatgtgtta ccatccgcat tatattaatt | 10500 |
| atttatccca acataaagtc agaatctgta atttctttgt tataaaatac agtaaatggt | 10560 |
| tccgtttaag ctgttagatg atttttgagt aaaaactaat gtaaaaaaaa caaaaaaaaa | 10620 |
| acaatgtagt tcataataca tgcatgtttt aaagaagttt cttgtttact atcaacttga | 10680 |
| atagtatttc acgaagtcaa aattgttcat tccgactttt ctatgtggag aaaaaaaatt | 10740 |
| ctatcattgt gcacaattta acagaatgta atttcttgta aaagaagagg aaacaattcg | 10800 |
| ctgttagtaa atgtgaagta tagaagtcta aaatgagata cctcaactag cttgaattaa | 10860 |
| gaaaaaaac aaaaactcta tcgacatgaa aaaggtcgca aatatttatc atttatcaat | 10920 |
| gccaaaggag tatttggttc acaaaatact gaatcattta tatagatata taattagctc | 10980 |
| taaattctac tataacttgc aaaataagta tactgactca attatatagc gtttaaaaat | 11040 |
| agacgatttg tatgatgagg tccatatata tggagatgtg catgcaacta tcgacatttt | 11100 |
| cacacgttga tatcgtcttt ctccaatgga gacttgaatt tgtgtaaact atgaatactc | 11160 |
| gtctctctaa gacctttttt cttcaaccat gccaactatt taggtaagat tttactgtct | 11220 |
| ttgattgata ttaaatactt agccgtggcg ttatcaatga atgataataa aaatgcggat | 11280 |
| aaaagccaaa ggtgttggaa ataaatccaa gaatgaagac gtagatgtcg atgggtattt | 11340 |
| taagaacttg aatttgtcac gactcacacg ttaaaatata ttatccgaat tgtttagtct | 11400 |
| aaagacacac atatattgaa aaagaaaagg taaatgaagc tcattggtgc ctaaatgtga | 11460 |
| aatgaagccg aaatgtgtta ggtgaacaca tttaaatata caaaaagaaa tataatagaa | 11520 |
| acaaaactaa ttaacaaagt cgcaatttgt attgtataaa atatctttcc gtctcccgtc | 11580 |
| atatttgaaa aaaaaaaat tacaaatctg ttaattttaa aactttctag aaaaacacaa | 11640 |
| gtatataatt ttctcttttc gtgcgtgttt gttttaaaat aacattgttt tgattggcga | 11700 |
| ctcaacatat tttagcattt acatatttct gcatatatta aatgatttat aaactcaact | 11760 |
| atagattaaa atataatttg acatctaata attttaacaa taatataaaa tatgagattt | 11820 |
| ataaattacg aatataaata ttcaagggag agaaaaagta gaacataatt caaaagataa | 11880 |
| gacttttag actttttaa caatattttt gatggataaa aattattcaa aagagaagaa | 11940 |
| agtaagaaga aaagatgttt ctgagaatta ctagaaacag catccgtttt tataatttaa | 12000 |
| ttttcttaca aaggtaggac caacatttgt gatctataaa tcttcctact acgttatata | 12060 |
| gagacccttc gacataacac ttaactcgtt tatatatttg ttttacttgt tttgcacata | 12120 |
| cacacaaaaa taaaaagac tttatatta tttactttt aatcacacgg attagctccg | 12180 |
| gcgaagtctg gtcgtcgtct tcatcttctt cctccatcat cagattttc cttaactgga | 12240 |
| agaaaccaaa cgaaactccg atcttctccg ttctcgtgtt ttcctctctg gctttattg | 12300 |

```
ctgggattgg gaatttctca ccgctctctt gcttttagt tgctgattct ttttccttcg   12360
actttctatt tccaatcttt cttcttctct ttgtgtatta gattatttt agttttattt   12420
ttctgtggta aaataaaaaa agttcgccgg agggtacctt cgacgacaag accgggccca   12480
caagtttgta caaaaaagct gaacgagaaa cgtaaaatga tataaatatc aatatattaa   12540
attagatttt gcataaaaaa cagactacat aatactgtaa aacacaacat atccagtcac   12600
tatgcgggcc gcattaggca ccccaggctt tacactttat gcttccggct cgtataatgt   12660
gtggattttg agttaggatc cgtcgagatt tcaggagct aaggaagcta aaatggagaa    12720
aaaaatcact ggatatacca ccgttgatat atcccaatgg catcgtaaag aacattttga   12780
ggcatttcag tcagttgctc aatgtaccta taaccagacc gttcagctgg atattacggc   12840
ctttttaaag accgtaaaga aaataagca caagttttat ccggccttta ttcacattct    12900
tgcccgcctg atgaatgctc atccggaatt ccgtatggca atgaaagacg gtgagctggt   12960
gatatgggat agtgttcacc cttgttacac cgttttccat gagcaaactg aaacgttttc   13020
atcgctctgg agtgaatacc acgacgattt ccggcagttt ctacacatat attcgcaaga   13080
tgtggcgtgt tacggtgaaa acctggccta tttccctaaa gggtttattg agaatatgtt   13140
tttcgtctca gccaatccct gggtgagttt caccagtttt gatttaaacg tggccaatat   13200
ggacaacttc ttcgccccg ttttcaccat gggcaaatat tatacgcaag gcgacaaggt    13260
gctgatgccg ctggcgattc aggttcatca tgccgtttgt gatggcttcc atgtcggcag   13320
aatgcttaat gaattacaac agtactgcga tgagtggcag ggcggggcgt aaagatctgg   13380
atccggctta ctaaaagcca gataacagta tgcgtatttg cgcgctgatt tttgcggtat   13440
aagaatatat actgatatgt atacccgaag tatgtcaaaa agaggtatgc tatgaagcag   13500
cgtattacag tgacagttga cagcgacagc tatcagttgc tcaaggcata tatgatgtca   13560
atatctccgg tctggtaagc acaaccatgc agaatgaagc ccgtcgtctg cgtgccgaac   13620
gctggaaagc ggaaaatcag gaagggatgg ctgaggtcgc ccggtttatt gaaatgaacg   13680
gctcttttgc tgacgagaac aggggctggt gaaatgcagt ttaaggttta cacctataaa   13740
agagagagcc gttatcgtct gtttgtggat gtacagagtg atattattga cacgcccggg   13800
cgacggatgg tgatccccct ggccagtgca cgtctgctgt cagataaagt ctcccgtgaa   13860
ctttacccgg tggtgcatat cggggatgaa agctggcgca tgatgaccac cgatatggcc   13920
agtgtgccgg tctccgttat cggggaagaa gtggctgatc tcagccaccg cgaaaatgac   13980
atcaaaaacg ccattaacct gatgttctgg ggaatataaa tgtcaggctc ccttatacac   14040
agccagtctg caggtcgacc atagtgactg gatatgttgt gttttacagt attatgtagt   14100
ctgttttta tgcaaaatct aatttaatat attgatattt atatcatttt acgtttctcg   14160
ttcagctttc ttgtacaaag tggtaggggc ccggctcttc tcctcactcg agccgctcga   14220
atttccccga tcgttcaaac atttggcaat aaagtttctt aagattgaat cctgttgccg   14280
gtcttgcgat gattatcata taatttctgt tgaattacgt taagcatgta ataattaaca   14340
tgtaatgcat gacgttattt atgagatggg ttttatgat tagagtcccg caattataca    14400
tttaatacgc gatagaaaac aaaatatagc gcgcaaacta ggataaatta tcgcgcgcgg   14460
tgtcatctat gttactagat cgggaatt                                     14488
```

<210> SEQ ID NO 134
<211> LENGTH: 12194
<212> TYPE: DNA

<213> ORGANISM: Artificial Sequence
<220> FEATURE:
<223> OTHER INFORMATION: Plasmid pGX179
<220> FEATURE:
<221> NAME/KEY: misc_feature
<222> LOCATION: (8909)..(12189)
<223> OTHER INFORMATION: Insert region

<400> SEQUENCE: 134

```
cgtaatcatg gtcatagctg tttcctgtgt gaaattgtta ccgctcaca attccacaca      60
acatacgagc cggaagcata agtgtaaag cctggggtgc ctaatgagtg agctaactca     120
cattaattgc gttgcgctca ctgcccgctt tccagtcggg aaacctgtcg tgccagctgc    180
attaatgaat cggccaacgc gcggggagag gcggtttgcg tattggctag cagcttgc     240
caacatggtg gagcacgaca ctctcgtcta ctccaagaat atcaaagata cagtctcaga   300
agaccaaagg gctattgaga cttttcaaca aggggtaata tcgggaaacc tcctcggatt   360
ccattgccca gctatctgtc acttcatcaa aaggacagta gaaaaggaag gtggcaccta   420
caaatgccat cattgcgata aaggaaaggc tatcgttcaa gatgcctctg ccgacagtgg   480
tcccaaagat ggacccccac ccacgaggag catcgtggaa aaagaagacg ttccaaccac   540
gtcttcaaag caagtggatt gatgtgataa catggtggag cacgacactc tcgtctactc   600
caagaatatc aaagatacag tctcagaaga ccaaagggct attgagactt ttcaacaaag   660
ggtaatatcg ggaaacctcc tcggattcca ttgcccagct atctgtcact tcatcaaaag   720
gacagtagaa aaggaaggtg gcacctacaa atgccatcat tgcgataaag gaaaggctat   780
cgttcaagat gcctctgccg acagtggtcc caaagatgga ccccccaccca cgaggagcat   840
cgtggaaaaa gaagacgttc caaccacgtc ttcaaagcaa gtggattgat gtgatatctc   900
cactgacgta agggatgacg cacaatccca ctatccttcg caagaccttc ctctatataa   960
ggaagttcat ttcatttgga gaggacacgc tgaaatcacc agtctctctc tacaaatcta  1020
tctctctcga gctttcgcag atcccggggg gcaatgagat atgaaaaagc ctgaactcac  1080
cgcgacgtct gtcgagaagt ttctgatcga aaagttcgac agcgtctccg acctgatgca  1140
gctctcggag ggcgaagaat ctcgtgcttt cagcttcgat gtaggagggc gtggatatgt  1200
cctgcgggta aatagctgcg ccgatggttt ctacaaagat cgttatgttt atcggcactt  1260
tgcatcggcc gcgctcccga ttccggaagt gcttgacatt ggggagttta gcgagagcct  1320
gacctattgc atctcccgcc gtgcacaggg tgtcacgttg caagacctgc ctgaaaccga  1380
actgcccgct gttctacaac cggtcgcgga ggctatggat gcgatcgctg cggccgatct  1440
tagccagacg agcgggttcg gcccattcgg accgcaagga atcggtcaat acactacatg  1500
gcgtgatttc atatgcgcga ttgctgatcc ccatgtgtat cactggcaaa ctgtgatgga  1560
cgacaccgtc agtgcgtccg tcgcgcaggc tctcgatgag ctgatgcttt gggccgagga  1620
ctgccccgaa gtccggcacc tcgtgcacgc ggatttcggc tccaacaatg tcctgacgga  1680
caatggccgc ataacagcgg tcattgactg gagcgaggcg atgttcgggg attcccaata  1740
cgaggtcgcc aacatcttct tctggaggcc gtggttggct tgtatggagc agcagacgcg  1800
ctacttcgag cggaggcatc cggagcttgc aggatcgcca cgactccggg cgtatatgct  1860
ccgcattggt cttgaccaac tctatcagag cttggttgac ggcaatttcg atgatgcagc  1920
ttgggcgcag ggtcgatgcg acgcaatcgt ccgatccgga gccgggactg tcgggcgtac  1980
acaaatcgcc cgcagaagcg cggccgtctg gaccgatggc tgtgtagaag tactcgccga  2040
tagtggaaac cgacgcccca gcactcgtcc gagggcaaag aaatagagta gatgccgacc  2100
```

```
ggatctgtcg atcgacaagc tcgagtttct ccataataat gtgtgagtag ttcccagata  2160
agggaattag ggttcctata gggtttcgct catgtgttga gcatataaga aacccttagt  2220
atgtatttgt atttgtaaaa tacttctatc aataaaattt ctaattccta aaaccaaaat  2280
ccagtactaa aatccagatc ccccgaatta attcggcgtt aattcagtac attaaaaacg  2340
tccgcaatgt gttattaagt tgtctaagcg tcaatttgtt tacaccacaa tatatcctgc  2400
caccagccag ccaacagctc cccgaccggc agctcggcac aaaatcacca ctcgatacag  2460
gcagcccatc agtccgggac ggcgtcagcg ggagagccgt tgtaaggcgg cagactttgc  2520
tcatgttacc gatgctattc ggaagaacgg caactaagct gccgggtttg aaacacggat  2580
gatctcgcgg agggtagcat gttgattgta acgatgacag agcgttgctg cctgtgatca  2640
ccgcggtttc aaaatcggct ccgtcgatac tatgttatac gccaactttg aaaacaactt  2700
tgaaaaagct gttttctggt atttaaggtt ttagaatgca aggaacagtg aattggagtt  2760
cgtcttgtta taattagctt cttggggtat ctttaaatac tgtagaaaag aggaaggaaa  2820
taataaatgg ctaaaatgag aatatcaccg gaattgaaaa aactgatcga aaaataccgc  2880
tgcgtaaaag atacggaagg aatgtctcct gctaaggtat ataagctggt gggagaaaat  2940
gaaaacctat atttaaaaat gacggacagc cggtataaag ggaccaccta tgatgtggaa  3000
cgggaaaagg acatgatgct atggctggaa ggaaagctgc ctgttccaaa ggtcctgcac  3060
tttgaacggc atgatggctg gagcaatctg ctcatgagtg aggccgatgg cgtcctttgc  3120
tcggaagagt atgaagatga acaaagccct gaaaagatta tcgagctgta tgcggagtgc  3180
atcaggctct ttcactccat cgacatatcg gattgtccct atacgaatag cttagacagc  3240
cgcttagccg aattggatta cttactgaat aacgatctgg ccgatgtgga ttgcgaaaac  3300
tgggaagaag acactccatt taaagatccg cgcgagctgt atgatttttt aaagacggaa  3360
aagcccgaag aggaacttgt cttttcccac ggcgacctgg gagacagcaa catctttgtg  3420
aaagatggca aagtaagtgg ctttattgat cttgggagaa gcggcagggc ggacaagtgg  3480
tatgacattg ccttctgcgt ccggtcgatc agggaggata tcggggaaga acagtatgtc  3540
gagctatttt ttgacttact ggggatcaag cctgattggg agaaaataaa atattatatt  3600
ttactggatg aattgtttta gtacctagaa tgcatgacca aaatcccta acgtgagttt  3660 tcgttccact gagcgtcaga ccccgtagaa aagatcaaag gatcttcttg agatcctttt  3720
tttctgcgcg taatctgctg cttgcaaaca aaaaaaccac cgctaccagc ggtggtttgt  3780
ttgccggatc aagagctacc aactcttttt ccgaaggtaa ctggcttcag cagagcgcag  3840
ataccaaata ctgtccttct agtgtagccg tagttaggcc accacttcaa gaactctgta  3900
gcaccgccta catacctcgc tctgctaatc ctgttaccag tggctgctgc cagtggcgat  3960
aagtcgtgtc ttaccgggtt ggactcaaga cgatagttac cggataaggc gcagcggtcg  4020
ggctgaacgg ggggttcgtg cacacagccc agcttggagc gaacgaccta caccgaactg  4080
agatacctac agcgtgagct atgagaaagc gccacgcttc ccgaagggag aaaggcggac  4140
aggtatccgg taagcggcag ggtcggaaca ggagagcgca cgagggagct tccaggggga  4200
aacgcctggt atctttatag tcctgtcggg tttcgccacc tctgacttga gcgtcgattt  4260
ttgtgatgct cgtcaggggg gcggagccta tggaaaaacg ccagcaacgc ggccttttta  4320
cggttcctgg ccttttgctg gccttttgct cacatgttct ttcctgcgtt atcccctgat  4380
tctgtggata accgtattac cgcctttgag tgagctgata ccgctcgccg cagccgaacg  4440
```

```
accgagcgca gcgagtcagt gagcgaggaa gcggaagagc gcctgatgcg gtattttctc    4500
cttacgcatc tgtgcggtat ttcacaccgc atatggtgca ctctcagtac aatctgctct    4560
gatgccgcat agttaagcca gtatacactc cgctatcgct acgtgactgg gtcatggctg    4620
cgccccgaca cccgccaaca cccgctgacg cgccctgacg ggcttgtctg ctcccggcat    4680
ccgcttacag acaagctgtg accgtctccg ggagctgcat gtgtcagagg ttttcaccgt    4740
catcaccgaa acgcgcgagg cagggtgcct tgatgtgggc gccggcggtc gagtggcgac    4800
ggcgcggctt gtccgcgccc tggtagattg cctggccgta ggccagccat ttttgagcgg    4860
ccagcggccg cgataggccg acgcgaagcg cggggcgta gggagcgcag cgaccgaagg     4920
gtaggcgctt tttgcagctc ttcggctgtg cgctggccag acagttatgc acaggccagg    4980
cgggttttaa gagttttaat aagttttaaa gagttttagg cggaaaaatc gcctttttc     5040 tcttttatat cagtcactta catgtgtgac cggttcccaa tgtacggctt tgggttccca    5100
atgtacgggt tccggttccc aatgtacggc tttgggttcc caatgtacgt gctatccaca    5160
ggaaagagac cttttcgacc tttttcccct gctagggcaa tttgccctag catctgctcc    5220
gtacattagg aaccggcgga tgcttcgccc tcgatcaggt tgcggtagcg catgactagg    5280
atcgggccag cctgccccgc ctcctccttc aaatcgtact ccggcaggtc atttgacccg    5340
atcagcttgc gcacggtgaa acagaacttc ttgaactctc cggcgctgcc actgcgttcg    5400
tagatcgtct tgaacaacca tctggcttct gccttgcctg cggcgcggcg tgccaggcgg    5460
tagagaaaac ggccgatgcc gggatcgatc aaaaagtaat cggggtgaac cgtcagcacg    5520
tccgggttct tgccttctgt gatctcgcgg tacatccaat cagctagctc gatctcgatg    5580
tactccggcc gccgggtttc gctctttacg atcttgtagc ggctaatcaa ggcttcaccc    5640
tcggataccg tcaccaggcg gccgttcttg gccttcttcg tacgctgcat ggcaacgtgc    5700
gtggtgttta accgaatgca ggtttctacc aggtcgtctt tctgctttcc gccatcggct    5760
cgccggcaga acttgagtac gtccgcaacg tgtggacgga acacgcggcc gggcttgtct    5820
cccttccctt cccggtatcg gttcatggat tcggttagat gggaaaccgc catcagtacc    5880
aggtcgtaat cccacacact ggccatgccg ccggccctg cggaaacctc tacgtgcccg     5940
tctggaagct cgtagcggat cacctcgcca gctcgtcggt cacgcttcga cagacggaaa    6000
acggccacgt ccatgatgct gcgactatcg cgggtgccca cgtcatagag catcggaacg    6060
aaaaaatctg gttgctcgtc gcccttgggc ggcttcctaa tcgacggcgc accggctgcc    6120
ggcggttgcc gggattcttt gcggattcga tcagcggccg cttgccacga ttcaccgggg    6180
cgtgcttctg cctcgatgcg ttgccgctgg gcggcctgcg cggccttcaa cttctccacc    6240
aggtcatcac ccagcgccgc gccgatttgt accgggccgg atggtttgcg accgtcacgc    6300
cgattcctcg ggcttggggg ttccagtgcc attgcagggc cggcagacaa cccagccgct    6360
tacgcctggc caaccgcccg ttcctccaca catgggcat tccacggcgt cggtgcctgg     6420
ttgttcttga ttttccatgc cgcctccttt agccgctaaa attcatctac tcatttattc    6480
atttgctcat ttactctggt agctgcgcga tgtattcaga tagcagctcg gtaatggtct    6540
tgccttggcg taccgcgtac atcttcagct tggtgtgatc ctccgccggc aactgaaagt    6600
tgacccgctt catggctggc gtgtctgcca ggctggccaa cgttgcagcc ttgctgctgc    6660
gtgcgctcgg acggcggca cttagcgtgt ttgtgctttt gctcattttc tctttacctc     6720
attaactcaa atgagttttg atttaatttc agcggccagc gcctgacct cgcgggcagc     6780 gtcgccctcg ggttctgatt caagaacggt tgtgccggcg gcggcagtgc ctgggtagct    6840
```

```
cacgcgctgc gtgatacggg actcaagaat gggcagctcg tacccggcca gcgcctcggc    6900
aacctcaccg ccgatgcgcg tgcctttgat cgcccgcgac acgacaaagg ccgcttgtag    6960
ccttccatcc gtgacctcaa tgcgctgctt aaccagctcc accaggtcgg cggtggccca    7020
tatgtcgtaa gggcttggct gcaccggaat cagcacgaag tcggctgcct tgatcgcgga    7080
cacagccaag tccgccgcct ggggcgctcc gtcgatcact acgaagtcgc gccggccgat    7140
ggccttcacg tcgcggtcaa tcgtcgggcg gtcgatgccg acaacggtta gcggttgatc    7200
ttcccgcacg gccgcccaat cgcgggcact gccctgggga tcggaatcga ctaacagaac    7260
atcgccccg gcgagttgca gggcgcgggc tagatgggtt gcgatggtcg tcttgcctga     7320
cccgcctttc tggttaagta cagcgataac cttcatgcgt tccccttgcg tatttgttta    7380
tttactcatc gcatcatata cgcagcgacc gcatgacgca agctgtttta ctcaaataca    7440
catcaccttt ttagacggcg gcgctcggtt tcttcagcgg ccaagctggc cggccaggcc    7500
gccagcttgg catcagacaa accgccagg atttcatgca gccgcacggt tgagacgtgc     7560
gcgggcggct cgaacacgta cccggccgcg atcatctccg cctcgatctc ttcggtaatg    7620
aaaaacggtt cgtcctggcc gtcctggtgc ggtttcatgc ttgttcctct tggcgttcat    7680
tctcggcggc cgccagggcg tcggcctcgg tcaatgcgtc ctcacggaag gcaccgcgcc    7740
gcctggcctc ggtgggcgtc acttcctcgc tgcgctcaag tgcgcggtac agggtcgagc    7800
gatgcacgcc aagcagtgca gccgcctctt tcacggtgcg gccttcctgg tcgatcagct    7860
cgcgggcgtg cgcgatctgt gccggggtga gggtagggcg ggggccaaac ttcacgcctc    7920
gggccttggc ggcctcgcgc ccgctccggg tgcggtcgat gattagggaa cgctcgaact    7980
cggcaatgcc ggcgaacacg gtcaacacca tgccggccgc cggcgtggtg gtgtcggccc    8040
acggctctgc caggctacgc aggcccgcgc cggcctcctg gatgcgctcg gcaatgtcca    8100
gtaggtcgcg ggtgctgcgg gccaggcggt ctagcctggt cactgtcaca acgtcgccag    8160
ggcgtaggtg gtcaagcatc ctggccagct ccgggcggtc gcgcctggtg ccggtgatct    8220
tctcggaaaa cagcttggtg cagccggccg cgtgcagttc ggcccgttgg ttggtcaagt    8280
cctggtcgtc ggtgctgacg cgggcatagc ccagcaggcc agcggcggcg ctcttgttca    8340
tggcgtaatg tctccggttc tagtcgcaag tattctactt tatgcgacta aaacacgcga    8400
caagaaaacg ccaggaaaag ggcagggcgg cagcctgtcg cgtaacttag gcttgtgcg     8460
acatgtcgtt ttcagaagac ggctgcactg aacgtcagaa gccgactgca ctatagcagc    8520
ggaggggttg gatcaaagta ctttgatccc gagggaacc ctgtggttgg catgcacata     8580
caaatggacg aacggataaa ccttttcacg ccctttaaa tatccgttat tctaataaac     8640
gctcttttct cttaggttta cccgccaata tatcctgtca aacactgata gtttaaactg    8700
aaggcgggaa acgacaatct gatccaagct caagctgctc tagcattcgc cattcaggct    8760
gcgcaactgt tgggaagggc gatcggtgcg ggcctcttcg ctattacgcc agctggcgaa    8820
aggggggatgt gctgcaaggc gattaagttg ggtaacgcca gggttttccc agtcacgacg   8880
ttgtaaaacg acggccagtg ccaagcttgc atgcctgcag gtcaacatgg tggagcacga    8940
cactctcgtc tactccaaga atatcaaaga tacagtctca gaagaccaga gggctattga    9000
gacttttcaa caaagggtaa tatcgggaaa cctcctcgga ttccattgcc cagctatctg    9060
tcacttcatc gaaaggacag tagaaaagga agatggcttc tacaaatgcc atcattgcga    9120
taaaggaaag gctatcgttc aagatgcctc taccgacagt ggtcccaaag atggacccc    9180
```

| | | | | | |
|---|---|---|---|---|---|
| acccacgagg | aacatcgtgg | aaaaagaaga | cgttccaacc | acgtcttcaa | agcaagtgga | 9240 |
| ttgatgtgat | ggtcaacatg | gtggagcacg | acactctcgt | ctactccaag | aatatcaaag | 9300 |
| atacagtctc | agaagaccag | agggctattg | agacttttca | acaaagggta | aatcgggaa | 9360 |
| acctcctcgg | attccattgc | ccagctatct | gtcacttcat | cgaaaggaca | gtagaaaagg | 9420 |
| aagatggctt | ctacaaatgc | catcattgcg | ataaaggaaa | ggctatcgtt | caagatgcct | 9480 |
| ctaccgacag | tggtcccaaa | gatggacccc | cacccacgag | gaacatcgtg | gaaaagaag | 9540 |
| acgttccaac | cacgtcttca | aagcaagtgg | attgatgtga | tatctccact | gacgtaaggg | 9600 |
| atgacgcaca | atcccactat | ccttcgcaag | acccttcctc | tatataagga | agttcatttc | 9660 |
| atttggagag | gccggtctag | aaacagcatc | cgtttttata | atttaatttt | cttacaaagg | 9720 |
| taggaccaac | atttgtgatc | tataaatctt | cctactacgt | tatatagaga | cccttcgaca | 9780 |
| taacacttaa | ctcgtttata | tatttgtttt | acttgttttg | cacatacaca | caaaaataaa | 9840 |
| aaagacttta | tatttattta | ctttttaatc | acacggatta | gctccggcga | agtctggtcg | 9900 |
| tcgtcttcat | cttcttcctc | catcatcaga | ttttccttat | actggaagaa | accaaacgaa | 9960 |
| actccgatct | tctccgttct | cgtgtttccc | tctctggctt | ttattgctgg | gattgggaat | 10020 |
| ttctcaccgc | tctcttgctt | tttagttgct | gattctttt | ccttcgactt | tctatttcca | 10080 |
| atctttcttc | ttctctttgt | gtattagatt | attttttagtt | ttattttct | gtggtaaaat | 10140 |
| aaaaaaagtt | cgccggaggg | taccttcgac | gacaagaccg | ggcccacaag | tttgtacaaa | 10200 |
| aaagctgaac | gagaaacgta | aaatgatata | aatatcaata | tattaaatta | gattttgcat | 10260 |
| aaaaaacaga | ctacataata | ctgtaaaaca | caacatatcc | agtcactatg | gcggccgcat | 10320 |
| taggcacccc | aggctttaca | ctttatgctt | ccggctcgta | taatgtgtgg | attttgagtt | 10380 |
| aggatccgtc | gagattttca | ggagctaagg | aagctaaaat | ggagaaaaaa | atcactggat | 10440 |
| ataccaccgt | tgatatatcc | caatggcatc | gtaaagaaca | ttttgaggca | tttcagtcag | 10500 |
| ttgctcaatg | tacctataac | cagaccgttc | agctggatat | tacggccttt | ttaaagaccg | 10560 |
| taaagaaaaa | taagcacaag | ttttatccgg | cctttattca | cattcttgcc | cgcctgatga | 10620 |
| atgctcatcc | ggaattccgt | atggcaatga | aagacggtga | gctggtgata | tgggatagtg | 10680 |
| ttcacccttg | ttacaccgtt | ttccatgagc | aaactgaaac | gttttcatcg | ctctggagtg | 10740 |
| aataccacga | cgatttccgg | cagtttctac | acatatattc | gcaagatgtg | gcgtgttacg | 10800 |
| gtgaaaacct | ggcctatttc | cctaaagggt | ttattgagaa | tatgtttttc | gtctcagcca | 10860 |
| atccctgggt | gagtttcacc | agttttgatt | taaacgtggc | caatatggac | aacttcttcg | 10920 |
| cccccgtttt | caccatgggc | aaatattata | cgcaaggcga | caaggtgctg | atgccgctgg | 10980 |
| cgattcaggt | tcatcatgcc | gtttgtgatg | gcttccatgt | cggcagaatg | cttaatgaat | 11040 |
| tacaacagta | ctgcgatgag | tggcagggcg | gggcgtaaag | atctggatcc | ggcttactaa | 11100 |
| aagccagata | acagtatgcg | tatttgcgcg | ctgattttg | cggtataaga | atatatactg | 11160 |
| atatgtatac | ccgaagtatg | tcaaaaagag | gtatgctatg | aagcagcgta | ttacagtgac | 11220 |
| agttgacagc | gacagctatc | agttgctcaa | ggcatatatg | atgtcaatat | ctccggtctg | 11280 |
| gtaagcacaa | ccatgcagaa | tgaagcccgt | cgtctgcgtg | ccgaacgctg | aaagcggaa | 11340 |
| aatcaggaag | ggatggctga | ggtcgcccgg | tttattgaaa | tgaacggctc | ttttgctgac | 11400 |
| gagaacaggg | gctggtgaaa | tgcagtttaa | ggtttacacc | tataaaagag | agagccgtta | 11460 |
| tcgtctgttt | gtggatgtac | agagtgatat | tattgacacg | cccgggcgac | ggatggtgat | 11520 |
| ccccctggcc | agtgcacgtc | tgctgtcaga | taaagtctcc | cgtgaacttt | acccggtggt | 11580 |

```
gcatatcggg gatgaaagct ggcgcatgat gaccaccgat atggccagtg tgccggtctc    11640
cgttatcggg gaagaagtgg ctgatctcag ccaccgcgaa aatgacatca aaaacgccat    11700
taacctgatg ttctggggaa tataaatgtc aggctccctt atacacagcc agtctgcagg    11760
tcgaccatag tgactggata tgttgtgttt tacagtatta tgtagtctgt tttttatgca    11820
aaatctaatt taatatattg atatttatat cattttacgt ttctcgttca gctttcttgt    11880
acaaagtggt aggggcccgg ctcttctcct cactcgagcc gctcgaattt ccccgatcgt    11940
tcaaacattt ggcaataaag tttcttaaga ttgaatcctg ttgccggtct tgcgatgatt    12000
atcatataat ttctgttgaa ttacgttaag catgtaataa ttaacatgta atgcatgacg    12060
ttatttatga gatgggtttt tatgattaga gtcccgcaat tatacattta atacgcgata    12120
gaaaacaaaa tatagcgcgc aaactaggat aaattatcgc gcgcggtgtc atctatgtta    12180
ctagatcggg aatt                                                      12194
```

<210> SEQ ID NO 135
<211> LENGTH: 12187
<212> TYPE: DNA
<213> ORGANISM: Artificial Sequence
<220> FEATURE:
<223> OTHER INFORMATION: pGX180
<220> FEATURE:
<221> NAME/KEY: misc_feature
<222> LOCATION: (8909)..(12183)
<223> OTHER INFORMATION: Insert region

<400> SEQUENCE: 135

```
cgtaatcatg gtcatagctg tttcctgtgt gaaattgtta tccgctcaca attccacaca      60
acatacgagc cggaagcata aagtgtaaag cctggggtgc ctaatgagtg agctaactca     120
cattaattgc gttgcgctca ctgcccgctt tccagtcggg aaacctgtcg tgccagctgc     180
attaatgaat cggccaacgc gcggggagag gcggtttgcg tattggctag agcagcttgc     240
caacatggtg gagcacgaca ctctcgtcta ctccaagaat atcaaagata cagtctcaga     300
agaccaaagg ctattgagac ttttcaaca aagggtaata tcgggaaacc tcctcggatt     360
ccattgccca gctatctgtc acttcatcaa aggacagta gaaaaggaag gtggcaccta     420
caaatgccat cattgcgata aaggaaaggc tatcgttcaa gatgcctctg ccgacagtgg     480
tcccaaagat ggacccccac ccacgaggag catcgtggaa aaagaagacg ttccaaccac     540
gtcttcaaag caagtggatt gatgtgataa catggtggag cacgacactc tcgtctactc     600
caagaatatc aaagatacag tctcagaaga ccaagggct attgagactt tcaacaaag     660 ggtaatatcg ggaaacctcc tcggattcca ttgcccagct atctgtcact tcatcaaaag     720
gacagtagaa aaggaaggtg gcacctacaa atgccatcat tgcgataaag gaaaggctat     780
cgttcaagat gcctctgccg acagtggtcc caaagatgga ccccacccca cgaggagcat     840
cgtggaaaaa gaagacgttc caaccacgtc ttcaaagcaa gtggattgat gtgatatctc     900
cactgacgta agggatgacg cacaatccca ctatccttcg caagaccttc ctctatataa     960
ggaagttcat ttcatttgga gaggacacgc tgaaatcacc agtctctctc tacaaatcta    1020
tctctctcga gctttcgcag atcccggggg gcaatgagat atgaaaaagc ctgaactcac    1080
cgcgacgtct gtcgagaagt ttctgatcga aaagttcgac agcgtctccg acctgatgca    1140
gctctcggag gcgaagaat ctcgtgcttt cagcttcgat gtaggagggc gtggatatgt    1200
cctgcgggta aatagctgcg ccgatggttt ctacaaagat cgttatgttt atcggcactt    1260
```

```
tgcatcggcc gcgctcccga ttccggaagt gcttgacatt ggggagttta gcgagagcct    1320
gacctattgc atctcccgcc gtgcacaggg tgtcacgttg caagacctgc ctgaaaccga    1380
actgcccgct gttctacaac cggtcgcgga ggctatggat gcgatcgctg cggccgatct    1440
tagccagacg agcgggttcg gcccattcgg accgcaagga atcggtcaat acactacatg    1500
gcgtgatttc atatgcgcga ttgctgatcc ccatgtgtat cactggcaaa ctgtgatgga    1560
cgacaccgtc agtgcgtccg tcgcgcaggc tctcgatgag ctgatgcttt gggccgagga    1620
ctgccccgaa gtccggcacc tcgtgcacgc ggatttcggc tccaacaatg tcctgacgga    1680
caatggccgc ataacagcgg tcattgactg gagcgaggcg atgttcgggg attcccaata    1740
cgaggtcgcc aacatcttct tctggaggcc gtggttggct tgtatggagc agcagacgcg    1800
ctacttcgag cggaggcatc cggagcttgc aggatcgcca cgactccggg cgtatatgct    1860
ccgcattggt cttgaccaac tctatcagag cttggttgac ggcaatttcg atgatgcagc    1920
ttgggcgcag ggtcgatgcg acgcaatcgt ccgatccgga gccgggactg tcgggcgtac    1980
acaaatcgcc cgcagaagcg cggccgtctg gaccgatggc tgtgtagaag tactcgccga    2040
tagtggaaac cgacgcccca gcactcgtcc gagggcaaag aaatagagta gatgccgacc    2100
ggatctgtcg atcgacaagc tcgagtttct ccataataat gtgtgagtag ttcccagata    2160
agggaattag ggttcctata gggtttcgct catgtgttga gcatataaga aacccttagt    2220
atgtatttgt atttgtaaaa tacttctatc aataaaattt ctaattccta aaaccaaaat    2280
ccagtactaa aatccagatc ccccgaatta attcggcgtt aattcagtac attaaaaacg    2340
tccgcaatgt gttattaagt tgtctaagcg tcaatttgtt tacaccacaa tatatcctgc    2400
caccagccag ccaacagctc cccgaccggc agctcggcac aaaatcacca ctcgatacag    2460
gcagcccatc agtccgggac ggcgtcagcg ggagagccgt tgtaaggcgg cagactttgc    2520
tcatgttacc gatgctattc ggaagaacgg caactaagct gccgggtttg aaacacggat    2580
gatctcgcgg agggtagcat gttgattgta acgatgacag agcgttgctg cctgtgatca    2640
ccgcggtttc aaaatcggct ccgtcgatac tatgttatac gccaactttg aaaacaactt    2700
tgaaaaagct gttttctggt atttaaggtt ttagaatgca aggaacagtg aattggagtt    2760
cgtcttgtta taattagctt cttggggtat ctttaaatac tgtagaaaag aggaaggaaa    2820
taataaatgg ctaaaatgag aatatcaccg gaattgaaaa aactgatcga aaaataccgc    2880
tgcgtaaaag atacggaagg aatgtctcct gctaaggtat ataagctggt gggagaaaat    2940
gaaaacctat atttaaaaat gacgacagcc ggtataaag ggaccaccta tgatgtggaa    3000
cgggaaaagg acatgatgct atggctggaa ggaaagctgc ctgttccaaa ggtcctgcac    3060
tttgaacggc atgatggctg gagcaatctg ctcatgagtg aggccgatgg cgtcctttgc    3120
tcggaagagt atgaagatga acaaagccct gaaaagatta tcgagctgta tgcggagtgc    3180
atcaggctct ttcactccat cgacatatcg gattgtccct atacgaatag cttagacagc    3240
cgcttagccg aattggatta cttactgaat aacgatctgg ccgatgtgga ttgcgaaaac    3300
tgggaagaag acactccatt taaagatccg cgcgagctgt atgattttt aaagacggaa    3360 aagcccgaag aggaacttgt cttttcccac ggcgacctgg agacagcaa catctttgtg    3420 aaagatggca agtaagtgg ctttattgat cttgggagaa gcggcagggc ggacaagtgg    3480
tatgacattg ccttctgcgt ccggtcgatc agggaggata tcgggaagac agtatgtc    3540 gagctatttt ttgacttact ggggatcaag cctgattggg agaaaataaa atattatatt    3600
ttactggatg aattgttta gtacctagaa tgcatgacca aaatccctta acgtgagttt    3660
```

```
tcgttccact gagcgtcaga ccccgtagaa aagatcaaag gatcttcttg agatccttt   3720
tttctgcgcg taatctgctg cttgcaaaca aaaaaaccac cgctaccagc ggtggtttgt   3780
ttgccggatc aagagctacc aactcttttt ccgaaggtaa ctggcttcag cagagcgcag   3840
ataccaaata ctgtccttct agtgtagccg tagttaggcc accacttcaa gaactctgta   3900
gcaccgccta catacctcgc tctgctaatc ctgttaccag tggctgctgc cagtggcgat   3960
aagtcgtgtc ttaccgggtt ggactcaaga cgatagttac cggataaggc gcagcggtcg   4020
ggctgaacgg ggggttcgtg cacacagccc agcttggagc gaacgaccta caccgaactg   4080
agatacctac agcgtgagct atgagaaagc gccacgcttc ccgaagggag aaaggcggac   4140
aggtatccgg taagcggcag ggtcggaaca ggagagcgca cgagggagct ccagggggga   4200
aacgcctggt atctttatag tcctgtcggg tttcgccacc tctgacttga gcgtcgattt   4260
ttgtgatgct cgtcaggggg gcggagccta tggaaaaacg ccagcaacgc ggccttttta   4320
cggttcctgg ccttttgctg gccttttgct cacatgttct ttcctgcgtt atcccctgat   4380
tctgtggata accgtattac cgcctttgag tgagctgata ccgctcgccg cagccgaacg   4440
accgagcgca gcgagtcagt gagcgaggaa gcggaagagc gcctgatgcg gtattttctc   4500
cttacgcatc tgtgcggtat ttcacaccgc atatggtgca ctctcagtac aatctgctct   4560
gatgccgcat agttaagcca gtatacactc cgctatcgct acgtgactgg gtcatggctg   4620
cgccccgaca cccgccaaca cccgctgacg cgccctgacg ggcttgtctg ctcccggcat   4680
ccgcttacag acaagctgtg accgtctccg ggagctgcat gtgtcagagg ttttcaccgt   4740
catcaccgaa acgcgcgagg cagggtgcct tgatgtgggc gccggcggtc gagtggcgac   4800
ggcgcggctt gtccgcgccc tggtagattg cctggccgta ggccagccat ttttgagcgg   4860
ccagcggccg cgataggccg acgcgaagcg gcggggcgta gggagcgcag cgaccgaagg   4920
gtaggcgctt tttgcagctc ttcggctgtg cgctggccag acagttatgc acaggccagg   4980
cgggttttaa gagttttaat aagttttaaa gagttttagg cggaaaaatc gcctttttc   5040
tcttttatat cagtcactta catgtgtgac cggttcccaa tgtacggctt tgggttccca   5100
atgtacgggt tccggttccc aatgtacggc tttgggttcc caatgtacgt gctatccaca   5160
ggaaagagac ctttcgacc ttttccct gctagggcaa tttgccctag catctgctcc   5220
gtacattagg aaccggcgga tgcttcgccc tcgatcaggt tgcggtagcg catgactagg   5280
atcgggccag cctgccccgc ctcctccttc aaatcgtact ccggcaggtc atttgacccg   5340
atcagcttgc gcacggtgaa acagaacttc ttgaactctc cggcgctgcc actgcgttcg   5400
tagatcgtct tgaacaacca tctggcttct gccttgcctg cggcgcggcg tgccaggcgg   5460
tagagaaaac ggccgatgcc gggatcgatc aaaaagtaat cggggtgaac cgtcagcacg   5520
tccgggttct tgccttctgt gatctcgcgg tacatccaat cagctagctc gatctcgatg   5580
tactccggcc gccggtttc gctctttacg atccttgtagc ggctaatcaa ggcttcaccc   5640
tcggataccg tcaccaggcg gccgttcttg gccttcttcg tacgctgcat ggcaacgtgc   5700
gtggtgttta accgaatgca ggtttctacc aggtcgtctt tctgctttcc gccatcggct   5760
cgccggcaga acttgagtac gtccgcaacg tgtggacgga acacgcggcc gggcttgtct   5820
cccttccctt cccggtatcg gttcatggat tcggttagat gggaaaccgc catcagtacc   5880
aggtcgtaat cccacacact ggccatgccg gccggccctg cggaaacctc tacgtgcccg   5940
tctggaagct cgtagcggat cacctcgcca gctcgtcggt cacgcttcga cagacggaaa   6000
```

-continued

```
acggccacgt ccatgatgct gcgactatcg cgggtgccca cgtcatagag catcggaacg    6060
aaaaaatctg gttgctcgtc gcccttgggc ggcttcctaa tcgacggcgc accggctgcc    6120
ggcggttgcc gggattcttt gcggattcga tcagcggccg cttgccacga ttcaccgggg    6180
cgtgcttctg cctcgatgcg ttgccgctgg gcggcctgcg cggccttcaa cttctccacc    6240
aggtcatcac ccagcgccgc gccgatttgt accgggccgg atggtttgcg accgtcacgc    6300
cgattcctcg ggcttggggg ttccagtgcc attgcagggc cggcagacaa cccagccgct    6360
tacgcctggc caaccgcccg ttcctccaca catggggcat tccacggcgt cggtgcctgg    6420
ttgttcttga ttttccatgc cgcctccttt agccgctaaa attcatctac tcatttattc    6480
atttgctcat ttactctggt agctgcgcga tgtattcaga tagcagctcg gtaatggtct    6540
tgccttggcg taccgcgtac atcttcagct tggtgtgatc ctccgccggc aactgaaagt    6600
tgacccgctt catggctggc gtgtctgcca ggctggccaa cgttgcagcc ttgctgctgc    6660
gtgcgctcgg acggccggca cttagcgtgt ttgtgctttt gctcattttc tctttacctc    6720
attaactcaa atgagttttg atttaatttc agcggccagc gcctgaccct cgcgggcagc    6780
gtcgccctcg ggttctgatt caagaacggt tgtgccggcg cggcagtgc ctgggtagct     6840
cacgcgctgc gtgatacggg actcaagaat gggcagctcg tacccggcca cgcctcggc    6900
aacctcaccg ccgatgcgcg tgcctttgat cgcccgcgac acgacaaagg ccgcttgtag    6960
ccttccatcc gtgacctcaa tgcgctgctt aaccagctcc accaggtcgg cggtggccca    7020
tatgtcgtaa gggcttggct gcaccggaat cagcacgaag tcggctgcct tgatcgcgga    7080
cacagccaag tccgccgcct ggggcgctcc gtcgatcact acgaagtcgc gccggccgat    7140
ggccttcacg tcgcggtcaa tcgtcgggcg gtcgatgccg acaacggtta gcggttgatc    7200
ttcccgcacg gccgcccaat cgcgggcact gccctgggga tcggaatcga ctaacagaac    7260
atcggccccg gcgagttgca gggcgcgggc tagatgggtt gcgatggtcg tcttgcctga    7320
cccgcctttc tggttaagta cagcgataac cttcatgcgt tccccttgcg tatttgttta    7380
tttactcatc gcatcatata cgcagcgacc gcatgacgca agctgtttta ctcaaataca    7440
catcaccttt ttagacggcg gcgctcggtt tcttcagcgg ccaagctggc cggccaggcc    7500
gccagcttgg catcagacaa accggccagg atttcatgca gccgcacggt tgagacgtgc    7560
gcgggcggct cgaacacgta cccggccgcg atcatctccg cctcgatctc ttcggtaatg    7620
aaaaacggtt cgtcctggcc gtcctggtgc ggtttcatgc ttgttcctct tggcgttcat    7680
tctcggcggc cgccagggcg tcggcctcgg tcaatgcgtc ctcacggaag gcaccgcgcc    7740
gcctggcctc ggtgggcgtc acttcctcgc tgcgctcaag tgcgcggtac agggtcgagc    7800
gatgcacgcc aagcagtgca gccgcctctt tcacggtgcg gccttcctgg tcgatcagct    7860
cgcgggcgtg cgcgatctgt gccggggtga gggtagggcg ggggccaaac ttcacgcctc    7920
gggccttggc ggcctcgcgc ccgctccggg tgccggtcgat gattagggaa cgctcgaact    7980
cggcaatgcc ggcgaacacg gtcaacacca tgcggccggc cggcgtggtg gtgtcggccc    8040
acggctctgc caggctacgc aggcccgcgc cggcctcctg gatgcgctcg gcaatgtcca    8100
gtaggtcgcg ggtgctgcgg gccaggcggt ctagcctggt cactgtcaca acgtcgccag    8160
ggcgtaggtg gtcaagcatc ctggccagct ccgggcggtc gcgcctggtg ccggtgatct    8220
tctcggaaaa cagcttggtg cagcggccg cgtgcagttc ggcccgttgg ttggtcaagt    8280
cctggtcgtc ggtgctgacg cgggcatagc ccagcaggcc agcggcggcg ctcttgttca    8340
tggcgtaatg tctccggttc tagtcgcaag tattctactt tatgcgacta aaacacgcga    8400
```

```
caagaaaacg ccaggaaaag ggcagggcgg cagcctgtcg cgtaacttag gacttgtgcg   8460
acatgtcgtt ttcagaagac ggctgcactg aacgtcagaa gccgactgca ctatagcagc   8520
ggaggggttg gatcaaagta ctttgatccc gaggggaacc ctgtggttgg catgcacata   8580
caaatggacg aacggataaa ccttttcacg ccctttaaa tatccgttat tctaataaac   8640
gctcttttct cttaggttta cccgccaata tatcctgtca aacactgata gtttaaactg   8700
aaggcgggaa acgacaatct gatccaagct caagctgctc tagcattcgc cattcaggct   8760
gcgcaactgt tgggaagggc gatcggtgcg ggcctcttcg ctattacgcc agctggcgaa   8820 aggggggatgt gctgcaaggc gattaagttg gtaacgcca gggttttccc agtcacgacg   8880
ttgtaaaacg acggccagtg ccaagcttgc atgcctgcag gtcaacatgg tggagcacga   8940
cactctcgtc tactccaaga atatcaaaga tacagtctca gaagaccaga gggctattga   9000
gacttttcaa caaagggtaa tatcgggaaa cctcctcgga ttccattgcc cagctatctg   9060
tcacttcatc gaaaggacag tagaaaagga agatggcttc tacaaatgcc atcattgcga   9120
taaaggaaag gctatcgttc aagatgcctc taccgacagt ggtcccaaag atggacccc   9180 acccacgagg aacatcgtgg aaaaagaaga cgttccaacc acgtcttcaa agcaagtgga   9240
ttgatgtgat ggtcaacatg gtggagcacg acactctcgt ctactccaag aatatcaaag   9300
atacagtctc agaagaccag agggctattg agacttttca acaaagggta atatcgggaa   9360
acctcctcgg attccattgc ccagctatct gtcacttcat cgaaaggaca gtagaaaagg   9420
aagatggctt ctacaaatgc catcattgcg ataaaggaaa ggctatcgtt caagatgcct   9480
ctaccgacag tggtcccaaa gatggacccc cacccacgag gaacatcgtg gaaaaagaag   9540
acgttccaac cacgtcttca aagcaagtgg attgatgtga tatctccact gacgtaaggg   9600
atgacgcaca atcccactat ccttcgcaag acccttcctc tatataagga agttcatttc   9660
atttggagag gccggtctag aaacagcatc cgttatttaa tttcttacaa aggtaggacc   9720
aacatttgtg atctataaat cttcctacta cgttatatag agacccttcg acataacact   9780
taactcgttt atatatttgt tttacttgtt ttgcacatac acacaaaaat aaaaaagact   9840
ttatatttat ttacttttta atcacacgga ttagctccgg cgaagtatgg tcgtcgtctt   9900
catcttcttc ctccatcatc agattttcc ttaaatggaa gaaaccaaac gaaactccga   9960
tcttctccgt tctcgtgttt tcctctctgg cttttattgc tgggattggg aatttctcac  10020
cgctctcttg cttttagtt gctgattctt tttccttcga cttctctattt ccaatctttc  10080 ttcttctctt tgtgtattag attattttta gttttatttt tctgtggtaa aataaaaaaa  10140
gttcgccgga gggtaccttc gacgacaaga ccgggcccac aagtttgtac aaaaaagctg  10200
aacgagaaac gtaaaatgat ataaatatca atatattaaa ttagattttg cataaaaaac  10260
agactacata atactgtaaa acacaacata tccagtcact atggcggccg cattaggcac  10320
cccaggcttt acactttatg cttccggctc gtataatgtg tggattttga gttaggatcc  10380
gtcgagattt tcaggagcta aggaagctaa aatggagaaa aaaatcactg gatataccac  10440
cgttgatata tcccaatggc atcgtaaaga acatttgag gcatttcagt cagttgctca  10500
atgtacctat aaccagaccg ttcagctgga tattacggcc ttttttaaaga ccgtaaagaa  10560 aaataagcac aagttttatc cggcctttat tcacattctt gcccgcctga tgaatgctca  10620
tccggaattc cgtatggcaa tgaaagacg tgagctggtg atatgggata gtgttcaccc  10680
ttgttacacc gttttccatg agcaaactga aacgttttca tcgctctgga gtgaatacca  10740
```

-continued

```
cgacgatttc cggcagtttc tacacatata ttcgcaagat gtggcgtgtt acggtgaaaa    10800
cctggcctat ttccctaaag ggtttattga gaatatgttt ttcgtctcag ccaatccctg    10860
ggtgagtttc accagttttg atttaaacgt ggccaatatg gacaacttct tcgcccccgt    10920
tttcaccatg ggcaaatatt atacgcaagg cgacaaggtg ctgatgccgc tggcgattca    10980
ggttcatcat gccgtttgtg atggcttcca tgtcggcaga atgcttaatg aattacaaca    11040
gtactgcgat gagtggcagg gcggggcgta aagatctgga tccggcttac taaaagccag    11100
ataacagtat gcgtatttgc gcgctgattt ttgcggtata agaatatata ctgatatgta    11160
tacccgaagt atgtcaaaaa gaggtatgct atgaagcagc gtattacagt gacagttgac    11220
agcgacagct atcagttgct caaggcatat atgatgtcaa tatctccggt ctggtaagca    11280
caaccatgca gaatgaagcc cgtcgtctgc gtgccaacg ctggaaagcg aaaatcagg    11340 aagggatggc tgaggtcgcc cggtttattg aaatgaacgg ctcttttgct gacgagaaca    11400
ggggctggtg aaatgcagtt taaggtttac acctataaaa gagagagccg ttatcgtctg    11460
tttgtggatg tacagagtga tattattgac acgcccgggc gacggatggt gatcccctg    11520 gccagtgcac gtctgctgtc agataaagtc tcccgtgaac tttacccggt ggtgcatatc    11580
ggggatgaaa gctggcgcat gatgaccacc gatatggcca gtgtgccggt ctccgttatc    11640
ggggaagaag tggctgatct cagccaccgc gaaaatgaca tcaaaaacgc cattaacctg    11700
atgttctggg gaatataaat gtcaggctcc cttatacaca gccagtctgc aggtcgacca    11760
tagtgactgg atatgttgtg ttttacagta ttatgtagtc tgttttttat gcaaaatcta    11820
atttaatata ttgatattta tatcatttta cgtttctcgt tcagctttct tgtacaaagt    11880
ggtaggggcc cggctcttct cctcactcga gccgctcgaa tttccccgat cgttcaaaca    11940
tttggcaata aagtttctta agattgaatc ctgttgccgg tcttgcgatg attatcatat    12000
aatttctgtt gaattacgtt aagcatgtaa taattaacat gtaatgcatg acgttattta    12060
tgagatgggt ttttatgatt agagtcccgc aattatacat ttaatacgcg atagaaaaca    12120
aaatatagcg cgcaaactag gataaattat cgcgcgcggt gtcatctatg ttactagatc    12180
gggaatt                                                             12187
```

<210> SEQ ID NO 136
<211> LENGTH: 11726
<212> TYPE: DNA
<213> ORGANISM: Artificial Sequence
<220> FEATURE:
<223> OTHER INFORMATION: Intermediate plasmid pGX0
<220> FEATURE:
<221> NAME/KEY: misc_feature
<222> LOCATION: (9672)..(9697)
<223> OTHER INFORMATION: 35S promoter
<220> FEATURE:
<221> NAME/KEY: misc_feature
<222> LOCATION: (9712)..(9717)
<223> OTHER INFORMATION: LIC1
<220> FEATURE:
<221> NAME/KEY: misc_feature
<222> LOCATION: (11425)..(11429)
<223> OTHER INFORMATION: Gateway region
<220> FEATURE:
<221> NAME/KEY: misc_feature
<222> LOCATION: (11444)..(11466)
<223> OTHER INFORMATION: LIC2
<220> FEATURE:
<221> NAME/KEY: misc_feature
<222> LOCATION: (11721)..(11722)
<223> OTHER INFORMATION: NOS

<400> SEQUENCE: 136

```
cgtaatcatg gtcatagctg tttcctgtgt gaaattgtta tccgctcaca attccacaca    60
acatacgagc cggaagcata aagtgtaaag cctggggtgc ctaatgagtg agctaactca   120
cattaattgc gttgcgctca ctgcccgctt tccagtcggg aaacctgtcg tgccagctgc   180
attaatgaat cggccaacgc gcggggagag gcggtttgcg tattggctag cagcagcttgc 240 caacatggtg gagcacgaca ctctcgtcta ctccaagaat atcaaagata cagtctcaga   300
agaccaaagg gctattgaga cttttcaaca aagggtaata tcgggaaacc tcctcggatt   360
ccattgccca gctatctgtc acttcatcaa aaggacagta gaaaggaag gtggcaccta    420 caaatgccat cattgcgata aaggaaaggc tatcgttcaa gatgcctctg ccgacagtgg   480
tcccaaagat ggaccccccac ccacgaggag catcgtggaa aagaagacg ttccaaccac   540 gtcttcaaag caagtggatt gatgtgataa catggtggag cacgcactc tcgtctactc    600 caagaatatc aaagatacag tctcagaaga ccaaagggct attgagactt tcaacaaag    660 ggtaatatcg ggaaacctcc tcggattcca ttgcccagct atctgtcact tcatcaaaag   720
gacagtagaa aaggaaggtg gcacctacaa atgccatcat tgcgataaag gaaaggctat   780
cgttcaagat gcctctgccg acagtggtcc caaagatgga ccccccaccca cgaggagcat 840 cgtggaaaaa gaagacgttc aaccacgtc ttcaaagcaa gtggattgat gtgatatctc    900
cactgacgta agggatgacg cacaatccca ctatccttcg caagaccttc ctctatataa   960
ggaagttcat ttcatttgga gaggacacgc tgaaatcacc agtctctctc tacaaatcta  1020
tctctctcga gctttcgcag atcccggggg gcaatgagat atgaaaaagc tgaactcac   1080 cgcgacgtct gtcgagaagt ttctgatcga aaagttcgac agcgtctccg acctgatgca  1140
gctctcggag ggcgaagaat ctcgtgcttt cagcttcgat gtaggagggc gtggatatgt  1200
cctgcgggta aatagctgcg ccgatggttt ctacaaagat cgttatgttt atcggcactt  1260
tgcatcggcc gcgctcccga ttccggaagt gcttgacatt ggggagttta gcgagagcct  1320
gacctattgc atctcccgcc gtgcacaggg tgtcacgttg caagacctgc ctgaaaccga  1380
actgcccgct gttctacaac cggtcgcgga ggctatggat gcgatcgctg cggccgatct  1440
tagccagacg agcgggttcg gcccattcgg accgcaagga atcggtcaat acactacatg  1500
gcgtgatttc atatgcgcga ttgctgatcc ccatgtgtat cactggcaaa ctgtgatgga  1560
cgacaccgtc agtgcgtccg tcgcgcaggc tctcgatgag ctgatgcttt gggccgagga  1620
ctgccccgaa gtccggcacc tcgtgcacgc ggatttcggc tccaacaatg tcctgacgga  1680
caatggccgc ataacagcgg tcattgactg gagcgaggcg atgttcgggg attcccaata  1740
cgaggtcgcc aacatcttct tctggaggcc gtggttggct tgtatggagc agcagacgcg  1800
ctacttcgag cggaggcatc cggagcttgc aggatcgcca cgactccggg cgtatatgct  1860
ccgcattggt cttgaccaac tctatcagag cttggttgac ggcaatttcg atgatgcagc  1920
ttgggcgcag ggtcgatgcg acgcaatcgt ccgatccgga gccgggactg tcgggcgtac  1980
acaaatcgcc cgcagaagcg cggccgtctg gaccgatggc tgtgtagaag tactcgccga  2040
tagtggaaac cgacgcccca gcactcgtcc gagggcaaag aaatagagta gatgccgacc  2100
ggatctgtcg atcgacaagc tcgagtttct ccataataat gtgtgagtag ttcccagata  2160
agggaattag ggttcctata gggtttcgct catgtgttga gcatataaga aaccccttagt 2220 atgtatttgt atttgtaaaa tacttctatc aataaaattt ctaattccta aaaccaaaat  2280
ccagtactaa aatccagatc ccccgaatta attcggcgtt aattcagtac attaaaaacg  2340
```

```
tccgcaatgt gttattaagt tgtctaagcg tcaatttgtt tacaccacaa tatatcctgc    2400
caccagccag ccaacagctc cccgaccggc agctcggcac aaaatcacca ctcgatacag    2460
gcagcccatc agtccgggac ggcgtcagcg ggagagccgt tgtaaggcgg cagactttgc    2520
tcatgttacc gatgctattc ggaagaacgg caactaagct gccgggtttg aaacacggat    2580
gatctcgcgg agggtagcat gttgattgta acgatgacag agcgttgctg cctgtgatca    2640
ccgcggtttc aaaatcggct ccgtcgatac tatgttatac gccaactttg aaaacaactt    2700
tgaaaaagct gttttctggt atttaaggtt ttagaatgca aggaacagtg aattggagtt    2760
cgtcttgtta taattagctt cttggggtat ctttaaatac tgtagaaaag aggaaggaaa    2820
taataaatgg ctaaaatgag aatatcaccg gaattgaaaa aactgatcga aaaataccgc    2880
tgcgtaaaag atacggaagg aatgtctcct gctaaggtat ataagctggt gggagaaaat    2940
gaaaacctat atttaaaaat gacggacagc cggtataaag ggaccaccta tgatgtggaa    3000
cgggaaaagg acatgatgct atggctggaa ggaaagctgc ctgttccaaa ggtcctgcac    3060
tttgaacggc atgatggctg gagcaatctg ctcatgagtg aggccgatgg cgtcctttgc    3120
tcggaagagt atgaagatga acaaagcccc gaaaagatta cgagctgta tgcggagtgc    3180 atcaggctct ttcactccat cgacatatcg gattgtccct atacgaatag cttagacagc    3240
cgcttagccg aattggatta cttactgaat aacgatctgg ccgatgtgga ttgcgaaaac    3300
tgggaagaag acactccatt taaagatccg cgcgagctgt atgatttttt aaagacggaa    3360
aagcccgaag aggaacttgt cttttcccac ggcgacctgg agacagcaa catctttgtg    3420 aaagatggca agtaagtgg ctttattgat cttgggagaa gcggcagggc ggacaagtgg    3480
tatgacattg ccttctgcgt ccggtcgatc agggaggata tcggggaaga acagtatgtc    3540
gagctatttt ttgacttact ggggatcaag cctgattggg agaaaataaa atattatatt    3600
ttactggatg aattgtttta gtacctagaa tgcatgacca aaatccctta acgtgagttt    3660
tcgttccact gagcgtcaga ccccgtagaa aagatcaaag gatcttcttg agatcctttt    3720
tttctgcgcg taatctgctg cttgcaaaca aaaaaaccac cgctaccagc ggtggtttgt    3780
ttgccggatc aagagctacc aactcttttt ccgaaggtaa ctggcttcag cagagcgcag    3840
ataccaaata ctgtccttct agtgtagccg tagttaggcc accacttcaa gaactctgta    3900
gcaccgccta catcctcgc tctgctaatc ctgttaccag tggctgctgc cagtggcgat    3960
aagtcgtgtc ttaccgggtt ggactcaaga cgatagttac cggataaggc gcagcggtcg    4020
ggctgaacgg ggggttcgtg cacacagccc agcttggagc gaacgaccta caccgaactg    4080
agatacctac agcgtgagct atgagaaagc gccacgcttc ccgaagggag aaaggcggac    4140
aggtatccgg taagcggcag ggtcggaaca ggagagcgca cgagggagct tccaggggga    4200
aacgcctggt atctttatag tcctgtcggg tttcgccacc tctgacttga gcgtcgattt    4260
ttgtgatgct cgtcaggggg gcggagccta tggaaaaacg ccagcaacgc ggccttttta    4320
cggttcctgg ccttttgctg ccttttgct cacatgttct ttcctgcgtt atcccctgat    4380
tctgtggata accgtattac cgcctttgag tgagctgata ccgctcgccg cagccgaacg    4440
accgagcgca gcgagtcagt gagcgaggaa gcggaagagc gcctgatgcg gtattttctc    4500
cttacgcatc tgtgcggtat ttcacaccgc atatggtgca ctctcagtac aatctgctct    4560
gatgccgcat agttaagcca gtatacactc cgctatcgct acgtgactgg gtcatggctg    4620
cgccccgaca cccgccaaca cccgctgacg cgccctgacg ggcttgtctg ctcccggcat    4680
ccgcttacag acaagctgtg accgtctccg ggagctgcat gtgtcagagg ttttcaccgt    4740
```

```
catcaccgaa acgcgcgagg cagggtgcct tgatgtgggc gccggcggtc gagtggcgac    4800
ggcgcggctt gtccgcgccc tggtagattg cctggccgta ggccagccat ttttgagcgg    4860
ccagcggccg cgataggccg acgcgaagcg gcggggcgta gggagcgcag cgaccgaagg    4920
gtaggcgctt tttgcagctc ttcggctgtg cgctggccag acagttatgc acaggccagg    4980
cgggttttaa gagttttaat aagttttaaa gagttttagg cggaaaaatc gcctttttc     5040 tcttttatat cagtcactta catgtgtgac cggttcccaa tgtacggctt tgggttccca    5100
atgtacgggt tccggttccc aatgtacggc tttgggttcc caatgtacgt gctatccaca    5160
ggaaagagac cttttcgacc ttttccccct gctagggcaa tttgccctag catctgctcc    5220
gtacattagg aaccggcgga tgcttcgccc tcgatcaggt tgcggtagcg catgactagg    5280
atcgggccag cctgccccgc ctcctccttc aaatcgtact ccggcaggtc atttgacccg    5340
atcagcttgc gcacggtgaa acagaacttc ttgaactctc cggcgctgcc actgcgttcg    5400
tagatcgtct tgaacaacca tctggcttct gccttgcctg cggcgcggcg tgccaggcgg    5460
tagagaaaac ggccgatgcc gggatcgatc aaaaagtaat cggggtgaac cgtcagcacg    5520
tccgggttct tgccttctgt gatctcgcgg tacatccaat cagctagctc gatctcgatg    5580
tactccggcc gccgggtttc gctctttacg atcttgtagc ggctaatcaa ggcttcaccc    5640
tcggataccg tcaccaggcg gccgttcttg gccttcttcg tacgctgcat ggcaacgtgc    5700
gtggtgttta accgaatgca ggtttctacc aggtcgtctt tctgctttcc gccatcggct    5760
cgccggcaga acttgagtac gtccgcaacg tgtggacgga acacgcggcc gggcttgtct    5820
cccttccctt cccggtatcg gttcatggat tcggttagat gggaaaccgc catcagtacc    5880
aggtcgtaat cccacacact ggccatgccg gccggccctg cggaaacctc tacgtgcccg    5940
tctggaagct cgtagcggat cacctcgcca gctcgtcggt cacgcttcga cagacggaaa    6000
acggccacgt ccatgatgct gcgactatcg cgggtgccca cgtcatagag catcggaacg    6060
aaaaaatctg gttgctcgtc gcccttgggc ggcttcctaa tcgacggcgc accggctgcc    6120
ggcggttgcc gggattcttt gcggattcga tcagcggccg cttgccacga ttcaccgggg    6180
cgtgcttctg cctcgatgcg ttgccgctgg gcggcctgcg cggccttcaa cttctccacc    6240
aggtcatcac ccagcgccgc gccgatttgt accgggccgg atggtttgcg accgtcacgc    6300
cgattcctcg ggcttggggg ttccagtgcc attgcagggc cggcagacaa cccagccgct    6360
tacgcctggc caaccgcccg ttcctccaca catgggcat tccacggcgt cggtgcctgg    6420
ttgttcttga ttttccatgc cgcctccttt agccgctaaa attcatctac tcatttattc    6480
atttgctcat ttactctggt agctgcgcga tgtattcaga tagcagctcg gtaatggtct    6540
tgccttggcg taccgcgtac atcttcagct tggtgtgatc ctccgccggc aactgaaagt    6600
tgacccgctt catggctggc gtgtctgcca ggctggccaa cgttgcagcc ttgctgctgc    6660
gtgcgctcga acgccggca cttagcgtgt ttgtgctttt gctcattttc tctttacctc    6720
attaactcaa atgagttttg atttaatttc agcggccagc gcctggacct cgcgggcagc    6780
gtcgccctcg ggttctgatt caagaacggt tgtgccggcg gcggcagtgc ctgggtagct    6840
cacgcgctgc gtgatacggg actcaagaat gggcagctcg tacccggcca gcgcctcggc    6900
aacctcaccg ccgatgcgcg tgcctttgat cgcccgcgac acgacaaagg ccgcttgtag    6960
ccttccatcc gtgacctcaa tgcgctgctt aaccagctcc accaggtcgg cggtggccca    7020
tatgtcgtaa gggcttggct gcaccggaat cagcacgaag tcggctgcct tgatcgcgga    7080
```

```
cacagccaag tccgccgcct ggggcgctcc gtcgatcact acgaagtcgc gccggccgat    7140
ggccttcacg tcgcggtcaa tcgtcgggcg gtcgatgccg acaacggtta gcggttgatc    7200
ttcccgcacg gccgcccaat cgcgggcact gccctgggga tcggaatcga ctaacagaac    7260
atcggccccg gcgagttgca gggcgcgggc tagatgggtt gcgatggtcg tcttgcctga    7320
cccgcctttc tggttaagta cagcgataac cttcatgcgt tccccttgcg tatttgttta    7380
tttactcatc gcatcatata cgcagcgacc gcatgacgca agctgtttta ctcaaataca    7440
catcaccttt ttagacggcg gcgctcggtt tcttcagcgg ccaagctggc cggccaggcc    7500
gccagcttgg catcagacaa accgccagg atttcatgca gccgcacggt tgagacgtgc    7560
gcgggcggct cgaacacgta cccggccgcg atcatctccg cctcgatctc ttcggtaatg    7620
aaaaacggtt cgtcctggcc gtcctggtgc ggtttcatgc ttgttcctct tggcgttcat    7680
tctcggcggc cgccagggcg tcggcctcgg tcaatgcgtc ctcacggaag gcaccgcgcc    7740
gcctggcctc ggtgggcgtc acttcctcgc tgcgctcaag tgcgcggtac agggtcgagc    7800
gatgcacgcc aagcagtgca gccgcctctt tcacggtgcg gccttcctgg tcgatcagct    7860
cgcgggcgtg cgcgatctgt gccggggtga gggtagggcg ggggccaaac ttcacgcctc    7920
gggccttggc ggcctcgcgc ccgctccggg tgcggtcgat gattagggaa cgctcgaact    7980
cggcaatgcc ggcgaacacg gtcaacacca tgcggccggc cggcgtggtg gtgtcggccc    8040
acggctctgc caggctacgc aggcccgcgc cggcctcctg gatgcgctcg gcaatgtcca    8100
gtaggtcgcg ggtgctgcgg gccaggcggt ctagcctggt cactgtcaca acgtcgccag    8160
ggcgtaggtg gtcaagcatc ctggccagct ccgggcggtc gcgcctggtg ccggtgatct    8220
tctcggaaaa cagcttggtg cagccggccg cgtgcagttc ggcccgttgg ttggtcaagt    8280
cctggtcgtc ggtgctgacg cgggcatagc ccagcaggcc agcggcggcg ctcttgttca    8340
tggcgtaatg tctccggttc tagtcgcaag tattctactt tatgcgacta aaacacgcga    8400
caagaaaacg ccaggaaaag ggcagggcgg cagcctgtcg cgtaacttag gacttgtgcg    8460
acatgtcgtt ttcagaagac ggctgcactg aacgtcagaa gccgactgca ctatagcagc    8520
ggaggggttg gatcaaagta ctttgatccc gaggggaacc ctgtggttgg catgcacata    8580
caaatggacg aacggataaa ccttttcacg ccctttaaa tatccgttat ctaataaac    8640 gctcttttct cttaggtta cccgccaata tatcctgtca aacactgata gtttaaactg    8700
aaggcgggaa acgacaatct gatccaagct caagctgctc tagcattcgc cattcaggct    8760
gcgcaactgt tgggaagggc gatcggtgcg ggcctcttcg ctattacgcc agctggcgaa    8820
agggggatgt gctgcaaggc gattaagttg ggtaacgcca gggttttccc agtcacgacg    8880
ttgtaaaacg acggccagtg ccaagcttgc atgcctgcag gtcaacatgg tggagcacga    8940
cactctcgtc tactccaaga atatcaaaga tacagtctca gaagaccaga gggctattga    9000
gacttttcaa caagggtaa tatcgggaaa cctcctcgga ttccattgcc cagctatctg    9060
tcacttcatc gaaaggacag tagaaaagga agatggcttc tacaaatgcc atcattgcga    9120
taaaggaaag gctatcgttc aagatgcctc taccgacagt ggtcccaaag atggacccc    9180 acccacgagg aacatcgtgg aaaaagaaga cgttccaacc acgtcttcaa agcaagtgga    9240
ttgatgtgat ggtcaacatg gtggagcacg acactctcgt ctactccaag aatatcaaag    9300
atacagtctc agaagaccag agggctattg agacttttca acaagggta atatcgggaa    9360 acctcctcga ttccattgc ccagctatct gtcacttcat cgaaaggaca gtagaaaagg    9420
aagatggctt ctacaaatgc catcattgcg ataaaggaaa ggctatcgtt caagatgcct    9480
```

```
ctaccgacag tggtcccaaa gatggacccc cacccacgag gaacatcgtg gaaaaagaag   9540
acgttccaac cacgtcttca aagcaagtgg attgatgtga tatctccact gacgtaaggg   9600
atgacgcaca atcccactat ccttcgcaag acccttcctc tatataagga agttcatttc   9660
atttggagag gccggtctag aggatccccg ggtaccttcg acgacaagac cgggcccaca   9720
agtttgtaca aaaaagctga acgagaaacg taaaatgata taaatatcaa tatattaaat   9780
tagattttgc ataaaaaaca gactacataa tactgtaaaa cacaacatat ccagtcacta   9840
tggcggccgc attaggcacc ccaggcttta cactttatgc ttccggctcg tataatgtgt   9900
ggattttgag ttaggatccg tcgagatttt caggagctaa ggaagctaaa atggagaaaa   9960
aaatcactgg atataccacc gttgatatat cccaatggca tcgtaaagaa cattttgagg  10020
catttcagtc agttgctcaa tgtacctata accagaccgt tcagctggat attacggcct  10080
ttttaaagac cgtaaagaaa aataagcaca agttttatcc ggcctttatt cacattcttg  10140
cccgcctgat gaatgctcat ccggaattcc gtatggcaat gaaagacggt gagctggtga  10200
tatgggatag tgttcacect tgttacaccg ttttccatga gcaaactgaa acgttttcat  10260
cgctctggag tgaataccac gacgatttcc ggcagtttct acacatatat tcgcaagatg  10320
tggcgtgtta cggtgaaaac ctggcctatt tccctaaagg gtttattgag aatatgtttt  10380
tcgtctcagc caatccctgg gtgagtttca ccagttttga tttaaacgtg gccaatatgg  10440
acaacttctt cgcccccgtt ttcaccatgg gcaaatatta tacgcaaggc gacaaggtgc  10500
tgatgccgct ggcgattcag gttcatcatg ccgtttgtga tggcttccat gtcggcagaa  10560
tgcttaatga attacaacag tactgcgatg agtggcaggg cggggcgtaa agatctggat  10620
ccggcttact aaaagccaga taacagtatg cgtatttgcg cgctgatttt tgcggtataa  10680
gaatatatac tgatatgtat acccgaagta tgtcaaaaag aggtatgcta tgaagcagcg  10740
tattacagtg acagttgaca gcgacagcta tcagttgctc aaggcatata tgatgtcaat  10800
atctccggtc tggtaagcac aaccatgcag aatgaagccc gtcgtctgcg tgccgaacgc  10860
tggaaagcgg aaaatcagga agggatggct gaggtcgccc ggtttattga aatgaacggc  10920
tcttttgctg acgagaacag gggctggtga atgcagtttt aaggtttaca cctataaaag  10980
agagagccgt tatcgtctgt ttgtggatgt acagagtgat attattgaca cgcccgggcg  11040
acggatggta atcccctggg ccagtgcacg tctgctgtca gataaagtct cccgtgaact  11100
ttacccggtg gtgcatatcg ggatgaaag ctggcgcatg atgaccaccg atatggccag  11160
tgtgccggtc tccgttatcg gggaagaagt ggctgatctc agccaccgcg aaaatgacat  11220
caaaaacgcc attaacctga tgttctgggg aatataaatg tcaggctccc ttatacacag  11280
ccagtctgca ggtcgaccat agtgactgga tatgttgtgt tttacagtat tatgtagtct  11340
gttttttatg caaaatctaa tttaatatat tgatatttat atcatttttac gtttctcgtt  11400 cagctttctt gtacaaagtg gtaggggccc ggctcttctc ctcactcgag ccgctcgaat  11460
ttccccgatc gttcaaacat ttggcaataa agtttcttaa gattgaatcc tgttgccggt  11520
cttgcgatga ttatcatata atttctgttg aattacgtta agcatgtaat aattaacatg  11580
taatgcatga cgttatttat gagatgggtt tttatgatta gagtcccgca attatacatt  11640
taatacgcga tagaaaacaa aatatagcgc gcaaactagg ataaattatc gcgcgcggtg  11700
tcatctatgt tactagatcg ggaatt                                      11726
```

<210> SEQ ID NO 137

```
<211> LENGTH: 1653
<212> TYPE: DNA
<213> ORGANISM: Photinus pyralis
<220> FEATURE:
<221> NAME/KEY: CDS
<222> LOCATION: (1)..(1650)
<223> OTHER INFORMATION: Firely luciferase, protein ID AHC94771.1,
      db_xref=GI567768057

<400> SEQUENCE: 137
```

| | | | | | | | | | | | | | | | | |
|---|---|---|---|---|---|---|---|---|---|---|---|---|---|---|---|---|
| atg | gaa | gac | gcc | aaa | aac | ata | aag | aaa | ggc | ccg | gcg | cca | ttc | tat | ccg | 48 |
| Met | Glu | Asp | Ala | Lys | Asn | Ile | Lys | Lys | Gly | Pro | Ala | Pro | Phe | Tyr | Pro | |
| 1 | | | | 5 | | | | | 10 | | | | | 15 | | |
| ctg | gaa | gat | gga | acc | gct | gga | gag | caa | ctg | cat | aag | gct | atg | aag | aga | 96 |
| Leu | Glu | Asp | Gly | Thr | Ala | Gly | Glu | Gln | Leu | His | Lys | Ala | Met | Lys | Arg | |
| | | | 20 | | | | | 25 | | | | | 30 | | | |
| tac | gcc | ctg | gtt | cct | gga | aca | att | gct | ttt | aca | gat | gca | cat | atc | gag | 144 |
| Tyr | Ala | Leu | Val | Pro | Gly | Thr | Ile | Ala | Phe | Thr | Asp | Ala | His | Ile | Glu | |
| | | 35 | | | | | 40 | | | | | 45 | | | | |
| gtg | gac | atc | act | tac | gct | gag | tac | ttc | gaa | atg | tcc | gtt | cgg | ttg | gca | 192 |
| Val | Asp | Ile | Thr | Tyr | Ala | Glu | Tyr | Phe | Glu | Met | Ser | Val | Arg | Leu | Ala | |
| | 50 | | | | | 55 | | | | | 60 | | | | | |
| gaa | gct | atg | aaa | cga | tat | ggg | ctg | aat | aca | aat | cac | aga | atc | gtc | gta | 240 |
| Glu | Ala | Met | Lys | Arg | Tyr | Gly | Leu | Asn | Thr | Asn | His | Arg | Ile | Val | Val | |
| 65 | | | | | 70 | | | | | 75 | | | | | 80 | |
| tgc | agt | gaa | aac | tct | ctt | caa | ttc | ttt | atg | ccg | gtg | ttg | ggc | gcg | tta | 288 |
| Cys | Ser | Glu | Asn | Ser | Leu | Gln | Phe | Phe | Met | Pro | Val | Leu | Gly | Ala | Leu | |
| | | | | 85 | | | | | 90 | | | | | 95 | | |
| ttt | atc | gga | gtt | gca | gtt | gcg | ccc | gcg | aac | gac | att | tat | aat | gaa | cgt | 336 |
| Phe | Ile | Gly | Val | Ala | Val | Ala | Pro | Ala | Asn | Asp | Ile | Tyr | Asn | Glu | Arg | |
| | | | 100 | | | | | 105 | | | | | 110 | | | |
| gaa | ttg | ctc | aac | agt | atg | ggc | att | tcg | cag | cct | acc | gtg | gtg | ttc | gtt | 384 |
| Glu | Leu | Leu | Asn | Ser | Met | Gly | Ile | Ser | Gln | Pro | Thr | Val | Val | Phe | Val | |
| | | 115 | | | | | 120 | | | | | 125 | | | | |
| tcc | aaa | aag | ggg | ttg | caa | aaa | att | ttg | aac | gtg | caa | aaa | aag | ctc | cca | 432 |
| Ser | Lys | Lys | Gly | Leu | Gln | Lys | Ile | Leu | Asn | Val | Gln | Lys | Lys | Leu | Pro | |
| | 130 | | | | | 135 | | | | | 140 | | | | | |
| atc | atc | caa | aaa | att | att | atc | atg | gat | tct | aaa | acg | gat | tac | cag | gga | 480 |
| Ile | Ile | Gln | Lys | Ile | Ile | Ile | Met | Asp | Ser | Lys | Thr | Asp | Tyr | Gln | Gly | |
| 145 | | | | | 150 | | | | | 155 | | | | | 160 | |
| ttt | cag | tcg | atg | tac | acg | ttc | gtc | aca | tct | cat | cta | cct | ccc | ggt | ttt | 528 |
| Phe | Gln | Ser | Met | Tyr | Thr | Phe | Val | Thr | Ser | His | Leu | Pro | Pro | Gly | Phe | |
| | | | | 165 | | | | | 170 | | | | | 175 | | |
| aat | gaa | tac | gat | ttt | gtg | cca | gag | tcc | ttc | gat | agg | gac | aag | aca | att | 576 |
| Asn | Glu | Tyr | Asp | Phe | Val | Pro | Glu | Ser | Phe | Asp | Arg | Asp | Lys | Thr | Ile | |
| | | | 180 | | | | | 185 | | | | | 190 | | | |
| gca | ctg | atc | atg | aac | tcc | tct | gga | tct | act | ggt | ctg | cct | aaa | ggt | gtc | 624 |
| Ala | Leu | Ile | Met | Asn | Ser | Ser | Gly | Ser | Thr | Gly | Leu | Pro | Lys | Gly | Val | |
| | | 195 | | | | | 200 | | | | | 205 | | | | |
| gct | ctg | cct | cat | aga | act | gcc | tgc | gtg | aga | ttc | tcg | cat | gcc | aga | gat | 672 |
| Ala | Leu | Pro | His | Arg | Thr | Ala | Cys | Val | Arg | Phe | Ser | His | Ala | Arg | Asp | |
| | 210 | | | | | 215 | | | | | 220 | | | | | |
| cct | att | ttt | ggc | aat | caa | atc | att | ccg | gat | act | gcg | att | tta | agt | gtt | 720 |
| Pro | Ile | Phe | Gly | Asn | Gln | Ile | Ile | Pro | Asp | Thr | Ala | Ile | Leu | Ser | Val | |
| 225 | | | | | 230 | | | | | 235 | | | | | 240 | |
| gtt | cca | ttc | cat | cac | ggt | ttt | gga | atg | ttt | act | aca | ctc | gga | tat | ttg | 768 |
| Val | Pro | Phe | His | His | Gly | Phe | Gly | Met | Phe | Thr | Thr | Leu | Gly | Tyr | Leu | |
| | | | | 245 | | | | | 250 | | | | | 255 | | |
| ata | tgt | gga | ttt | cga | gtc | gtc | tta | atg | tat | aga | ttt | gaa | gaa | gag | ctg | 816 |
| Ile | Cys | Gly | Phe | Arg | Val | Val | Leu | Met | Tyr | Arg | Phe | Glu | Glu | Glu | Leu | |
| | | | 260 | | | | | 265 | | | | | 270 | | | |

|  |  |
|---|---|
| ttt ctg agg agc ctt cag gat tac aag att caa agt gcg ctg ctg gtg<br>Phe Leu Arg Ser Leu Gln Asp Tyr Lys Ile Gln Ser Ala Leu Leu Val<br>275 280 285 | 864 |
| cca acc cta ttc tcc ttc ttc gcc aaa agc act ctg att gac aaa tac<br>Pro Thr Leu Phe Ser Phe Phe Ala Lys Ser Thr Leu Ile Asp Lys Tyr<br>290 295 300 | 912 |
| gat tta tct aat tta cac gaa att gct tct ggt ggc gct ccc ctc tct<br>Asp Leu Ser Asn Leu His Glu Ile Ala Ser Gly Gly Ala Pro Leu Ser<br>305 310 315 320 | 960 |
| aag gaa gtc ggg gaa gcg gtt gcc aag agg ttc cat ctg cca ggt atc<br>Lys Glu Val Gly Glu Ala Val Ala Lys Arg Phe His Leu Pro Gly Ile<br>325 330 335 | 1008 |
| agg caa gga tat ggg ctc act gag act aca tca gct att ctg att aca<br>Arg Gln Gly Tyr Gly Leu Thr Glu Thr Thr Ser Ala Ile Leu Ile Thr<br>340 345 350 | 1056 |
| ccc gag ggg gat gat aaa ccg ggc gcg gtc ggt aaa gtt gtt cca ttt<br>Pro Glu Gly Asp Asp Lys Pro Gly Ala Val Gly Lys Val Val Pro Phe<br>355 360 365 | 1104 |
| ttt gaa gcg aag gtt gtg gat ctg gat acc ggg aaa acg ctg ggc gtt<br>Phe Glu Ala Lys Val Val Asp Leu Asp Thr Gly Lys Thr Leu Gly Val<br>370 375 380 | 1152 |
| aat caa aga ggc gaa ctg tgt gtg aga ggt cct atg att atg tcc ggt<br>Asn Gln Arg Gly Glu Leu Cys Val Arg Gly Pro Met Ile Met Ser Gly<br>385 390 395 400 | 1200 |
| tat gta aac aat ccg gaa gcg acc aac gcc ttg att gac aag gat gga<br>Tyr Val Asn Asn Pro Glu Ala Thr Asn Ala Leu Ile Asp Lys Asp Gly<br>405 410 415 | 1248 |
| tgg cta cat tct gga gac ata gct tac tgg gac gaa gac gaa cac ttc<br>Trp Leu His Ser Gly Asp Ile Ala Tyr Trp Asp Glu Asp Glu His Phe<br>420 425 430 | 1296 |
| ttc atc gtt gac cgc ctg aag tct ctg att aag tac aaa ggc tat cag<br>Phe Ile Val Asp Arg Leu Lys Ser Leu Ile Lys Tyr Lys Gly Tyr Gln<br>435 440 445 | 1344 |
| gtg gct ccc gct gaa ttg gaa tcc atc ttg ctc caa cac ccc aac atc<br>Val Ala Pro Ala Glu Leu Glu Ser Ile Leu Leu Gln His Pro Asn Ile<br>450 455 460 | 1392 |
| ttc gac gca ggt gtc gca ggt ctt ccc gac gat gac gcc ggt gaa ctt<br>Phe Asp Ala Gly Val Ala Gly Leu Pro Asp Asp Asp Ala Gly Glu Leu<br>465 470 475 480 | 1440 |
| ccc gcc gcc gtt gtt gtt ttg gag cac gga aag acg atg acg gaa aaa<br>Pro Ala Ala Val Val Val Leu Glu His Gly Lys Thr Met Thr Glu Lys<br>485 490 495 | 1488 |
| gag atc gtg gat tac gtc gcc agt caa gta aca acc gcg aaa aag ttg<br>Glu Ile Val Asp Tyr Val Ala Ser Gln Val Thr Thr Ala Lys Lys Leu<br>500 505 510 | 1536 |
| cgc gga gga gtt gtg ttt gtg gac gaa gta ccg aaa ggt ctt acc gga<br>Arg Gly Gly Val Val Phe Val Asp Glu Val Pro Lys Gly Leu Thr Gly<br>515 520 525 | 1584 |
| aaa ctc gac gca aga aaa atc aga gag atc ctc ata aag gcc aag aag<br>Lys Leu Asp Ala Arg Lys Ile Arg Glu Ile Leu Ile Lys Ala Lys Lys<br>530 535 540 | 1632 |
| ggc gga aag atc gcc gtg taa<br>Gly Gly Lys Ile Ala Val<br>545 550 | 1653 |

<210> SEQ ID NO 138
<211> LENGTH: 550
<212> TYPE: PRT
<213> ORGANISM: Photinus pyralis

<400> SEQUENCE: 138

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415
```

```
Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
            530                 535                 540

Gly Gly Lys Ile Ala Val
545                 550

<210> SEQ ID NO 139
<211> LENGTH: 2532
<212> TYPE: DNA
<213> ORGANISM: Artificial Sequence
<220> FEATURE:
<223> OTHER INFORMATION: NPR1-EGFP
<220> FEATURE:
<221> NAME/KEY: CDS
<222> LOCATION: (1)..(1779)
<223> OTHER INFORMATION: CDS: Arabidopsis NPR1 coding sequence without
      stop codon; AT1G64280
<220> FEATURE:
<221> NAME/KEY: CDS
<222> LOCATION: (1780)..(1815)
<223> OTHER INFORMATION: Linker sequence between NPR1 and EGFP
<220> FEATURE:
<221> NAME/KEY: CDS
<222> LOCATION: (1816)..(2529)
<223> OTHER INFORMATION: EGFP coding region without start codon

<400> SEQUENCE: 139 atg gac acc acc att gat gga ttc gcc gat tct tat gaa atc agc agc      48
Met Asp Thr Thr Ile Asp Gly Phe Ala Asp Ser Tyr Glu Ile Ser Ser
1               5                  10                  15 act agt ttc gtc gct acc gat aac acc gac tcc tct att gtt tat ctg     96
Thr Ser Phe Val Ala Thr Asp Asn Thr Asp Ser Ser Ile Val Tyr Leu
            20                  25                  30 gcc gcc gaa caa gta ctc acc gga cct gat gta tct gct ctg caa ttg    144
Ala Ala Glu Gln Val Leu Thr Gly Pro Asp Val Ser Ala Leu Gln Leu
        35                  40                  45 ctc tcc aac agc ttc gaa tcc gtc ttt gac tcg ccg gat gat ttc tac    192
Leu Ser Asn Ser Phe Glu Ser Val Phe Asp Ser Pro Asp Asp Phe Tyr
    50                  55                  60 agc gac gct aag ctt gtt ctc tcc gac ggc cgg gaa gtt tct ttc cac    240
Ser Asp Ala Lys Leu Val Leu Ser Asp Gly Arg Glu Val Ser Phe His
65                  70                  75                  80 cgg tgc gtt ttg tca gcg aga agc tct ttc ttc aag agc gct tta gcc    288
Arg Cys Val Leu Ser Ala Arg Ser Ser Phe Phe Lys Ser Ala Leu Ala
                85                  90                  95 gcc gct aag aag gag aaa gac tcc aac aac acc gcc gcc gtg aag ctc    336
Ala Ala Lys Lys Glu Lys Asp Ser Asn Asn Thr Ala Ala Val Lys Leu
            100                 105                 110 gag ctt aag gag att gcc aag gat tac gaa gtc ggt ttc gat tcg gtt    384
Glu Leu Lys Glu Ile Ala Lys Asp Tyr Glu Val Gly Phe Asp Ser Val
```

```
                Glu Leu Lys Glu Ile Ala Lys Asp Tyr Glu Val Gly Phe Asp Ser Val
                        115                 120                 125 gtg act gtt ttg gct tat gtt tac agc agc aga gtg aga ccg ccg cct        432
Val Thr Val Leu Ala Tyr Val Tyr Ser Ser Arg Val Arg Pro Pro Pro
        130                 135                 140 aaa gga gtt tct gaa tgc gca gac gag aat tgc tgc cac gtg gct tgc        480
Lys Gly Val Ser Glu Cys Ala Asp Glu Asn Cys Cys His Val Ala Cys
145                 150                 155                 160 cgg ccg gcg gtg gat ttc atg ttg gag gtt ctc tat ttg gct ttc atc        528
Arg Pro Ala Val Asp Phe Met Leu Glu Val Leu Tyr Leu Ala Phe Ile
                165                 170                 175 ttc aag atc cct gaa tta att act ctc tat cag agg cac tta ttg gac        576
Phe Lys Ile Pro Glu Leu Ile Thr Leu Tyr Gln Arg His Leu Leu Asp
                180                 185                 190 gtt gta gac aaa gtt gtt ata gag gac aca ttg gtt ata ctc aag ctt        624
Val Val Asp Lys Val Val Ile Glu Asp Thr Leu Val Ile Leu Lys Leu
                195                 200                 205 gct aat ata tgt ggt aaa gct tgt atg aag cta ttg gat aga tgt aaa        672
Ala Asn Ile Cys Gly Lys Ala Cys Met Lys Leu Leu Asp Arg Cys Lys
        210                 215                 220 gag att att gtc aag tct aat gta gat atg gtt agt ctt gaa aag tca        720
Glu Ile Ile Val Lys Ser Asn Val Asp Met Val Ser Leu Glu Lys Ser
225                 230                 235                 240 ttg ccg gaa gag ctt gtt aaa gag ata att gat aga cgt aaa gag ctt        768
Leu Pro Glu Glu Leu Val Lys Glu Ile Ile Asp Arg Arg Lys Glu Leu
                245                 250                 255 ggt ttg gag gta cct aaa gta aag aaa cat gtc tcg aat gta cat aag        816
Gly Leu Glu Val Pro Lys Val Lys Lys His Val Ser Asn Val His Lys
        260                 265                 270 gca ctt gac tcg gat gat att gag tta gtc aag ttg ctt ttg aaa gag        864
Ala Leu Asp Ser Asp Asp Ile Glu Leu Val Lys Leu Leu Leu Lys Glu
        275                 280                 285 gat cac acc aat cta gat gat gcg tgt gct ctt cat ttc gct gtt gca        912
Asp His Thr Asn Leu Asp Asp Ala Cys Ala Leu His Phe Ala Val Ala
        290                 295                 300 tat tgc aat gtg aag acc gca aca gat ctt tta aaa ctt gat ctt gcc        960
Tyr Cys Asn Val Lys Thr Ala Thr Asp Leu Leu Lys Leu Asp Leu Ala
305                 310                 315                 320 gat gtc aac cat agg aat ccg agg gga tat acg gtg ctt cat gtt gct       1008
Asp Val Asn His Arg Asn Pro Arg Gly Tyr Thr Val Leu His Val Ala
                325                 330                 335 gcg atg cgg aag gag cca caa ttg ata cta tct cta ttg gaa aaa ggt       1056
Ala Met Arg Lys Glu Pro Gln Leu Ile Leu Ser Leu Leu Glu Lys Gly
        340                 345                 350 gca agt gca tca gaa gca act ttg gaa ggt aga acc gca ctc atg atc       1104
Ala Ser Ala Ser Glu Ala Thr Leu Glu Gly Arg Thr Ala Leu Met Ile
        355                 360                 365 gca aaa caa gcc act atg gcg gtt gaa tgt aat aat atc ccg gag caa       1152
Ala Lys Gln Ala Thr Met Ala Val Glu Cys Asn Asn Ile Pro Glu Gln
        370                 375                 380 tgc aag cat tct ctc aaa ggc cga cta tgt gta gaa ata cta gag caa       1200
Cys Lys His Ser Leu Lys Gly Arg Leu Cys Val Glu Ile Leu Glu Gln
385                 390                 395                 400 gaa gac aaa cga gaa caa att cct aga gat gtt cct ccc tct ttt gca       1248
Glu Asp Lys Arg Glu Gln Ile Pro Arg Asp Val Pro Pro Ser Phe Ala
                405                 410                 415 gtg gcg gcc gat gaa ttg aag atg acg ctg ctc gat ctt gaa aat aga       1296
Val Ala Ala Asp Glu Leu Lys Met Thr Leu Leu Asp Leu Glu Asn Arg
                420                 425                 430
```

```
gtt gca ctt gct caa cgt ctt ttt cca acg gaa gca caa gct gca atg    1344
Val Ala Leu Ala Gln Arg Leu Phe Pro Thr Glu Ala Gln Ala Ala Met
    435             440                 445 gag atc gcc gaa atg aag gga aca tgt gag ttc ata gtg act agc ctc    1392
Glu Ile Ala Glu Met Lys Gly Thr Cys Glu Phe Ile Val Thr Ser Leu
450             455                 460 gag cct gac cgt ctc act ggt acg aag aga aca tca ccg ggt gta aag    1440
Glu Pro Asp Arg Leu Thr Gly Thr Lys Arg Thr Ser Pro Gly Val Lys
465             470                 475                 480 ata gca cct ttc aga atc cta gaa gag cat caa agt aga cta aaa gcg    1488
Ile Ala Pro Phe Arg Ile Leu Glu Glu His Gln Ser Arg Leu Lys Ala
            485                 490                 495 ctt tct aaa acc gtg gaa ctc ggg aaa cga ttc ttc ccg cgc tgt tcg    1536
Leu Ser Lys Thr Val Glu Leu Gly Lys Arg Phe Phe Pro Arg Cys Ser
        500                 505                 510 gca gtg ctc gac cag att atg aac tgt gag gac ttg act caa ctg gct    1584
Ala Val Leu Asp Gln Ile Met Asn Cys Glu Asp Leu Thr Gln Leu Ala
    515                 520                 525 tgc gga gaa gac gac act gct gag aaa cga cta caa aag aag caa agg    1632
Cys Gly Glu Asp Asp Thr Ala Glu Lys Arg Leu Gln Lys Lys Gln Arg
530                 535                 540 tac atg gaa ata caa gag aca cta aag aag gcc ttt agt gag gac aat    1680
Tyr Met Glu Ile Gln Glu Thr Leu Lys Lys Ala Phe Ser Glu Asp Asn
545                 550                 555                 560 ttg gaa tta gga aat tcg tcc ctg aca gat tcg act tct tcc aca tcg    1728
Leu Glu Leu Gly Asn Ser Ser Leu Thr Asp Ser Thr Ser Ser Thr Ser
            565                 570                 575 aaa tca acc ggt gga aag agg tct aac cgt aaa ctc tct cat cgt cgt    1776
Lys Ser Thr Gly Gly Lys Arg Ser Asn Arg Lys Leu Ser His Arg Arg
        580                 585                 590 cgg tac cca gct ttc ttg tac aaa gtg gtg ata tca atg gtg agc aag    1824
Arg Tyr Pro Ala Phe Leu Tyr Lys Val Val Ile Ser Met Val Ser Lys
    595                 600                 605 ggc gag gag ctg ttc acc ggg gtg gtg ccc atc ctg gtc gag ctg gac    1872
Gly Glu Glu Leu Phe Thr Gly Val Val Pro Ile Leu Val Glu Leu Asp
610                 615                 620 ggc gac gta aac ggc cac aag ttc agc gtg tcc ggc gag ggc gag ggc    1920
Gly Asp Val Asn Gly His Lys Phe Ser Val Ser Gly Glu Gly Glu Gly
625                 630                 635                 640 gat gcc acc tac ggc aag ctg acc ctg aag ttc atc tgc acc acc ggc    1968
Asp Ala Thr Tyr Gly Lys Leu Thr Leu Lys Phe Ile Cys Thr Thr Gly
            645                 650                 655 aag ctg ccc gtg ccc tgg ccc acc ctc gtg acc acc ctg acc tac ggc    2016
Lys Leu Pro Val Pro Trp Pro Thr Leu Val Thr Thr Leu Thr Tyr Gly
        660                 665                 670 gtg cag tgc ttc agc cgc tac ccc gac cac atg aag cag cac gac ttc    2064
Val Gln Cys Phe Ser Arg Tyr Pro Asp His Met Lys Gln His Asp Phe
    675                 680                 685 ttc aag tcc gcc atg ccc gaa ggc tac gtc cag gag cgc acc atc ttc    2112
Phe Lys Ser Ala Met Pro Glu Gly Tyr Val Gln Glu Arg Thr Ile Phe
690                 695                 700 ttc aag gac gac ggc aac tac aag acc cgc gcc gag gtg aag ttc gag    2160
Phe Lys Asp Asp Gly Asn Tyr Lys Thr Arg Ala Glu Val Lys Phe Glu
705                 710                 715                 720 ggc gac acc ctg gtg aac cgc atc gag ctg aag ggc atc gac ttc aag    2208
Gly Asp Thr Leu Val Asn Arg Ile Glu Leu Lys Gly Ile Asp Phe Lys
            725                 730                 735 gag gac ggc aac atc ctg ggg cac aag ctg gag tac aac tac aac agc    2256
Glu Asp Gly Asn Ile Leu Gly His Lys Leu Glu Tyr Asn Tyr Asn Ser
        740                 745                 750
```

```
cac aac gtc tat atc atg gcc gac aag cag aag aac ggc atc aag gtg          2304
His Asn Val Tyr Ile Met Ala Asp Lys Gln Lys Asn Gly Ile Lys Val
        755                 760                 765 aac ttc aag atc cgc cac aac atc gag gac ggc agc gtg cag ctc gcc          2352
Asn Phe Lys Ile Arg His Asn Ile Glu Asp Gly Ser Val Gln Leu Ala
    770                 775                 780 gac cac tac cag cag aac acc ccc atc ggc gac ggc ccc gtg ctg ctg          2400
Asp His Tyr Gln Gln Asn Thr Pro Ile Gly Asp Gly Pro Val Leu Leu
785                 790                 795                 800 ccc gac aac cac tac ctg agc acc cag tcc gcc ctg agc aaa gac ccc          2448
Pro Asp Asn His Tyr Leu Ser Thr Gln Ser Ala Leu Ser Lys Asp Pro
            805                 810                 815 aac gag aag cgc gat cac atg gtc ctg ctg gag ttc gtg acc gcc gcc          2496
Asn Glu Lys Arg Asp His Met Val Leu Leu Glu Phe Val Thr Ala Ala
        820                 825                 830 ggg atc act ctc ggc atg gac gag ctg tac aag taa                          2532
Gly Ile Thr Leu Gly Met Asp Glu Leu Tyr Lys
    835                 840

<210> SEQ ID NO 140
<211> LENGTH: 843
<212> TYPE: PRT
<213> ORGANISM: Artificial Sequence
<220> FEATURE:
<223> OTHER INFORMATION: Synthetic Construct

<400> SEQUENCE: 140

Met Asp Thr Thr Ile Asp Gly Phe Ala Asp Ser Tyr Glu Ile Ser Ser
1               5                   10                  15

Thr Ser Phe Val Ala Thr Asp Asn Thr Asp Ser Ser Ile Val Tyr Leu
            20                  25                  30

Ala Ala Glu Gln Val Leu Thr Gly Pro Asp Val Ser Ala Leu Gln Leu
        35                  40                  45

Leu Ser Asn Ser Phe Glu Ser Val Phe Asp Ser Pro Asp Asp Phe Tyr
    50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
        115                 120                 125

Val Thr Val Leu Ala Tyr Val Tyr Ser Ser Arg Val Arg Pro Pro Pro
    130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
            180                 185                 190

Val Val Asp Lys Val Val Ile Glu Asp Thr Leu Val Ile Leu Lys Leu
        195                 200                 205

Ala Asn Ile Cys Gly Lys Ala Cys Met Lys Leu Leu Asp Arg Cys Lys
    210                 215                 220

Glu Ile Ile Val Lys Ser Asn Val Asp Met Val Ser Leu Glu Lys Ser
225                 230                 235                 240
```

-continued

```
Leu Pro Glu Glu Leu Val Lys Glu Ile Ile Asp Arg Arg Lys Glu Leu
            245                 250                 255

Gly Leu Glu Val Pro Lys Val Lys Lys His Val Ser Asn Val His Lys
            260                 265                 270

Ala Leu Asp Ser Asp Asp Ile Glu Leu Val Lys Leu Leu Leu Lys Glu
            275                 280                 285

Asp His Thr Asn Leu Asp Asp Ala Cys Ala Leu His Phe Ala Val Ala
            290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
            325                 330                 335

Ala Met Arg Lys Glu Pro Gln Leu Ile Leu Ser Leu Leu Glu Lys Gly
            340                 345                 350

Ala Ser Ala Ser Glu Ala Thr Leu Glu Gly Arg Thr Ala Leu Met Ile
            355                 360                 365

Ala Lys Gln Ala Thr Met Ala Val Glu Cys Asn Asn Ile Pro Glu Gln
            370                 375                 380

Cys Lys His Ser Leu Lys Gly Arg Leu Cys Val Glu Ile Leu Glu Gln
385                 390                 395                 400

Glu Asp Lys Arg Glu Gln Ile Pro Arg Asp Val Pro Pro Ser Phe Ala
            405                 410                 415

Val Ala Ala Asp Glu Leu Lys Met Thr Leu Leu Asp Leu Glu Asn Arg
            420                 425                 430

Val Ala Leu Ala Gln Arg Leu Phe Pro Thr Glu Ala Gln Ala Ala Met
            435                 440                 445

Glu Ile Ala Glu Met Lys Gly Thr Cys Glu Phe Ile Val Thr Ser Leu
            450                 455                 460

Glu Pro Asp Arg Leu Thr Gly Thr Lys Arg Thr Ser Pro Gly Val Lys
465                 470                 475                 480

Ile Ala Pro Phe Arg Ile Leu Glu Glu His Gln Ser Arg Leu Lys Ala
            485                 490                 495

Leu Ser Lys Thr Val Glu Leu Gly Lys Arg Phe Phe Pro Arg Cys Ser
            500                 505                 510

Ala Val Leu Asp Gln Ile Met Asn Cys Glu Asp Leu Thr Gln Leu Ala
            515                 520                 525

Cys Gly Glu Asp Asp Thr Ala Glu Lys Arg Leu Gln Lys Lys Gln Arg
530                 535                 540

Tyr Met Glu Ile Gln Glu Thr Leu Lys Lys Ala Phe Ser Glu Asp Asn
545                 550                 555                 560

Leu Glu Leu Gly Asn Ser Ser Leu Thr Asp Ser Thr Ser Ser Thr Ser
            565                 570                 575

Lys Ser Thr Gly Gly Lys Arg Ser Asn Arg Lys Leu Ser His Arg Arg
            580                 585                 590

Arg Tyr Pro Ala Phe Leu Tyr Lys Val Val Ile Ser Met Val Ser Lys
            595                 600                 605

Gly Glu Glu Leu Phe Thr Gly Val Val Pro Ile Leu Val Glu Leu Asp
            610                 615                 620

Gly Asp Val Asn Gly His Lys Phe Ser Val Ser Gly Glu Gly Glu Gly
625                 630                 635                 640

Asp Ala Thr Tyr Gly Lys Leu Thr Leu Lys Phe Ile Cys Thr Thr Gly
            645                 650                 655
```

```
Lys Leu Pro Val Pro Trp Pro Thr Leu Val Thr Thr Leu Thr Tyr Gly
                660                 665                 670

Val Gln Cys Phe Ser Arg Tyr Pro Asp His Met Lys Gln His Asp Phe
            675                 680                 685

Phe Lys Ser Ala Met Pro Glu Gly Tyr Val Gln Glu Arg Thr Ile Phe
        690                 695                 700

Phe Lys Asp Asp Gly Asn Tyr Lys Thr Arg Ala Glu Val Lys Phe Glu
705                 710                 715                 720

Gly Asp Thr Leu Val Asn Arg Ile Glu Leu Lys Gly Ile Asp Phe Lys
                725                 730                 735

Glu Asp Gly Asn Ile Leu Gly His Lys Leu Glu Tyr Asn Tyr Asn Ser
            740                 745                 750

His Asn Val Tyr Ile Met Ala Asp Lys Gln Lys Asn Gly Ile Lys Val
        755                 760                 765

Asn Phe Lys Ile Arg His Asn Ile Glu Asp Gly Ser Val Gln Leu Ala
        770                 775                 780

Asp His Tyr Gln Gln Asn Thr Pro Ile Gly Asp Gly Pro Val Leu Leu
785                 790                 795                 800

Pro Asp Asn His Tyr Leu Ser Thr Gln Ser Ala Leu Ser Lys Asp Pro
                805                 810                 815

Asn Glu Lys Arg Asp His Met Val Leu Leu Glu Phe Val Thr Ala Ala
            820                 825                 830

Gly Ile Thr Leu Gly Met Asp Glu Leu Tyr Lys
                835                 840

<210> SEQ ID NO 141
<211> LENGTH: 780
<212> TYPE: DNA
<213> ORGANISM: Artificial Sequence
<220> FEATURE:
<223> OTHER INFORMATION: HA-mBax
<220> FEATURE:
<221> NAME/KEY: CDS
<222> LOCATION: (1)..(129)
<223> OTHER INFORMATION: 3x Hemagglutinin (HA) tag coding region
<220> FEATURE:
<221> NAME/KEY: CDS
<222> LOCATION: (130)..(201)
<223> OTHER INFORMATION: Linker region
<220> FEATURE:
<221> NAME/KEY: CDS
<222> LOCATION: (202)..(777)
<223> OTHER INFORMATION: Mus musculus BCL2-associated X protein
      (Bax);/gene="Bax"
      /product="apoptosis regulator BAX"/protein_id="NP_031553.1"
      /db_xref="GI:6680770"

<400> SEQUENCE: 141 atg ggg tta att aac atc ttt tac cca tac gat gtt cct gac tat gcg     48
Met Gly Leu Ile Asn Ile Phe Tyr Pro Tyr Asp Val Pro Asp Tyr Ala
1               5                   10                  15 ggc tat ccc tat gac gtc ccg gac tat gca gga tcc tat cca tat gac    96
Gly Tyr Pro Tyr Asp Val Pro Asp Tyr Ala Gly Ser Tyr Pro Tyr Asp
                20                  25                  30 gtt cca gat tac gct gct cag tgc agc tct aga gga ggt ggc tca tct   144
Val Pro Asp Tyr Ala Ala Gln Cys Ser Ser Arg Gly Gly Gly Ser Ser
            35                  40                  45 ggc gga ggt cag atc tcg tac gcg tcc cgg ggc ggt acc ttc gac gac   192
Gly Gly Gly Gln Ile Ser Tyr Ala Ser Arg Gly Gly Thr Phe Asp Asp
        50                  55                  60 aag acc gtc atg gac ggg tcc ggg gag cag ctt ggg agc ggc ggg ccc   240
Lys Thr Val Met Asp Gly Ser Gly Glu Gln Leu Gly Ser Gly Gly Pro
```

```
acc agc tct gaa cag atc atg aag aca ggg gcc ttt ttg cta cag ggt        288
Thr Ser Ser Glu Gln Ile Met Lys Thr Gly Ala Phe Leu Leu Gln Gly
                85                  90                  95 ttc atc cag gat cga gca ggg agg atg gct ggg gag aca cct gag ctg        336
Phe Ile Gln Asp Arg Ala Gly Arg Met Ala Gly Glu Thr Pro Glu Leu
            100                 105                 110 acc ttg gag cag ccg ccc cag gat gcg tcc acc aag aag ctg agc gag        384
Thr Leu Glu Gln Pro Pro Gln Asp Ala Ser Thr Lys Lys Leu Ser Glu
        115                 120                 125 tgt ctc cgg cga att gga gat gaa ctg gac agc aat atg gag ctg cag        432
Cys Leu Arg Arg Ile Gly Asp Glu Leu Asp Ser Asn Met Glu Leu Gln
    130                 135                 140 agg atg att gct gac gtg gac acg gac tcc ccc cga gag gtc ttc ttc        480
Arg Met Ile Ala Asp Val Asp Thr Asp Ser Pro Arg Glu Val Phe Phe
145                 150                 155                 160 cgg gtg gca gct gac atg ttt gct gat ggc aac ttc aac tgg ggc cgc        528
Arg Val Ala Ala Asp Met Phe Ala Asp Gly Asn Phe Asn Trp Gly Arg
                165                 170                 175 gtg gtt gcc ctc ttc tac ttt gct agc aaa ctg gtg ctc aag gcc ctg        576
Val Val Ala Leu Phe Tyr Phe Ala Ser Lys Leu Val Leu Lys Ala Leu
            180                 185                 190 tgc act aaa gtg ccc gag ctg atc aga acc atc atg ggc tgg aca ctg        624
Cys Thr Lys Val Pro Glu Leu Ile Arg Thr Ile Met Gly Trp Thr Leu
        195                 200                 205 gac ttc ctc cgt gag cgg ctg ctt gtc tgg atc caa gac cag ggt ggc        672
Asp Phe Leu Arg Glu Arg Leu Leu Val Trp Ile Gln Asp Gln Gly Gly
    210                 215                 220 tgg gaa ggc ctc ctc tcc tac ttc ggg acc ccc aca tgg cag aca gtg        720
Trp Glu Gly Leu Leu Ser Tyr Phe Gly Thr Pro Thr Trp Gln Thr Val
225                 230                 235                 240 acc atc ttt gtg gct gga gtc ctc acc gcc tcg ctc acc atc tgg aag        768
Thr Ile Phe Val Ala Gly Val Leu Thr Ala Ser Leu Thr Ile Trp Lys
                245                 250                 255 aag atg ggc tga                                                         780
Lys Met Gly <210> SEQ ID NO 142
<211> LENGTH: 259
<212> TYPE: PRT
<213> ORGANISM: Artificial Sequence
<220> FEATURE:
<223> OTHER INFORMATION: Synthetic Construct

<400> SEQUENCE: 142

Met Gly Leu Ile Asn Ile Phe Tyr Pro Tyr Asp Val Pro Asp Tyr Ala
1               5                   10                  15

Gly Tyr Pro Tyr Asp Val Pro Asp Tyr Ala Gly Ser Tyr Pro Tyr Asp
            20                  25                  30

Val Pro Asp Tyr Ala Ala Gln Cys Ser Ser Arg Gly Gly Ser Ser
        35                  40                  45

Gly Gly Gly Gln Ile Ser Tyr Ala Ser Arg Gly Gly Thr Phe Asp Asp
    50                  55                  60

Lys Thr Val Met Asp Gly Ser Glu Gln Leu Gly Ser Gly Gly Pro
65                  70                  75                  80

Thr Ser Ser Glu Gln Ile Met Lys Thr Gly Ala Phe Leu Leu Gln Gly
                85                  90                  95

Phe Ile Gln Asp Arg Ala Gly Arg Met Ala Gly Glu Thr Pro Glu Leu
            100                 105                 110
```

```
Thr Leu Glu Gln Pro Pro Gln Asp Ala Ser Thr Lys Lys Leu Ser Glu
        115                 120                 125

Cys Leu Arg Arg Ile Gly Asp Glu Leu Asp Ser Asn Met Glu Leu Gln
        130                 135                 140

Arg Met Ile Ala Asp Val Asp Thr Asp Ser Pro Arg Glu Val Phe Phe
145                 150                 155                 160

Arg Val Ala Ala Asp Met Phe Ala Asp Gly Asn Phe Asn Trp Gly Arg
                165                 170                 175

Val Val Ala Leu Phe Tyr Phe Ala Ser Lys Leu Val Leu Lys Ala Leu
                180                 185                 190

Cys Thr Lys Val Pro Glu Leu Ile Arg Thr Ile Met Gly Trp Thr Leu
        195                 200                 205

Asp Phe Leu Arg Glu Arg Leu Leu Val Trp Ile Gln Asp Gln Gly Gly
        210                 215                 220

Trp Glu Gly Leu Leu Ser Tyr Phe Gly Thr Pro Thr Trp Gln Thr Val
225                 230                 235                 240

Thr Ile Phe Val Ala Gly Val Leu Thr Ala Ser Leu Thr Ile Trp Lys
                245                 250                 255

Lys Met Gly

<210> SEQ ID NO 143
<211> LENGTH: 792
<212> TYPE: DNA
<213> ORGANISM: Artificial Sequence
<220> FEATURE:
<223> OTHER INFORMATION: mGFP5
<220> FEATURE:
<221> NAME/KEY: CDS
<222> LOCATION: (1)..(789)
<223> OTHER INFORMATION: modified green fluorescent protein GFP5-ER
      (mgfp5-ER) mRNA, complete cds; GenBank: U87974.1

<400> SEQUENCE: 143 atg aag act aat ctt ttt ctc ttt ctc atc ttt tca ctt ctc cta tca      48
Met Lys Thr Asn Leu Phe Leu Phe Leu Ile Phe Ser Leu Leu Leu Ser
1               5                   10                  15 tta tcc tcg gcc gaa ttc agt aaa gga gaa gaa ctt ttc act gga gtt      96
Leu Ser Ser Ala Glu Phe Ser Lys Gly Glu Glu Leu Phe Thr Gly Val
                20                  25                  30 gtc cca att ctt gtt gaa tta gat ggt gat gtt aat ggg cac aaa ttt     144
Val Pro Ile Leu Val Glu Leu Asp Gly Asp Val Asn Gly His Lys Phe
            35                  40                  45 tct gtc agt gga gag ggt gaa ggt gat gca aca tac gga aaa ctt acc     192
Ser Val Ser Gly Glu Gly Glu Gly Asp Ala Thr Tyr Gly Lys Leu Thr
        50                  55                  60 ctt aaa ttt att tgc act act gga aaa cta cct gtt ccc tgg cca aca     240
Leu Lys Phe Ile Cys Thr Thr Gly Lys Leu Pro Val Pro Trp Pro Thr
65                  70                  75                  80 ctt gtc act act ttc tct tat ggt gtt caa tgc ttt tca aga tac cca     288
Leu Val Thr Thr Phe Ser Tyr Gly Val Gln Cys Phe Ser Arg Tyr Pro
                85                  90                  95 gat cat atg aag cgg cac gac ttc ttc aag agc gcc atg cct gag gga     336
Asp His Met Lys Arg His Asp Phe Phe Lys Ser Ala Met Pro Glu Gly
            100                 105                 110 tac gtg cag gag agg acc atc ttc ttc aag gac gac ggg aac tac aag     384
Tyr Val Gln Glu Arg Thr Ile Phe Phe Lys Asp Asp Gly Asn Tyr Lys
        115                 120                 125 aca cgt gct gaa gtc aag ttt gag gga gac acc ctc gtc aac agg atc     432
Thr Arg Ala Glu Val Lys Phe Glu Gly Asp Thr Leu Val Asn Arg Ile
```

```
gag ctt aag gga atc gat ttc aag gag gac gga aac atc ctc ggc cac        480
Glu Leu Lys Gly Ile Asp Phe Lys Glu Asp Gly Asn Ile Leu Gly His
145                 150                 155                 160 aag ttg gaa tac aac tac aac tcc cac aac gta tac atc atg gcc gac        528
Lys Leu Glu Tyr Asn Tyr Asn Ser His Asn Val Tyr Ile Met Ala Asp
                165                 170                 175 aag caa aag aac ggc atc aaa gcc aac ttc aag acc cgc cac aac atc        576
Lys Gln Lys Asn Gly Ile Lys Ala Asn Phe Lys Thr Arg His Asn Ile
            180                 185                 190 gaa gac ggc ggc gtg caa ctc gct gat cat tat caa caa aat act cca        624
Glu Asp Gly Gly Val Gln Leu Ala Asp His Tyr Gln Gln Asn Thr Pro
        195                 200                 205 att ggc gat ggc cct gtc ctt tta cca gac aac cat tac ctg tcc aca        672
Ile Gly Asp Gly Pro Val Leu Leu Pro Asp Asn His Tyr Leu Ser Thr
210                 215                 220 caa tct gcc ctt tcg aaa gat ccc aac gaa aag aga gac cac atg gtc        720
Gln Ser Ala Leu Ser Lys Asp Pro Asn Glu Lys Arg Asp His Met Val
225                 230                 235                 240 ctt ctt gag ttt gta aca gct gct ggg att aca cat ggc atg gat gaa        768
Leu Leu Glu Phe Val Thr Ala Ala Gly Ile Thr His Gly Met Asp Glu
                245                 250                 255 cta tac aaa cat gat gag ctt taa                                         792
Leu Tyr Lys His Asp Glu Leu
            260

<210> SEQ ID NO 144
<211> LENGTH: 263
<212> TYPE: PRT
<213> ORGANISM: Artificial Sequence
<220> FEATURE:
<223> OTHER INFORMATION: Synthetic Construct

<400> SEQUENCE: 144

Met Lys Thr Asn Leu Phe Leu Phe Leu Ile Phe Ser Leu Leu Leu Ser
1               5                   10                  15

Leu Ser Ser Ala Glu Phe Ser Lys Gly Glu Glu Leu Phe Thr Gly Val
                20                  25                  30

Val Pro Ile Leu Val Glu Leu Asp Gly Asp Val Asn Gly His Lys Phe
            35                  40                  45

Ser Val Ser Gly Glu Gly Glu Gly Asp Ala Thr Tyr Gly Lys Leu Thr
        50                  55                  60

Leu Lys Phe Ile Cys Thr Thr Gly Lys Leu Pro Val Pro Trp Pro Thr
65                  70                  75                  80

Leu Val Thr Thr Phe Ser Tyr Gly Val Gln Cys Phe Ser Arg Tyr Pro
                85                  90                  95

Asp His Met Lys Arg His Asp Phe Phe Lys Ser Ala Met Pro Glu Gly
                100                 105                 110

Tyr Val Gln Glu Arg Thr Ile Phe Phe Lys Asp Asp Gly Asn Tyr Lys
            115                 120                 125

Thr Arg Ala Glu Val Lys Phe Glu Gly Asp Thr Leu Val Asn Arg Ile
        130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Ala Asn Phe Lys Thr Arg His Asn Ile
            180                 185                 190
```

```
Glu Asp Gly Gly Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr His Gly Met Asp Glu
                245                 250                 255

Leu Tyr Lys His Asp Glu Leu
            260

<210> SEQ ID NO 145
<211> LENGTH: 936
<212> TYPE: DNA
<213> ORGANISM: Artificial Sequence
<220> FEATURE:
<223> OTHER INFORMATION: Bax inhibitor 1-HA region
<220> FEATURE:
<221> NAME/KEY: CDS
<222> LOCATION: (1)..(741)
<223> OTHER INFORMATION: Arabidopsis Bax inhibitor-1 (BI-1) without stop
      codon, At5g47120
<220> FEATURE:
<221> NAME/KEY: CDS
<222> LOCATION: (742)..(810)
<223> OTHER INFORMATION: Linker region between BI-1 and HA tag
<220> FEATURE:
<221> NAME/KEY: CDS
<222> LOCATION: (811)..(933)
<223> OTHER INFORMATION: 3x Hemagglutinin (HA) tag coding region

<400> SEQUENCE: 145 atg gat gcg ttc tct tcc ttc ttc gat tct caa cct ggt agc aga agc      48
Met Asp Ala Phe Ser Ser Phe Phe Asp Ser Gln Pro Gly Ser Arg Ser
1               5                   10                  15 tgg agc tat gat tct ctt aaa aac ttc cgt cag att tct cca gcc gtt      96
Trp Ser Tyr Asp Ser Leu Lys Asn Phe Arg Gln Ile Ser Pro Ala Val
            20                  25                  30 cag aat cat ctt aaa cgg gtt tat ttg acc tta tgt tgt gct ctt gtg     144
Gln Asn His Leu Lys Arg Val Tyr Leu Thr Leu Cys Cys Ala Leu Val
        35                  40                  45 gcg tct gcc ttt gga gct tac ctc cat gtg ctc tgg aat atc ggc ggt     192
Ala Ser Ala Phe Gly Ala Tyr Leu His Val Leu Trp Asn Ile Gly Gly
    50                  55                  60 att ctt aca acg att gga tgt att gga act atg att tgg ctc ctt tca     240
Ile Leu Thr Thr Ile Gly Cys Ile Gly Thr Met Ile Trp Leu Leu Ser
65                  70                  75                  80 tgt cct cct tat gaa cac caa aaa agg ctt tct ctt ctg ttt gtg tct     288
Cys Pro Pro Tyr Glu His Gln Lys Arg Leu Ser Leu Leu Phe Val Ser
                85                  90                  95 gct gtt ctt gaa ggt gct tct gtt ggc ccc ttg atc aaa gtg gca att     336
Ala Val Leu Glu Gly Ala Ser Val Gly Pro Leu Ile Lys Val Ala Ile
            100                 105                 110 gat gtt gac cca agc atc ctt atc act gca ttt gtt gga act gcg ata     384
Asp Val Asp Pro Ser Ile Leu Ile Thr Ala Phe Val Gly Thr Ala Ile
        115                 120                 125 gcg ttt gtc tgt ttc tca gca gca gca atg tta gca aga cgc agg gag     432
Ala Phe Val Cys Phe Ser Ala Ala Ala Met Leu Ala Arg Arg Arg Glu
    130                 135                 140 tat ctc tac ctt gga gga ctg ctt tca tct ggc ttg tct atg cta atg     480
Tyr Leu Tyr Leu Gly Gly Leu Leu Ser Ser Gly Leu Ser Met Leu Met
145                 150                 155                 160
```

```
tgg ctc cag ttt gcc tct tca atc ttt ggt ggc tct gca tct atc ttt        528
Trp Leu Gln Phe Ala Ser Ser Ile Phe Gly Gly Ser Ala Ser Ile Phe
            165                 170                 175 aag ttt gag ttg tac ttt gga ctt ttg atc ttt gtg gga tac atg gtg        576
Lys Phe Glu Leu Tyr Phe Gly Leu Leu Ile Phe Val Gly Tyr Met Val
            180                 185                 190 gtg gac aca caa gag att ata gaa aag gca cac ctc ggt gac atg gac        624
Val Asp Thr Gln Glu Ile Ile Glu Lys Ala His Leu Gly Asp Met Asp
            195                 200                 205 tat gta aaa cat tcg ttg acc ctt ttc act gac ttt gta gct gtg ttt        672
Tyr Val Lys His Ser Leu Thr Leu Phe Thr Asp Phe Val Ala Val Phe
210                 215                 220 gtt cgg att ctc atc ata atg ttg aag aac tca gca gat aaa gaa gag        720
Val Arg Ile Leu Ile Ile Met Leu Lys Asn Ser Ala Asp Lys Glu Glu
225                 230                 235                 240 aag aag aag aaa agg aga aac gca cgg ctc ttc tcc tca ctc gac cag        768
Lys Lys Lys Lys Arg Arg Asn Ala Arg Leu Phe Ser Ser Leu Asp Gln
            245                 250                 255 atc tcg tac gcg tcc cgg ggc ggt ggc tca tct ggc gga ggt atg ggg        816
Ile Ser Tyr Ala Ser Arg Gly Gly Gly Ser Ser Gly Gly Gly Met Gly
            260                 265                 270 tta att aac atc ttt tac cca tac gat gtt cct gac tat gcg ggc tat        864
Leu Ile Asn Ile Phe Tyr Pro Tyr Asp Val Pro Asp Tyr Ala Gly Tyr
            275                 280                 285 ccc tat gac gtc ccg gac tat gca gga tcc tat cca tat gac gtt cca        912
Pro Tyr Asp Val Pro Asp Tyr Ala Gly Ser Tyr Pro Tyr Asp Val Pro
290                 295                 300 gat tac gct gct cag tgc agc tga                                        936
Asp Tyr Ala Ala Gln Cys Ser
305                 310
```

<210> SEQ ID NO 146
<211> LENGTH: 311
<212> TYPE: PRT
<213> ORGANISM: Artificial Sequence
<220> FEATURE:
<223> OTHER INFORMATION: Synthetic Construct

<400> SEQUENCE: 146

```
Met Asp Ala Phe Ser Ser Phe Phe Asp Ser Gln Pro Gly Ser Arg Ser
1               5                   10                  15

Trp Ser Tyr Asp Ser Leu Lys Asn Phe Arg Gln Ile Ser Pro Ala Val
            20                  25                  30

Gln Asn His Leu Lys Arg Val Tyr Leu Thr Leu Cys Cys Ala Leu Val
        35                  40                  45

Ala Ser Ala Phe Gly Ala Tyr Leu His Val Leu Trp Asn Ile Gly Gly
    50                  55                  60

Ile Leu Thr Thr Ile Gly Cys Ile Gly Thr Met Ile Trp Leu Leu Ser
65                  70                  75                  80

Cys Pro Pro Tyr Glu His Gln Lys Arg Leu Ser Leu Leu Phe Val Ser
                85                  90                  95

Ala Val Leu Glu Gly Ala Ser Val Gly Pro Leu Ile Lys Val Ala Ile
            100                 105                 110

Asp Val Asp Pro Ser Ile Leu Ile Thr Ala Phe Val Gly Thr Ala Ile
        115                 120                 125

Ala Phe Val Cys Phe Ser Ala Ala Ala Met Leu Ala Arg Arg Arg Glu
    130                 135                 140

Tyr Leu Tyr Leu Gly Gly Leu Leu Ser Ser Gly Leu Ser Met Leu Met
145                 150                 155                 160
```

```
Trp Leu Gln Phe Ala Ser Ser Ile Phe Gly Gly Ser Ala Ser Ile Phe
            165                 170                 175

Lys Phe Glu Leu Tyr Phe Gly Leu Leu Ile Phe Val Gly Tyr Met Val
        180                 185                 190

Val Asp Thr Gln Glu Ile Ile Glu Lys Ala His Leu Gly Asp Met Asp
    195                 200                 205

Tyr Val Lys His Ser Leu Thr Leu Phe Thr Asp Phe Ala Val Phe
    210                 215                 220

Val Arg Ile Leu Ile Ile Met Leu Lys Asn Ser Ala Asp Lys Glu Glu
225                 230                 235                 240

Lys Lys Lys Lys Arg Arg Asn Ala Arg Leu Phe Ser Ser Leu Asp Gln
                245                 250                 255

Ile Ser Tyr Ala Ser Arg Gly Gly Gly Ser Ser Gly Gly Gly Met Gly
            260                 265                 270

Leu Ile Asn Ile Phe Tyr Pro Tyr Asp Val Pro Asp Tyr Ala Gly Tyr
        275                 280                 285

Pro Tyr Asp Val Pro Asp Tyr Ala Gly Ser Tyr Pro Tyr Asp Val Pro
    290                 295                 300

Asp Tyr Ala Ala Gln Cys Ser
305                 310
```

<210> SEQ ID NO 147
<211> LENGTH: 4950
<212> TYPE: DNA
<213> ORGANISM: Arabidopsis thaliana
<220> FEATURE:
<221> NAME/KEY: misc_feature
<222> LOCATION: (1)..(4947)
<223> OTHER INFORMATION: Genomic fragment of Arabidopsis snc1 mutant
      plant encoding constitutively active form of SNC1 (suppressor of
      NPR1, constitutive 1). Reference: Activation of an EDS1-Mediated
      R-Gene Pathway in the snc1 Mutant Leads to Constitutive,

<400> SEQUENCE: 147

```
atggagatag cttcttcttc tggcagccgg agatacgacg ttttcccaag ctttcgtgga    60
gaagatgtcc gtgactcatt cctcagccat cttctcaagg agctcagggg caaagcaatc   120
acattcatag atgatgagat cgagaggagc cgctcaatcg gcccggagct tttatcggca   180
ataaaagaat cgagaatagc aatcgttatc ttctctaaga actatgcttc atccacctgg   240
tgcctgaatg aattggtgga gattcacaag tgttatacga atttgaatca aatggtgatt   300
ccgattttct tccacgttga tgcttcggaa gttaaaaaac agaccggcga atttggaaag   360
gtctttgaag agacatgcaa ggctaaatca gaggatgaga acaaagttg gaagcaagct    420 ctagcagctg ttgcagttat ggccggatat gatcttcgga atggtatttt caatgaatag   480
acttcgtgat tttttgttt tgcgttgctt ctttaatgaa acagttgact attgttatta    540
ggcctagtga agcagccatg attgaagagc ttgccgagga tgttttgaga aaaactatga   600
caccatcgga tgatttggc gacttagtcg gaattgaaaa tcatatagag gcaataaaat    660
cagtattgtg cttggaatcc aaggaagcta gaataatggt cgggatttgg ggacaatcag   720
ggattggtaa gagtaccata ggaagagctc tttacagtaa actctctatc cagttccacc   780
atcgcgcttt cataacatat aaaagcacca gcggtagtga cgtctctggc atgaagttga   840
ggtgggaaaa agaacttctc tcggaaatct taggtcaaaa ggacataaag atagagcatt   900
ttggtgtggt ggagcaaagg ttaaagcaac agaaagttct tatccttctt gatgatgtgg   960
atagtctaga gtttcttaag accttggtgg gaaaagctga atggtttgga tctggaagca  1020
```

```
gaataattgt gatcactcaa gataggcaac ttctcaaggc tcatgagatt gaccttatat   1080
atgaggtgga gttcccatct gaacatcttg ctcttacgat gttatgccga tctgcttttg   1140
ggaaagactc tccacctgat gattttaagg aactagcatt tgaagttgcg aagcttgccg   1200
gtaatcttcc gttgggtctt agtgtccttg gttcgtcttt aaagggaagg accaaagaat   1260
ggtggatgga gatgatgcct aggctccgaa atggtttgaa cggagatatt atgaaaacat   1320
taagagtcag ctacgataga ttacatcaaa aagatcaaga tatgttcctt tacatcgcgt   1380
gtttattcaa tggttttgaa gtcagttacg tcaaagattt acttaaagat aatgttgggt   1440
ttacaatgtt gactgagaag tccctcatac gtattacacc ggatggatat atagagatgc   1500
acaatttgct agagaaattg ggtagagaaa ttgatcgtgc aaagtccaag ggtaatcctg   1560
gaaaacgtcg atttctgacg aattttgaag atattcatga agtagtgacc gagaaaactg   1620 taagttttt tcgcagctcc gtttgaatgc atgactttat attaatataa tcgtaatttg   1680
gggattgata aacttaagca attgttgcct catgcgtaat taaaatgtag ctttgatgtg   1740
tcagaaaatt aaaaagggtt gcgattgtta agattatatt agttttcttc ggattttttt   1800
tcaggggaca gaaactcttc ttggaatacg tttgccattc gaggaatatt tttcgacaag   1860
gccgttatta atagataaag aatcgttcaa aggcatgcgt aatctgcaat atctaaaaat   1920
tggttattac ggggatctac ctcagagcct cgtttatttg cccttaaac tcagattgct   1980 agactgggat gattgtccat gaagtctttt gccatctact tttaaggcgg aatatctagt   2040
taacctcata tgaagtata gtaagcttga gaaactgtgg gaaggaactc tggtacgaat   2100
tctaaatttt attagttgtc agttttaga acagaactgt ggtatatttg tgaacgtgtg   2160
tattctcttt ttccatattt tgttttcagc cccttggaag tctcaaggag atgaatttga   2220
ggtattccaa caatttgaaa gaaattccag atctttcttt agccataaac ctcgaggaat   2280
tagatcttgt tggatgcaaa tctttggtga cacttccttc ctcgattcag aatgccacta   2340
aactgatcta tttagatatg agtgattgca aaaagctaga gagttttcca accgatctca   2400
acttggaatc tctcgagtac ctcaatctca ctggatgccc gaatttgaga aactttccag   2460
caatcaaaat gggatgttca gacgttgact ttccggaagg gagaaatgag atcgtggtag   2520
aagattgttt ctggaacaag aatctccctg ctggactaga ttatctcgac tgccttacga   2580
gatgtatgcc ttgtgaattt cgcccagaac aactcgcttt tctcaatgtg aggggctaca   2640
agcatgagaa gctatgggaa ggcatccagg tacattgtta atgctatgct gattttgtt   2700 taccttctgt tatataacta attaactata cccaaatttg ttattatggc ttgtgatcca   2760
cggttatgtc ttaccacggt tatgtcttat aataatgttt aattataatt ttaaacatat   2820
acagtataaa attaaaatga ttatcatcga taatgattga agcataccaa tgtttttttc   2880
agtcgcttgg aagtctcgaa gggatggatc tgtcagaatc tgaaaacctg acagaaattc   2940
cagatctttc aaaggccacc aagctcgagt ctttgatact caacaactgc aaaagtttgg   3000
tgacacttcc ttctacaatt gggaatcttc atagattggt gaggttggaa atgaaagaat   3060
gcacagggct ggaggttctt ccgaccgatg tcaacttgtc atctctcgaa accctcgatc   3120
tcagtggttg ctcaagtttg agaagttttc ctctgatttc aactaatatt gtatggctct   3180
atctggaaaa caccgccatt gaagaaattc cttctacaat tgggaatctt catagattgg   3240
tgaggttaga aatgaaaaaa tgcacagggc tggaggttct tccgaccgat gtcaacttgt   3300
catctctcga aaccctcgat ctcagtggtt gctcaagttt gagaagtttt cctctgattt   3360
```

```
cagagagtat caaatggctc tatctggaaa acaccgccat tgaagaaatt ccagatcttt    3420
caaaggccac taatctgaag aatttgaaac tcaacaattg caaaagtttg gtgacacttc    3480
ctactactat aggaaatctc caaaaattgg tgagctttga aatgaaagaa tgcacagggc    3540
tggaggttct tccgatcgat gtcaacttgt catctcttat gatcctcgat ctcagtggtt    3600
gctcaagtct gagaactttt cctctgattt caactaatat tgtatggctc tatctggaaa    3660
acaccgccat tgaagaaatc ccttctacaa ttgggaatct tcatagattg gtgaagttag    3720
aaatgaaaga atgcacaggg ctggaggttc ttccgaccga tgtcaacttg tcatctctta    3780
tgatcctcga tctcagtggt tgctcaagtc tgagaacttt tcctctgatt caactagaa     3840 tcgaatgtct ctatctgcaa acaccgcca ttgaagaagt tccctgctgc attgaggatt      3900
tcacgaggct cactgtactt atgatgtatt gttgccagag gttgaaaacc atctccccaa    3960
acattttcag acttacaaga cttgagctcg ccgactttac agactgtaga ggtgtcatca    4020
aggcgttgag tgatgcaact gtggtagcga caatggaaga ccacgtttct tgtgtaccat    4080
tatctgaaaa cattgaatat atctgggata agttgtatcg tgttgcatac ctccaggaac    4140
attttagctt ccgtaattgc ttcaaattgg atagagatgc gcgagagctc atcctacgat    4200
catgcttcaa gcctgtggcc ttaccaggtg aagaaatccc taagtatttc acgtatcgag    4260
cttatggaga ttccctaact gtcattgtac ctcagagctc tctttctcaa aatttcttgc    4320
gatttaaggc ttgcgtcgtg gttgaacctc tctccaaggg caagggtttt tatccattct    4380
tgaaggtaaa cgttggcttc aatggcaaac agtatcagaa atcatttcct aaagatgcag    4440
aactggagct ttgtaagacg gatcatctgt ttttctgttc cttcaagttc cggtctgaag    4500
atcttccatc taaattgaat ttcaacgatg tggagtttaa gttttgttgc tccaatagga    4560
tcaaagaatg cggtgtacga ctcatgtatg tctctcaaga agagaacaac caacagacta    4620
cgagaagcga gaagcggatg cgggtatctt ttgactttg atttgatttt ccaggatcga    4680
aataccatag ggacagacta tttaatagaa tctatcgttt gatttataat gcagatgaca    4740
tcggggacat ctgaagaaga tatcaactta ccctatggcc taattgtagc ggacacagga    4800
ttggccgctc taaatatgga gctttcgtta gggcagggag aaccatcatc atcaacatct    4860
ctagaggggg aagctttgtg tgttgattac atgataactg aagaacaaga taaaggaatt    4920
cctatcttgt ttcctgtttc tggtaactga                                    4950
```

<210> SEQ ID NO 148
<211> LENGTH: 5244
<212> TYPE: DNA
<213> ORGANISM: Artificial Sequence
<220> FEATURE:
<223> OTHER INFORMATION: snc1-cMyc
<220> FEATURE:
<221> NAME/KEY: misc_feature
<222> LOCATION: (1)..(5244)
<223> OTHER INFORMATION: Encoding Snc1-linker-cMyc fusion polypeptide,
      where snc1 region has 6 exons and 5 introns upstream from linker
      region and cMyc region
<220> FEATURE:
<221> NAME/KEY: exon
<222> LOCATION: (1)..(491)
<223> OTHER INFORMATION: Exon 1: 1-491
<220> FEATURE:
<221> NAME/KEY: Intron
<222> LOCATION: (492)..(568)
<223> OTHER INFORMATION: Intron 1: 492-568
<220> FEATURE:
<221> NAME/KEY: exon
<222> LOCATION: (569)..(1646)
<223> OTHER INFORMATION: Exon 2: 569-1646

```
<220> FEATURE:
<221> NAME/KEY: Intron
<222> LOCATION: (1647)..(1831)
<223> OTHER INFORMATION: Intron 2: 1647-1831
<220> FEATURE:
<221> NAME/KEY: exon
<222> LOCATION: (1832)..(2119)
<223> OTHER INFORMATION: Exon 3: 1832-2119
<220> FEATURE:
<221> NAME/KEY: Intron
<222> LOCATION: (2120)..(2216)
<223> OTHER INFORMATION: Intron 3: 2120-2216
<220> FEATURE:
<221> NAME/KEY: exon
<222> LOCATION: (2217)..(2696)
<223> OTHER INFORMATION: Exon 4: 2217-2696
<220> FEATURE:
<221> NAME/KEY: Intron
<222> LOCATION: (2697)..(2909)
<223> OTHER INFORMATION: Intron 4: 2697-2909
<220> FEATURE:
<221> NAME/KEY: exon
<222> LOCATION: (2910)..(4670)
<223> OTHER INFORMATION: exon 5: 2910-4670
<220> FEATURE:
<221> NAME/KEY: Intron
<222> LOCATION: (4671)..(4761)
<223> OTHER INFORMATION: Intron 5: 4671-4761
<220> FEATURE:
<221> NAME/KEY: exon
<222> LOCATION: (4762)..(4974)
<223> OTHER INFORMATION: exon 6: 4762-4974
<220> FEATURE:
<221> NAME/KEY: CDS
<222> LOCATION: (4975)..(5007)
<223> OTHER INFORMATION: linker region
<220> FEATURE:
<221> NAME/KEY: CDS
<222> LOCATION: (5008)..(5241)
<223> OTHER INFORMATION: cMyc

<400> SEQUENCE: 148 atg atg gat aca tcc aaa gat gat gat atg gag ata gct tct tct tct      48
Met Met Asp Thr Ser Lys Asp Asp Asp Met Glu Ile Ala Ser Ser Ser
1               5                   10                  15 ggc agc cgg aga tac gac gtt ttc cca agc ttt cgt gga gaa gat gtc      96
Gly Ser Arg Arg Tyr Asp Val Phe Pro Ser Phe Arg Gly Glu Asp Val
            20                  25                  30 cgt gac tca ttc ctc agc cat ctt ctc aag gag ctc agg ggc aaa gca     144
Arg Asp Ser Phe Leu Ser His Leu Leu Lys Glu Leu Arg Gly Lys Ala
        35                  40                  45 atc aca ttc ata gat gat gag atc gag agg agc cgc tca atc ggc ccg     192
Ile Thr Phe Ile Asp Asp Glu Ile Glu Arg Ser Arg Ser Ile Gly Pro
    50                  55                  60 gag ctt tta tcg gca ata aaa gaa tcg aga ata gca atc gtt atc ttc     240
Glu Leu Leu Ser Ala Ile Lys Glu Ser Arg Ile Ala Ile Val Ile Phe
65                  70                  75                  80 tct aag aac tat gct tca tcc acc tgg tgc ctg aat gaa ttg gtg gag     288
Ser Lys Asn Tyr Ala Ser Ser Thr Trp Cys Leu Asn Glu Leu Val Glu
                85                  90                  95 att cac aag tgt tat acg aat ttg aat caa atg gtg att ccg att ttc     336
Ile His Lys Cys Tyr Thr Asn Leu Asn Gln Met Val Ile Pro Ile Phe
            100                 105                 110 ttc cac gtt gat gct tcg gaa gtt aaa aaa cag acc ggc gaa ttt gga     384
Phe His Val Asp Ala Ser Glu Val Lys Lys Gln Thr Gly Glu Phe Gly
        115                 120                 125 aag gtc ttt gaa gag aca tgc aag gct aaa tca gag gat gag aaa caa     432
Lys Val Phe Glu Glu Thr Cys Lys Ala Lys Ser Glu Asp Glu Lys Gln
    130                 135                 140
```

```
agt tgg aag caa gct cta gca gct gtt gca gtt atg gcc gga tat gat      480
Ser Trp Lys Gln Ala Leu Ala Ala Val Ala Val Met Ala Gly Tyr Asp
145                 150                 155                 160 ctt cgg aaa tg  gtatttcaat gaatagactt cgtgatttt ttgttttgcg           531
Leu Arg Lys Trp ttgcttcttt aatgaaacag ttgactattg ttattag g cct agt gaa gca gcc       584
                                          Pro Ser Glu Ala Ala
                                                      165 atg att gaa gag ctt gcc gag gat gtt ttg aga aaa act atg aca cca      632
Met Ile Glu Glu Leu Ala Glu Asp Val Leu Arg Lys Thr Met Thr Pro
170                 175                 180                 185 tcg gat gat ttt ggc gac tta gtc gga att gaa aat cat ata gag gca      680
Ser Asp Asp Phe Gly Asp Leu Val Gly Ile Glu Asn His Ile Glu Ala
                    190                 195                 200 ata aaa tca gta ttg tgc ttg gaa tcc aag gaa gct aga ata atg gtc      728
Ile Lys Ser Val Leu Cys Leu Glu Ser Lys Glu Ala Arg Ile Met Val
                205                 210                 215 ggg att tgg gga caa tca ggg att ggt aag agt acc ata gga aga gct      776
Gly Ile Trp Gly Gln Ser Gly Ile Gly Lys Ser Thr Ile Gly Arg Ala
220                 225                 230 ctt tac agt aaa ctc tct atc cag ttc cac cat cgc gct ttc ata aca      824
Leu Tyr Ser Lys Leu Ser Ile Gln Phe His His Arg Ala Phe Ile Thr
        235                 240                 245 tat aaa agc acc agc ggt agt gac gtc tct ggc atg aag ttg agg tgg      872
Tyr Lys Ser Thr Ser Gly Ser Asp Val Ser Gly Met Lys Leu Arg Trp
250                 255                 260                 265 gaa aaa gaa ctt ctc tcg gaa atc tta ggt caa aag gac ata aag ata      920
Glu Lys Glu Leu Leu Ser Glu Ile Leu Gly Gln Lys Asp Ile Lys Ile
                270                 275                 280 gag cat ttt ggt gtg gtg gag caa agg tta aag caa cag aaa gtt ctt      968
Glu His Phe Gly Val Val Glu Gln Arg Leu Lys Gln Gln Lys Val Leu
            285                 290                 295 atc ctt ctt gat gat gtg gat agt cta gag ttt ctt aag acc ttg gtg     1016
Ile Leu Leu Asp Asp Val Asp Ser Leu Glu Phe Leu Lys Thr Leu Val
300                 305                 310 gga aaa gct gaa tgg ttt gga tct gga agc aga ata att gtg atc act     1064
Gly Lys Ala Glu Trp Phe Gly Ser Gly Ser Arg Ile Ile Val Ile Thr
        315                 320                 325 caa gat agg caa ctt ctc aag gct cat gag att gac ctt ata tat gag     1112
Gln Asp Arg Gln Leu Leu Lys Ala His Glu Ile Asp Leu Ile Tyr Glu
330                 335                 340                 345 gtg gag ttc cca tct gaa cat ctt gct ctt acg atg tta tgc cga tct     1160
Val Glu Phe Pro Ser Glu His Leu Ala Leu Thr Met Leu Cys Arg Ser
                350                 355                 360 gct ttt ggg aaa gac tct cca cct gat gat ttt aag gaa cta gca ttt     1208
Ala Phe Gly Lys Asp Ser Pro Pro Asp Asp Phe Lys Glu Leu Ala Phe
            365                 370                 375 gaa gtt gcg aag ctt gcc ggt aat ctt ccg ttg ggt ctt agt gtc ctt     1256
Glu Val Ala Lys Leu Ala Gly Asn Leu Pro Leu Gly Leu Ser Val Leu
380                 385                 390 ggt tcg tct tta aag gga agg acc aaa gaa tgg tgg atg gag atg atg     1304
Gly Ser Ser Leu Lys Gly Arg Thr Lys Glu Trp Trp Met Glu Met Met
        395                 400                 405 cct agg ctc cga aat ggt ttg aac gga gat att atg aaa aca tta aga     1352
Pro Arg Leu Arg Asn Gly Leu Asn Gly Asp Ile Met Lys Thr Leu Arg
410                 415                 420                 425 gtc agc tac gat aga tta cat caa aaa gat caa gat atg ttc ctt tac     1400
Val Ser Tyr Asp Arg Leu His Gln Lys Asp Gln Asp Met Phe Leu Tyr
                430                 435                 440
```

| | |
|---|---|
| atc gcg tgt tta ttc aat ggt ttt gaa gtc agt tac gtc aaa gat tta<br>Ile Ala Cys Leu Phe Asn Gly Phe Glu Val Ser Tyr Val Lys Asp Leu<br>                445                    450                 455 | 1448 |
| ctt aaa gat aat gtt ggg ttt aca atg ttg act gag aag tcc ctc ata<br>Leu Lys Asp Asn Val Gly Phe Thr Met Leu Thr Glu Lys Ser Leu Ile<br>           460                    465                    470 | 1496 |
| cgt att aca ccg gat gga tat ata gag atg cac aat ttg cta gag aaa<br>Arg Ile Thr Pro Asp Gly Tyr Ile Glu Met His Asn Leu Leu Glu Lys<br>475                    480                    485 | 1544 |
| ttg ggt aga gaa att gat cgt gca aag tcc aag ggt aat cct gga aaa<br>Leu Gly Arg Glu Ile Asp Arg Ala Lys Ser Lys Gly Asn Pro Gly Lys<br>490                    495                    500                    505 | 1592 |
| cgt cga ttt ctg acg aat ttt gaa gat att cat gaa gta gtg acc gag<br>Arg Arg Phe Leu Thr Asn Phe Glu Asp Ile His Glu Val Val Thr Glu<br>                      510                    515                    520 | 1640 |
| aaa act gtaagttttt ttcgcagctc cgtttgaatg catgacttta tattaatata<br>Lys Thr | 1696 |
| atcgtaattt ggggattgat aaacttaagc aattgttgcc tcatgcgtaa ttaaaatgta | 1756 |
| gctttgatgt gtcagaaaat taaaaagggt tgcgattgtt aagattatat tagttttctt | 1816 |
| cggatttttt ttcag ggg aca gaa act ctt ctt gga ata cgt ttg cca ttc<br>                      Gly Thr Glu Thr Leu Leu Gly Ile Arg Leu Pro Phe<br>                             525                    530                    535 | 1867 |
| gag gaa tat ttt tcg aca agg ccg tta tta ata gat aaa gaa tcg ttc<br>Glu Glu Tyr Phe Ser Thr Arg Pro Leu Leu Ile Asp Lys Glu Ser Phe<br>                540                    545                    550 | 1915 |
| aaa ggc atg cgt aat ctg caa tat cta aaa att ggt tat tac ggg gat<br>Lys Gly Met Arg Asn Leu Gln Tyr Leu Lys Ile Gly Tyr Tyr Gly Asp<br>            555                    560                    565 | 1963 |
| cta cct cag agc ctc gtt tat ttg ccc ctt aaa ctc aga ttg cta gac<br>Leu Pro Gln Ser Leu Val Tyr Leu Pro Leu Lys Leu Arg Leu Leu Asp<br>            570                    575                    580 | 2011 |
| tgg gat gat tgt cca ttg aag tct ttg cca tct act ttt aag gcg gaa<br>Trp Asp Asp Cys Pro Leu Lys Ser Leu Pro Ser Thr Phe Lys Ala Glu<br>585                    590                    595 | 2059 |
| tat cta gtt aac ctc ata atg aag tat agt aag ctt gag aaa ctg tgg<br>Tyr Leu Val Asn Leu Ile Met Lys Tyr Ser Lys Leu Glu Lys Leu Trp<br>600                    605                    610                    615 | 2107 |
| gaa gga act ctg gtacgaattc taaatttat tagttgtcag tttttagaac<br>Glu Gly Thr Leu | 2159 |
| agaactgtgg tatatttgtg aacgtgtgta ttctcttttt ccatatttg ttttcag | 2216 |
| ccc ctt gga agt ctc aag gag atg aat ttg agg tat tcc aac aat ttg<br>Pro Leu Gly Ser Leu Lys Glu Met Asn Leu Arg Tyr Ser Asn Asn Leu<br>620                    625                    630                    635 | 2264 |
| aaa gaa att cca gat ctt tct tta gcc ata aac ctc gag gaa tta gat<br>Lys Glu Ile Pro Asp Leu Ser Leu Ala Ile Asn Leu Glu Glu Leu Asp<br>                640                    645                    650 | 2312 |
| ctt gtt gga tgc aaa tct ttg gtg aca ctt cct tcc tcg att cag aat<br>Leu Val Gly Cys Lys Ser Leu Val Thr Leu Pro Ser Ser Ile Gln Asn<br>            655                    660                    665 | 2360 |
| gcc act aaa ctg atc tat tta gat atg agt gat tgc aaa aag cta gag<br>Ala Thr Lys Leu Ile Tyr Leu Asp Met Ser Asp Cys Lys Lys Leu Glu<br>            670                    675                    680 | 2408 |
| agt ttt cca acc gat ctc aac ttg gaa tct ctc gag tac ctc aat ctc<br>Ser Phe Pro Thr Asp Leu Asn Leu Glu Ser Leu Glu Tyr Leu Asn Leu<br>685                    690                    695 | 2456 |
| act gga tgc ccg aat ttg aga aac ttt cca gca atc aaa atg gga tgt<br>Thr Gly Cys Pro Asn Leu Arg Asn Phe Pro Ala Ile Lys Met Gly Cys<br>700                    705                    710                    715 | 2504 |

```
tca gac gtt gac ttt ccg gaa ggg aga aat gag atc gtg gta gaa gat      2552
Ser Asp Val Asp Phe Pro Glu Gly Arg Asn Glu Ile Val Val Glu Asp
                720                 725                 730 tgt ttc tgg aac aag aat ctc cct gct gga cta gat tat ctc gac tgc      2600
Cys Phe Trp Asn Lys Asn Leu Pro Ala Gly Leu Asp Tyr Leu Asp Cys
            735                 740                 745 ctt acg aga tgt atg cct tgt gaa ttt cgc cca gaa caa ctc gct ttt      2648
Leu Thr Arg Cys Met Pro Cys Glu Phe Arg Pro Glu Gln Leu Ala Phe
        750                 755                 760 ctc aat gtg agg ggc tac aag cat gag aag cta tgg gaa ggc atc cag      2696
Leu Asn Val Arg Gly Tyr Lys His Glu Lys Leu Trp Glu Gly Ile Gln
    765                 770                 775 gtacattgtt aatgctatgc tgattttgt ttaccttctg ttatataact aattaactat     2756
acccaaattt gttattatgg cttgtgatcc acggttatgt cttaccacgg ttatgtctta    2816
taataatgtt taattataat tttaaacata tacagtataa aattaaaatg attatcatcg    2876
ataatgattg aagcatacca atgtttttt cag tcg ctt gga agt ctc gaa ggg      2930
                                    Ser Leu Gly Ser Leu Glu Gly
                                    780                 785 atg gat ctg tca gaa tct gaa aac ctg aca gaa att cca gat ctt tca      2978
Met Asp Leu Ser Glu Ser Glu Asn Leu Thr Glu Ile Pro Asp Leu Ser
                790                 795                 800 aag gcc acc aag ctc gag tct ttg ata ctc aac aac tgc aaa agt ttg      3026
Lys Ala Thr Lys Leu Glu Ser Leu Ile Leu Asn Asn Cys Lys Ser Leu
            805                 810                 815 gtg aca ctt cct tct aca att ggg aat ctt cat aga ttg gtg agg ttg      3074
Val Thr Leu Pro Ser Thr Ile Gly Asn Leu His Arg Leu Val Arg Leu
        820                 825                 830 gaa atg aaa gaa tgc aca ggg ctg gag gtt ctt ccg acc gat gtc aac      3122
Glu Met Lys Glu Cys Thr Gly Leu Glu Val Leu Pro Thr Asp Val Asn
835                 840                 845                 850 ttg tca tct ctc gaa acc ctc gat ctc agt ggt tgc tca agt ttg aga      3170
Leu Ser Ser Leu Glu Thr Leu Asp Leu Ser Gly Cys Ser Ser Leu Arg
                855                 860                 865 agt ttt cct ctg att tca act aat att gta tgg ctc tat ctg gaa aac      3218
Ser Phe Pro Leu Ile Ser Thr Asn Ile Val Trp Leu Tyr Leu Glu Asn
            870                 875                 880 acc gcc att gaa gaa att cct tct aca att ggg aat ctt cat aga ttg      3266
Thr Ala Ile Glu Glu Ile Pro Ser Thr Ile Gly Asn Leu His Arg Leu
        885                 890                 895 gtg agg tta gaa atg aaa aaa tgc aca ggg ctg gag gtt ctt ccg acc      3314
Val Arg Leu Glu Met Lys Lys Cys Thr Gly Leu Glu Val Leu Pro Thr
    900                 905                 910 gat gtc aac ttg tca tct ctc gaa acc ctc gat ctc agt ggt tgc tca      3362
Asp Val Asn Leu Ser Ser Leu Glu Thr Leu Asp Leu Ser Gly Cys Ser
915                 920                 925                 930 agt ttg aga agt ttt cct ctg att tca gag agt atc aaa tgg ctc tat      3410
Ser Leu Arg Ser Phe Pro Leu Ile Ser Glu Ser Ile Lys Trp Leu Tyr
                935                 940                 945 ctg gaa aac acc gcc att gaa gaa att cca gat ctt tca aag gcc act      3458
Leu Glu Asn Thr Ala Ile Glu Glu Ile Pro Asp Leu Ser Lys Ala Thr
            950                 955                 960 aat ctg aag aat ttg aaa ctc aac aat tgc aaa agt ttg gtg aca ctt      3506
Asn Leu Lys Asn Leu Lys Leu Asn Asn Cys Lys Ser Leu Val Thr Leu
        965                 970                 975 cct act act ata gga aat ctc caa aaa ttg gtg agc ttt gaa atg aaa      3554
Pro Thr Thr Ile Gly Asn Leu Gln Lys Leu Val Ser Phe Glu Met Lys
    980                 985                 990
```

```
gaa tgc aca ggg ctg gag gtt ctt ccg atc gat gtc aac ttg tca      3599
Glu Cys Thr Gly Leu Glu Val Leu Pro Ile Asp Val Asn Leu Ser
995                 1000                1005 tct ctt atg atc ctc gat ctc agt ggt tgc tca agt ctg aga act      3644
Ser Leu Met Ile Leu Asp Leu Ser Gly Cys Ser Ser Leu Arg Thr
1010                1015                1020 ttt cct ctg att tca act aat att gta tgg ctc tat ctg gaa aac      3689
Phe Pro Leu Ile Ser Thr Asn Ile Val Trp Leu Tyr Leu Glu Asn
1025                1030                1035 acc gcc att gaa gaa atc cct tct aca att ggg aat ctt cat aga      3734
Thr Ala Ile Glu Glu Ile Pro Ser Thr Ile Gly Asn Leu His Arg
1040                1045                1050 ttg gtg aag tta gaa atg aaa gaa tgc aca ggg ctg gag gtt ctt      3779
Leu Val Lys Leu Glu Met Lys Glu Cys Thr Gly Leu Glu Val Leu
1055                1060                1065 ccg acc gat gtc aac ttg tca tct ctt atg atc ctc gat ctc agt      3824
Pro Thr Asp Val Asn Leu Ser Ser Leu Met Ile Leu Asp Leu Ser
1070                1075                1080 ggt tgc tca agt ctg aga act ttt cct ctg att tca act aga atc      3869
Gly Cys Ser Ser Leu Arg Thr Phe Pro Leu Ile Ser Thr Arg Ile
1085                1090                1095 gaa tgt ctc tat ctg caa aac acc gcc att gaa gaa gtt ccc tgc      3914
Glu Cys Leu Tyr Leu Gln Asn Thr Ala Ile Glu Glu Val Pro Cys
1100                1105                1110 tgc att gag gat ttc acg agg ctc act gta ctt atg atg tat tgt      3959
Cys Ile Glu Asp Phe Thr Arg Leu Thr Val Leu Met Met Tyr Cys
1115                1120                1125 tgc cag agg ttg aaa acc atc tcc cca aac att ttc aga ctt aca      4004
Cys Gln Arg Leu Lys Thr Ile Ser Pro Asn Ile Phe Arg Leu Thr
1130                1135                1140 aga ctt gag ctc gcc gac ttt aca gac tgt aga ggt gtc atc aag      4049
Arg Leu Glu Leu Ala Asp Phe Thr Asp Cys Arg Gly Val Ile Lys
1145                1150                1155 gcg ttg agt gat gca act gtg gta gcg aca atg gaa gac cac gtt      4094
Ala Leu Ser Asp Ala Thr Val Val Ala Thr Met Glu Asp His Val
1160                1165                1170 tct tgt gta cca tta tct gaa aac att gaa tat atc tgg gat aag      4139
Ser Cys Val Pro Leu Ser Glu Asn Ile Glu Tyr Ile Trp Asp Lys
1175                1180                1185 ttg tat cgt gtt gca tac ctc cag gaa cat ttt agc ttc cgt aat      4184
Leu Tyr Arg Val Ala Tyr Leu Gln Glu His Phe Ser Phe Arg Asn
1190                1195                1200 tgc ttc aaa ttg gat aga gat gcg cga gag ctc atc cta cga tca      4229
Cys Phe Lys Leu Asp Arg Asp Ala Arg Glu Leu Ile Leu Arg Ser
1205                1210                1215 tgc ttc aag cct gtg gcc tta cca ggt gaa gaa atc cct aag tat      4274
Cys Phe Lys Pro Val Ala Leu Pro Gly Glu Glu Ile Pro Lys Tyr
1220                1225                1230 ttc acg tat cga gct tat gga gat tcc cta act gtc att gta cct      4319
Phe Thr Tyr Arg Ala Tyr Gly Asp Ser Leu Thr Val Ile Val Pro
1235                1240                1245 cag agc tct ctt tct caa aat ttc ttg cga ttt aag gct tgc gtc      4364
Gln Ser Ser Leu Ser Gln Asn Phe Leu Arg Phe Lys Ala Cys Val
1250                1255                1260 gtg gtt gaa cct ctc tcc aag ggc aag ggt ttt tat cca ttc ttg      4409
Val Val Glu Pro Leu Ser Lys Gly Lys Gly Phe Tyr Pro Phe Leu
1265                1270                1275 aag gta aac gtt ggc ttc aat ggc aaa cag tat cag aaa tca ttt      4454
Lys Val Asn Val Gly Phe Asn Gly Lys Gln Tyr Gln Lys Ser Phe
1280                1285                1290
```

```
tct aaa gat gca gaa ctg gag ctt tgt aag acg gat cat ctg ttt      4499
Ser Lys Asp Ala Glu Leu Glu Leu Cys Lys Thr Asp His Leu Phe
1295                1300                1305 ttc tgt tcc ttc aag ttc cgg tct gaa gat ctt cca tct aaa ttg      4544
Phe Cys Ser Phe Lys Phe Arg Ser Glu Asp Leu Pro Ser Lys Leu
1310                1315                1320 aat ttc aac gat gtg gag ttt aag ttt tgt tgc tcc aat agg atc      4589
Asn Phe Asn Asp Val Glu Phe Lys Phe Cys Cys Ser Asn Arg Ile
1325                1330                1335 aaa gaa tgc ggt gta cga ctc atg tat gtc tct caa gaa gag aac      4634
Lys Glu Cys Gly Val Arg Leu Met Tyr Val Ser Gln Glu Glu Asn
1340                1345                1350 aac caa cag act acg aga agc gag aag cgg atg cgg gtatcttttg       4680
Asn Gln Gln Thr Thr Arg Ser Glu Lys Arg Met Arg
1355                1360                1365 actttgatt tgattttcca ggatcgaaat accataggga cagactattt aatagaatct  4740
atcgtttgat ttataatgca g atg aca tcg ggg aca tct gaa gaa gat atc  4791
                        Met Thr Ser Gly Thr Ser Glu Glu Asp Ile
                                   1370                1375 aac tta ccc tat ggc cta att gta gcg gac aca gga ttg gcc gct      4836
Asn Leu Pro Tyr Gly Leu Ile Val Ala Asp Thr Gly Leu Ala Ala
1380                1385                1390 cta aat atg gag ctt tcg tta ggg cag gga gaa cca tca tca tca      4881
Leu Asn Met Glu Leu Ser Leu Gly Gln Gly Glu Pro Ser Ser Ser
1395                1400                1405 aca tct cta gag ggg gaa gct ttg tgt gtt gat tac atg ata act      4926
Thr Ser Leu Glu Gly Glu Ala Leu Cys Val Asp Tyr Met Ile Thr
1410                1415                1420 gaa gaa caa gat aaa gga att cct atc ttg ttt cct gtt tct ggt      4971
Glu Glu Gln Asp Lys Gly Ile Pro Ile Leu Phe Pro Val Ser Gly
1425                1430                1435 aac tgg cgg ccg ctc gag agg tat cga ttc aaa gct atg gaa caa      5016
Asn Trp Arg Pro Leu Glu Arg Tyr Arg Phe Lys Ala Met Glu Gln
1440                1445                1450 aag ctc att tct gaa gag gac ttg aat gaa atg gag caa aag ctc      5061
Lys Leu Ile Ser Glu Glu Asp Leu Asn Glu Met Glu Gln Lys Leu
1455                1460                1465 att tct gaa gag gac ttg aat gaa atg gag caa aag ctc att tct      5106
Ile Ser Glu Glu Asp Leu Asn Glu Met Glu Gln Lys Leu Ile Ser
1470                1475                1480 gaa gag gac ttg aat gaa atg gag caa aag ctc att tct gaa gag      5151
Glu Glu Asp Leu Asn Glu Met Glu Gln Lys Leu Ile Ser Glu Glu
1485                1490                1495 gac ttg aat gaa atg gag agc ttg ggc gac ctc acc atg gag caa      5196
Asp Leu Asn Glu Met Glu Ser Leu Gly Asp Leu Thr Met Glu Gln
1500                1505                1510 aag ctc att tct gaa gag gac ttg aat tgg gta ccc cgg gtt ctc      5241
Lys Leu Ile Ser Glu Glu Asp Leu Asn Trp Val Pro Arg Val Leu
1515                1520                1525 tag                                                               5244

<210> SEQ ID NO 149
<211> LENGTH: 11
<212> TYPE: PRT
<213> ORGANISM: Artificial Sequence
<220> FEATURE:
<223> OTHER INFORMATION: Synthetic Construct

<400> SEQUENCE: 149
```

```
Trp Arg Pro Leu Glu Arg Tyr Arg Phe Lys Ala
1               5                   10
```

<210> SEQ ID NO 150
<211> LENGTH: 78
<212> TYPE: PRT
<213> ORGANISM: Artificial Sequence
<220> FEATURE:
<223> OTHER INFORMATION: Synthetic Construct

<400> SEQUENCE: 150

```
Met Glu Gln Lys Leu Ile Ser Glu Glu Asp Leu Asn Glu Met Glu Gln
1               5                   10                  15
Lys Leu Ile Ser Glu Glu Asp Leu Asn Glu Met Glu Gln Lys Leu Ile
            20                  25                  30
Ser Glu Glu Asp Leu Asn Glu Met Glu Gln Lys Leu Ile Ser Glu Glu
        35                  40                  45
Asp Leu Asn Glu Met Glu Ser Leu Gly Asp Leu Thr Met Glu Gln Lys
    50                  55                  60
Leu Ile Ser Glu Glu Asp Leu Asn Trp Val Pro Arg Val Leu
65                  70                  75
```

<210> SEQ ID NO 151
<211> LENGTH: 619
<212> TYPE: DNA
<213> ORGANISM: Artificial Sequence
<220> FEATURE:
<223> OTHER INFORMATION: Synthetic

<400> SEQUENCE: 151

```
atacgtatca aagtagatat ccgcaaatat cacaaaaaaa ttcggatatt caaaattccg      60
gatatccgga aagtttcgaa tcaaagcaaa tcataaaatc aagtattcga ttaaaacgaa     120
tcaaataaca aatatcacaa tttttccgga tatttgcttc gtgtccaggc ctatccgcct     180
ttataggccc atagacagta tgtgttaaat tataatccaa tattgtacgg atgattatac     240
tatatagttc cgaatatata tcattgtgtt acagctggga atgaatcaaa ttaacgtaat     300
gtacggaaga agaactatag aagctttgtt ttttgtgggc ttcaaatttc aatatgtcaa     360
ttatgagaat aatcaagtaa atattgtaaa tacatactct aataagaaaa taaggcctaa     420
agtttaggat atgagaatgt tagagtgcaa tttaagaaaa tgtccggtgc aacgcgacat     480
ttgcgtgttt ttcacatcca tgcatgcgta ctatatgtat ccccgcaatc ttagtcaaat     540
atcaaatatt caaacgagag atttcatcta ccgctgattc atttgcttcg cgtatatcac     600
tatatggatt tgataatta                                                   619
```

<210> SEQ ID NO 152
<211> LENGTH: 2100
<212> TYPE: DNA
<213> ORGANISM: Artificial Sequence
<220> FEATURE:
<223> OTHER INFORMATION: Synthetic

<400> SEQUENCE: 152

```
attcttcatt gctgcgaacc gtggctcctt gggctgaaac ttgaccctg cataaagctt       60
catgtagtca tcaaagacga aactcgggta ctcggaatct ttctcgacaa gcgaagtagc    120
tggtgagatc tccgcatcgc ttcccggggtt gtaaaacgat gcaaccgaca tcctgttttcc    180
ttcttgttga gtcaccacac ggtgcagcac actcttatac ttcccgttgg ttatcaccta    240
cagacaattc agatcggttt agctgtaccg aatcatactc aattaagatt gcatgtcgtt    300
```

```
cttccggttt aactcggtta taacatttac taaccgtttc ctatagttcc atcaaaccga      360
gactaaacca taacacattg gttttgttag caaaaagata ttttgaaaat gtggtgtgaa      420
catgacatac ctcaagttgg tcaccaagat tgatgacaat agagtggttg agaggaggaa      480
catcaatcca gtcaccatct ttaagaagct ggagaccact gaccttgtcg tcttgaaaca      540
acaagatgat gcctcctgca tcagtgtggg ccctaagacc tttgatcatc tctggtttag      600
gacatggtgg ataattgctc acctttgtcc caaggttgg gccttttgtt ccatgaaaca       660 cttcttcaa atacccttc tctaaaccta gattctcaca cagtagatcc aacaaatcct       720
cagcaagatt ctccagtctc ttaccaaagt ctttcatggc cgtcctgcca aatcagaata      780
tattacataa tatttcccaa aaagaaaat gattatgctt cactatgcaa gtttcaagtt       840
acttttaagt aaaataataa ttttaaatg ggttttaaca ataaaatatt taccaataaa       900
tatcacaaaa agtcagaaat tcttaaactc atgcatgtga gaaaaagtaa aaagtaagaa      960
aatatttata attaaaggta aaagaggtag agtgtacaac tgaaattttt ttacagtcaa     1020
tttgagattt atttaagaaa aatagaatta aattcggtcc tacaaataag tgataattaa     1080
ctggccttat tggtattcat gtatcctaag agatgttatg attaaggggg agttttgtg      1140 tggtgactaa ttttttttcat agaagaaaat aaatattatt tatcactaaa tgaatataac     1200
attcgatcta aaatagtatt tttctaaaaa cattatgtac ctgtattcat cagcacatc      1260 tgaaatgtca ttgagattgg attgagggag gtgacgaacg tagaaagtgc tttcccaatc     1320
gacatcttcg acttctgtct caagattatc caaaccttg gacttgagca tgtcattgaa     1380
cttttgttct tggcatgtct tgtaatggtc ctttgtcatc ttctcgatct tgtccattaa     1440
gtcatgtggt aatccatggt tcactatctg aaaaatgaaa ttaacaaaag atcaacctta     1500
ccactaagag ctagctatag tcaaatcttt tcaaacaata atatgttaga tattgtgtat     1560
gtacctcaaa gaagccccaa ttctcacaag cttcattgat tagagccatg gtttggtctc     1620
tctcttcccc attgagcttg gacaagtcta ctactggaaa cttcatgttc ttctccatct     1680
ttctttctct ctctcttctt tgaaagtaat ctatttgaag ttacaagttg tgtatttgtt     1740
aattgctttg atgtgagact tgtagaatga gagagggttg ctatttatag gcgcaaatga    1800
gagagattgg cttcaataa aataaataaa attctgagaa aatatgtgcg agtcatagtc     1860
atagataaga tgtataaata tgtttcattc aaattgttaa aaagaagaa gttaaagtaa      1920 aagaaacaag agttcgtgga gcatgtatgt gagcacatca tagatggacc cctaccatct     1980
cctttcttta agagattgat tcatttggca ttttcctttt gggtctctat ttatacactt     2040
caattggttt cttttctctt cccttttggg gttattttat tcgaaatagt ttgaaaaatt    2100
```

<210> SEQ ID NO 153
<211> LENGTH: 1082
<212> TYPE: DNA
<213> ORGANISM: Artificial Sequence
<220> FEATURE:
<223> OTHER INFORMATION: Synthetic

<400> SEQUENCE: 153

```
acttgggttc agttaaaaat ctcaaattgg agacattatt ggtgtttata tatttgagag       60
agagagccag agaggagacg ttgaattgaa tgaagggtgt ggtcggaaga gaagacgtgt     120
agaagagacg agacaagtaa atttaagcat tggccccatt tacagccaca agtccgctac     180
aacaaattat ttccaagaaa ctctgagata acgtcgtgat gaaacggctc atgctgctgt     240
```

```
tgtgattcgt gaattagagg tttatctttt gggttttga atgttactta attggacggt      300
cgatttttca aactgggtgt gaaatgtgaa tgggtcattc ataatgggct tttgttttaa      360
tgtgaagcca ttcacacact ctttgtcctt cttttctatt attcataact gtcactcttt      420
gttcttcgaa atagtaaaga gcaaatcgat tctttgttga tctgggccgt aaaatttcca      480
tggttgtggg aagtattctc gcagctgatc tgggccgtca atgctacagt ttcatgtcag      540
agagaggtca agaatcaaca cgtggccaac catgatttta aaccaaagca aacacacgat      600
tagaccccac attgtttgtt caccaacccc cgtggaccct cctttagccg acgtgtccac      660
gtcaatagtg gttttctc ctttcaaagt acacaaattc cattctttct catttactt      720 tttggattac gttgttgtta taaactggta aatgaatta tgaatgcaaa taaatttcat      780
ttaagttttg ttggcttcta atatttttt cacctaaaat tctaataaac tacacagcca      840
tgagccatcg tatgaaaaga agaagaaaaa aaatgtcttt ttctagaagg atctttcaac      900
gactaaaaaa gattttaagc ttttgactaa ttttgtcaat aatatacaca aatttacact      960
caattatagc catcaaatgt gtgctatgca gaaacaccaa ttatttcatc acacatacgc     1020
atacgttacg tttccaactt tctctatata tatatatagt aatacacaca cataaacagc     1080
aa                                                                   1082
```

<210> SEQ ID NO 154
<211> LENGTH: 1176
<212> TYPE: DNA
<213> ORGANISM: Artificial Sequence
<220> FEATURE:
<223> OTHER INFORMATION: Synthetic

<400> SEQUENCE: 154

```
cgacaagaat cttgttttgt gatgctgccg aggatcattt tcttgtatta agaatcttgt       60
attatatatc actgtaactt ctacatccat cagtggagaa tcttacattc ttagtttttt      120
ttggcaacat acatgatcta tacatgtctt ttggccaaat cttatttta tatttttaat      180 acatgatcta taacatgtat taagtttgaa aacataacaa aattttgta acaaaaataa      240 ccaaatatt atttgaaaaa gaaatatcca agtttaat agtaataata caaaaataga      300
agtttgaaaa cattttttaa taaataaaaa agtgttaaaa atttatcaca acgctaacaa      360
acaaattcac ctaaccgttt acttttagaa tcagaaataa acaacaaaaa taaactttca      420
gaaagttgca gtttcacata tgttacaaac atcatcagat tctttgaaac aaaacagtaa      480
ccaagaagtt tcttatgcat agctttgttc aaaatcaata ctttggagtt agtcaattaa      540
attcatatgc aaatctctga cctttttgctt ttgtaagcta aatgcattga aaaagggag      600 aggctctgga tcagtgtgct catggtgggc cggcccatca ctatgggctg tctaaaacaa      660
aaacaatttt ggaaggcaaa aggtataata acccccgtccc tgtatgttgg gctaggcctg      720
tccagtatcc accaccacta actcaattcc cccattatta caaatttaca atctctccac      780
caattggcca acaatggagt atatattaac tataaagcaa atcataaagc ttctatagta      840
acatcaagct atgaatattt ttatacgttc tgcaagaaac gtgacatcaa catttttgtga     900 ttaaaccgat tcttaatttg tccctttcta tcatcaagtt aaaaacgtga catcaacact     960
ttgattaaga gaatcaagaa acgtgacgtc aatatttga tgaagcttgt gaaatgtgga    1020
cagctatttt atcctcgatg atattcgat tgttttaata aaaatcattt cagctatttt    1080
tagtcaatat agacggtttt gccaaactca aaagtcaaaa gtcaaggtc aaggagtcc    1140 attatataaa ccatagctta atcatttgat tactaa                             1176
```

<210> SEQ ID NO 155
<211> LENGTH: 1853
<212> TYPE: DNA
<213> ORGANISM: Artificial Sequence
<220> FEATURE:
<223> OTHER INFORMATION: Synthetic

<400> SEQUENCE: 155

```
gcaacgatac cgtgtttact aagctcaggt tttaggtctc aaattaggtc ttatataaga      60
caatagtaaa aaggaaatat tttctcctta gttaaaatta atgaacaagt cccctgaatt     120
aaaataaaat accaaatcgc ccgttttta aacagatttc agtattgaac ctgttaaaa      180
ccggtttgaa aactaaagta atattaaaaa cgataacaat taacaacaca tcgttatata     240
tacattatgt tgtgttactg gaatttcggt gttcagtttt ttaaaccgaa ctcaccaaat     300
tcgtataaga aaatctatgg atttatcgta taaagaactt ttctatgctg ctttcaaact     360
ttttttaaga tccctccctt gattttggta taccttcaaa tgtacatgta tacacaaaaa     420
aaaaatgaaa gacagaaaga tacacttaca caatgtaact tgcttgatga ttcatagtca     480
taggatttga gacttctcta acaatgcact aaactagtct ctttcttgga agatttcttg     540
atggagacac gagtaagctt taggggaaag aagaatttat catgtttcag gtgactcgtt     600
cacacgattg tgcaggtata ctgacaatat ttctattttt tattagaaaa atatggattt     660
ggtcataaat atctaattt ctggaaaaaa aaagagaaa aagaaacac caacgaagac       720
aaatgaatga agagtaaaat aaaattagag aacaacaggg aaagaaaag acatgttgca     780
tgaatgaaaa agaatggtcg tattagagta gtttgctaaa tgatttattt aaagaatgtg     840
cattatagta ttaacaaaat cttttcatgt cttttaaaa gccaacgctc tagagttgac     900
tctatgtatt tcttcttctt cttcttcatg atatgaagtc tgaccccaa caaaaaagga     960
tgaaagtatt tttggggaaa tggtcattta tcgcttctgg ataagctact cgcatttcga    1020
aactatattg tactaatact aaaattacga cttacgaaag atgacacaat taataacaaa    1080
aagatgcttt tatcagattc tataataaat gttgtttcct atcggatcaa catgcatgca    1140
ctttgacaaa tcgggtagaa aatttccttc cttcggattg aatcataaaa atatgtttta    1200
cctaagcaat ctccataata ttatcagaaa atttggtatc aacacttatt cgcaagtaat    1260
gatatttata tatttgattt gatttatact tatctgcaac aacaattaga aaaaatacta    1320
agagatccaa tgtaaacata actttatatt atctatattt attaattgaa agatgtctaa    1380
gttttattgg ttaagtaata atggacagca aaaaaaaaga taacttctat gcataaaatt    1440
agacaagaga tatagcaata tggttaagaa cttgagattc ttaagaacct cacgtgtgat    1500
gcaaacaatg acacgcaata acgcgtttta actgacaact ttctttcttt atttttgtct    1560
cttaaatttc ttttccttta agtggttaca gatttctact ttcgattctc gtcgactcta    1620
aaaatctcac tcgtatttgt ataaccgtcc cacgttgttg tccacttctg gaagataagt    1680
gaggtgtgtg attgattgcc gtttccaacc tcttttcaat taaatgcttc tctctatctt    1740
caattggtaa tattggcttt ggtcaattca tcatcatcat catattatta ttataccaaa    1800
gacaatgtca catgaacctt ataatataca caactgttat accttataaa caa           1853
```

<210> SEQ ID NO 156
<211> LENGTH: 2002
<212> TYPE: DNA
<213> ORGANISM: Artificial Sequence
<220> FEATURE:

<223> OTHER INFORMATION: Synthetic

<400> SEQUENCE: 156

```
aaaatacgtc acaaatataa tactaggcaa ataattattt tattataagt caatagagtg      60
gttgttgtaa aattgatttt ttgatattga aagagttcat ggacggatgt gtatgcgcca     120
aatggtaagc ccttgtactg tgccgcgcgt atattttaac caccactagt tgtttctctt     180
tttcaaaaaa cacaaaaaaa aaataatttg ttttcttaac ggcgtcaaat ctgacggcgt     240
ctcaatacgt tcaattttt tctttctttc acatggtttc tcatagcttt gcattgacca     300
taggtaaagg gataaggata atggttttt ctcttgtttg ttttatcctt attattcaaa     360
aaggataaaa aaacagtgat atttagattt ctttgattaa aaaagtcatt gaaattcata     420
tttgatttt tgctaaatgt caacacagag acacaaacgt aatgcactgt cgccaatatt     480
catggatcat gacaataaat atcactagaa taattaaaaa tcagtagaat gcaaacaaag     540
cattttctaa gtaaaacagt cttttatatt cacgtaattg gaatttcctt tttttttttt     600
tgtcgtaatt ggaatttcct ttatcaaacc caaagtccaa acaatcggc aatgttttgc      660
aaaatgttca aaactattgg cgggttggtc tatccgaatt gaagatcttt tctccatatg     720
atagaccaac gaaattcggc atacgtgttt tttttttgt tttgaaaacc ctttaaacaa      780
ccttaattca aaatactaat gtaactttat tgaacgtgca tctaaaaatt ttgaactttg     840
cttttgagaa ataatcaatg taccaataaa gaagatgtag tacatacatt ataattaaat     900
acaaaaaagg aatcaccata tagtacatgg tagacaatga aaaactttaa aacatataca     960
atcaataata ctctttgtgc ataactttt ttgtcgtctc gagtttatat ttgagtactt     1020
atacaaacta ttagattaca aactgtgctc agatacatta agttaatctt atatacaaga    1080
gcactcgagt gttgtcctta agttaatctt aagatatctt gaggtaaata gaaatagttg    1140
actcgttttt atcttcttct tttttttacca tgagcaaaaa agatgaaata agttcaaaac    1200
gtgacgaatc tatatgttac tacttagtat gtgtcaatca ttaaatcggg aaaacttcat    1260
catttcagga gtattacaaa actcctaaga gtgagaacga ctacatagta catattttga    1320
taaaagactt gaaaacttgc taaaacgaat ttgcgaaaat ataatcatac aagtgccagt    1380
gattttgatc gaattattca tagctttgta ggatgaactt aattaaataa tatctcacaa    1440
aagtattgac agtaacctag tactatacta tctatgttag aatatgatta tgatataatt    1500
tatcccctca cttattcata tgatttttga agcaactact ttcgtttttt taacattttc    1560
ttttgttggt tattgttaat gagcatattt agtcgtttct taattccact gaaatagaaa    1620
atacaaagag aactttagtt aatagatatg aacataatct cacatcctcc tcctaccttc    1680
accaaacact tttacataca ctttgtggtc tttcttacc taccaccatc aacaacaaca    1740
ccaagcccca ctcacacaca cgcaatcacg ttaaatttaa cgccgtttat tatctcatca    1800
ttcaccaact cccacgtacc taacgccgtt taccttttgc cgttggtcct catttctcaa    1860
accaaccaaa cctctccctc ttataaaatc ctctctccct tctttatttc ttcctcagca    1920
gcttcttctg ctttcaatta ctctcgccga cgatttctc accggaaaaa aacaatatca    1980
ttgcggatac acaaactata at                                              2002
```

<210> SEQ ID NO 157
<211> LENGTH: 3002
<212> TYPE: DNA
<213> ORGANISM: Artificial Sequence
<220> FEATURE:
<223> OTHER INFORMATION: Synthetic

<400> SEQUENCE: 157

```
tatgtttatg atggtaatat ttgaattgaa aaacgtaaga ttggaataaa aataaatacg    60
taagattatg atgaaatatg atgcatttga agtttgaaat ggcaagtgtt ggtgattaac   120
aagttataca tacgtcaaag gtttgtttaa ttattattct tcaccttta acgaattaca    180
cttgttcact ctaattaata atcttcaaag gtgtagtccg cgtcatgctg atgctcggga   240
aggtcttttc ctttacttaa tattgttgta gtcggttatt tgaccaatga acatacatac   300
gaaaaaacaa atatcaaagc aaaaaaaaaa catcaaatta aaccaatatt caaaaaatcg   360
gtaggtcgta tctagacggt ccgtatgagc ctagcgccta gacaaataaa tcggggatta   420
agcggggtat gggaatacaa gataattaat ttcagggtta tttaaaatag ataatttta    480
aattattacc gaacataaac cagacattgc tcttgctcac ccctaagcaa tagtagtata   540
tattactagt tgttgtcgaa cataaaacaa attgttaacg cgattactca tgcaaccgta   600
agcaacagta tacattaatt taaaaccaaa aaaacagtat acattagttg ttgattttgt   660
tgtattaaac ttcccttagc ttgtcattta ttacacttgc tgctattcat tgactcgaac   720
aaaaggtcaa tgtgatgaat ttatttagat atgttaaaat gtaagaaaaa ataagttcta   780
tttgattgtt tctttacacg actatatcaa ccaatataaa aaaaatccca atccagtcaa   840
aagacccgat cgactccaag cagaaccagt ccataatgaa acacttataa caatggttta   900
gctgccaagc tgatgtaaga tatatagtat aattttgttt tcttaagttt tccaagctaa   960
tacgtaaatt aatcactaaa tagatttttt gagcgtatta gtgtaacaca attggattcg  1020
aagttagatt atgacacaac aacaacaaaa acaacaacaa catcgataca tattattcag  1080
ccacatggcc ttcaccttca tgccttgtca tacagtttac atggtatatt tttttttaaa  1140
gtgtcgacta atattttgct agatatttt gtttatagtt ttggtcgttg gatatcttac  1200
tatattattt gaaaagtaca ttttaaatgt aactttattt tttgtaatta attacatgac  1260
aataccatta aaaaaattta atcaaaaaca aaatctttta atgacgtcat taagattacc  1320
aaactcattt aactacaata ttcatttctt aaatataagg cttattggat ctaaaaacgg  1380
atcatcaaag atttcctaaa ctgaagcaaa atataccgaa tattcaaata tctatctgtt  1440
atcaaattat aaacaaataa gttcgtaaaa caatttaata tttttataaac gaaatcaatt  1500
aaatcttaat cacataaaaa ttagcacaaa aaaaagcatt caacatttaa aaaattatca  1560
aatctctgtg ttatataagt tttatactat attcaaataa agtgtaatat acctttcaa   1620
tttgtatttt ttaactagtt taagctaact aatatatttg ctaatcttat acctatcaaa  1680
accgactatc gtttcttatc tctatagtat ttttgcaaga cttttttggt ggatttgggt  1740
gaaagtgcat tcggatcata tggtacattc ccctattaaa taaatatggt gcactcctat  1800
gttattagct aaaatgttta gattataaat caaagtcata tcataaataa aattaatatt  1860
aataaaataa atggcttttt ggcaagacga atttggaggg acagtaaaat ataattaatc  1920
caccgtttca atacgggtta aatctttaat ttattaacat atcaaatcat cctaatttag  1980
aaagattat ataaaaccaa aaatgttatg tggtatatat aatgttacta tatataaaat  2040
taactataa aatataaatc tattagagaa tgatacaagt tgcaaaaatt ttatatataa  2100
taaataattc ttaaatttta aaaattacta ctataaaaaa aatcacgaga cgggtaaaga  2160
aattacagaa cggatttat tttggaattg ggttatatgg tagatgtatt tgaatcaata  2220
tttataaaat tttaaaatat tattaatatg ttgttttaat aaggattaaa acttcagttt  2280
```

```
tttaacaatt gtctcatgta ttcgtcgtat aacgttactt aataacaatt ataaactata    2340
aaatataaat attttataaa aataaaattt acaaattta atatatatta tctttaaaaa    2400
ataaatcgtc ccgcggtata gtgagggtta aaatctagta cttgtgctat gttttatca    2460 aaagtcaacg agattaacta agcaaccaca aaataggaaa acgcatcaaa cgcacatata    2520
tatgagatca tgtatatgat tatatcatga tgatactcat gggcgtagtc aatttacatt    2580
gtagaaagtc ttgtcttctt taaagagttg gtcaatttaa attgtccaat gaaacaaata    2640
ttatcacaat tcacaacttc ttcgtcacaa aaagattta aaaccaaatg gcccatgcag     2700
gtttcgaacc tgcgaccttc gcgttattag cacgacgctc taaccaactg agctaatggg    2760
ccatttgcta caaaactaaa atcatattta ctaatcttta aattatcatt tttatacaaa    2820
ttattagtcc aaaaaagatg caagaaatgt tgaaaaatat ttttcatacg ggttattggt    2880
caaagtatat gcaagaaatg ttgaaaaata tttttcatac gggttattag tcaaagtata    2940
tgcaagaaaa aaatggaaaa gtttgggata tatcatcgtg catggttggt cattatgtgt    3000
gt                                                                   3002

<210> SEQ ID NO 158
<211> LENGTH: 2498
<212> TYPE: DNA
<213> ORGANISM: Artificial Sequence
<220> FEATURE:
<223> OTHER INFORMATION: Synthetic

<400> SEQUENCE: 158
tttgtgttca atttcttagt ttattagaaa tctaattacc gatttatgaa gaaaaatgta     60
acaacttgag tgctcttaag gttgatcata aaagtatact gatcactgtg ggattaatat    120
ttgcatttct ctatgtgtgt gaagggtaag cccgtcaaag acgccagtga ggctacacca    180
ctctgattta aactaaagct aatagcaatc cgatgaaaga gatctattca tattgagaca    240
aagaaatcaa aagtcatttt aagatacttg aagcgttttt gttcatataa agatcttctc    300
gatctcaagc tgcccggccg atataataat tttgaaccct tagtaactta tgctaaacta    360
tctcctttgg aaccaaattg atcttgtttc ttatataata atttggaaac atcatttttgg   420 tcatctttat gaatcatttt aagacccttt tggacaaaat cctctcctac tctctctctc    480
tgaatttcca tgcttttctg tttggtatga ttattcagtg tttgatttga tggaagtgaa    540
agttgttgga tttctttaca aatagtttca ttgatttggt atctttttta ctaggcgaga    600
taacacaact taacggaatc gaacactgat gagaaaagcg gaatcaaatg gactttacca    660
cttgactaaa agcacatcat cgagagaaga tatctagttt gtaactaaat aaataaatat    720
attagattat ttttttcttg aactcatttt caacaaaaca ttgtattaat aaatatcagt    780
ttgattgctt acgagaatac cttgtaaaac aaaactaatc tatcaaccaa accaaaggcc    840
ccatatttct aaactgaatt tcattgactc ggtttggttt gttactttgt ttgatatgat    900
tgacgaaact acactcaaat gtgaacccac aacaaaaatt aggcacagta aatatggaag    960
ttttagttga ctttcgtttt gttaaaatat aaacccatgt ttataaagaa aagattatct   1020
atctatttga ccaagtcctc ctgtgtaaga cttatttttt ttttgtcaaa tttgggacac   1080
tatacctgtt ttatatattg aataaagaac cgtatacaaa ggttgaaaaa acagagaaat   1140
gaagtataga aatgggaatg aaaatgtcaa ctgataagac aattgtcggc taactaacct   1200
ggtcaagata agttacgtat atgaaaagtt acgagaaaac acaacgtggg atatttcttg   1260
agacacaagt caactatcaa accggaccgt atggttaaga gacgattgat tctcgtacta   1320
```

```
tattgaaggc agcaaagtca tgtcttagcc acttggttaa gttcaaccat tgaaccagtg   1380
ggtttattat ctactttaat tttcgtcctt aaacaatttg acccacgacc atttgctatc   1440
aaatgtttgg accggaccgg accgaaccag accggtgaga tgttaaatga gagacttgct   1500
taccaaattg taccaaaacg gtttatatta aaaggtgtaa aaagtggcct tttgttgtct   1560
ttttcagtac ttgacggtgg aggagtagta gtaggtgacc gtattaactc gtttaagcgt   1620
ttttcatgca tatggttgtg acagatcaaa atcaccgcgt tccatgtttt caaaaatctt   1680 attttatta tgaggtcttt aattattgta agaagaaag agaataaaaa ttgtggaaca     1740
atttattagg taaagatatc tttggtaatt ttctgtttaa ttgctatcaa attttttttt   1800
tttttttttt tttttttaaa agttgctatc aaatatgtta tctacgagtg gaaaatctat   1860
ggtaaacaca atgtattttt caagtgctat actatttta aagtttatat aatccatagt    1920
taaaattaat taaaatcaac aaatataaga taagcacatg tcacttatgt ttattttatt   1980
tatttattat aattcaaaat gacacagaaa ttcttctaat tattttaaa aattaaaata    2040 ttattacaaa acgtaaccgt cttatcttat tttaaattaa catatgtagt ttcttacctc   2100
gcaagataat gatttcacta ataaaaatat gaaagttaag atcaacccat taatgtttac   2160
cacataaaaa aaaatacca acctctatta gttttattt tattttctat atgcttacaa     2220
tgcaaaacaa aaaatttcta gaaaagaat caatgtaaaa gttaattttc accttaatta    2280
ggcaaacata taattttaaa aaatttgatc taatttcagt acttttgtag gtcagaaaaa   2340
ttatttttaa tttctttcgt cgttaattc aattcaacaa tcaacatcat tagatgtgaa    2400
agtcattaaa tgaaattaac atacaattaa aagtgattaa tgccactacg cgctcttgcc   2460
tccttcttag tggtcttcat ttaacaaacg ccttctct                           2498

<210> SEQ ID NO 159
<211> LENGTH: 2902
<212> TYPE: DNA
<213> ORGANISM: Artificial Sequence
<220> FEATURE:
<223> OTHER INFORMATION: Synthetic

<400> SEQUENCE: 159
tacccagaca aacgcacgag caatctcctt cgcaatcatg gtgaattctt cctctgaaac    60
attgaattat tttcttgcta ttaactcgaa cagaaatgaa taatgatatg atgattttct   120
cgtgcttgca gattatctca gagaagaatc gccgcgagat ctccaaatac cacctcttca   180
aaggtacaac tctttttatt ttgtttgcga atcgtcttaa ctttgatctg tatacgtgta   240
atcagataca gtacgtagat attctgaatc tcttgtactt agcccatcgt tttaacttta   300
gctgtttctg aattcgatgc cttacttact ttgaacatag ttagcaagaa caatgtgatt   360
cactaggatt acttagaaat gttactttta tttcgagaaa gttttgtatg ctaaaagagg   420
acttgaattt gccacaacat cccttgatcg agtgttccga atcctgcagg tgattaagct   480
tatgtagagc tttttgtcaa aggagtatgt caaagagact tttacttggg tacattacta   540
ctggttcctt aacaatgaag gcattaactt cctcaagact cacctcaatc tcccacctga   600
gattgttcct gcggtcctgc caccttaaaa agcagccttc tttttttttc cacgactgag   660
accttaatta aaagcagccg aataagcgac caatttttctg taaaaagcac ttactagatt   720
ttactttgtt aggctttccc ttttgtgtat ttttgtatgt ctcttaaaaa agataaggca   780
ttcacggtaa aacaaaacaa aaaatcaac gaaaataat tacggaaaca caaatattta    840
```

```
atgaaaataa aaaaccagtt taaacactt tatgggtcga ttttattt taaaaataaa      900
atcctttaaa aaaaaaacta aaaaggaga aaaaaatcgc tttgattta aaaacaagtg      960
atcgaattca ggagagggat cagatgataa agaaggaga gtgctcaata gtcgtaacag    1020
gctgagcgaa acactcttct cgcattaagc gagtttaata accactcctc atttcccctt   1080
taacttgcct gaaggatcat atttattcat tgccccacct ttaatctttt ttatagccaa   1140
ctaatcatat ccctcccgtc tcttctaacc gatgtgggac aaatatctct tcttcagttt   1200
ttcaaaaccc taattagcct accgaaaatg ggcttaggcc tggtaaaaat tacaacggcc   1260
caacaagacg acgatttctc agtatgacga ttacgatttc tgttgacaga gaaacttttt   1320
gaaatgatga ctactacgac gacgacgatt tctcagcata acttctatgg tgctggagat   1380
tcggaaactt gcatttctat tattgaggta ttaagctctc actggtaaac aatggcgatt   1440
tctaatcgag ctttcttctt tcgcgttttg ttttttccat cgtttgtttg tgatttgtgt   1500
gtatgtgtag aatttgaagg aagagtatgg attgtttgtt tggccttgta gcgttatcct   1560
cgctgagtat gtttggcaac acagatctcg atttcgtgat tcttcgatac tcgaggttaa   1620
tttctatttc aactactctt tgctaaaatc ccttgatttt gaattgatta cagaattggg   1680
atatgtgtgt ttgagctaat gaatcttaaa tatgttagga cctttttaac gttttcttag   1740
acttgtgttg atggaattta cagctaggag ctggtacttc cttgcctggt ttagtagctg   1800
caaaggttgg ggctaatgtc actcttactg atgatgcaac taaaccagag gtgtgaaatt   1860
taagttcttg tgttgagaag attttttgcta tttgggttta gagaatatga gcttatttag   1920
ttcgtttgta tcatatatat atgcaggttt tggataatat gagaagagtc tgtgagctta   1980
acaagctgaa ctgtaatgta atataaacta tcttcacctc tcttcaattt aacaacgcca   2040
aatttatcat ttacccggat cattatatgt tgcatatgta attcacgaag gttgttgggt   2100
tgattgctat ttacatttga aattcttgag agtttgcttc tagaacttct ctgtggttgt   2160
ctattgtagg tgttgggtct cacctggggt gtgtgggatg caccgatact cgacctgcga   2220
ccaaacatta tacttggggc tgatgtttta tatgattcaa gtggttcgtt tcatttgttt   2280
ttgttttggg tattggcctt ttctttttcc ccttgtgaat gagttgaaaa tctgaacttg   2340
gacacctctg ttgttaagca tttgatgatc tctttgcgac tgtctcattt cttctccaaa   2400
gttctcctga tgcagttttt attaccactt atcataacag gaggtacacg aattcttctt   2460
ctttcattct tcccggtcgt ctattatata tatccgcaac agatttaggg tgacgatttc   2520
ttccggattt catttgttca gttttgattt tgcagtgggc atcatctaat cgagttcctg   2580
atggtaaaat ggggactaaa gtgtgttaaa cttctggatg gcttctcatt cttgccctct   2640
caaaaggcat ctgtacttag tggaaacatt cagttggttg agatcgtatt gagttcccaa   2700
aatgaaaatc agcagcttta gactgtaaca accatctaag tggataataa ccagagatca   2760
aagaggtata acatttactt cattgtaata atacatggtt actctactat agaaagtggt   2820
tagcaggaat ctctggacta gggagtttag tttaatcaaa ctcatatact tggtaattct   2880
ttgcataaat tcaaatttat ct                                            2902
```

<210> SEQ ID NO 160
<211> LENGTH: 1548
<212> TYPE: DNA
<213> ORGANISM: Artificial Sequence
<220> FEATURE:
<223> OTHER INFORMATION: Synthetic

<400> SEQUENCE: 160

```
atttttttt ggggaaaaga agagaaatta gggtttcaaa atgtaagaga gagacttatg      60
tgatttgagg tgataagacg cagccttaat ttatagaaca ggtgtgacgt aataactagg     120
gttaaacatg ttttctaggg tttgctgaaa gatttgtttc aacttactct gattaagatg    180
tgtggttaat tgggttagtg gttaggccca catcatgtga gcattttcga taactaatga    240
ttttttctcc tcgtttcgag caaaaaatat ctttgtaaga atatctttta ttccttaaat    300
gacaattttg tccttcgtct cgtcgtcatt atgtcataca atagttgggt ctgagtttcg    360
tttattgggc ctatctaatt taattggaaa gattataact tccggcccaa tgaatctgac    420
ggcgaaatta gtaaaacaat aaaatgaaat aatatgcaaa gactatgacg ataatgtgct    480
atggatttac atatttgttt tgtcattaat tatgacatgc aataaattca tatgaaaaga    540
ttcttatcgc aatagcatcg tggacatgtt acagtctgta atatccaaac tttagcatag    600
acgttttttg ttgtacaaat attttggtat gttaagtgat attcaaatga aagctagatg    660
tgcagatatg tgaacatata aatctttcaa tggaattcaa ttttcaatca ttgaatattt    720
ggatacactc gctctgtact tgaaatattt tgactgtctg aatattattt ttttacagga    780
ttaattattt tgtataccaa aattagacgg atgaagaatg aagatgtagt agttatacaa    840
agtcaattac aaatggttca gtatcttgat ttcgattttt gtgctgaaaa tgctgactaa    900
agcgtgtaga agagcttttt caacaagaaa taacctggct aagatttttt taagaaatct    960
gattattaat atatcgcagg taatatgaaa aagtatcgtc gacttttat aagagtgaca    1020 actaaatcat tttgctcata ataaagccac aattattatt agtatatttt ggtcgtttta    1080
atacgaggaa aaataattgt catacaaaat ttacagaaat ggagtagcat cgtagctcct    1140
aggaattcaa ttatttattt gcaaaactac taaaatggtg gttatcatat taaacgtcag    1200
cagaaacttt aagtattttt gaaatgatat taatttaaga gttcgttaag ctgtcttggg    1260
cgggatcgtt gagagtcaaa ctcctcaaac gacgccgtat tcagaacttc actttcaatt    1320
actgtatctg cgtctcggtc acgagatcga accataaatc ttgggaacgt gcacgtatac    1380
aacgaaagat ccaccttctc tcactttttt tattttctta tactttcttc tcttttcttc    1440
gaacggccgc tgttcttgac cagtctgaag ctttctctgt ccagaacagt tctgtaagaa    1500
gaagttttta tcaaatatta tataaaaata tctgtttcgt attatatc                 1548
```